(12) United States Patent  (10) Patent No.: US 7,902,367 B2
Nomura et al.  (45) Date of Patent: Mar. 8, 2011

(54) CYCLIC AMINO BENZOIC ACID DERIVATIVE

(75) Inventors: Masahiro Nomura, Tochigi (JP); Yasuo Takano, Saitama (JP); Kazuhiro Yumoto, Tochigi (JP); Takehiro Shinozaki, Tochigi (JP); Shigeki Isogai, Tokyo (JP); Koji Murakami, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 968 days.

(21) Appl. No.: 11/659,854

(22) PCT Filed: Aug. 11, 2005

(86) PCT No.: PCT/JP2005/014718
§ 371 (c)(1),
(2), (4) Date: Mar. 5, 2007

(87) PCT Pub. No.: WO2006/016637
PCT Pub. Date: Feb. 16, 2006

(65) Prior Publication Data
US 2007/0249580 A1  Oct. 25, 2007

(30) Foreign Application Priority Data
Aug. 11, 2004 (JP) ................. 2004-234603

(51) Int. Cl.
C07D 401/00 (2006.01)
A01N 43/40 (2006.01)
(52) U.S. Cl. .......................... 546/209; 514/326
(58) Field of Classification Search ........... 546/209; 514/326
See application file for complete search history.

(56) References Cited

U.S. PATENT DOCUMENTS

| | | |
|---|---|---|
| 4,010,273 A | 3/1977 | Bormann et al. |
| 4,064,252 A | 12/1977 | Murai et al. |
| 4,113,871 A | 9/1978 | Stach et al. |
| 4,237,132 A | 12/1980 | Murai et al. |
| 5,227,490 A | 7/1993 | Hartman et al. |
| 5,411,972 A | 5/1995 | Komoto et al. |
| 5,461,066 A | 10/1995 | Gericke et al. |
| 5,847,005 A | 12/1998 | Kasahara et al. |
| 6,028,109 A | 2/2000 | Willson |
| 6,166,049 A | 12/2000 | Smith |
| 6,204,277 B1 | 3/2001 | Shinkai et al. |
| 6,291,459 B1 | 9/2001 | Bhatnagar et al. |
| 6,294,580 B1 | 9/2001 | Willson et al. |
| 6,376,503 B1 | 4/2002 | Patane et al. |
| 6,506,797 B1 | 1/2003 | Nomura et al. |
| 6,518,290 B1 | 2/2003 | Sierra |
| 6,562,828 B1 | 5/2003 | Katoh et al. |
| 6,635,655 B1 | 10/2003 | Jayyosi et al. |
| 6,673,817 B1 | 1/2004 | Zhu et al. |
| 6,706,763 B1 | 3/2004 | Satoh et al. |
| 6,734,199 B1 | 5/2004 | Miyachi et al. |
| 6,884,821 B1 | 4/2005 | Shinoda et al. |
| 7,005,440 B1 | 2/2006 | Jayyosi et al. |
| 2002/0019402 A1 | 2/2002 | Dominguez et al. |
| 2002/0028835 A1 | 3/2002 | Hu et al. |
| 2002/0032330 A1 | 3/2002 | Nomura et al. |
| 2002/0151545 A1 | 10/2002 | Bisacchi et al. |
| 2002/0165282 A1 | 11/2002 | Hayward et al. |
| 2002/0198195 A1 | 12/2002 | Nazare et al. |
| 2003/0032671 A1 | 2/2003 | Urbahns et al. |
| 2003/0040531 A1 | 2/2003 | Fujishima et al. |

(Continued)

FOREIGN PATENT DOCUMENTS

DE 24 61 601 7/1976
(Continued)

OTHER PUBLICATIONS

Michael R. Wood et al., "A novel, one-step method for the conversion of primary alcohols into carbamate-protected amines", Tetrahedron Letters, vol. 43, No. 21, pp. 3887-3890, 2002.

(Continued)

Primary Examiner — Rita J Desai
Assistant Examiner — John Mabry
(74) Attorney, Agent, or Firm — Wenderoth, Lind & Ponack, L.L.P.

(57) ABSTRACT

The present invention relates to cyclic amino benzoic acid derivatives which are effective in therapy of lipid metabolism abnormality, diabetes and the like as a human peroxisome proliferators-activated receptor (PPAR) agonist, in particular, as an agonist against human PPARα isoform, and addition salts thereof, and pharmaceutical compositions containing these compounds.

A cyclic amino benzoic acid derivative represented by the general formula (1)

[Chemical formula 1]

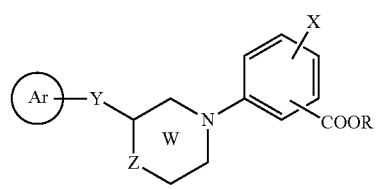

(1)

[wherein a ring Ar represents an aryl group which may have substituent, or the like; Y represents a $C_1$-$C_4$ alkylene, $C_2$-$C_4$ alkenylene, $C_2$-$C_4$ alkynylene, or the like; Z represents an oxygen atom, sulfur atom or —$(CH_2)_n$— (n represents 0, 1 or 2); X represents a hydrogen atom, halogen atom, lower alkyl group which may be substituted with a halogen atom, or the like; R represents a hydrogen atom or lower alkyl group, and —COOR substitutes for an ortho position or metha position of binding position of ring W] or a pharmaceutically acceptable salt thereof.

12 Claims, No Drawings

U.S. PATENT DOCUMENTS

| | | |
|---|---|---|
| 2003/0134885 A1 | 7/2003 | Bernardon et al. |
| 2003/0144332 A1 | 7/2003 | Glombik et al. |
| 2003/0187068 A1 | 10/2003 | Miyachi et al. |
| 2004/0102500 A1 | 5/2004 | Cano et al. |
| 2004/0157885 A1 | 8/2004 | Bagley et al. |
| 2004/0198786 A1 | 10/2004 | Gretzke et al. |
| 2004/0204462 A1 | 10/2004 | Goerlitzer et al. |
| 2004/0209873 A1 | 10/2004 | Stapper et al. |
| 2004/0214888 A1 | 10/2004 | Matsuura et al. |
| 2005/0032899 A1 | 2/2005 | Chen et al. |
| 2005/0054582 A1 | 3/2005 | Lehmann et al. |
| 2005/0054671 A1 | 3/2005 | Giannessi et al. |
| 2005/0059669 A1 | 3/2005 | Ajito et al. |
| 2005/0096468 A1 | 5/2005 | Van Emelen et al. |
| 2005/0101521 A1 | 5/2005 | Miyachi et al. |
| 2005/0113362 A1 | 5/2005 | Lindstedt et al. |
| 2005/0165016 A1 | 7/2005 | Van Emelen |
| 2005/0228044 A1 | 10/2005 | Shi et al. |
| 2005/0228050 A1 | 10/2005 | Orita et al. |
| 2006/0089404 A1 | 4/2006 | Desai et al. |
| 2007/0154543 A1 | 7/2007 | Hoshino et al. |
| 2007/0191429 A1 | 8/2007 | Bagley et al. |
| 2007/0225296 A1 | 9/2007 | Miyazaki et al. |
| 2009/0036489 A1 | 2/2009 | Nomura et al. |

FOREIGN PATENT DOCUMENTS

| | | |
|---|---|---|
| EP | 1 757 582 A1 | 2/2007 |
| JP | 52-83676 | 7/1977 |
| JP | 63-91354 | 4/1988 |
| JP | 5-271072 | 10/1993 |
| JP | 6-72861 | 3/1994 |
| WO | 00/23407 | 4/2000 |
| WO | 00/64876 | 11/2000 |
| WO | 01/25181 | 4/2001 |
| WO | 01/27082 | 4/2001 |
| WO | 01/27090 | 4/2001 |
| WO | 02/44127 | 6/2002 |
| WO | 02/44130 | 6/2002 |
| WO | 02/46146 | 6/2002 |
| WO | 02/46161 | 6/2002 |
| WO | 02/098840 | 12/2002 |
| WO | 03/030889 | 4/2003 |
| WO | 03/043988 | 5/2003 |
| WO | 03/050077 | 6/2003 |
| WO | 03/051821 | 6/2003 |
| WO | 03/055867 | 7/2003 |
| WO | 03/059875 | 7/2003 |
| WO | 03/075929 | 9/2003 |
| WO | 03/076438 | 9/2003 |
| WO | 03/099766 | 12/2003 |
| WO | 2004/009533 | 1/2004 |
| WO | 2004/010936 | 2/2004 |
| WO | 2004/010992 | 2/2004 |
| WO | 2004/048334 | 6/2004 |
| WO | 2004/075815 | 9/2004 |
| WO | 2004/076402 | 9/2004 |
| WO | 2004/076447 | 9/2004 |
| WO | 2004/091600 | 10/2004 |
| WO | WO 2004/089918 | * 10/2004 |
| WO | 2005/009942 | 2/2005 |
| WO | 2006/101108 | 9/2006 |

OTHER PUBLICATIONS

Supplementary European Search Report issued May 13, 2009 in European Application No. 05 77 0805.

P. Sarraf et al. "Differentiation and reversal of malignant changes in colon cancer through PPARγ", Nature Medicine, vol. 4, No. 9, pp. 1046-1052 (Sep. 1998).

K. Schoonjans et al. "Role of the peroxisome proliferator-activated receptor (PPAR) in mediating the effects of fibrates and fatty acids on gene expression", Journal of Lipid Research, vol. 37, pp. 907-925 (1996).

P. Costet et al. "Peroxisome Proliferator-activated Receptor α-Isoform Deficiency Leads to Progressive Dyslipidemia with Sexually Dimorphic Obesity and Steatosis", Journal of Biological Chemistry, vol. 273, No. 45, pp. 29577-29585 (1998).

O. Braissant et al. "Differential Expression of Peroxisome Proliferator-Activated Receptors (PPARs): Tissue Distribution of PPAR-α, -β, and —γ in the Adult Rat", Endocrinology, vol. 137, No. 1, pp. 354-366 (1996).

G. Picciola et al. "Composti Eterrociclici Contenenti IL Residuo Di Un Acido 4-Amminofenilalcanoico A Presunta Attivita Antiinfiammatoria", Farmaco, Edizione Scientifica, 36(1), pp. 47-60 (1981), with English abstract.

B. Forman et al. "Hypolipidemic drugs, polyunsaturated fatty acids, and eicosanoids are ligands for peroxisome proliferator-activated receptors α and δ", Proc. Natl. Acad. Sci. USA, vol. 94, pp. 4312-4317 (Apr. 1997).

Y. Wang et al. "Peroxisome-Proliferator-Activated Receptor δ Activates Fat Metabolism to Prevent Obesity", Cell, vol. 113, pp. 159-170 (Apr. 18, 2003).

M. Göttlicher et al. "Fatty acids activate a chimera of the clofibric acid-activated receptor and the glucocorticoid receptor", Proc. Natl. Acad. Sci. USA, vol. 89, pp. 4653-4657 (May 1992).

* cited by examiner

CYCLIC AMINO BENZOIC ACID DERIVATIVE

TECHNICAL FIELD

The present invention relates to cyclic amino benzoic acid derivatives which are effective in therapy of lipid metabolism abnormality, diabetes and the like as a human peroxisome proliferators-activated receptor (PPAR) agonist, in particular, as an agonist against human PPARα isoform, and addition salts thereof, and pharmaceutical compositions containing these compounds.

BACKGROUND ART

Peroxisome proliferators-activated receptor (PPAR) is a ligand-dependent transcription factor belonging to a nuclear receptor super-family likewise steroid receptors, retinoid receptors, thyroid receptors and the like. The receptor includes three isoforms (type α, type γ and type δ (or type β)), which have been identified in various animal species (Non-patent document 1). Among these, PPARα distributes in liver, kidney or the like having high fatty acid catabolic ability (Non-patent document 2), and positively or negatively controls expression of genes involved in fatty acid metabolism or intracellular transport (for example, acyl CoA synthetase, fatty acid binding protein or lipoprotein lipase) and genes of apolipoproteins (AI, AII, CIII) involved in metabolism of cholesterol and neutral lipid. PPARγ is highly expressed in adipocyte, and involved in differentiation of adipocyte (Non-patent document 3). PPARδ is universally expressed in biological tissues, mainly in nerve cells.

As to physiological significance of PPARδ, involvement in fatty acid burning is recently reported (Non-patent documents 4 and 7), however, there still remain a lot of unclear points. In this manner, each isoform of PPAR plays a specific role in a specific organ or tissue.

Furthermore, it is also reported that PPARα-knockout mouse exhibits hypertriglycemia with age, and gets obesity which is mainly associated with increase in white adipocyte (Non-patent document 5). This strongly suggests the relation between activation of PPARα and blood lipid (cholesterol and neutral lipid) lowering activity.

On the other hand, as antihyperlipidemic drugs that are dominantly used at the present day, statin drugs and fibrate drugs are known. Statin drugs, however, are poor in free fatty acid and triglyceride lowering ability, and fibrate drugs are poor in cholesterol lowering ability. As to fibrate drugs, various side effects that are attributable to exhibition of wide pharmacological property, such as gastrointestinal damages, eruption, headache, hepatic function disorder, renal function impairment, gallstone have been reported, and hence there is need for development of an antihyperlipidemic drug based on a specific mechanism that will not cause such side effects.

In consideration of the current cases of conventional antihyperlipidemic drugs and relationship between the role regarding lipid metabolism control function of transcription factor called PPARα, and clinical condition of hyperlipemia that has been revealed heretofore, creation of a compound that directly binds as a ligand to PPARα, in particular, to human PPARα and is able to potently activate human PPARα may provide a therapeutic agent exhibiting blood lipid (both cholesterol and neutral lipid) lowering activity according to an extremely specific mechanism.

As an endogenous ligand against PPARα, eicosanoid of hydroxyeicosatetraenoic acid (HETE) group generated through oxidation by cytochrome P-450, in particular 8-HETE, 8-HEPE and the like are reported as well as $LTB_4$ which is a metabolite of arachidonic acid (Non-patent document 6). These endogenous unsaturated fatty acid derivatives are instable in both metabolic and chemical aspects, so that they cannot be provided as pharmaceuticals.

On the other hand, as a compound which is reported to have PPARα agonist activity, compounds of the formulas (A) to (J) listed in Table 1 are known, however, none of these include compounds having a benzoic acid structure substituted with alicyclic amino group, and hence they differ in structure from compounds of the present invention.

TABLE 1

| Patent Document | Formula |
|---|---|
| 1 | (A) |
| 2 | (B) |

TABLE 1-continued
| Patent Document | Formula |
|---|---|
| 3 | 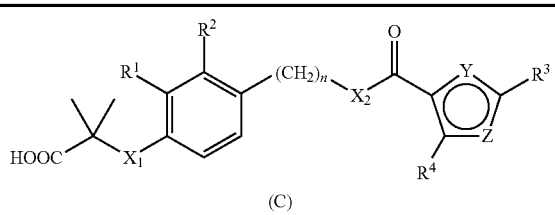<br>(C) |
| 4 | 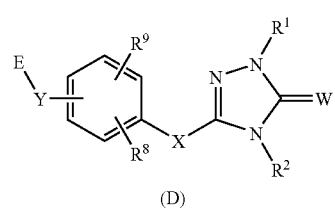<br>(D) |
| 5 | 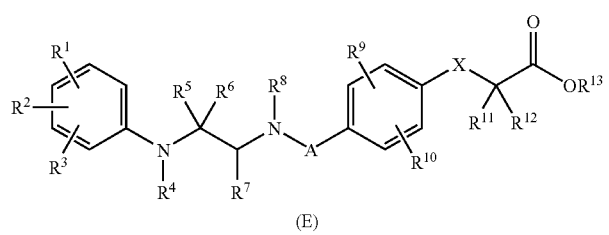<br>(E) |
| 6 | 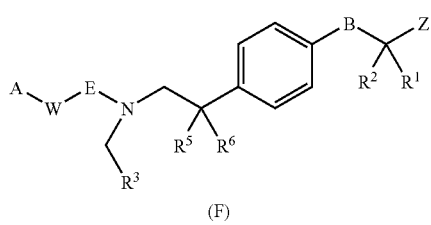<br>(F) |
| 7 | 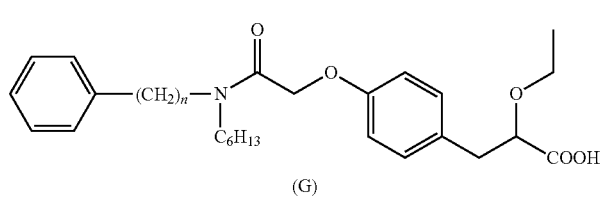<br>(G) |
| 8 | 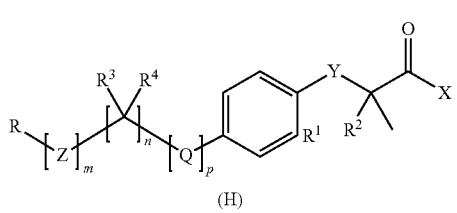<br>(H) |
| 9 | 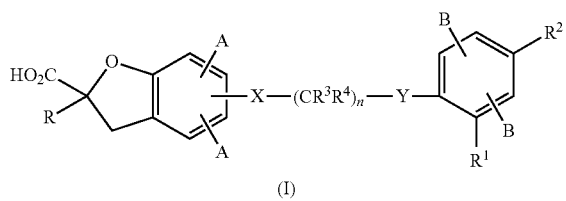<br>(I) |
| 10 | 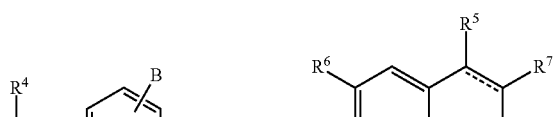 |

Furthermore, as a compound having a similar structure to compounds of the present invention and reported for PPARγ agonist activity, Patent document 11 discloses a compound represented by the general formula (K)

[Chemical formula 1]

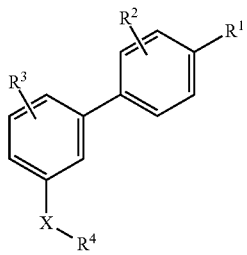
(K)

[wherein R¹ represents the general formula (K-a)

[Chemical formula 2]

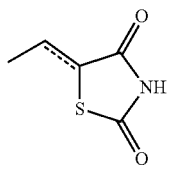
(K-a)

or general formula (K-b)

[Chemical formula 3]

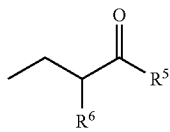
(K-b)

(wherein $R^5$ represents a hydroxyl group, or $C_1$-$C_9$ alkoxy group, and $R^6$ represents a $C_1$-$C_6$ alkyl group or the like); $R^2$ and $R^3$ represent a hydrogen atom, alkyl group or the like; X represents —$CH_2$—$NR^8CO$—, —$N(R^8)$—$COCH_2$— or the like; $R^4$ represents a phenyl group, benzyl group or the like; $R^8$ represents a hydrogen atom or $C_1$-$C_6$ alkyl group] (explanation for substituents is partly extracted), however this compound is a biphenyl alkanoic acid derivative, and is different in structure from compounds in accordance with the present invention.

Furthermore, as a compound having a similar structure to compounds in accordance with the present invention, and reported to have PPAR agonist activity, Patent document 12 discloses a compound represented by the general formula (L)

[Chemical formula 4]

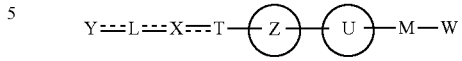
(L)

[wherein L represents a single bond, or a $C_1$-$C_6$ alkylene group which may have one or more substituents or the like; M represents a single bond, or a $C_1$-$C_6$ alkylene group which may have one or more substituents or the like; T represents a single bond or the like; W represents carboxyl group;

---- [Chemical formula 5]

represents a single bond or a double bond; X represents a single bond, an oxygen atom or the like; Y represents a 5 to 14-membered aromatic group which may have one or more substituents and one or more hetero atoms, or a $C_3$-$C_7$ alicyclic hydrocarbon group; rings Z and U represent 5 to 14-membered aromatic groups which may be identical or different, and may have one to four substituents, and one or more hetero atoms, and may be saturated in a part of the ring] (explanation for substituents is partly extracted). As a compound that is reported as a PPAR receptor ligand, Patent document 13 discloses a compound represented by the general formula (M)

[Chemical formula 6]

(M)

Ar I—(—)$_a$—A—(—)$_b$—Ar II—(—)$_c$—B—(—)$_d$—Ar III—(—)$_e$—D—(—)$_f$—E—Z with R1, R2 on first bracket; R3, R4 on second; R5, R6 on third; R7, R8 on fourth; R9, R10 on fifth; R11, R12 on sixth.

[wherein ring ArI, ring ARII, and ring ARIII independently represent an aryl, heteroaryl or the like; A represents an oxygen atom, sulfur atom or the like; B represents an oxygen atom, sulfur atom, a single bond or the like; D represents an oxygen atom, sulfur atom, single bond or the like; E represents a single bond or ethylene group; a, b, c and e represent 0 to 4; d represents 0 to 5; f represents 0 to 6, $R^1$, $R^3$, $R^5$, $R^7$, $R^9$ and $R^{11}$ independently represent a hydrogen atom, halogen atom or the like;

$R^2$, $R^4$, $R^6$, $R^8$, $R^{10}$ and $R^{12}$ independently represent —$(CH_2)_q$—X; q represents 0 to 3, X represents a hydrogen atom, halogen atom or the like; Z represents $R^{21}O_2C$—, $R^{21}CO$— and the like; $R^{21}$ represents a hydrogen or the like] (explanation for substituents is partly extracted). However, ring Z or ring ArII of these compounds (Patent documents 12 and 13) does not contain an alicyclic amino group which is characteristic of compounds in accordance with the present invention, and differs in structure from compounds in accordance with the present invention.

Furthermore, as a compound having a similar structure to compounds in accordance with the present invention and reported to have PPAR agonist activity, Patent document 14 discloses a compound represented by the general formula (N)

[Chemical formula 7]

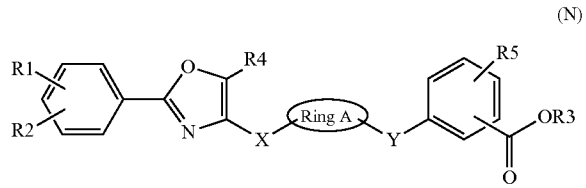

(N)

[wherein ring A represents a $C_3$-$C_8$ cycloalkyl which may contain an oxygen atom, or $C_3$-$C_8$ cycloalkenyl which may contain an oxygen atom; $R^1$, $R^2$, $R^4$ and $R^5$ represent a hydrogen atom, fluorine atom, chlorine atom, bromine atom, hydroxyl group, nitro group, trifluoromethyl group, trifluoromethoxy group, $C_1$-$C_6$ alkyl group, or $C_1$-$C_6$ alkoxy group; $R^3$ represents a hydrogen atom, or $C_1$-$C_6$ alkyl group; and X, Y represent a $C_1$-$C_6$ alkylene which may be substituted with an oxygen atom]. However, ring A does not contain an alicyclic amino group which is characteristic of compounds in accordance with the present invention, and ring A and the benzoic acid moiety are bound via Y, so that it is different in structure from compounds in accordance with the present invention.

Furthermore, as a compound having a similar structure to compounds in accordance with the present invention and reported to have triglyceride and cholesterol lowering activity, Patent documents 15 to 19 disclose a compound represented by the general formula (O)

[Chemical formula 8]

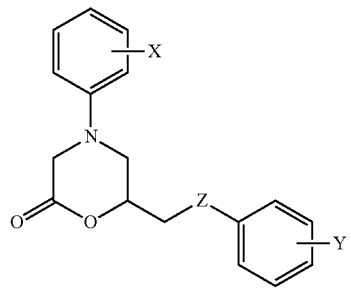

(O)

[wherein Z represents an oxygen atom or sulfur atom; X represents a hydrogen atom, halogen atom, lower alkyl group, carboxyl group, lower alkoxycarbonyl group or the like; Y represents a hydrogen atom, halogen atom, lower alkyl group when Z is a sulfur atom, and represents a hydrogen atom, halogen atom, lower alkyl group, lower alkoxy group or the like when Z is an oxygen atom] (explanation for substituents is partly extracted). However, this compound is a derivative of morpholin one which is different from an alicyclic amino group which is characteristic of compounds in accordance with the present invention, and has a different structure from compounds in accordance with the present invention because only para-substituted benzoic acid derivative (X=COOR) is described in Examples of the patent documents. Furthermore, the patent documents include no report about PPARα agonist activity.

As a compound having a cyclic amino benzoic acid structure, Patent document 20 discloses as a compound having integrin antagonist activity, a compound represented by the general formula (P)

[Chemical formula 9]

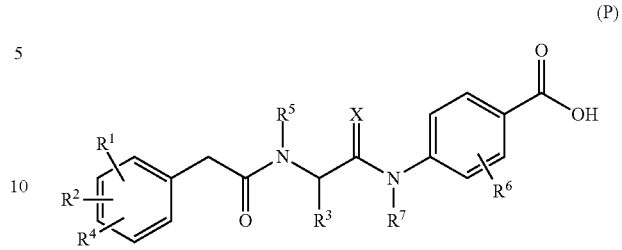

(P)

[wherein $R^1$ represents a hydrogen atom, hydroxyl group or the like; $R^2$ represents a hydrogen atom or halogen atom, or $R^1$ and $R^2$ together represent a 4 to 7-membered ring which may contain up to two oxygen atoms, nitrogen atoms, or sulfur atoms, and up to two double bonds; $R^3$ represents a hydrogen atom, $C_1$-$C_{10}$ alkyl group or the like; $R^4$ represents a hydrogen atom, halogen atom or the like; $R^5$ represents a hydrogen atom, $C_1$-$C_6$ alkyl group or the like, or $R^3$ and $R^5$ together represent a 4 to 7-membered ring which may contain up to two oxygen atoms, nitrogen atoms, or sulfur atoms, or up to two double bonds; $R^6$ represents a hydrogen atom, $C_1$-$C_4$ alkyl group or the like; $R^7$ represents a hydrogen atom or $C_1$-$C_4$ alkyl group, or $R^3$ and $R^7$ bind to each other to represent a ring; X represents an oxygen atom or two hydrogen atoms] (explanation for substituents is partly extracted). However, for this compound, no report about PPARα agonist activity is found, and the compound is a benzoic acid derivative having a cyclic amino group at para position of carboxylic acid, and hence differs in structure from compounds in accordance with the present invention.

Furthermore, as a compound having a cyclic amino benzoic acid structure, Patent document 21 discloses a compound having serine protease inhibitory activity, a compound represented by the general formula (Q)

[Chemical formula 10]

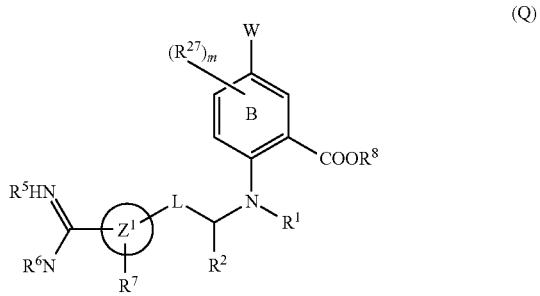

(Q)

[wherein ring B represents a phenyl group or pyridyl group, W represents a $C_2$-$C_{10}$ alkyl group and the like; $Z^1$ represents a 5 to 7-membered monocyclic or 8 to 11-membered bicyclic aryl group or the like; L represents —$(R^{18}R^{19})_s$—Y—$(R^{18a}R^{19a})_t$—; Y represents a carbonyl group or the like; $R^1$ and $R^2$ independently represent a hydrogen atom or the like, or $R^1$ and $R^2$ together represent a 5 to 7-membered saturated heterocycle which may be substituted with one or two $R^{26}$; $R^5$ and $R^6$ independently represent a hydrogen atom or the like; $R^7$ represents a hydrogen atom, halogen atom or the like; $R^8$ represents a hydrogen atom, alkyl group or the like; $R^{18}$, $R^{18a}$, $R^{19}$, and $R^{19a}$ represent a hydrogen atom, lower alkyl group or the like; $R^{26}$ and $R^{27}$ represent a hydrogen atom, alkyl group or the like; m represents 0, 1, or 2 when ring B is phenyl, or represents 0 or 1 when B is pyridyl; s, t independently represent 0, 1 or 2] (explanation for substituents is partly extracted). However, for this compound, no report about PPARα agonist activity is found. Furthermore, this compound is an amidine derivative, and differs in structure from compounds in accordance with the present invention in that the rings B and L to be substituted adjacently bind to the ring formed by $R^1$ and $R^2$.

As a compound having cyclic amino benzoic acid structure, Patent document 22 discloses as a compound having factor Xa inhibitory activity, a compound represented by the general formula (R)

[Chemical formula 11]

R⁰-Q-X-Q'-W-U-V-G-M (R)

[wherein $R^0$ represents aryl group or the like which may be substituted with $R^2$; Q, Q' represent a bonding hand, carbonyl or the like; X represents a bonding hand, 3 to 7-membered heteroaryl group or the like; W represents a 5 to 14-membered aryl group which may be substituted with $R^1$, 5 to 14-membered heteroaryl group which may be substituted with $R^1$ or the like; U and G represent a bonding hand, $-(CH_2)_m-$, $-(CH_2)_m-O-(CH_2)_m-$ or the like; V represents 3 to 7-membered cycle which may contain 1 to 4 oxygen atoms, nitrogen atom, and sulfur atom, and may be substituted with $R^{14}$, bonding hand, or the like; M represents a 6 to 14-membered aryl group which may be substituted with $R^{14}$, hydrogen atom or the like; $R^1$ represents a halogen atom, nitro group or the like; $R^2$ represents a halogen, nitro group or the like; $R^{14}$ represents a halogen atom, OH, COOH or the like] (explanation for substituents is partly extracted), and Patent document 23 discloses a compound represented by the general formula (S)

[Chemical formula 12]

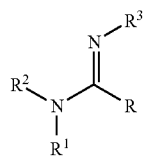

[wherein $R^1$, $R^2$ and $R^3$ which are identical or different, represent a hydrogen atom, hydroxyl group or the like; and R represents the general formula (S-a)

[Chemical formula 13]

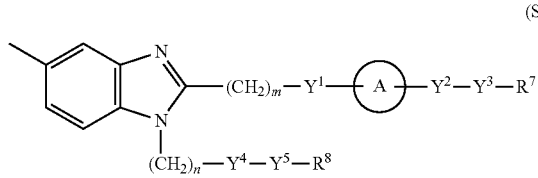

(wherein $R^7$ represents a hydrogen atom, lower alkyl group, or $-C(=R^9)R^{10}$; $R^8$ represents hydrogen atom, lower alkyl group or the like; $Y^1$ represents an oxygen atom, $-CONH-$ or the like; $Y^2$ represents an oxygen atom, sulfur atom, or a single bond; $Y^3$ represents a single bond,

[Chemical formula 14]

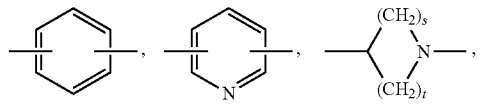

$Y^4$ represents an oxygen atom, a single bond or the like, $Y^5$ represents $-(CH_2)_p-$, a single bond or the like; A represents

[Chemical formula 15]

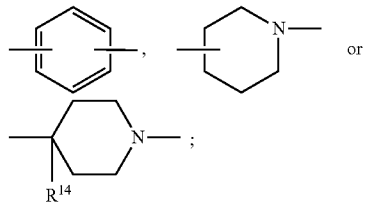

m and n which are identical or different, each represents 0 or an integer from 1 to 3; s, t which are identical or different, each represent an integer from 1 to 3; $R^9$ represents an oxygen atom, sulfur atom or the like; $R^{10}$ represents a lower alkyl, lower alkoxy group; $R^{14}$ represents a carboxyl group or the like) and so on] (explanation for substituents is partly extracted). However, as to the compound described in Patent document 22, no report about PPARα agonist activity is found. Furthermore, all the benzoic acid derivatives substituted with a cyclic amino group that are described in examples in patent specification are compounds in which 4-position of benzoic acid is substituted with an alicyclic amino group and hence are different from compounds in accordance with the present invention. Furthermore, as to the compound in Patent document 23, no report about PPARα agonist activity is found, and examples of the patent specification lack description on benzoic acid derivative substituted with an alicyclic amino group.

As a compound having a similar structure to compounds in accordance with the present invention, compounds shown by formulas (T) to (AA) in Table 2 having histone deacetylation inhibitory activity [in general formulas (T) to (AA), $R^1$ represents $-CONR^8R^9$ (wherein $R^8$ and $R^9$ each independently represent a hydrogen atom, hydroxyl group, $C_{1-6}$ alkyl group or the like), NHCOR$^{10}$ (wherein $R^{10}$ represents a hydrogen atom, $C_{1-6}$ alkyl group or the like) or the like, and in general formulas (T) to (Y), $R^2$ represents a hydrogen atom, halogen atom, hydroxyl group or the like] (explanation for substituents is partly extracted) are known. However, no reports about PPARα agonist activity are found for these compounds. In these compounds, the substituent $R^1$ is a functional group such as amide or hydroxamic acid, and a carboxyl group and a lower alkoxycarbonyl group which provide structural feature of the present invention are not contained. Therefore, these compounds are different in structure from compounds in accordance with the present invention. Furthermore, in examples of patent specifications of Patent documents 24 to 29, benzoic acid derivatives substituted with a cyclic amino group are described as intermediates, however, these compounds are also different in structure from compounds in accordance with the present invention because the cyclic amino group being bound thereto is 1-piperadyl group, 4-aminopiperidino group or the like, and no report about PPARα agonist activity is found. Furthermore, examples in patent specifications of Patent documents 30 and 31 completely lack description about benzoic acid derivatives.

known as a compound having integrin $\alpha_v\beta_3$ antagonist activity. In any of these compounds, however, a carboxyl group

TABLE 2

| Patent Document | Formula |
| --- | --- |
| 24 | 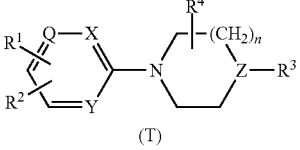<br>(T) |
| 25 | 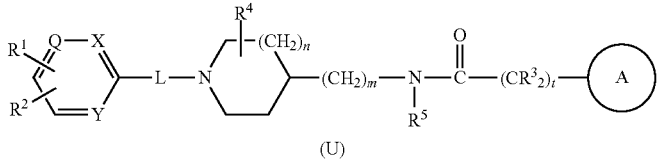<br>(U) |
| 26 | 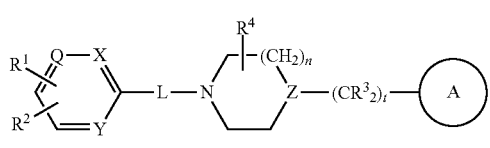<br>(V) |
| 27 | 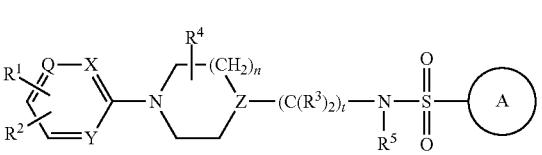<br>(W) |
| 28 | 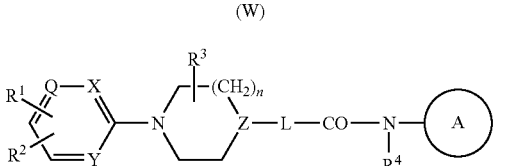<br>(X) |
| 29 | 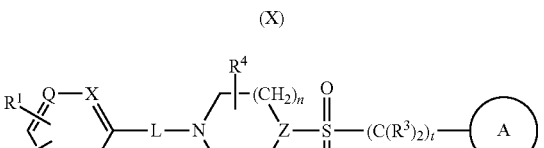<br>(Y) |
| 30 | 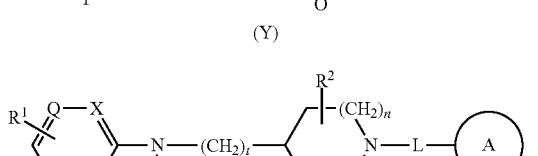<br>(Z) |
| 31 | 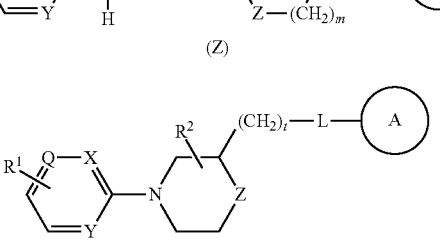<br>(AA) |

Furthermore, as a compound having a similar structure to compounds in accordance with the present invention, compounds shown by formulas (AB) to (AD) listed in Table 3 are binds to a benzene ring via a linker, and no report about PPARα agonist activity is found. Although benzoic acid derivatives substituted with an alicyclic amino group are described as intermediates in examples of the patent specifications, no report about PPARα agonist activity is found for these compounds.

TABLE 3

| Patent Document | Formula |
|---|---|
| 32 | 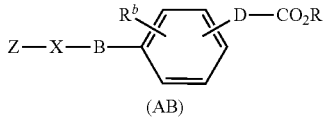<br>(AB) |
| 33 | 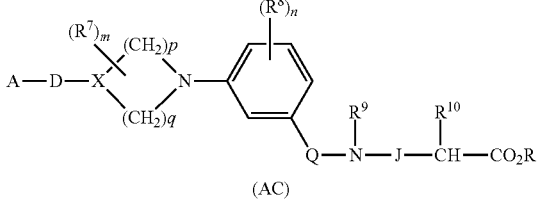<br>(AC) |
| 34 | 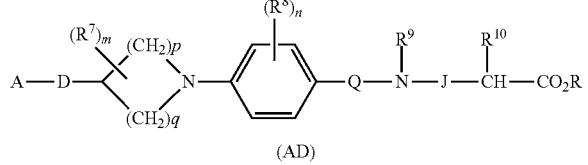<br>(AD) |

Furthermore, as a compound having a similar structure to compounds in accordance with the present invention, Patent document 35 discloses a compound represented by the general formula (AE) as an inhibitory agent of $Na^+/H^+$ alternate transport function:

[Chemical formula 16]

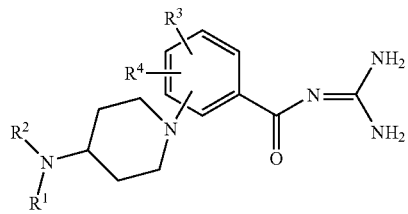

(AE)

[wherein $R^1$ and $R^2$ each independently represent a hydrogen atom, $C_1$-$C_6$ alkyl group, Ph, PhCO or the like; $R^3$ and $R^4$ each independently represent a hydrogen atom, $C_1$-$C_6$ alkyl group or the like] (explanation for substituents is partly extracted). However, no report about PPARα agonist activity is found for these compounds. Furthermore, this compound is characterized by a benzoyl guanidine structure, and is different in structure from compounds in accordance with the present invention in that the cyclic amino group that is to bind to a phenyl group is 4-aminopiperidino group. Furthermore, in examples of the patent specification, benzoic acid derivatives substituted with a cyclic amino group are described as intermediates, however, these compounds are also different in structure from compounds in accordance with the present invention, and no report about PPARα agonist activity is found. Furthermore, as a compound having a similar structure to compounds in accordance with the present invention and reported to be a PPAR receptor ligand, Patent document 36 discloses compound represented by the general formula (AF)

[Chemical formula 17]

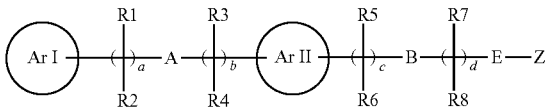

(AF)

[wherein ring ArI and ring ARII independently represent an aryl, heteroaryl or the like, A represents an oxygen atom, sulfur atom, compound represented by the general formula (AF-a)

[Chemical formula 18]

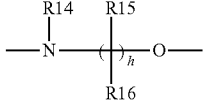

(AF-a)

(wherein h represents 1 to 4; $R^{14}$, $R^{15}$ and $R^{16}$ represent a hydrogen atom, alkyl group or the like, or $R^{14}$ and $R^{15}$ represent, together with nitrogen atom, 5-membered or 6-membered hetero cycle or the like) or the like, B represents an oxygen atom, sulfur atom or the like, E represents a single bond or an ethylene group, a and d represent 0 to 6, b and c represent 0 to 4, $R^1$, $R^3$, $R^5$ and $R^7$ independently represent a hydrogen atom, halogen atom or the like, $R^2$, $R^4$, $R^6$, and $R^8$ and $R^{12}$ independently represent —$(CH_2)_q$—X, q represents 0 to 3, X represents a hydrogen atom, halogen atom or the like, Z represents $R^{21}O_2C$—, $R^{21}CO$— or the like, and $R^{21}$ represents a hydrogen or the like] (explanation for substituents is partly extracted). However, in this compound, the cyclic amino group represented by the general formula (AF-a) binds to ring ArII via a linker, so that it is different in structure from compounds in accordance with the present invention. Furthermore, examples in patent specification lack description on a compound having a cyclic amino group. Furthermore, as a compound having a similar structure to compound of the present invention and reported to have PPARα agonist activity, Patent document 37 discloses a compound represented by the general formula (AG)

[Chemical formula 19]

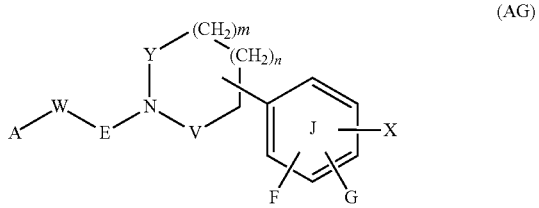

(AG)

[wherein Y and V represent methylene or carbonyl group; F and G represent a hydrogen atom, halogen atom or the like; X represents Z or —B—C($R^1R^2$)—Z; B represents an oxygen atom, sulfur atom or the like; Z represents —C(O)OH, —C(O)O—($C_1$-$C_6$) alkyl or the like; $R^1$ represents a hydrogen atom, ($C_1$-$C_6$)alkyl group or the like; $R^2$ represents a hydrogen atom, ($C_3$-$C_6$) cycloalkyl group or the like; E represents a carbonyl group, sulfonyl group, methylene; W represents a bonding hand, carbonyl group, —N(H)— or the like; and A represents a mono-N— or di-N,N—($C_1$-$C_6$)alkyl amino group, ($C_2$-$C_6$) alkanoyl amino group, partly or fully saturated or fully unsaturated 3 to 8-membered ring which may have 1 to 4 oxygen atom, sulfur atom, or nitrogen atom] (explanation for substituents is partly extracted). However, this compound is featured in that the ring J binds at a position other than nitrogen atom of the alicyclic amino group containing Y and V, and excludes compounds having the feature of compounds in accordance with the present invention that benzoic acid binds to a nitrogen atom of the alicyclic amino group, and hence is different in structure from compounds in accordance with the present invention. Furthermore, as a compound having a similar structure to compounds in accordance with the present invention and reported to have lipid lowering activity, Patent document 38 discloses a compound represented by the general formula (AH)

[Chemical formula 20]

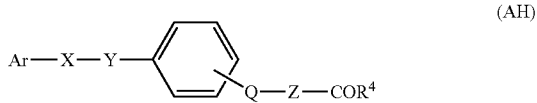

(AH)

[wherein Ar represents a naphthyl group, pyridyl group or the like; X represents —CO—, or —$SO_2$—, Y represents

[Chemical formula 21]

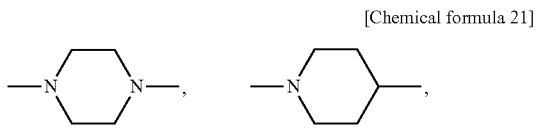

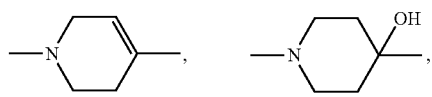

Q represents —O— or a single bond; Z represents a 1 to 3 alkylene group or —$CR^5R^6$— (wherein $R^5$ and $R^6$ represent an alkyl group); $R^4$ represents a hydroxyl group or —NH($CH_2$)$_m$COOH (wherein m represents a number from 1 to 3)] (explanation for substituents is partly extracted), and Patent document 39 discloses a compound represented by the general formula (AI)

[Chemical formula 22]

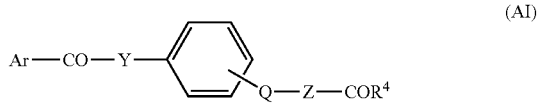

(AI)

[wherein Ar represents a naphthyl group, pyridyl group or the like; Y represents

[Chemical formula 23]

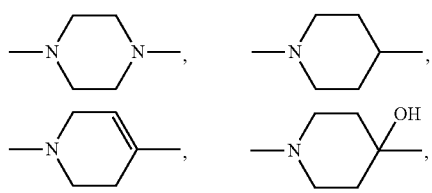

Q represents —O— or a single bond, Z represents a 1 to 3 alkylene group or —$CR^5R^6$— (wherein $R^5$ and $R^6$ represent an alkyl group), $R^4$ represents a hydroxyl group or —NH($CH_2$)$_m$COOH (wherein m represents a number from 1 to 3)] (explanation for substituents is partly extracted). In these compounds, however, substituent Ar—X or Ar—CO— binds to 4-position nitrogen atom of ring Y with respect to the phenyl group, and the substituted $COR^4$ of these compounds binds to phenyl group via -Q-Z—, so that they do not include a benzoic acid derivative and are different in structure from compounds in accordance with the present invention. Furthermore, for these compounds, no report about PPARα agonist activity is found.

As a compound having a cyclic amino benzoic acid structure, Patent document 40 discloses, as a compound having serine protease inhibitory activity, a compound represented by the general formula (AJ)

[Chemical formula 24]

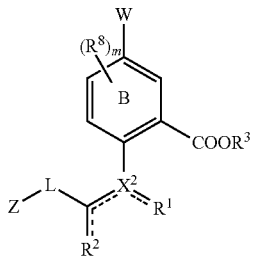

(AJ)

[wherein ring B represents a phenyl group or pyridyl group; $X^2$ represents N, CH or the like; W represents a $C_2$-$C_{10}$ alkyl group or the like; Z represents a 5 to 7-membered monocyclic or 8 to 11-membered bicyclic aryl group and the like; L represents —$(R^{18}R^{19})_s$—Y—$(R^{18a}R^{19a})_t$—; $R^1$ and $R^2$ independently represent a hydrogen atom or the like; $R^1$ and $R^2$ together represent an aromatic ring, heteroaromatic ring or the like; $R^8$ represents a hydrogen atom or the like; $R^3$ represents a hydrogen atom, alkyl group or the like; $R^{18}$, $R^{18a}$, $R^{19}$ and $R^{19a}$ represent a hydrogen atom, lower alkyl group or the like; Y represents CO or the like; m represents 0, 1 or 2 when ring B is a phenyl, or represents 0 or 1 when ring B is a pyridyl; and s, t independently represent 0, 1 or 2] (explanation for substituents is partly extracted). For this compound, however, no report about PPARα agonist activity is found. Furthermore, it is different in structure from compounds in accordance with the present invention in that substituent rings B and L bind adjacently to the ring formed by the $R^1$ and $R^2$.

Furthermore, as a compound having a similar structure to the present invention, Patent document 41 discloses as a compound having p38MAP kinase inhibitory activity, a compound represented by the general formula (AK)

[Chemical formula 25]

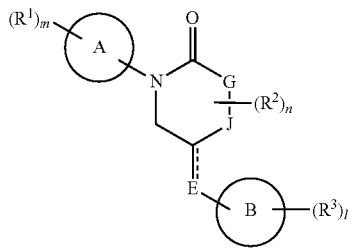

(AK)

[wherein A ring represents a $C_5$-$C_{10}$ monocyclic, bicyclic hydrocarbon ring or the like; $R^1$ represents $COOR^{11}$, $C_1$-$C_8$ alkyl group, $C_2$-$C_8$ alkenyl group or the like; $R^2$ represents a $C_1$-$C_8$ alkyl group; G and J each independently represent a carbon atom, nitrogen atom or the like; E represents a $C_1$-$C_8$ alkylene group, $C_2$-$C_8$ alkenylene group, —O— or the like; B ring represents a $C_5$-$C_{10}$ monocyclic, bicyclic hydrocarbon ring or the like; $R^3$ represents a $C_1$-$C_8$ alkyl group, $C_2$-$C_8$ alkenyl group or the like; $R^{11}$ represents a hydrogen atom, $C_1$ to $C_8$ alkyl group or the like; m represents 0 or integer from 1 to 5; n represents 0 or integer from 1 to 7; and l represents 0 or integer from 1 to 12, ---- [Chemical formula 26]

represents a single bond or double bond] (explanation for substituents is partly extracted). However, this compound is a cyclic amide derivative which is different from the alicyclic amino group that is characteristic of compounds in accordance with the present invention, and all the benzoic acid derivatives that are described in examples of patent specification are para-substituted compounds and hence are different in structure from compounds in accordance with the present invention. Furthermore, no report about PPARα agonist activity is found.

Furthermore, as a compound having a similar structure to the present invention, Patent document 42 discloses as a compound having $β_3$ adrenaline receptor agonist activity, a compound represented by the general formula (AL)

[Chemical formula 27]

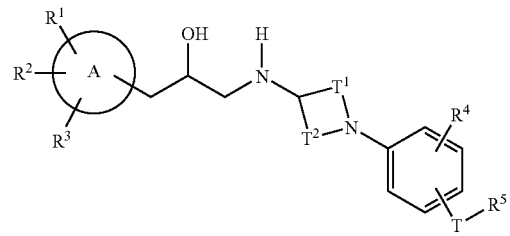

(AL)

[wherein ring A represents an aromatic ring or hetero ring; X represents —$OCH_2$—, —$SCH_2$—, or bonding hand; $T^1$ represents $(CH_2)_m$; $T^2$ represents $(CH_2)_n$; T represents a bonding hand, C1-C6 alkyl group which may be substituted with substituent $R^{11}$ or the like; $R^1$, $R^2$ and $R^3$ each independently represent a hydrogen atom, C1 to 6 alkyl group or the like; $R^4$ represents a hydrogen atom, C1 to 6 alkyl group or the like; $R^5$ represents a $COOR^6$, or a compound represented by the general formula (AL-a)

[Chemical formula 28]

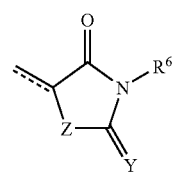

(AL-a)

(wherein Y, Z each independently represent $NR^7$, O or S; $R^6$ represents a hydrogen atom, $C_1$-$C_6$ alkyl group which may be substituted with $R^{11}$, $R^{12}$ and $R^{13}$, or the like; and a broken line represents a single bond or a double bond) or the like; m represents 1 to 3; n represents 1 to 3; $R^6$ represents a hydrogen atom, alkyl group having 1 to 6 carbon(s) and the like; $R^{11}$, $R^{12}$, $R^{13}$ each independently represent a $C_1$-$C_6$ alkyl group, halogen atom or the like] (explanation for substituents is partly extracted). However, this compound is featured by an amino ethanol structure, and the benzoic acid derivatives substituted with a cyclic amino group described in examples of patent specification are merely the compounds in which substitution with cyclic amino group occurs at para position of benzoic acid, and differ in structure from compounds in accordance with the present invention. Furthermore, no report about PPARα agonist activity is found.

As a compound having a similar structure to the present invention, Patent document 43 discloses as a compound having calcium receptor antagonist activity, a compound represented by the general formula (AM)

[Chemical formula 29]

(AM)

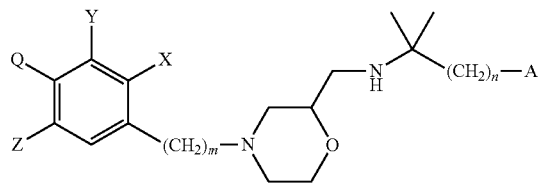

[wherein m represents an integer from 0 to 2; n represents an integer from 1 to 3; X represents a cyano group, nitro group or the like; Y represents a chlorine atom, fluorine atom or the like; Q and Z independently represent a hydrogen atom, $R_1$, $SO_2R_1'$, $C(O)OR_1''$ or the like; A represents a phenyl group or naphthyl group which may be substituted with a hydroxyl group, halogen atom or the like; $R_1$, $R_1'$ and $R_1''$ independently represent a hydrogen atom, $C_1$-$C_4$ alkyl group or the like] (explanation for substituents is partly extracted). However, no report about PPARα agonist activity of this compound is found. In examples of the patent specification, no description is found about a benzoic acid derivative substituted with a cyclic amino group.

As a compound having a similar structure to the present invention, Patent document 44 discloses as a compound having integrin inhibitory activity, a compound represented by the general formula (AN)

[Chemical formula 30]

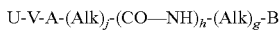

[wherein g, h and l each independently represent 0 or 1; Alk represents an alkylene; U represents an amidino group, guanidine group or -(G-Alk)$_k$-C(Q)-N(R)$R_1$ (wherein G represents a single bond, oxygen atom or the like, Q represents an oxygen atom, sulfur atom or the like, R represents a hydrogen atom, alkyl group or the like; R1 represents an alkyl group, aryl group or the like; k represents 0 or 1), V represents general formula (AN-a)

[Chemical formula 31]

(AN-a)

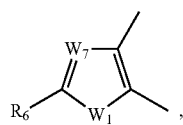

general formula (AN-b)

[Chemical formula 32]

(AN-b)

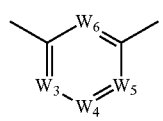

(wherein $W_1$ represents an oxygen atom, sulfur atom or the like; $W_3$, $W_4$, $W_5$ and $W_6$ represent N or C—$R_4$; $W_7$ represents a nitrogen atom or the like; $R_4$ represents a hydrogen atom, halogen atom or the like; $R_6$ represents a hydrogen atom, halogen atom or the like); A represents general formula (AN-c)

[Chemical formula 33]

(AN-c)

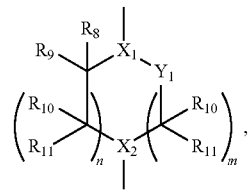

general formula (AN-d)

[Chemical formula 34]

(AN-d)

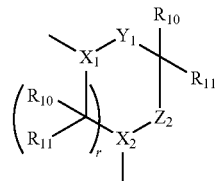

(wherein $X_1$ represents a nitrogen atom or C—H; $X_2$ represents C—H; $Y_1$ represents —C(O)—, —C(S)— or the like; $Z_2$ represents an oxygen atom, sulfur atom or the like; n, m each independently represent 0, 1 or 2, and n+m=1, 2, 3 or 4; r represents 1 or 2; $R_8$, $R_9$, $R_{10}$ and $R_{11}$ each independently represent a hydrogen atom, alkyl group or the like), B represents general formula (AN-e)

[Chemical formula 35]

(AN-e)

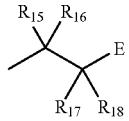

(wherein $R_{15}$ represents a hydrogen atom, alkyl group or the like; $R_{17}$ represents a hydrogen atom, alkyl group, aryl group or the like; $R_{16}$ and $R_{18}$ each independently represent a hydrogen atom, or alkyl group; E represents a carboxyl group, amide group or the like)] (explanation for substituents is partly extracted). However, this compound is a cyclic amide derivative and the like which is different from an alicyclic amino group which is characteristic of compounds in accordance with the present invention, and substituent U is amidino group, guanidine group or the like functional group. Therefore, the above compound lacks a carboxyl group and a lower alkoxycarbonyl group which are structural features of the present invention, and hence differs in stricture from compounds in accordance with the present invention. Furthermore, no report about PPARα agonist activity is found.

Furthermore, as a compound having a similar structure to compounds in accordance with the present invention, Patent document 45 discloses as a compound having integrin $α_vβ_3$ antagonist activity, a compound represented by the general formula (AO)

[Chemical formula 36]

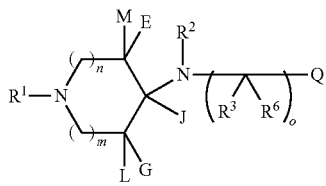
(AO)

[wherein Q represents general formula (AO-a)

[Chemical formula 37]

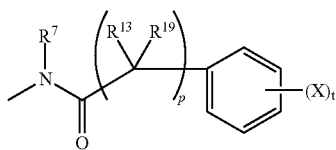
(AO-a)

(wherein $R^7$ represents a hydrogen atom, $C_{1-8}$ alkyl group or the like; $R^{13}$ represents a hydrogen atom, $C_{1-8}$ alkyl group or the like; $R^{19}$ represents a hydrogen atom, $C_{1-8}$ alkyl group or the like; X represents a halogen atom, cyano group or the like; p represents an integer from 0 to 4; t represents an integer from 0 to 5), E, G, L and M each independently represent a hydrogen atom, $C_{1-8}$ alkyl group or the like, J represents a hydrogen atom, $C_{1-8}$ alkyl group or the like, $R^1$ represents a halogen atom, phenyl group which may be substituted with $(CH_2)_{0-4}CO_2R^{16}$ or the like; $R^2$ represents a hydrogen atom, $C_{1-8}$ alkyl group or the like; $R^3$ and $R^6$ each independently represent a hydrogen atom, $C_{1-8}$ alkyl group or the like; $R^{16}$ represents a hydrogen atom, $C_{1-8}$ alkyl group or the like; m, n and p each independently represent an integer from 0 to 4; o represents an integer from 2 to 5] (explanation for substituents is partly extracted). However, this compound is featured in that an aminoalkyl amino group binds to a cyclic amino group; and any cyclic amino group that binds to a benzoic acid derivative described in examples of the patent specification is 4-aminopiperidino group, and hence is different in structure from compounds in accordance with the present invention. Furthermore, no report about PPARα agonist activity is found. As a compound having a similar structure to the present invention, Patent document 46 discloses as a compound having factor Xa inhibitory activity, a compound represented by the general formula (AP)

[Chemical formula 38]

A-Y-D-E-G-J-Z-L (AP)

[wherein A represents a phenyl group, $C_1$-$C_6$ alkyl group, or $C_3$-$C_8$ cycloalkyl group which may be substituted with 0 to 2 R1 or the like; Y represents a bonding hand, —C(=O)— or the like; D represents a bonding hand, phenyl group substituted with 0 to 2 $R^{1a}$ or the like; E represents —N($R^5$)—C(=O)—, —C(=O)—N($R^5$)— or the like; G represents a bonding hand, —$CR^7R^8$— or the like; J represents general formula (AP-a)

[Chemical formula 39]

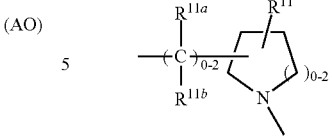
(AP-a)

(wherein $R^{11}$, $R^{11a}$ and $R^{11b}$ independently represent a hydrogen atom, hydroxyl group or the like) or the like, Z represents a phenyl substituted with 0 to 2 $R^{1b}$, naphthyl group substituted with 0 to 2 $R^{1b}$ or the like; L represents a hydrogen atom, cyano group, C(=O)$NR^{12}R^{13}$, C(=$NR^{12}$)$NR^{12}R^{13}$ or the like; $R^1$ represents a halogen atom, $C_{1-4}$ alkyl group or the like; $R^{1a}$ represents a halogen atom, $C_{1-4}$ alkyl group or the like; $R^{1b}$ represents a halogen atom, —$OCH2$-$COOR^{2b}$ or the like; $R^{2b}$ represents a hydrogen atom, $C_{1-4}$ alkyl group or the like; $R^{12}$ and $R^{13}$ independently represent a hydrogen atom, $C_{1-4}$ alkyl group or the like] (explanation for substituents is partly extracted). This compound dose not include benzoic acid derivatives which are substituted with a cyclic amino group, and differs in structure from compounds in accordance with the present invention. Furthermore, no report about PPARα agonist activity is found.

[Patent document 1] WO00/23407 pamphlet
[Patent document 2] WO00/75103 pamphlet
[Patent document 3] WO01/40207 pamphlet
[Patent document 4] WO02/38553 pamphlet
[Patent document 5] WO02/28821 pamphlet
[Patent document 6] WO02/064549 pamphlet
[Patent document 7] WO03/051821 pamphlet
[Patent document 8] WO03/059875 pamphlet
[Patent document 9] WO2004/010936 pamphlet
[Patent document 10] WO2004/010992 pamphlet
[Patent document 11] WO03/055867 pamphlet
[Patent document 12] WO02/098840 pamphlet
[Patent document 13] WO00/64876 pamphlet
[Patent document 14] WO03/020269 pamphlet
[Patent document 15] Japanese Patent Laid-Open Publication No. Sho 52-83676
[Patent document 16] Japanese Patent Laid-Open Publication No. Sho 51-149234
[Patent document 17] Japanese Patent Laid-Open Publication No. Sho 51-149235
[Patent document 18] Japanese Patent Laid-Open Publication No. Sho 51-146478
[Patent document 19] Japanese Patent Laid-Open Publication No. Sho 51-146479
[Patent document 20] WO03/030889 pamphlet
[Patent document 21] WO02/37937 pamphlet
[Patent document 22] WO02/051831 pamphlet
[Patent document 23] Japanese Patent Laid-Open Publication No. 2000-136190
[Patent document 24] WO03/075929 pamphlet
[Patent document 25] WO03/076395 pamphlet
[Patent document 26] WO03/076400 pamphlet
[Patent document 27] WO03/076401 pamphlet
[Patent document 28] WO03/076421 pamphlet
[Patent document 29] WO03/076422 pamphlet
[Patent document 30] WO03/076430 pamphlet
[Patent document 31] WO03/076438 pamphlet
[Patent document 32] WO01/54726 pamphlet
[Patent document 33] WO01/27090 pamphlet
[Patent document 34] WO01/27082 pamphlet
[Patent document 35] Japanese Patent Laid-Open Publication No. Hei 7-267926

[Patent document 36] WO00/64888 pamphlet
[Patent document 37] WO2004/048334 pamphlet
[Patent document 38] WO93/12086 pamphlet
[Patent document 39] EP0607536 pamphlet
[Patent document 40] WO02/42273 pamphlet
[Patent document 41] WO03/043988 pamphlet
[Patent document 42] WO02/06232 pamphlet
[Patent document 43] WO00/09132 pamphlet
[Patent document 44] WO01/44230 pamphlet
[Patent document 45] WO98/57638 pamphlet
[Patent document 46] WO00/71515 pamphlet
[Non-patent document 1] Proc. Natl. Acad. Sci., 1992, 89, 4653
[Non-patent document 2] Endocrinology, 1996, 137, 354
[Non-patent document 3] J. Lipid. Res., 1996, 37, 907
[Non-patent document 4] Nat. Med., 1998, 4, 1046
[Non-patent document 5] J. Biol. Chem., 1998, 273, 29577
[Non-patent document 6] Proc. Natl. Acad. Sci., 1997, 94, 4312
[Non-patent document 7] Cell, 2003, 113, 159

DISCLOSURE OF THE INVENTION

Means to be Solved by the Invention

It is an object of the present invention to provide compounds which are different in chemical structure from known compounds described above, and has potent PPARα agonist activity while exhibiting potent effect in biological bodies.

Means for Solving the Problem

The inventors of the present invention made diligent efforts in light of a specific role of human PPARα to lipid metabolism for creating a structurally novel pharmaceutical having excellent efficacy, sustention and safety as an antihyperlipidemic drug, and found that novel cyclic aminobenzoic acid derivatives of the present invention, namely, cyclic amino benzoic acids and cyclic amino benzoic acid esters and addition salts thereof have excellent human PPARα transcription activating activity, and exhibit excellent lipid lowering activity in a biological body.

That is, the present invention relates to (1) to (20) below.
(1) The cyclic amino benzoic acid derivatives represented by the general formula (1)

[Chemical formula 40]

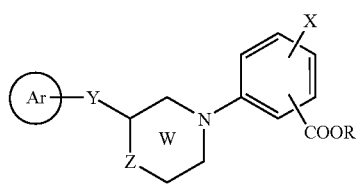
(1)

[wherein a ring Ar represents an aryl group which may have substituent, 5-membered or 6-membered aromatic heterocyclic group which may have substituent or condensed ring group thereof,
Y represents a $C_1$-$C_4$ alkylene, $C_2$-$C_4$ alkenylene, $C_2$-$C_4$ alkynylene or the general formula (2)

[Chemical formula 41]

-T-A-U- (2)

(wherein T represents a single bond, $C_1$-$C_4$ alkylene, $C_2$-$C_4$ alkenylene or $C_2$-$C_4$ alkynylene,
U represents a single bond, $C_1$-$C_4$ alkylene or $C_2$-$C_4$ alkenylene,
A represents a carbonyl group, oxygen atom, sulfur atom, —$NR^1$— ($R^1$ represents a hydrogen atom, lower alkyl group which may be substituted with a halogen atom, aralkyl group which may have substituent, aryl group which may have substituent or 5-membered or 6-membered aromatic heterocyclic group which may have substituent or condensed ring group thereof), the general formula (3)

[Chemical formula 42]

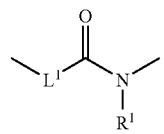
(3)

(wherein $L^1$ represents a single bond, oxygen atom or —$NR^1$—, and $R^1$ is as defined above) or the general formula (4)

[Chemical formula 43]

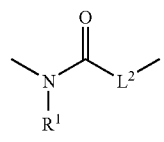
(4)

(wherein $L^2$ represents a single bond or oxygen atom, and $R^1$ is as defined above)),
Z represents an oxygen atom, sulfur atom or —$(CH_2)_n$— (n represents 0, 1 or 2),
X represents a hydrogen atom, halogen atom, lower alkyl group which may be substituted with a halogen atom, lower alkoxy group which may be substituted with a halogen atom, hydroxyl group, nitro group, cyano group, optionally substituted amino group, aryl group which may have substituent, 5-membered or 6-membered aromatic heterocyclic group which may have substituent and condensed ring group thereof, aralkyl group which may have substituent, aryloxy group which may have substituent or aralkyloxy group which may have substituent,
R represents a hydrogen atom or lower alkyl group, and —COOR is substituted at ortho position or metha position of binding position of ring W], or the pharmaceutically acceptable salt thereof,
(2) The cyclic amino benzoic acid derivative as described in the above (1) and the pharmaceutically acceptable salt thereof, wherein in the general formula (1), Y is represented by the general formula (2a)

[Chemical formula 44]

-$T^1$-$A^1$-$U^1$- (2a)

(wherein $T^1$ represents a single bond, $C_1$-$C_4$ alkylene or $C_2$-$C_4$ alkenylene, $U^1$ represents a single bond or $C_1$-$C_4$ alkylene, and $A^1$ represents an oxygen atom, sulfur atom, the general formula (3)

[Chemical formula 45]

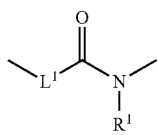
(3)

(wherein $L^1$ represents a single bond, oxygen atom or —$NR^1$—, and $R^1$ is as defined above) or the general formula (4)

[Chemical formula 46]

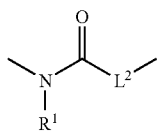
(4)

(wherein $L^2$ represents a single bond or oxygen atom, and $R^1$ is as defined above)),
(3) The cyclic amino benzoic acid derivative as described in the above (1) or the pharmaceutically acceptable salt thereof, wherein in the general formula (1), Y is represented by the general formula (2b)

[Chemical formula 47]

-$T^1$-$A^2$-$U^1$-   (2b)

(wherein $T^1$ represents a single bond, $C_1$-$C_4$ alkylene or $C_2$-$C_4$ alkenylene, $U^1$ represents a single bond or $C_1$-$C_4$ alkylene,
$A^2$ represents an oxygen atom, sulfur atom, the general formula (3a)

[Chemical formula 48]

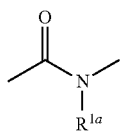
(3a)

(wherein $R^{1a}$ represents a hydrogen, alkyl group which may be substituted with halogen atom or aralkyl group which may have substituent), or represented by the general formula (4a)

[Chemical formula 49]

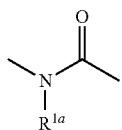
(4a)

(wherein $R^{1a}$ is as defined above)),
(4) The cyclic amino benzoic acid derivative as described in the above (1) or the pharmaceutically acceptable salt thereof, wherein in the general formula (1), Y is represented by the general formula (2c)

[Chemical formula 50]

-$T^1$-$A^3$-$U^2$-   (2c)

(wherein $T^1$ represents a single bond, $C_1$-$C_4$ alkylene or $C_2$-$C_4$ alkenylene,
$U^2$ represents a single bond or methylene,
$A^3$ represents the general formula (3a)

[Chemical formula 51]

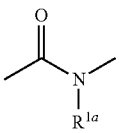
(3a)

(wherein $R^{1a}$ represents a hydrogen atom, alkyl group which may be substituted with halogen atom or aralkyl group which may have substituent) or the general formula (4a)

[Chemical formula 52]

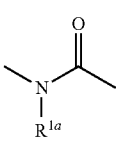
(4a)

(wherein $R^{1a}$ is as defined above)),
(5) The cyclic amino benzoic acid derivative as described in any one of the above (1) to (4) or the pharmaceutically acceptable salt thereof, wherein in the general formula (1), Z represents an oxygen atom, sulfur atom or methylene,
(6) The cyclic amino benzoic acid derivative as described in any one of the above (1) to (5) or the pharmaceutically acceptable salt thereof, wherein in the general formula (1), Z represents methylene,
(7) The cyclic amino benzoic acid derivative as described in any one of the above (1) to (6) or the pharmaceutically acceptable salt thereof, wherein in the general formula (1), X represents a hydrogen atom, halogen atom, lower alkyl group which may be substituted with a halogen atom, lower alkoxy group which may be substituted with a halogen atom, hydroxyl group or optionally substituted amino group,
(8) The cyclic amino benzoic acid derivative as described in any one of the above (1) to (7) or the pharmaceutically acceptable salt thereof, wherein in the general formula (1), ring Ar represents 5-membered or 6-membered aromatic heterocyclic group which may have substituent,
(9) The cyclic amino benzoic acid derivative as described in any one of the above (1) to (8) or the pharmaceutically acceptable salt thereof, wherein in the general formula (1), ring Ar represents the general formula (5)

[Chemical formula 53]

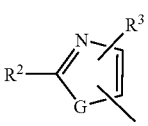
(5)

(wherein R² represents a lower alkyl group which may be substituted with a halogen atom, cyclic alkyl group, lower alkoxy group which may be substituted with a halogen atom, optionally substituted amino group, 5-membered or 6-membered cyclic amino group, aryl group which may have substituent or 5-membered or 6-membered aromatic heterocyclic group which may have substituent, R³ represents a hydrogen atom, lower alkyl group which may be substituted with a halogen atom or cycloalkyl group, and G represents an oxygen atom or sulfur atom),

(10) The cyclic amino benzoic acid derivative as described in the above (1) or the pharmaceutically acceptable salt thereof, wherein the compound represented by the general formula (1) is 2-[3-[[2-(4-chlorophenyl)-4-methylthiazol-5-yl]methoxymethyl]piperidin-1-yl]benzoic acid,
3-[3-[[2-(4-chlorophenyl)-4-methylthiazol-5-yl]methoxymethyl]piperidin-1-yl]benzoic acid,
3-[3-[[2-(4-chlorophenyl)-4-methylthiazol-5-yl]methoxy]piperidin-1-yl]benzoic acid,
2-[3-[[2-(4-chlorophenyl)-4-methylthiazol-5-yl]carbonylaminomethyl]piperidin-1-yl]benzoic acid,
3-[3-[[2-(4-chlorophenyl)-4-methylthiazol-5-yl]carbonylaminomethyl]piperidin-1-yl]benzoic acid,
3-[3-[[2-(4-chlorophenyl)-4-methylthiazol-5-yl]carbonylamino]piperidin-1-yl]benzoic acid,
2-[3-[N-[[2-(4-chlorophenyl)-4-methylthiazol-5-yl]methyl]carbamoyl]piperidin-1-yl]benzoic acid,
(S)-2-[3-[[2-(4-chlorophenyl)-4-methylthiazol-5-yl]methoxymethyl]piperidine-1-yl]benzoic acid,
(R)-2-[3-[[2-(4-chlorophenyl)-4-methylthiazol-5-yl]methoxymethyl]piperidin-1-yl]benzoic acid,
(S)-3-[3-[[2-(4-chlorophenyl)-4-methylthiazol-5-yl]methoxymethyl]piperidin-1-yl]benzoic acid,
(R)-3-[3-[[2-(4-chlorophenyl)-4-methylthiazol-5-yl]methoxymethyl]piperidin-1-yl]benzoic acid,
(S)-3-[3-[[2-(4-chlorophenyl)-4-methylthiazol-5-yl]methoxy]piperidin-1-yl]benzoic acid,
(R)-3-[3-[[2-(4-chlorophenyl)-4-methylthiazol-5-yl]methoxy]piperidin-1-yl]benzoic acid,
(S)-2-[3-[[2-(4-chlorophenyl)-4-methylthiazol-5-yl]carbonylaminomethyl]piperidin-1-yl]benzoic acid,
(R)-2-[3-[[2-(4-chlorophenyl)-4-methylthiazol-5-yl]carbonylaminomethyl]piperidin-1-yl]benzoic acid,
(S)-3-[3-[[2-(4-chlorophenyl)-4-methylthiazol-5-yl]carbonylaminomethyl]piperidin-1-yl]benzoic acid,
(R)-3-[3-[[2-(4-chlorophenyl)-4-methylthiazol-5-yl]carbonylaminomethyl]piperidin-1-yl]benzoic acid,
(S)-3-[3-[[2-(4-chlorophenyl)-4-methylthiazol-5-yl]carbonylamino]piperidin-1-yl]benzoic acid,
(R)-3-[3-[[2-(4-chlorophenyl)-4-methylthiazol-5-yl]carbonylamino]piperidin-1-yl]benzoic acid,
(S)-2-[3-[N-[[2-(4-chlorophenyl)-4-methylthiazol-5-yl]methyl]carbamoyl]piperidin-1-yl]benzoic acid, or
(R)-2-[3-[N-[[2-(4-chlorophenyl)-4-methylthiazol-5-yl]methyl]carbamoyl]piperidin-1-yl]benzoic acid,

(11) A pharmaceutical comprising at least one of the cyclic amino benzoic acid derivative or the pharmaceutically acceptable salt thereof as described in any one of the above (1) to (10) as an active ingredient,

(12) A PPARα agonist comprising at least one of the cyclic amino benzoic acid derivative or the pharmaceutically acceptable salt thereof as described in any one of the above (1) to (10) as an active ingredient,

(13) A PPAR α, γ dual agonist comprising at least one of the cyclic amino benzoic acid derivative or the pharmaceutically acceptable salt thereof as described in any one of the above (1) to (10) as an active ingredient,

(14) A PPAR α, δ dual agonist comprising at least one of the cyclic amino benzoic acid derivative or the pharmaceutically acceptable salt thereof as described in any one of the above (1) to (10) as an active ingredient,

(15) A PPAR α, γ, δ triple agonist comprising at least one of the cyclic amino benzoic acid derivative or the pharmaceutically acceptable salt thereof as described in any one of the above (1) to (10) as an active ingredient,

(16) A PPAR modulator comprising at least one of the cyclic amino benzoic acid derivative or the pharmaceutically acceptable salt thereof as described in any one of the above (1) to (10) as an active ingredient,

(17) A lipid lowering agent comprising at least one of the cyclic amino benzoic acid derivative or the pharmaceutically acceptable salt thereof as described in any one of the above (1) to (10) as an active ingredient,

(18) A prophylactic or therapeutic agent for arteriosclerosis, comprising at least one of the cyclic amino benzoic acid derivative or the pharmaceutically acceptable salt thereof as described in any one of the above (1) to (10) as an active ingredient,

(19) A prophylactic or therapeutic agent for diabetes, comprising at least one of the cyclic amino benzoic acid derivative or the pharmaceutically acceptable salt thereof as described in any one of the above (1) to (10) as an active ingredient, and

(20) A prophylactic or therapeutic agent for obesity, comprising at least one of the cyclic amino benzoic acid derivative or the pharmaceutically acceptable salt thereof as described in any one of the above (1) to (10) as an active ingredient.

Effect of the Invention

The novel cyclic amino benzoic acid derivative or the addition salt thereof according to the present invention has excellent human PPARα transcription activating ability, and exhibits excellent lipid lowering activity in a living body.

These compounds of the present invention are effective as a lipid lowering agent, in particular, as a lipid lowering agent in liver and an inhibitor against development of arteriosclerosis.

BEST MODE FOR CARRYING OUT THE INVENTION

For the compound represented by the general formula (1) of the present invention, definitions in the formula will be concretely explained below.

The term "halogen atom" includes fluorine, chlorine, bromine, and iodine.

The term "lower alkyl group" includes straight chain or branched chain group consisting of 1 to 6 carbons such as methyl, ethyl, n-propyl, i-propyl and the like.

The term "cycloalkyl group" includes the ring group consisting of 3 to 7 carbons such as cyclopropyl, cyclopentyl, cyclohexyl and the like.

The term "lower alkoxy group" includes straight chain or branched chain group consisting of 1 to 5 carbons such as methoxy, ethoxy, n-propoxy, i-propoxy and the like.

The term "lower alkyl group which may be substituted with a halogen atom" includes the aforementioned lower alkyl group, and lower alkyl group substituted with a halogen atom such as chloromethyl group, trifluoromethyl group and the like.

The term "lower alkoxy group which may be substituted with a halogen atom" includes the aforementioned lower alkoxy group, and lower alkoxy group substituted with a halogen atom such as trifluoromethoxy group.

The term "aryl group" includes an aromatic hydrocarbon group such as phenyl group, naphthyl group and the like.

The term "aryloxy group" includes a phenoxy group, naphthoxy group and the like.

The term "aralkyl group" includes a benzyl group, diphenylmethyl group, triphenyl methyl group, phenethyl group, phenylpropyl group and the like.

The term "aralkyloxy group" includes a benzyloxy group, phenethyloxy group and the like.

The term "5-membered or 6-membered aromatic heterocyclic group" in "5-membered or 6-membered aromatic heterocyclic group and condensed ring group thereof" means 5-membered or 6-membered aromatic ring group which may contain 1 to 3 nitrogen, oxygen, sulfur atom, and examples thereof include furanyl group, thienyl group, pyrazolyl group, imidazolyl group, oxazolyl group, thiazolyl group, isoxazolyl group, isothiazolyl group, triazolyl group, oxadiazolyl group, thiadiazolyl group, pyridyl group, pyrimidyl group, pyridadyl group, and pyrazinyl group, and the term "condensed ring group thereof" means a benzene condensed ring group of the aforementioned "5-membered or 6-membered aromatic heterocyclic group" or condenced ring consisting of two rings arbitrarily selected from the aforementioned "5-membered or 6-membered aromatic heterocyclic group", and examples thereof include indolyl group, benzoxazolyl group, benzothiazolyl group, benzofuranyl group, benzothienyl group, benzimidazolyl group, quinolyl group, isoquinolyl group, quinazolyl group, quinoxalinyl group, imidazopyridyl group, pyrazolopyridyl group, imidazopyrimidyl group and the like.

The term "optionally substituted amino group" includes unsubstituted amino group or amino group which is substituted with acyl group such as acetyl group, lower alkylsulfonyl group which may be substituted with a halogen atom such as methanesulfonyl group, and trifluoromethane sulofnyl group, aryl sulfonyl group which may have substituent such as phenylsulfonyl group, and tolylsulfonyl, lower alkyl group which may be substituted with a halogen atom, aryl group which may have substituent, or aralkyl group which may have substituent.

The term "5-membered or 6-membered cyclic amino group" includes a pyrrolidinyl group, piperidinyl group, piperadinyl group, morpholinyl group, thiomorpholinyl group or the like.

The term "substituent" used in the wordings "aryl group which may have substituent", "5-membered or 6-membered aromatic heterocyclic group which may have substituent or condensed ring group thereof", "aralkyl group which may have substituent", "aralkyloxy group which may have substituent", and "aryloxy group which may have substituent" means a halogen atom, hydroxyl group, lower alkyl group which may be substituted with a halogen atom, cycloalkyl group; lower alkoxy group which may be substituted with a halogen atom, lower alkylthio group, lower alkoxycarbonyl group, nitro group, optionally substituted amino group, 5-membered or 6-membered cyclic amino group, cyano group, carboxyl group, aldehyde group, aryl group which may have substituent, aralkyl group which may have substituent, aralkyloxy group which may have substituent, aryloxy group which may have substituent, or 5-membered or 6-membered aromatic heterocyclic group which may have substituent or condensed ring thereof, and the term "lower alkylthio group" indicates straight-chained or branched-chained group consisting of 1 to 5 carbon(s) such as methylthio group, ethylthio group, propylthio group or the like, and the term "lower alkoxycarbonyl group" indicates the like straight-chained or branched-chained group having 1 to 6 carbon(s) such as methoxycarbonyl group, ethoxycarbonyl group or the like. The substituent used herein refers to the "substituent" as explained above.

The compound represented by general formula (1) of the present invention may be in the form of a pharmaceutically acceptable salt as needed. Examples of the pharmaceutically acceptable salt include inorganic salts with "hydrochloric acid, hydrobromic acid, sulfuric acid" and the like, organic salts with "acetic acid, fumaric acid, maleic acid, oxalic acid, citric acid, methane sulfonic acid, tosylic acid" and the like, and salts with base such as "sodium salt, potassium salt, calcium salt" and the like.

Furthermore, the compound represented by the general formula (1) of the present invention and its pharmaceutically acceptable salt may be in the form of its intramolecular salt thereof, anhydride, hydrate, or solvate thereof.

Furthermore, the compound represented by the general formula (1) of the present invention includes optical isomers based on asymmetric carbon, geometrical isomers, stereo isomers, tautomers and the like, and all of these isomers and mixture thereof are encompassed by the scope of the present invention.

The compound represented by the general formula (1) which is a compound of the present invention can be prepared by a method described in Production method 1 or by combination of known methods.

[Production Method 1]

[Chemical formula 54]

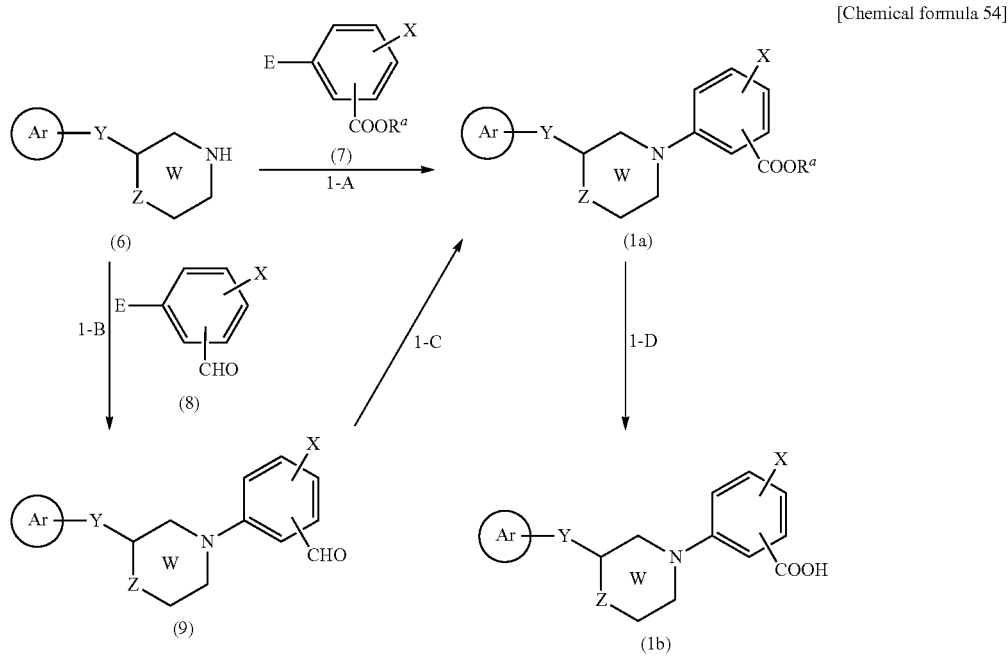

[wherein E represents a leaving group, $R^a$ represents a lower alkyl group, and ring Ar, W, X, Y, and Z are defined above]

As the leaving group denoted by E, a halogen atom, sulfonyloxy group such as trifluoromethanesulfonyloxy group and p-tolylsulfonyloxy group, trialkylsutanyl group such as trimethylstanyl group, $(HO)_2B—$ and the like can be exemplified.

Conversion from the compounds represented by the general formula (6) and the general formula (7) to the compound represented by the general formula (1a) (Step 1-A) can be performed, when the leaving group E in the compound represented by the general formula (7) represents a halogen atom, or sulfonyloxy group, at room temperature to 120° C. for 12 to 48 hours in an appropriate solvent, for example, toluene, 1,4-dioxane, t-butylalcohol, N,N-dimethylformamide, tetrahydrofuran, a mixture thereof or the like, in the presence of ligand such as 2,2'-bis(diphenylphosphino)-1,1'-binaphthyl, 1,1'-bis(diphenylphosphino)ferrocene or the like ligand, and base such as sodium carbonate, potassium carbonate, cesium carbonate, sodium tert-butoxide, potassium tert-butoxide, tripotassium phosphate, triethylamine, pyridine or the like base, by using palladium catalyst such as palladium (II) acetate, tris (dibenzylidene acetone)dipalladium (0), or [1,1'-bis(diphenylphosphino)ferrocene]dichloropalladium (II), or nickel catalyst such as bis(1,5-cyclooctadiene) nickel (0).

When the leaving group E is a halogen atom, the conversion can be performed at room temperature to 160° C. for 1 to 70 hours in an appropriate solvent such as toluene, N,N-dimethylformamide, N,N-dimethylacetamide, dimethylsulfoxide, isopropanol, 1,2-dimethoxyethane, 1,4-dioxane or the like, in the presence of a base such as potassium carbonate, sodium carbonate, cesium carbonate, cesium acetate, tripotassium phosphate or the like, and, if need be, by using a cuprous salt such as copper iodide (I), copper bromide (I) or the like, and, if need be, by using a ligand such as proline, N-methyl glycine, ethylene glycol, ethylene diamine, and, if need be, by using a phase transfer catalyst such as tetrabutyl ammonium iodide or the like.

When the leaving group E in the compound represented by the general formula (7) represents a trialkylstanyl group, or $(HO)_2B—$, the conversion can be performed at 0 to 60° C. for 6 to 70 hours in an appropriate solvent, for example, dichloromethane, 1,4-dioxane, N-methylpyrrolidone, tetrahydrofuran, N,N-dimethylformamide, N,N-dimethylacetamide or the like, in the presence of a base such as triethylamine, pyridine, 2,6-lutidine, tetrabutyl ammonium fluoride or the like, in the presence of copper (II) acetate, and, if need be, by using molecular sieves, and, if need be, by using an appropriate reaction auxiliary agent such as pyridine N-oxide, 1,1,6,6-tetramethylpiperidinyloxy radical, myristic acid or the like cooxidant.

Conversion from the compounds represented by the general formula (6) and the general formula (8) to the compound represented by the general formula (9) (Step 1-B) can be performed in a similar manner as described in Step 1-A.

Conversion from the compound represented by the general formula (9) to the compound represented by the general formula (1a) (Step 1-C) can be performed at 0 to 100° C. for 1 to 24 hours in a mixture of an alcohol such as methanol, ethanol or the like and an appropriate solvent such as dichloromethane, tetrahydrofuran or the like, in the presence of acid such as acetic acid or the like if need be, by using manganese dioxide and cyamide salt such as potassium cyamide, sodium cyamide or the like.

Conversion from the compound represented by the general formula (1a) to the compound represented by the general formula (1b) (Step 1-D) can be performed by hydrolysis using acid such as hydrochloric acid, sulfuric acid or nitric acid or the like or base such as lithium hydroxide, sodium hydroxide, potassium hydroxide, sodium carbonate, potassium carbonate or the like at 0 to 100° C. for 1 to 48 hours in the absence or in the presence of an appropriate solvent such as water, acetic acid, methanol, ethanol, tetrahydrofuran, 1,4-dioxane, a mixture thereof or the like.

Among compounds represented by the general formula (1a), a compound represented by the general formula (1c) can also be prepared by a synthesis method described in Production method 2.

[Production Method 2]

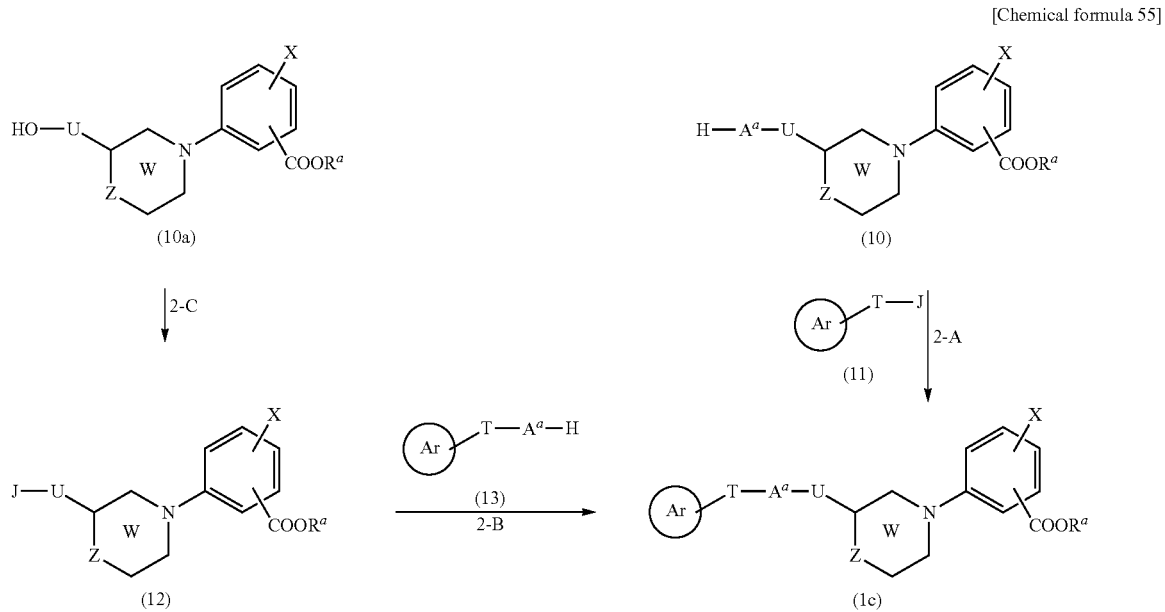

[wherein $A^a$ represents an oxygen atom, sulfur atom, or —$NR^1$—, J represents a leaving group, and ring Ar, T, U, W, X, Z, $R^1$, and $R^a$ are as defined above]

As a leaving group denoted by J, a halogen atom, lower alkylsulfonyloxy group which may be substituted with halogen atom such as methanesulfonyloxy group and trifluoromethanesulfonyloxy group, arylsulfonyloxy group which may be substituted with lower alkyl group such as phenylsulfonyloxy group and p-tolylsulfonyloxy group can be exemplified.

Conversion from the compounds represented by the general formula (10) and the general formula (11) to the compound represented by the general formula (1c) (Step 2-A) can be performed at −15 to 120° C. for 1 to 24 hours, in an appropriate solvent for example, toluene, hexane, tetrahydrofuran, diethyl ether, dichloromethane, N,N-dimethylformamide, dimethylsulfoxide, acetone, a mixture thereof or the like, in the presence of a base such as sodium hydroxide, potassium hydroxide, sodium carbonate, potassium carbonate, sodium hydride, sodium methoxide, potassium t-butoxide, pyridine, triethylamine, N,N-dimethyl aniline or the like, with addition of an appropriate iodide salt, for example, sodium iodide, potassium iodide, tetrabutyl ammonium iodide and the like if need be.

Conversion from the compounds represented by the general formula (12) and the general formula (13) to the compound represented by the general formula (1c) (Step 2-B) can be performed in a similar manner as described in Step 2-A.

Conversion from the compound represented by the general formula (10a) to the compound represented by the general formula (12) (Step 2-C) can be performed by using a halogenating agent such as thionyl chloride, phosphorous oxychloride, thionyl bromide or the like at −20 to 80° C. for 0.5 to 6 hours in the absence or in the presence of an appropriate solvent for example, dichloromethane, chloroform, tetrahydrofuran, benzene, a mixture thereof or the like, in the presence of a base such as pyridine or the like if need be, or by using an appropriate sulfonylating agent for example, methane sulfonyl chloride, trifluoromethane sulfonic anhydride or the like at −20 to 60° C. for 0.5 to 3 hours in an appropriate solvent, for example, dichloromethane, tetrahydrofuran, N,N-dimethylformamide, a mixture thereof or the like, in the presence of a base such as triethylamine, pyridine or the like.

The conversion can also be performed at −20 to 60° C. for 0.5 to 6 hours in the absence or in the presence of an appropriate solvent for example, dichloromethane, chloroform, tetrahydrofuran, benzene, a mixture thereof or the like, in the presence of imidazole if need be, by using triphenylphosphine and carbon tetrabromide, carbon tetrachloride or iodide.

Among compounds represented by the general formula (1a), a compound represented by the general formula (1d) can also be prepared by a synthesis method described in Production method 3.

[Production Method 3]

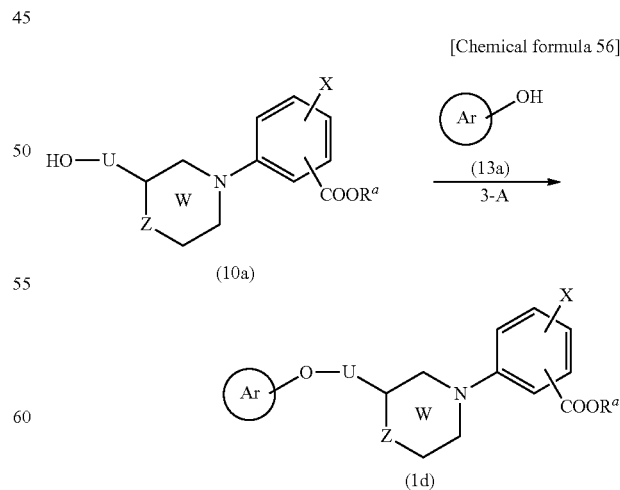

[wherein ring Ar, U, W, X, Z, and $R^a$ are as defined above]

Conversion from the compounds represented by the general formula (10a) and the general formula (13a) to the compound represented by the general formula (1d) (Step 3-A) can be performed by using an electrophilic agent such as diethyl azodicarbonate, diisopropyl azodicarbonate, dipiperidine azodicarbonate or the like at 0 to 60° C. for 3 to 24 hours, in an appropriate solvent, for example, toluene, hexane, tetrahydrofuran, a mixture thereof or the like, in the presence of organic phosphorous compound such as triphenylphosphine, tributylphosphine or the like, or by using a phosphorane compound such as cyanomethylene tributylphosphorane, cyanomethylene trimethylphosphorane or the like at room to 120° C. for 1 to 24 hours in an appropriate solvent, for example, toluene, benzene, hexane, tetrahydrofuran, a mixture thereof or the like.

Among compound represented by the general formula (1a), a compound represented by the general formula (1e) can also be prepared by a synthesis method described in Production method 4.

[Production Method 4]

Conversion from the compounds represented by the general formula (10b) and the general formula (14) to the compound represented by the general formula (1e) (Step 4-A) can be performed by using a reducing agent such as lithium borohydride, sodium borohydride, sodium cyanoborohydride, sodium triacetoxyborohydride or the like at 0 to 60° C. for 1 to 24 hours in an appropriate solvent, for example, methanol, ethanol, dichloromethane, chloroform, tetrahydrofuran a mixture thereof or the like, in the presence of acid such as hydrochloric acid, hydrobromic acid, acetic acid or the like or Lewis acid such as aluminum chloride, zinc chloride or the like if need be.

Conversion from the compounds represented by the general formula (15) and the general formula (13b) to the compound represented by the general formula (1e) (Step 4-B) can be performed in a similar manner as described in Step 4-A.

Among compounds represented by the general formula (1a), compounds represented by the general formula (1f) and

[Chemical formula 57]

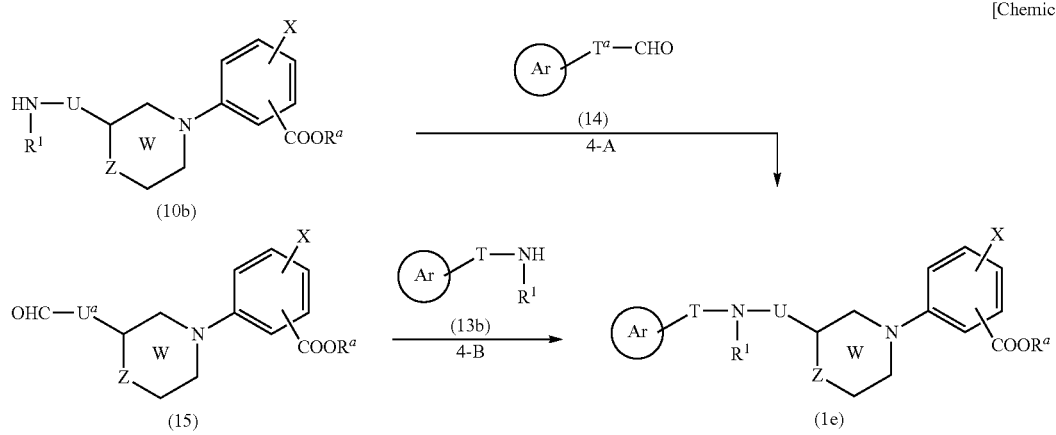

[wherein $T^a$ represents a single bond, $C_1$-$C_3$ alkylene, $C_2$-$C_3$ alkenylene, or $C_2$-$C_3$ alkynylene, $U^a$ represents a single bond, $C_1$-$C_3$ alkylene, or $C_2$-$C_3$ alkenylene, and ring Ar, T, U, W, X, Z, $R^1$, and $R^a$ are as defined above]

the general formula (1g) can also be prepared by a synthesis method described in Production method 5.

[Production Method 5]

[Chemical formula 58]

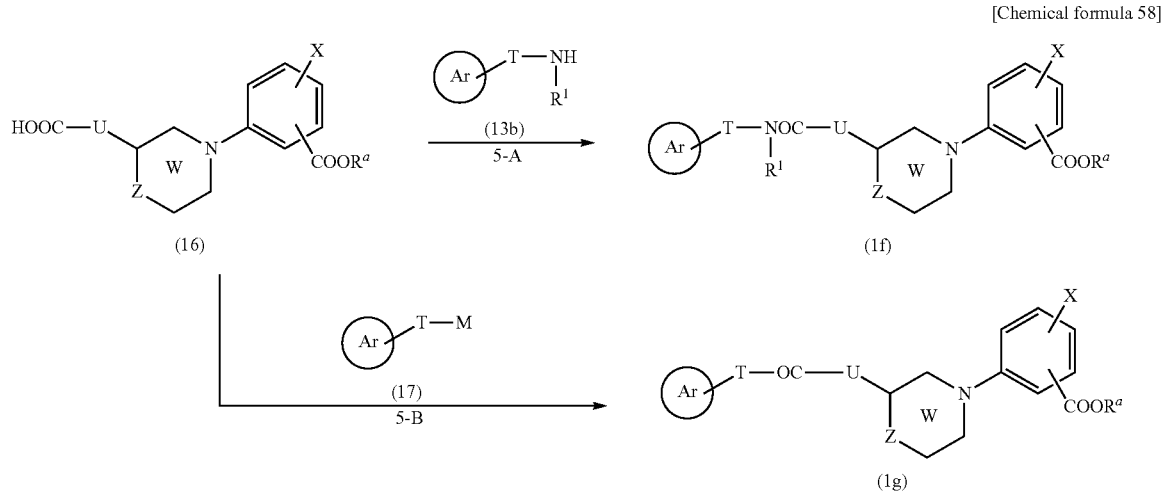

[wherein M represents a leaving group, and Ar, T, U, W, X, Z. $R^1$, and $R^a$ are as defined above]

Here, as a leaving group denoted by M, lithium atom, copper atom, —$MgX^1$ ($X^1$ represents halogen atom) and the like can be exemplified.

Conversion from the compounds represented by the general formula (16) and the general formula (13b) to the compound represented by the general formula (1f) (Step 5-A) can be performed by using a condensing agent such as dicyclohexylcarbodiimide, 3-(3-dimethylaminopropyl)-1-ethylcarbodiimide hydrochloride, diethyl cyanophosphate, azide diphenylphosphate, carbonyldiimidazole or the like at −15 to 120° C. for 1 to 24 hours, in an appropriate solvent, for example, dichloromethane, chloroform, tetrahydrofuran, diethyl ether, N,N-dimethylformamide, a mixture thereof or the like, in the presence of a base such as pyridine, triethylamine, N-methylmorpholine, 4-(dimethylamino)pyridine or the like, in the presence of a reaction auxiliary agent such as N-hydroxybenzotriazole, N-hydroxy succinimide, 3,4-dihydro-3-hydroxy-4-oxo-1,2,3-benzotriazine or the like if need be.

Alternatively, the conversion can also be performed first by letting the compound represented by the general formula (16) reacts with thionyl chloride, thionyl bromide, acetic anhydride, ethyl chlorocarbonate or the like, in the presence of a base such as pyridine, triethylamine or the like if need be, at −15 to 50° C. for 5 minutes to 3 hours, in the absence or in the presence of an appropriate solvent, for example, toluene, tetrahydrofuran, dichloromethane, N,N-dimethylformamide, a mixture thereof or the like if need be, so that a carboxyl group is made into a reactive derivative group such as acid chloride, acid bromide, acid anhydride or the like, and then reaction with the compound represented by the general formula (13b) is conducted at −15 to 50° C. for 30 minutes to 6 hours in an appropriate solvent, for example, toluene, tetrahydrofuran, dichloromethane, N,N-dimethylformamide, a mixture thereof or the like, in the presence of a base such as pyridine, triethylamine, 4-(dimethylamino)pyridine or the like.

Conversion from the compounds represented by the general formula (16) and the general formula (17) to the compound represented by the general formula (1g) (Step 5-B) can be performed first by letting the compound represented by the general formula (16) react with thionyl chloride, thionyl bromide, acetic anhydride, ethyl chlorocarbonate or the like at −15 to 50° C. for 5 minutes to 3 hours in the absence or in the presence of an appropriate solvent, for example, toluene, tetrahydrofuran, dichloromethane, a mixture thereof or the like, in the presence of a base such as pyridine, triethylamine or the like if need be, so that a carboxyl group is made into a reactive derivative group such as acid chloride, acid bromide or acid anhydride, and then reaction with the compound represented by the general formula (17) is conducted at −78 to 50° C. for 0.5 to 12 hours in an appropriate solvent, for example, toluene, tetrahydrofuran, diethyl ether, a mixture thereof or the like.

Among compounds represented by the general formula (1a), a compound represented by the general formula (1h) can also be prepared by a synthesis method described in Production method 6.

[Production Method 6]

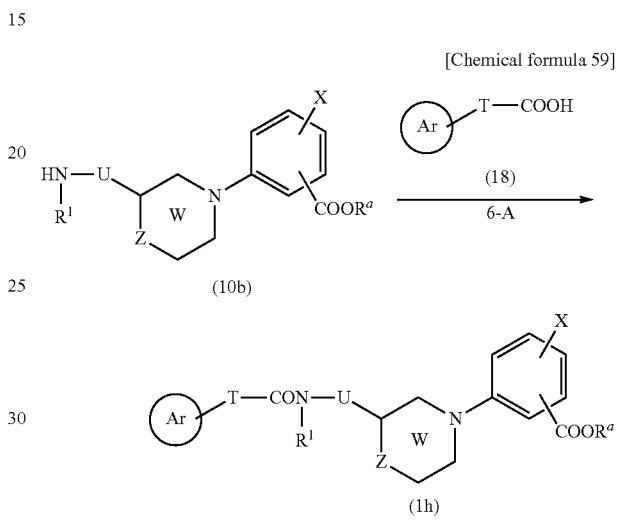

[Chemical formula 59]

[wherein ring Ar, T, U, W, X, Z, $R^1$, and $R^a$ are as defined above]

Conversion from the compounds represented by the general formula (10b) and the general formula (18) to the compound represented by the general formula (1h) (Step 6-A) can be performed in a similar manner as described in Step 5-A.

Among compounds represented by the general formula (1a), a compound represented by the general formula (1i) can also be prepared by a synthesis method described in Production method 7.

[Production Method 7]

[Chemical formula 60]

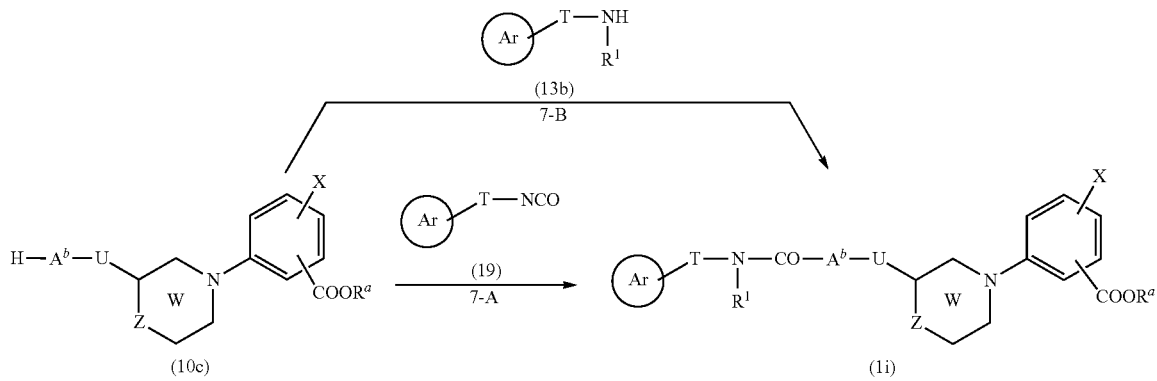

[wherein $A^b$ represents an oxygen atom, or $-NR^1-$, and ring Ar, T, U, W, X, Z, $R^1$, and $R^a$ are as defined above]

Conversion from the compounds represented by the general formula (10c) and the general formula (19) to the compound represented by the general formula (1i) (Step 7-A) can be performed at 0 to 100° C. for 0.5 to 12 hours in an appropriate solvent, for example, toluene, tetrahydrofuran, dichloromethane, N,N-dimethylformamide, a mixture thereof or the like, in the presence of a base such as pyridine or triethylamine if need be.

Conversion from the compounds represented by the general formula (10c) and the general formula (13b) to the compound represented by the general formula (1i) (Step 7-B) can be performed reacting at 0 to 60° C. for 0.5 to 12 hours in an appropriate solvent, for example, toluene, tetrahydrofuran, dichloromethane, N,N-dimethylformamide, a mixture thereof or the like, in the presence of a base such as pyridine, triethylamine or the like if need be, by using carbonyl diimidazole.

Among compounds represented by the general formula (1a), a compound represented by the general formula (1j) can also be prepared by a synthesis method described in Production method 8.

[Production Method 8]

-continued

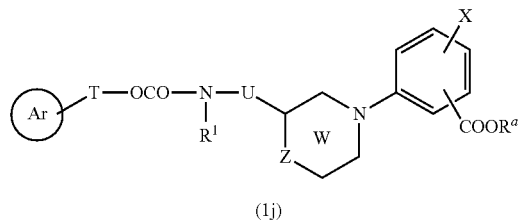

[wherein ring Ar, T, U, W, X, Z, $R^1$, and $R^a$ are as defined above]

Conversion from the compounds represented by the general formula (10b) and the general formula (13c) to the compound represented by the general formula (1j) (Step 8-A) can be performed in a similar manner as described in Step 7-B.

Among compounds represented by the general formula (1a), compounds represented by the general formula (1k) and the general formula (1l) can also be prepared by a synthesis method described in Production method 9.

[Production Method 9]

[Chemical formula 61]

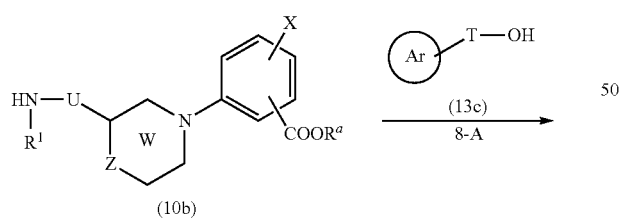

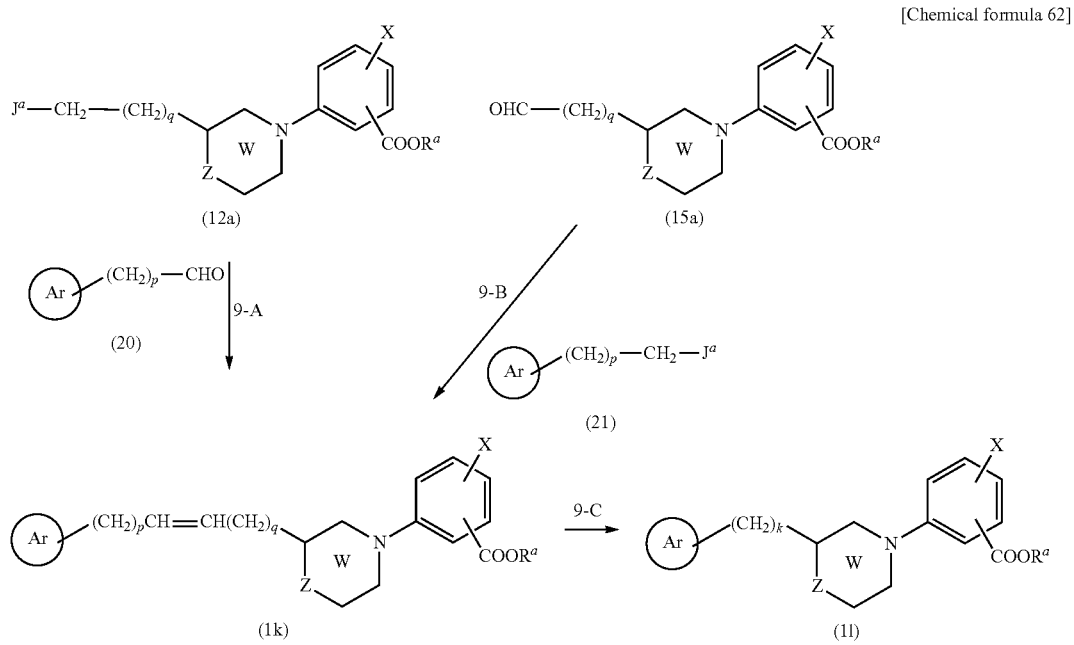

[wherein $J^a$ represents a halogen atom; p, q which are identical or different, represent 0, 1 or 2, and p+q represents 0, 1 or 2; k represents 2, 3 or 4, and ring Ar, W, X, Z, and $R^a$ are as defined above]

Conversion from the compounds represented by the general formula (12a) and the general formula (20) to the compound represented by the general formula (1k) (Step 9-A) can be performed first by letting the compound represented by the general formula (12a) react with an organic phosphorous compound such as triphenylphosphine, triethyl phosphate or the like at −78 to 120° C. for 1 hour to 12 hours in the absence or in the presence of an appropriate solvent, for example, toluene, tetrahydrofuran, benzene, a mixture thereof or the like, and then letting the same react with the compound represented by the general formula (20) at −78 to 120° C. for 1 to 12 hours in an appropriate solvent, for example, toluene, tetrahydrofuran, diethyl ether, dimethylsulfoxide, a mixture thereof or the like, in the presence of a base such as sodium hydride, n-butyl lithium, lithium diisopropyl amide, lithium bis(trimethylsilyl)amide, potassium t-butoxide, sodium hydroxide or the like.

Conversion from the compounds represented by the general formula (15a) and the general formula (21) to the compound represented by the general formula (1k) (Step 9-B) can be performed in a similar manner as described in Step 9-A.

Conversion from the compounds represented by the general formula (1k) to the general formula (1l) (Step 9-C) can be performed at 0 to 80° C. for 0.5 to 12 hours in hydrogen atmosphere at atmospheric pressure to 0.5 MPa in an appropriate solvent, for example, methanol, ethanol, ethyl acetate, tetrahydrofuran, N,N-dimethylformamide, a mixture thereof or the like, in the presence of metal catalyst such as palladium on activated carbon, palladium on activated carbon-ethylene diamine complex, platinum on activated carbon, platinum oxide, rhodium on aluminum or the like.

Among compounds represented by the general formula (1a), a compound represented by the general formula (1m) can also be prepared by a synthesis method described in Production method 10.

[Production Method 10]

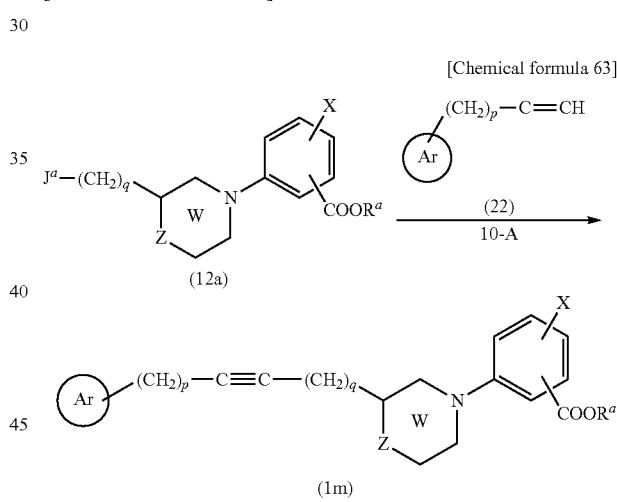

[wherein ring Ar, W, X, Z, $R^a$, $J^a$, p, and q are as defined above]

Conversion from the compounds represented by the general formula (12a) and the general formula (22) to the compound represented by the general formula (1m) (Step 10-A) can be performed at −78° C. to room temperature for 1 to 12 hours, in an appropriate solvent, for example, toluene, tetrahydrofuran, diethyl ether, dimethylsulfoxide, hexamethylphosphoric triamide, a mixture thereof or the like, in the presence of a base such as sodium hydride, n-butyl lithium, lithium amide, potassium carbonate or the like, with addition of appropriate iodide salt such as sodium iodide, copper (I) iodide, tetrabutyl ammonium iodide, or the like if need be.

In Production method 1, among compounds represented by the general formula (6), a compound represented by the general formula (6a) can be prepared by a synthesis method described in Production method 11.

[Production Method 11]

[Chemical formula 64]

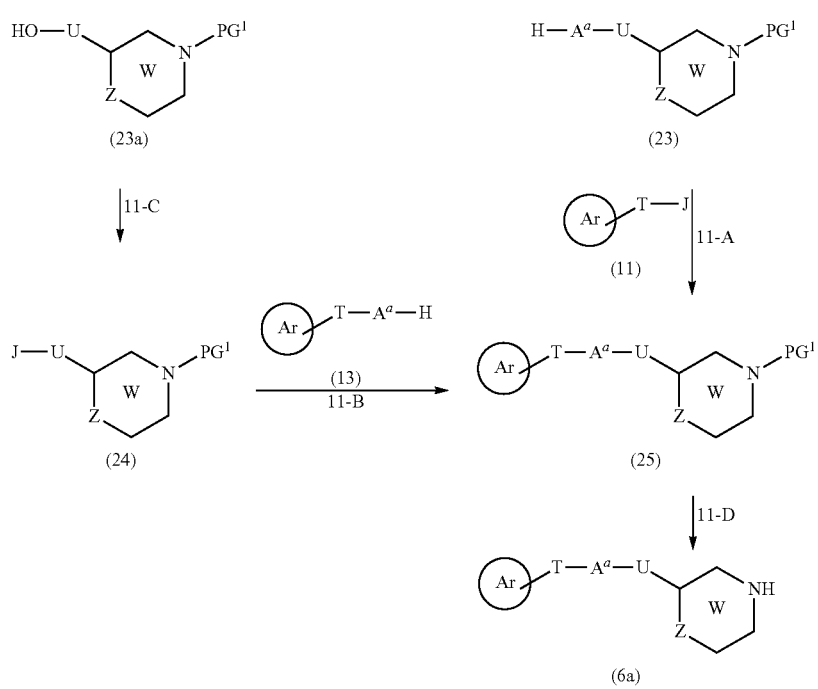

[wherein PG$^1$ represents a protecting group, and ring Ar, T, U, W, Z, A$^a$, and J are as defined above]

As a protecting group shown by PG$^1$, acyl group such as acetyl group or trifluoroacetyl group, lower alkoxycarbonyl group such as t-butoxycarbonyl group, aralkyloxy carbonyl group which may have substituent such as benzyloxycarbonyl group, or aralkyl group which may have substituent such as benzyl group or p-methoxybenzyl group can be exemplified.

Conversion from the compounds represented by the general formula (23) and the general formula (11) to the compound represented by the general formula (25) (Step 11-A) can be performed in a similar manner as described in Step 2-A.

Conversion from the compounds represented by the general formula (24) and the general formula (13) to the compound represented by the general formula (25) (Step 11-B) can be performed in a similar manner as described in Step 2-B.

Conversion from the compound represented by the general formula (23a) to the compound represented by the general formula (24) (Step 11-C) can be performed in a similar manner as described in Step 2-C.

Conversion from the compound represented by the general formula (25) to the compound represented by the general formula (6a) (Step 11-D) can be performed by deprotection according to a known method, for example, those disclosed in "Protecting Groups in Organic Synthesis (published by John Wily and Sons (1999))".

As such a method, methods using acids, bases, ultraviolet rays, hydrazine, tetrabutyl ammonium fluoride, trimethylsilyl iodide and the like, as well as a reducing method can be exemplified.

In Production method 11, among compounds represented by the general formula (25), a compound represented by the general formula (25a) can also be prepared by a synthesis method shown by Production method 12.

[Production Method 12]

[Chemical formula 65]

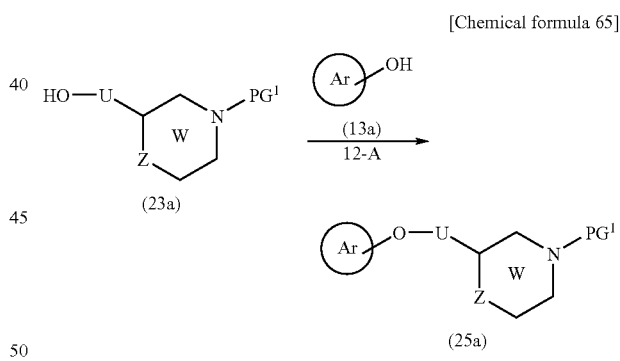

[wherein ring Ar, U, W, Z, and PG$^1$ are as defined above]

Conversion from the compounds represented by the general formula (23a) and the general formula (13a) to the compound represented by the general formula (25a) (Step 12-A) can be performed in a similar manner as described in Step 3-A.

In Production method 11, among compounds represented by the general formula (25), a compound represented by the general formula (25b) can also be prepared by a synthesis method described in Production method 13.

[Production Method 13]

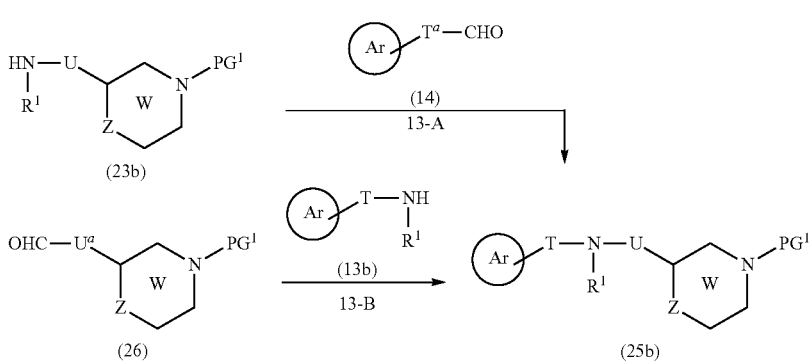

[wherein ring Ar, T, $T^a$, U, $U^a$, W, Z, $R^1$, and $PG^1$ are as defined above]

Conversion from the compounds represented by the general formula (23b) and the general formula (14) to the compound represented by the general formula (25b) (Step 13-A) can be performed in a similar manner as described in Step 4-A.

Conversion from the compounds represented by the general formula (26) and the general formula (13b) to the compound represented by the general formula (25b) (Step 13-B) can be performed in a similar manner as described in Step 4-B.

In Production method 1, among compounds represented by the general formula (6), a compound represented by the general formula (6b) can be prepared by a synthesis method described in Production method 14.

[Production Method 14]

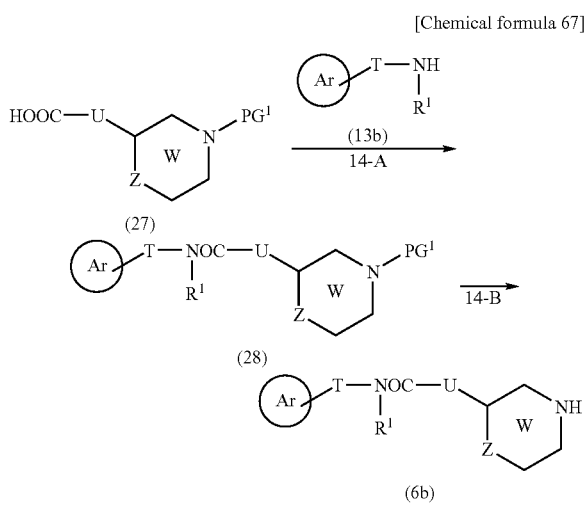

[wherein ring Ar, T, U, W, Z, $R^1$, and $PG^1$ are as defined above]

Conversion from the compounds represented by the general formula (27) and the general formula (13b) to the compound represented by the general formula (28) (Step 14-A) can be performed in a similar manner as described in Step 5-A.

Conversion from the compound represented by the general formula (28) to the compound represented by the general formula (6b) (Step 14-B) can be performed in a similar manner as described in Step 11-D.

In Production method 1, among compounds represented by the general formula (6), a compound represented by the general formula (6c) can be prepared by a synthesis method described in Production method 15.

[Production Method 15]

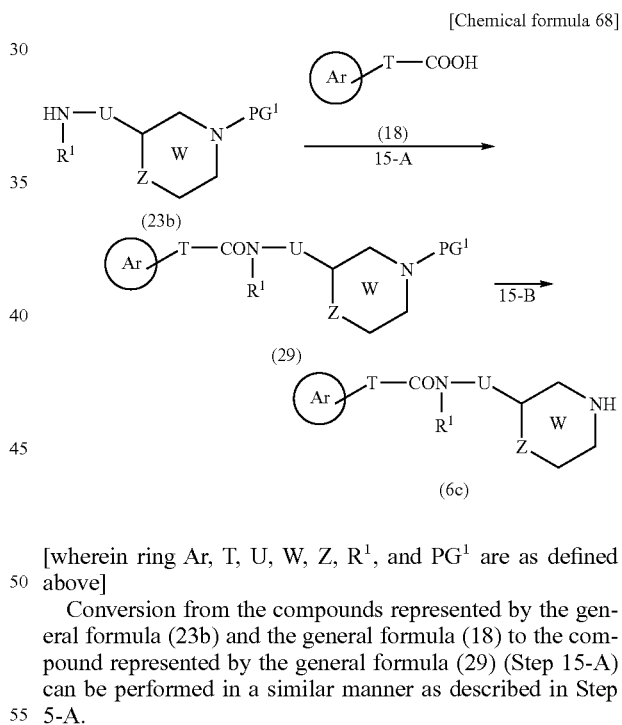

[wherein ring Ar, T, U, W, Z, $R^1$, and $PG^1$ are as defined above]

Conversion from the compounds represented by the general formula (23b) and the general formula (18) to the compound represented by the general formula (29) (Step 15-A) can be performed in a similar manner as described in Step 5-A.

Conversion from the compound represented by the general formula (29) to the compound represented by the general formula (6c) (Step 15-B) can be performed in a similar manner as described in Step 11-D.

In Production method 1, among compounds represented by the general formula (6), a compound represented by the general formula (6d) can be prepared by a synthesis method described in Production method 16.

[Production Method 16]

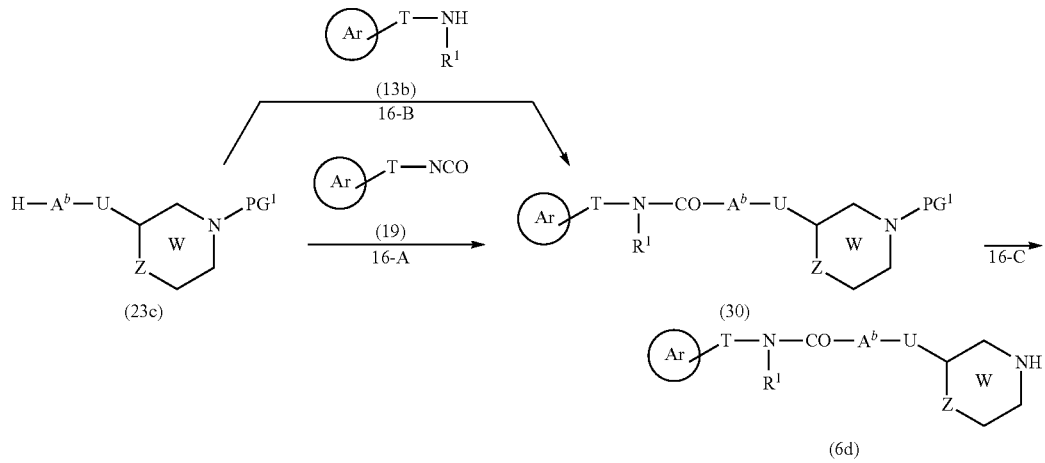

[wherein ring Ar, $A^b$, T, U, W, Z, $R^1$, and $PG^1$ are as defined above]

Conversion from the compounds represented by the general formula (23c) and the general formula (19) to the compound represented by the general formula (30) (Step 16-A) can be performed in a similar manner as described in Step 7-A.

Conversion from the compounds represented by the general formula (23c) and the general formula (13b) to the compound represented by the general formula (30) (Step 16-B) can be performed in a similar manner as described in Step 7-B.

Conversion from the compound represented by the general formula (30) to the compound represented by the general formula (6d) (Step 16-C) can be performed in a similar manner as described in Step 11-D.

In Production method 1, among compounds represented by the general formula (6), a compound represented by the general formula (6e) can be prepared by a synthesis method described in Production method 17.

[Production Method 17]

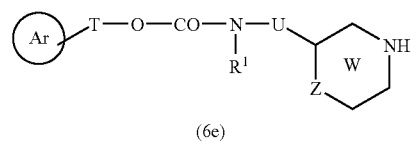

[wherein ring Ar, T, U, W, Z, $R^1$, and $PG^1$ are as defined above]

Conversion from the compounds represented by the general formula (23b) and the general formula (13c) to the compound represented by the general formula (31) (Step 17-A) can be performed in a similar manner as described in Step 7-B.

Conversion from the compound represented by the general formula (31) to the compound represented by the general formula (6e) (Step 17-B) can be performed in a similar manner as described in Step 11-D.

In Production method 1, among compounds represented by the general formula (6), compounds represented by the general formulas (6f) and (6g) can be prepared by a synthesis method described in Production method 18.

[Production Method 18]

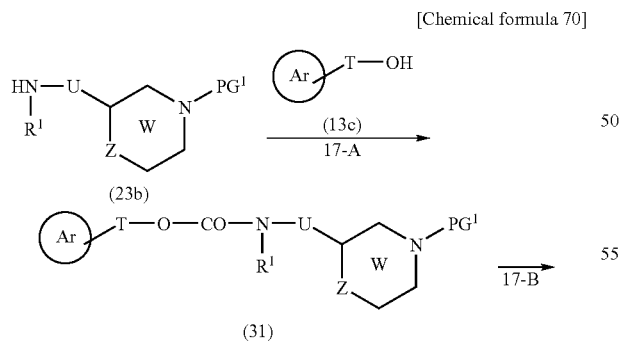

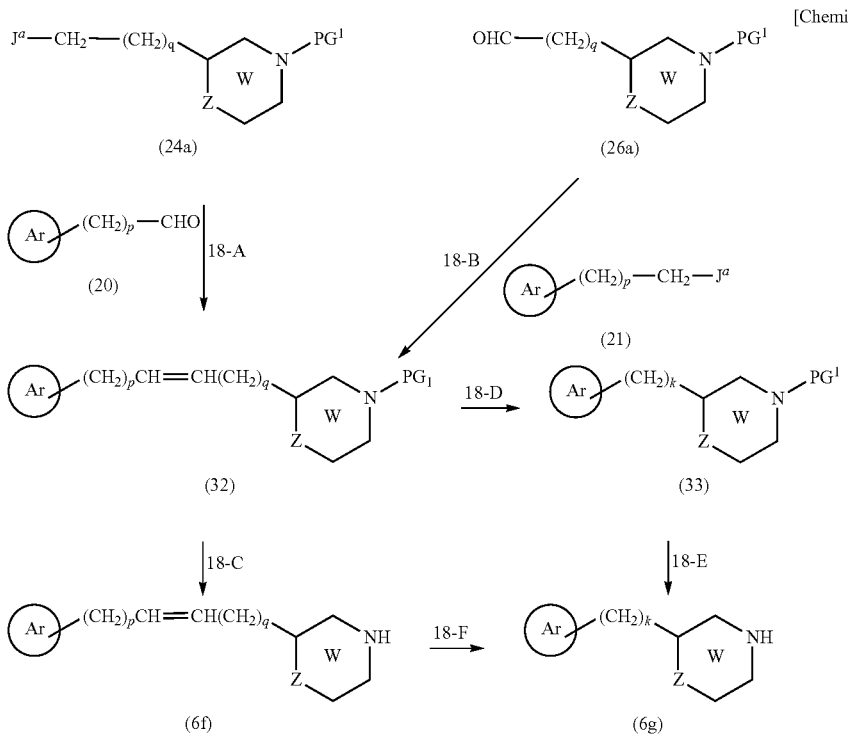

[wherein ring Ar, W, Z, J$^a$, p, q, k, and PG$^1$ are as defined above]

Conversion from the compounds represented by the general formula (24a) and the general formula (20) to the compound represented by the general formula (32) (Step 18-A) can be performed in a similar manner as described in Step 9-A.

Conversion from the compounds represented by the general formula (26a) and the general formula (21) to the compound represented by the general formula (32) (Step 18-B) can be performed in a similar manner as described in Step 9-B.

Conversion from the compound represented by the general formula (32) to the compound represented by the general formula (6f) (Step 18-C) can be performed in a similar manner as described in Step 11-D.

Conversion from the compound represented by the general formula (32) to the compound represented by the general formula (33) (Step 18-D) can be performed in a similar manner as described in Step 9-C.

Conversion from the compound represented by the general formula (33) to the compound represented by the general formula (6g) (Step 18-E) can be performed in a similar manner as described in Step 11-D.

Conversion from the compound represented by the general formula (6f) to the compound represented by the general formula (6g) (Step 18-F) can be performed in a similar manner as described in Step 9-C.

In Production method 1, among compounds represented by the general formula (6), a compound represented by the general formula (6h) can be prepared by a synthesis method described in Production method 19.

[Production Method 19]

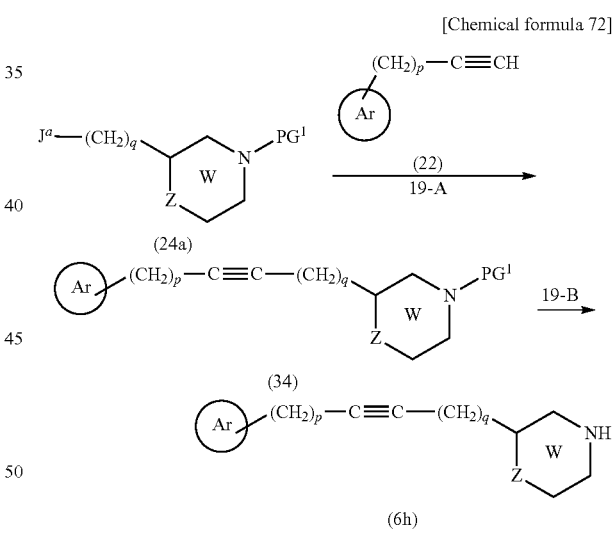

[wherein ring Ar, W, Z, J$^a$, p, q, and PG$^1$ are as defined above]

Conversion from the compounds represented by the general formula (24a) and the general formula (22) to the compound represented by the general formula (34) (Step 19-A) can be performed in a similar manner as described in Step 10-A.

Conversion from the compound represented by the general formula (34) to the compound represented by the general formula (6h) (Step 19-B) can be performed in a similar manner as described in Step 11-D.

In Production methods 2 to 10, compounds represented by the general formulas (10), (15) and (16) can be prepared by a synthesis method described in Production method 20.

[Production Method 20]

[Chemical formula 73]
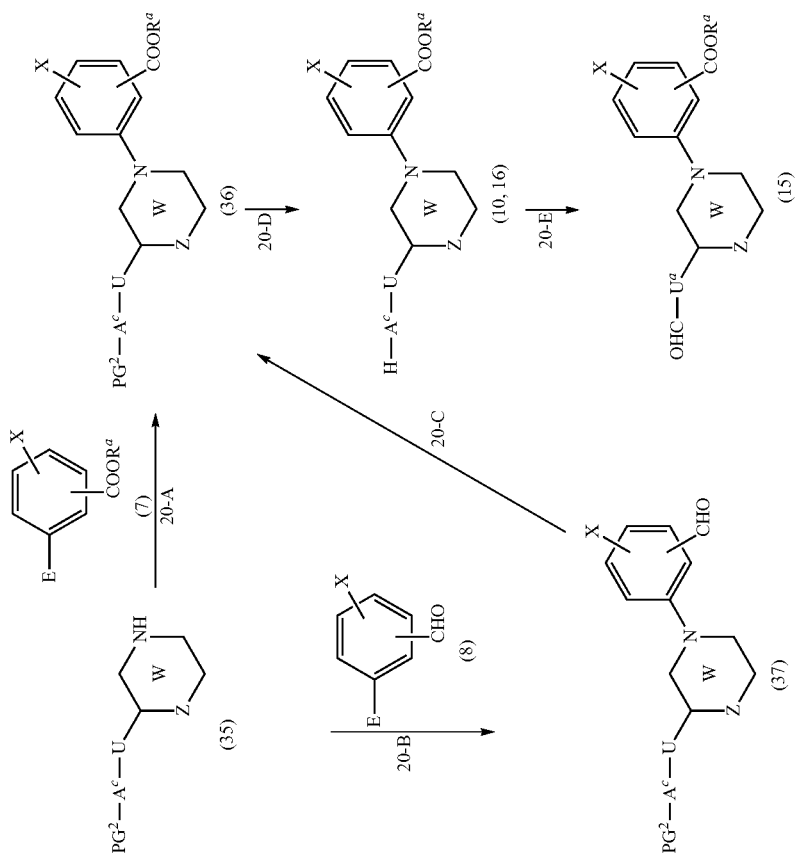

[wherein PG² represents a protecting group or hydrogen atom, A^c represents an oxygen atom, sulfur atom, —NR¹—, or —OOC—, and U, U^a, W, X, Z, R¹, R^a, and E are as defined above]

As a protecting group shown by PG¹, acyl group such as acetyl group or trifluoroacetyl group, lower alkoxycarbonyl group such as t-butoxycarbonyl group, aralkyloxy carbonyl group which may have substituent such as benzyloxycarbonyl group, aralkyl groups which have substituent such as benzyl group, p-methoxybenzyl group or triphenyl group, silyl group such as trimethylsilyl group or t-butyldimethylsilyl, phthaloyl group or the like can be exemplified.

Conversion from the compounds represented by the general formula (35) and the general formula (7) to the compound represented by the general formula (36) (Step 20-A) can be performed in a similar manner as described in Step 1-A.

Conversion from the compounds represented by the general formula (35) and the general formula (8) to the compound represented by the general formula (37) (Step 20-B) can be performed in a similar manner as described in Step 1-B.

Conversion from the compound represented by the general formula (37) to the compound represented by the general formula (36) (Step 20-C) can be performed in a similar manner as described in Step 1-C.

In the general formula (36), conversion from a compound in which PG² represents a protecting group to the compound represented by the general formulas (10), or (16) (Step 20-D) can be performed by deprotection according to a known method, for example, those disclosed in "Protecting Groups in Organic Synthesis (published by John Wily and Sons (1999))".

As such a method, methods using acid, base, ultraviolet rays, hydrazine, tetrabutyl ammonium fluoride, trimethylsilyl iodide and the like, as well as a reducing method can be exemplified.

In the general formula (10), conversion from a compound in which A^c is an oxygen atom (excluding compound in which U represents a single bond) to the compound represented by the general formula (15) (Step 20-E) can be performed at −78 to 50° C. for 15 minutes to 6 hours in an appropriate solvent, for example, dichloromethane, tetrahydrofuran, diethyl ether, a mixture thereof or the like, in the presence of a base such as triethylamine, pyridine, diisopropylethylamine or the like, and in the presence of dimethylsulfoxide, and, if need be, acid such as trifluoro acetic acid, by using an electrophilic agent such as oxalyl chloride, dicyclohexyl carbodiimide, sulfur trioxide pyridine complex, or acetic anhydride.

Alternatively, the compound represented by the general formula (15) can be prepared by reaction at 0 to 50° C. for 30 minutes to 12 hours in an appropriate solvent, for example, dichloromethane, dichloromethane, acetonitrile or the like, using Dess-Martin periodinane (1,1,1-tris(acetoxy)-1,1-dihydro-1,2-benziodoxol-3-(1H)-one).

Furthermore, it can be prepared by reaction at 0 to 50° C. for 10 minutes to 36 hours in an appropriate solvent, for example, chloroform, dichloromethane, acetonitrile or the like, using tetrapropyl ammonium perrutenate in the presence of 4-methylmorpholine N-oxide.

Furthermore, it can be prepared by reaction at 0 to 50° C. for 0.5 to 6 hours in an appropriate solvent, for example, chloroform, dichloromethane, benzene, toluene or the like, in the presence of a cooxidant such as sodium hypochlorite, a reaction auxiliary agent such as potassium bromide and a buffer such as sodium hydrogen carbonate aqueous solution, using 2,2,6,6-tetramethylpiperidine N-oxide.

In the general formula (10), the compound in which A^c represents an oxygen atom can be converted into a compound in which A^c represents NH, for example, by Gabriel reaction in accordance with a known method, for example, "Jikken Kagaku Koza (Experimental Chemistry Lecture) (published by Maruzen)."

Among compounds represented by the general formula (1a), a compound represented by the general formula (1o) can also be prepared by a synthesis method described in Production method 21.

[Production Method 21]

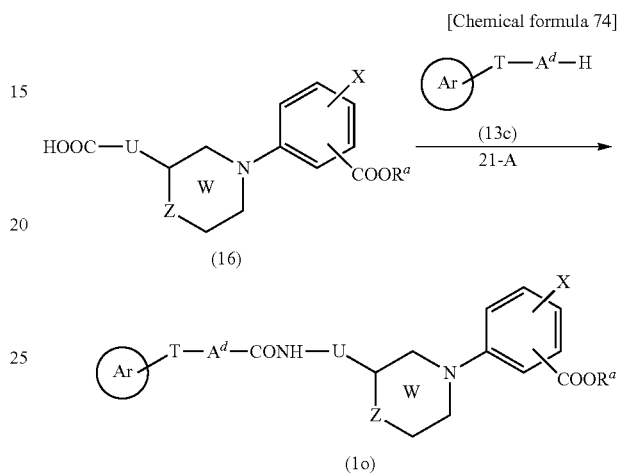

[Chemical formula 74]

[wherein A^d represents an oxygen atom, or —NR¹—, and ring Ar, T, U, W, X, Z, R¹, R^a are as defined above]

Conversion from the compounds represented by the general formula (16) and the general formula (13c) to the compound represented by the general formula (1o) (Step 21-A) can be performed first by letting the compound represented by general formula (16) react at room temperature to 150° C. for 3 to 12 hours in an appropriate solvent, for example, benzene, toluene, tetrahydrofuran, 1,4-dioxane, a mixture thereof or the like, in the presence of a base such as pyridine, triethylamine, N-methylmorpholine, 4-(dimethylamino)pyridine or the like, using phosphonic azide such as diphenylphosphonic azide or the like to convert a carboxyl group into an isocyanate group, and then conducting reaction with the compound represented by the general formula (13c) at 0 to 150° C. for 0.5 to 12 hours in an appropriate solvent, for example, benzene, toluene, tetrahydrofuran, 1,4-dioxane, a mixture thereof or the like, in the presence of a base such as pyridine, triethylamine, N-methylmorpholine, or 4-(dimethylamino)pyridine if need be.

The conversion may be performed by letting the compound represented by the general formula (16) react at −15 to 50° C. for 5 minutes to 3 hours in the absence or in the presence of an appropriate solvent, for example, benzene, toluene, tetrahydrofuran, dichloromethane, a mixture thereof or the like, in the presence of a base such as pyridine or triethylamine if need be, using thionyl chloride, thionyl bromide, acetic anhydride or ethyl chlorocarbonate, thereby making a carboxyl group into a reactive derivative group such as acid chloride, acid bromide or acid anhydride, and then conducting reacting at 0 to 50° C. for 0.5 to 6 hours in an appropriate solvent, for example, water, acetone, 1,4-dioxane, tetrahydrofuran, benzene, toluene, dichloromethane, a mixture thereof or the like, in the presence of an auxiliary agent such as 18-crown-6 if need be, using salt azide such sodium azide or silyl azide such as trimethylsilyl azide, and then conducting reaction at room temperature to 150° C. for 3 to 12 hours in an appropriate solvent, for example, benzene, toluene, tetrahydrofuran, 1,4-dioxane, a mixture thereof or the like, thereby making a carboxyl group into an isocyanate group, and then conducting reaction with the compound represented by the general formula (13c) at 0 to 150° C. for 0.5 to 12 hours in an appropriate solvent, for example, benzene, toluene, tetrahydrofuran, 1,4-dioxane, a mixture thereof or the like, in the presence of a base such as pyridine, triethylamine, N-methylmorpholine, 4-(dimethylamino)pyridine or the like if need be.

Among compounds represented by the general formula (1a), a compound represented by the general formula (1g) can also be prepared by a synthesis method described in Production method 22.

[Production Method 22]

by the general formula (40) react with the compound represented by the general formula (12) at −78 to 60° C. for 1 to 12 hours in an appropriate solvent, for example, benzene, toluene, tetrahydrofuran, diethyl ether, 1,4-dioxane, N,N-dimethylformamide, dimethylsulfoxide, a mixture thereof or the like, in the presence of a base such as sodium hydride, lithium diisopropyl amide, lithium bis(trimethylsilyl)amide, potassium t-butoxide or the like, and then conducting reaction at 0 to 100° C. for 1 to 48 hours in the absence or in the presence of an appropriate solvent, for example, water, acetic acid, methanol, ethanol, ethyleneglycol, tetrahydrofuran, 1,4-dioxane, a mixture thereof or the like, using acid such as hydrochloric acid, sulfuric acid, nitric acid or the like.

Conversion from the compounds represented by the general formula (41) and the general formula (39) to the com-

[Chemical formula 75]

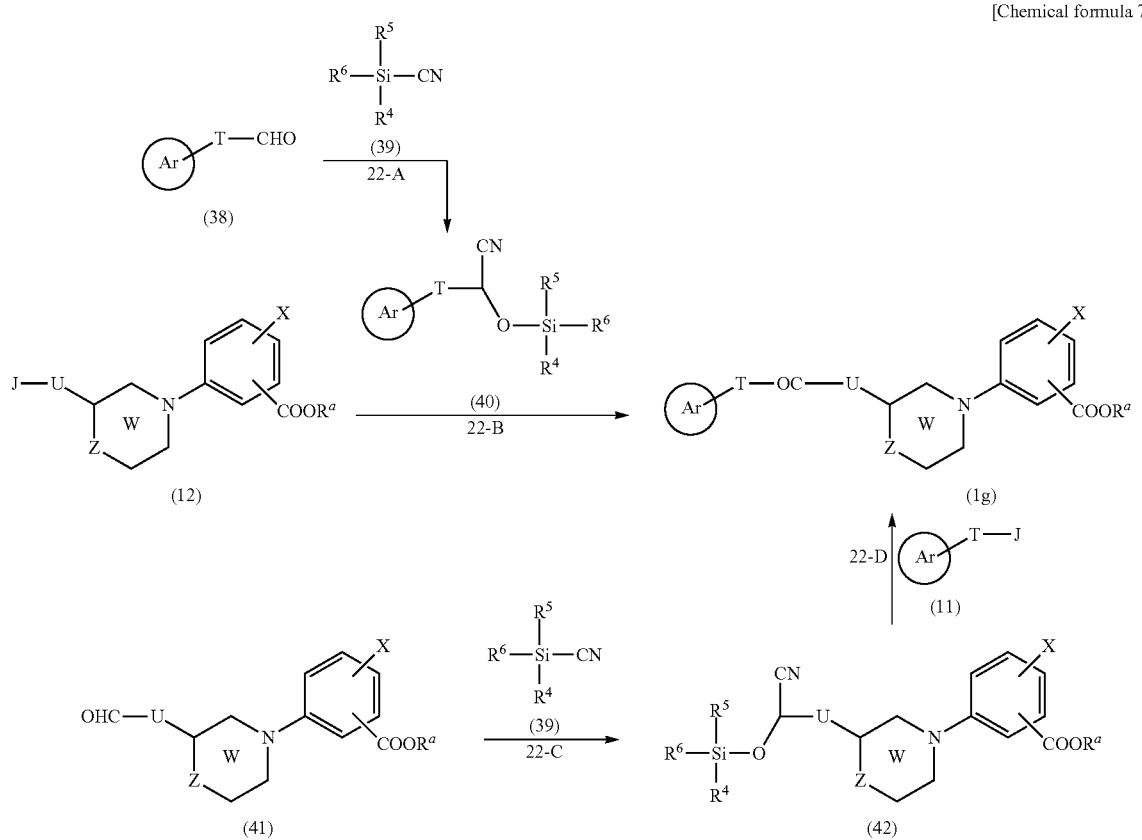

[wherein $R^4$, $R^5$ and $R^6$ which are identical or different, represent a lower alkyl group or aryl group, and ring Ar, T, U, W, X, Z, $R^a$, and J are as defined above]

Conversion from the compounds represented by the general formula (38) and the general formula (39) to the compound represented by the general formula (40) (Step 22-A) can be performed at 0 to 60° C. for 3 to 24 hours in the absence or in the presence of an appropriate solvent, for example, dichloromethane, chloroform, tetrahydrofuran, diethyl ether, N,N-dimethylformamide, 1,4-dioxane, acetonitrile, a mixture thereof or the like, in the presence of Lewis acid such as zinc iodide if need be.

Conversion from the compounds represented by the general formula (12) and the general formula (40) to the compound represented by the general formula (1g) (Step 22-B) can be performed first by letting the compound represented pound represented by the general formula (42) (Step 22-C) can be performed in a similar manner as described in Step 22-A.

Conversion from the compounds represented by the general formula (42) and the general formula (11) to the compound represented by the general formula (1g) (Step 22-D) can be performed in a similar manner as described in Step 22-B.

Compounds represented by the general formula (1b) can also be prepared by a synthesis method described in Production method 23.

[Production Method 23]

[Chemical formula 76]

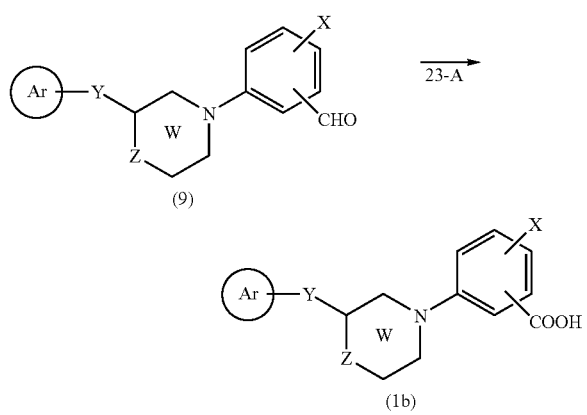

[wherein ring Ar, Y, W, X, and Z are as defined above]

Conversion from the compound represented by the general formula (9) to the compound represented by the general formula (1b) (Step 23-A) can be performed at room temperature to 50° C. for 1 to 12 hours in water or in mixture of water and appropriate organic solvent such as t-butyl alcohol, 2-propanol, acetonitrile or the like, by using isobutylene, chlorite such as sodium chlorite or the like, and sodium dihydrogenphosphate.

Alternatively, the conversion can also be performed at room temperature to refluxing temperatures for 1 to 6 hours in water or in mixture of water and appropriate organic solvent such as tetrahydrofuran, 1,4-dioxane or the like, by using silver (I) oxide and a base such as sodium hydroxide, potassium hydroxide, barium hydroxide, potassium carbonate or the like.

Furthermore, it can also be performed at room temperature to refluxing temperatures for 1 to 6 hours in water or in mixture of water and appropriate organic solvent such as t-butyl alcohol, dichloromethane or the like, by using permanganate such as potassium permanganate or the like.

Among compounds represented by the general formula (1b), a compound represented by the general formula (1q) can also be prepared by a synthesis method described in Production method 24.

[Production Method 24]

[Chemical formula 77]

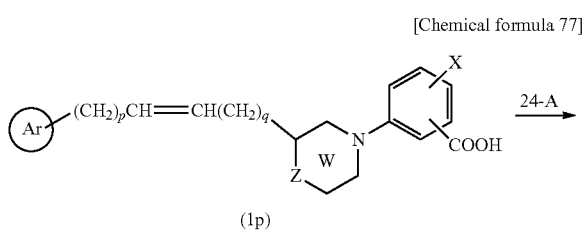

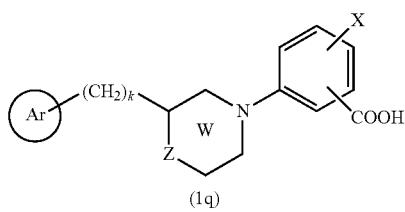

[wherein p, q, k, ring Ar, W, X, and Z are as defined above]

Conversion from the compound represented by the general formula (1p) to the compound represented by the general formula (1q) (Step 24-A) can be performed in a similar manner as described in Step 9-C. In Production method 1, among compounds represented by the general formula (6), a compound represented by the general formula (6i) can be prepared by a synthesis method described in Production method 25.

[Production Method 25]

[Chemical formula 78]

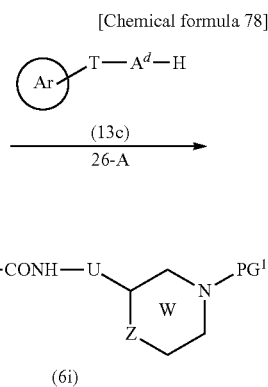

[wherein ring Ar, T, U, W, X, Z, $R^1$, $A^d$, and $PG^1$ are as defined above]

Conversion from the compounds represented by the general formula (27) and the general formula (13c) to the compound represented by the general formula (6i) (Step 25-A) can be performed in a similar manner as described in Step 21-A. In Production method 1, among compounds represented by the general formula (6), a compound represented by the general formula (6j) can be prepared by a synthesis method described in Production method 26.

[Production Method 26]

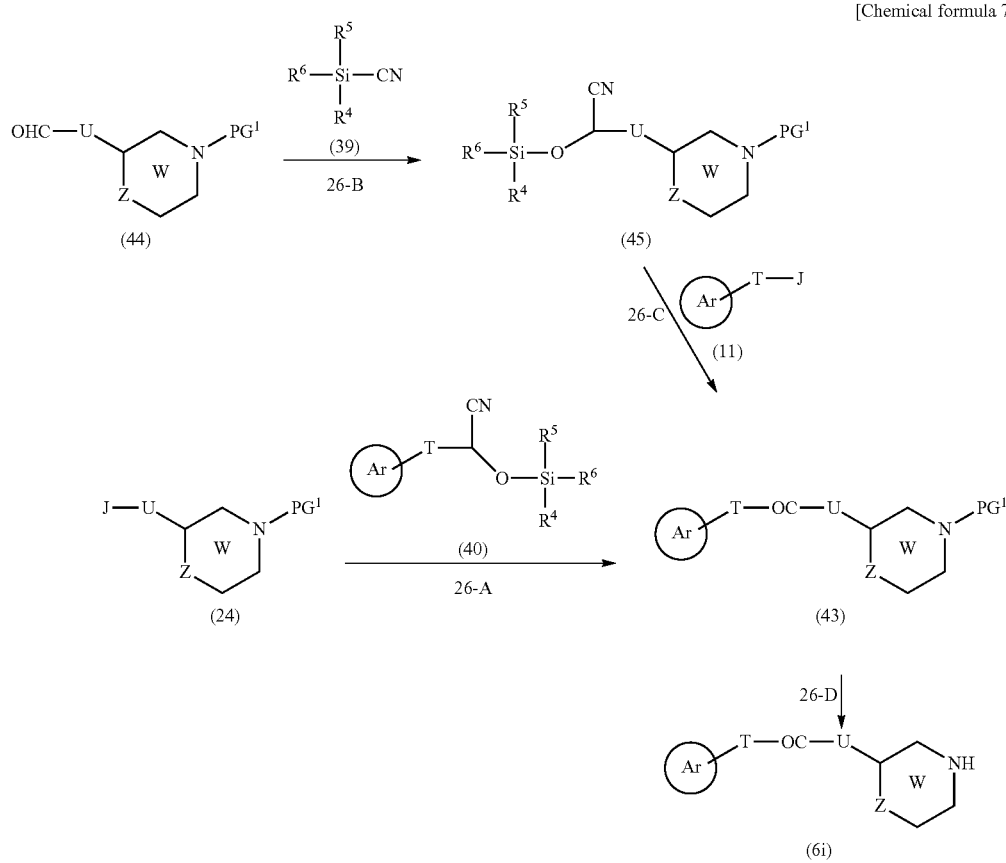

[Chemical formula 79]

[wherein ring Ar, T, U, W, Z, J, $R^4$, $R^5$, $R^6$, and $PG^1$ are as defined above]

Conversion from the compounds represented by the general formula (24) and the general formula (40) to the compound represented by the general formula (43) (Step 26-A) can be performed in a similar manner as described in Step 22-B.

Conversion from the compounds represented by the general formula (44) and the general formula (39) to the compound represented by the general formula (45) (Step 26-B) can be performed in a similar manner as described in Step 22-C.

Conversion from the compounds represented by the general formula (45) and the general formula (11) to the compound represented by the general formula (43) (Step 26-C) can be performed in a similar manner as described in Step 22-D.

Conversion from the compound represented by the general formula (43) to the compound represented by the general formula (6j) (Step 26-D) can be performed in a similar manner as described in Step 11-D.

In Production method 22, among compounds represented by the general formula (41) can be prepared by a synthesis method described in Production method 27.

[Production Method 27]

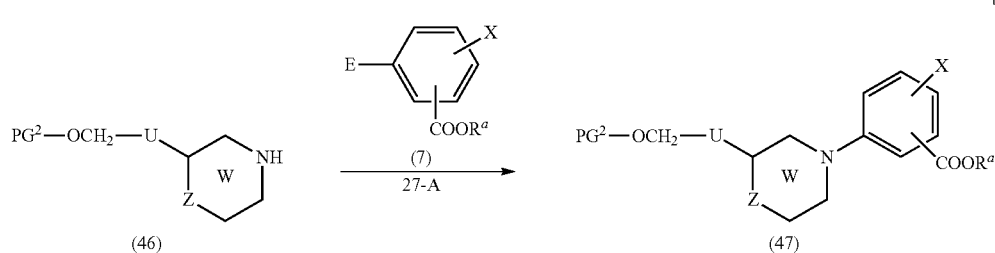

[Chemical formula 80]

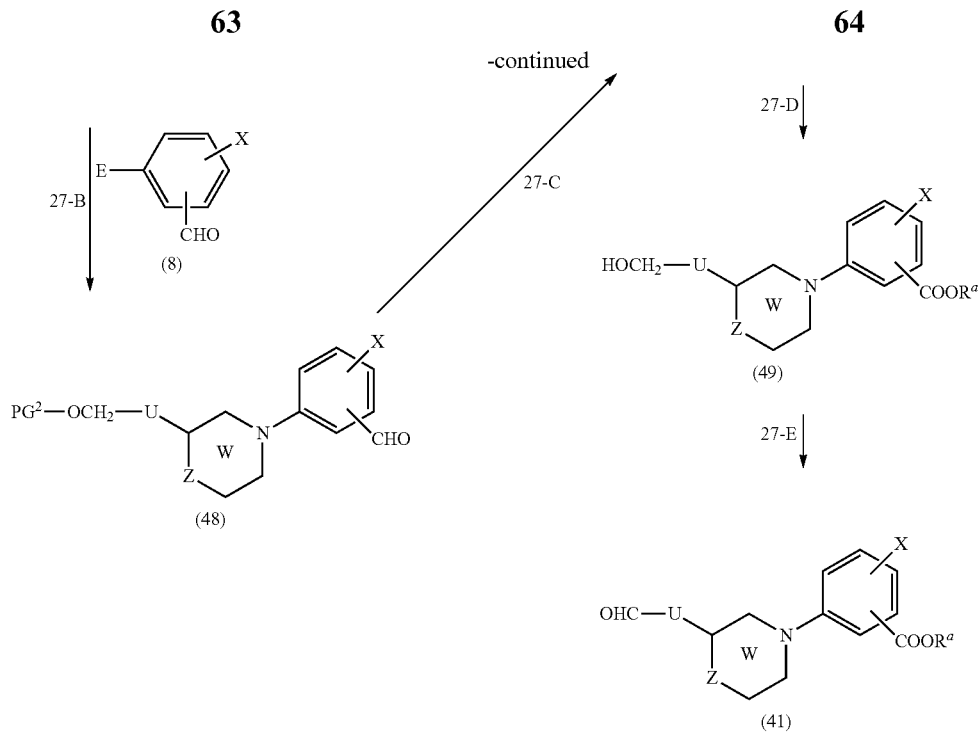

[wherein U, W, X, Z, $R^a$, and $PG^2$ are as defined above]

Conversion from the compounds represented by the general formula (46) and the general formula (7) to the compound represented by the general formula (47) (Step 27-A) can be performed in a similar manner as described in Step 1-A.

Conversion from the compounds represented by the general formula (46) and the general formula (8) to the compound represented by the general formula (48) (Step 27-B) can be performed in a similar manner as described in Step 1-B.

Conversion from the compound represented by the general formula (48) to the compound represented by the general formula (47) (Step 27-C) can be performed in a similar manner as described in Step 1-C.

Conversion from the compound represented by the general formula (47) to the compound represented by the general formula (49) (Step 27-D) can be performed in a similar manner as described in Step 20-D.

In the general formula (49), conversion from a compound in which $PG^2$ represents a protecting group to the compound represented by the general formula (41) (Step 27-E) can be performed in a similar manner as described in Step 20-E.

In Production methods 1 to 27, compounds having a ring Ar represented by the general formulas (11), (13), (14), and (17) to (23) can be prepared according to known methods, for example, "Heterocyclic Chemistry (published by Chapman and Hall (1995))", "Synthetic Communication, 20(16), 2537-2547 (1990)", "Heterocycles, 47(2), 857-864 (1998)", "Journal of Organic Chemistry, 61(19), 6496-6497 (1996)", "Journal of American Chemical Society, 71, 2328 (1949)", "Synthesis Communication, 19(16), 2921-2924 (1989)" and the like.

Substituents X and $R^1$ in compounds shown in Production methods 1 to 27 can be converted according to a known method, such as "Jikken Kagaku Kouza (published by Maruzen)." For example, a compound in which the substituent X represents nitro group can be converted into a compound in which the substituent X represents amino group, by a reduction process using metal such as iron powder or zinc powder, or by a reduction process using palladium on activated carbon or the like, while a compound in which substituent $R^1$ represents a hydrogen atom may be converted into a compound in which the substituent $R^1$ represents an alkyl group by alkylation using a halogenated alkyl such as methyl iodide, or reductive amination using aldehyde such as acetaldehyde and a reducing agent such as sodium borohydride.

Optical isomers of compounds represented by the general formula (1) can be prepared by using optically active material compounds according to the aforementioned Production methods 1 to 27.

Racemic compounds represented by the general formula (1) may be prepared by functional crystallization using optically active acid or base, or by separating diastereomeric ester derivative or oxazolidin one derivative obtained by reacting with optically active alcohol derivative or optically active oxazolidin one derivative through either technique of functional crystallization or chromatography, and followed by hydrolysis.

Furthermore, they can also be prepared by a chromatographic technique using a chiral support.

EXAMPLES

The present invention will now be described in further detail with reference to examples, which are not intended to limit the scope of the invention in any way.

Reference Example 1

1-benzyl-2-oxoperhydroazepine

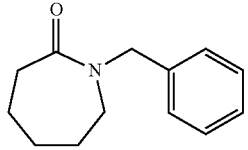

[Chemical formula 81]

ε-Caprolactum (3.00 g, 26.5 mmol) was dissolved in tetrahydrofuran (30 mL). To this solution, potassium hydride (3.34 g, 29.2 mmol) was added and the mixture was stirred at room temperature for 10 min. Benzyl chloride (3.36 mL, 29.2 mmol) and sodium iodide (100 mg) were added and the reaction mixture was further stirred at room temperature for 3 hours. Subsequently, water was added and the mixture was extracted with ethylacetate. The extract was washed with brine, dried over magnesium sulfate and concentrated. Purification of the residue by silica gel column chromatography (hexane:ethyl acetate=10:1->2:1) gave 3.04 g (57%) of the desired compound as a colorless oil.

$^1$H NMR (400 MHz, CDCl$_3$) δ 1.46-1.51 (2H, m), 1.66-1.74 (4H, m), 2.60-2.62 (2H, m), 3.28-3.30 (2H, m), 4.59 (2H, s), 7.25-7.33 (5H, m).

FAB$^+$ (m/z): 204 (M+H).

Reference Example 2

Methyl 1-benzyl-2-oxoperhydroazepine-3-carboxylate

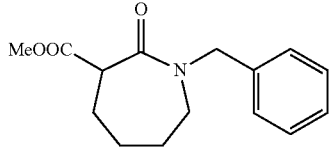

[Chemical formula 82]

Diisopropylamine (2.95 mL, 21.0 mmol) and n-butyllithium (11.3 mL, 18.0 mmol) were dissolved in diethyl ether (50 mL) at −78° C. and the mixture was stirred for 10 min. 1-benzylperhydroazepine (3.04 g, 15.0 mmol) in diethyl ether (3 mL) was then added and the mixture was further stirred at room temperature for 10 min. The mixture was then stirred for another 10 min while bubbled with carbon dioxide. Subsequently, the reaction mixture was added to ice water and the aqueous layer was collected. 2 mol/L hydrochloric acid was added to make the mixture acidic. The mixture was then extracted with ethyl acetate and the extract washed with brine and dried over magnesium sulfate, followed by evaporation of the solvent. The resulting colorless oil (2.97 g) was dissolved in a 10% hydrogen chloride/methanol solution and the mixture was stirred at room temperature for 2 hours. The mixture was then concentrated. Water was added to the residue and the mixture was extracted with ethyl acetate. The extract was then washed with brine and was dried over magnesium sulfate, followed by evaporation of the solvent. Purification of the residue by silica gel column chromatography (hexane:ethyl acetate=10:1->2:1) gave 2.39 g (61%) of the desired compound as a colorless oil.

$^1$H NMR (400 MHz, CDCl$_3$) δ 1.24-1.33 (1H, m), 1.49-1.66 (2H, m), 1.82-1.94 (2H, m), 2.04-2.12 (1H, m), 3.19-3.25 (1H, m), 3.32-3.41 (1H, m), 3.70 (1H, dd, J=2.4, 11.0 Hz), 3.79 (3H, s), 4.55 (1H, d, J=14.7 Hz), 4.65 (1H, d, J=14.7 Hz), 7.23-7.37 (5H, m).

FAB$^+$ (m/z): 262 (M+H).

Reference Example 3

1-Benzyl perhydroazepin-3-yl methanol

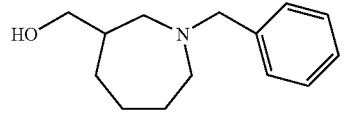

[Chemical formula 83]

Methyl 1-benzyl-2-oxoperhydroazepine-3-carboxylate (2.39 g, 9.15 mmol) was dissolved in tetrahydrofuran (50 mL). To this solution, lithium aluminum hydride (868 mg, 18.3 mmol) was added and the mixture was stirred for 2 hours while being refluxed. Subsequently, ice water and a 10% aqueous sodium hydroxide solution were added and the mixture was stirred at room temperature for 1 hour. The reaction mixture was then filtered through Celite. The filtrate was extracted with ethyl acetate and the extract washed with brine, followed by drying over magnesium sulfate and evaporation of the solvent. Purification of the residue by silica gel column chromatography (Chromatorex NH-DM2035 (Fuji Sylysia Chemical Co., Ltd.) hexane:ethyl acetate=20:1->3:1) gave 1.30 g (65%) of the desired compound as a colorless oil.

$^1$H NMR (400 MHz, CDCl$_3$) δ 1.49-1.65 (3H, m), 1.70-1.86 (4H, m), 2.22-2.29 (1H, m), 2.70-2.80 (3H, m), 3.45 (1H, dd, J=10.4, 4.3 Hz), 3.57-3.60 (3H, m), 7.23-7.29 (1H, m), 7.30-7.38 (4H, m).

FAB$^+$ (m/z): 220 (M+H).

Reference Example 4

1-(tert-Butoxycarbonyl)perhydroazepin-3-yl methanol

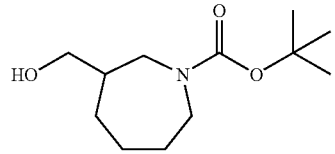

[Chemical formula 84]

1-Benzyl perhydroazepin-3-yl methanol (1.30 g, 5.93 mmol) was dissolved in a 4.4% formic acid/methanol solution (30 mL). To this solution, 10% palladium on activated carbon (1.30 g) was added and the mixture was stirred at room temperature for 2 hours. Subsequently, water was added and the mixture was filtered through Celite. The filtrate was concentrated. The resulting residue was dissolved in acetonitrile (15 mL). While the solution was ice-chilled and stirred, triethylamine (1.81 mL, 13.0 mmol) and t-butyl dicarbonate (1.42 g, 6.52 mmol) were added. The reaction mixture was then stirred at room temperature for 4 hours. Subsequently, the mixture was concentrated and ethyl acetate was added. The mixture was sequentially washed with a 5% aqueous citric acid solution, a saturated aqueous sodium bicarbonate solution and brine, followed by drying over magnesium sulfate. Evaporation of the solvent gave 1.13 g (83%) of the desired compound as a colorless oil.

$^1$H NMR (400 MHz, CDCl$_3$) δ 1.36-1.43 (1H, m), 1.47 (9H, s), 1.60-1.69 (3H, m), 1.93-1.99 (1H, m), 2.96-3.03 (1H, m), 3.11-3.16 (1H, m), 3.39-3.54 (4H, m), 3.68-3.74 (1H, m), 3.77-3.85 (2H, m).

FAB$^+$ (m/z): 230 (M+H).

Reference Example 5

N-[[1-(tert-Butoxycarbonyl)perhydroazepin-3-yl]methyl]phthalimide

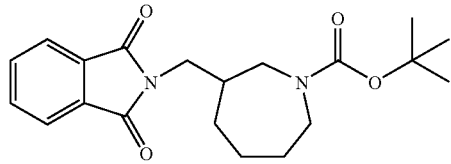

[Chemical formula 85]

1-(tert-Butoxycarbonyl)perhydroazepin-3-yl methanol (1.13 g, 4.93 mmol) was dissolved in tetrahydrofuran (10 mL). To this solution, triphenylphosphine (1.60 g, 5.92 mmol) and phthalimide (871 mg, 5.92 mmol) were added and the mixture was stirred at room temperature for 5 min. A 40% toluene solution of diethyl azodicarboxylate (3.23 mL, 7.40 mmol) was then added and the mixture was stirred at room temperature for 4 hours. Subsequently, water was added and the mixture was extracted with ethyl acetate. The extract washed with brine and was dried over magnesium sulfate, followed by evaporation of the solvent. Purification of the residue by silica gel column chromatography (hexane:ethyl acetate=10:1->2:1) gave 1.27 g (72%) of the desired compound as a colorless powder.

$^1$H NMR (400 MHz, CDCl$_3$) δ 1.14-1.44 (11H, m), 1.52-1.94 (4H, m), 2.13-2.35 (1H, m), 2.79-3.05 (1H, m), 3.11-3.27 (1H, m), 3.41-3.71 (4H, m), 7.69-7.74 (2H, m), 7.82-7.86 (2H, m).

EI$^+$ (m/z): 358 (M+).

Reference Example 6

1-(tert-Butoxycarbonyl)perhydroazepin-3-yl methylamine

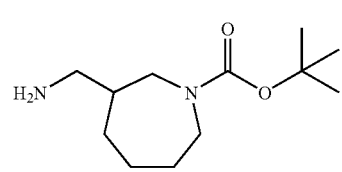

[Chemical formula 86]

N-[[(1-tert-Butoxycarbonyl)perhydroazepin-3-yl]methyl]phthalimide (1.27 g, 3.54 mmol) was dissolved in methanol (30 mL). To this solution, hydrazine monohydrate (0.343 mL, 7.08 mol) was added and the mixture was stirred for 3 hours while being refluxed. The mixture was then allowed to cool and the precipitates were removed by filtration. The filtrate was concentrated and ethyl acetate was added to the residue. The mixture was then washed sequentially with a 1 mol/L aqueous potassium hydroxide solution and brine and was dried over magnesium sulfate. The solvent was evaporated to give 712 mg (88%) of the desired compound as a colorless oil.

$^1$H NMR (400 MHz, CDCl$_3$) δ 1.16-1.62 (14H, m), 1.67-1.85 (4H, m), 2.51-2.70 (2H, m), 2.91-3.14 (1H, m), 3.27-3.60 (3H, m).

EI$^+$ (M/Z): 228 (M+).

Reference Example 7

3-(tert-Butyldimethylsilyloxymethyl)piperidine

Step A1) 1-(Benzyloxycarbonyl)piperidin-3-yl methanol

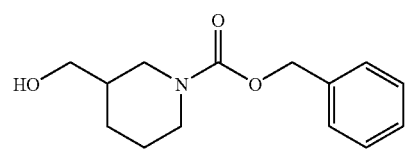

[Chemical formula 87]

An aqueous solution (20 mL) of sodium carbonate (6.90 g, 65.1 mmol) was added to 3-piperidinylmethanol (5.00 g, 43.4 mmol) in tetrahydrofuran (20 mL). While the mixture was chilled in an ice bath, benzyloxycarbonyl chloride (9.36 g, 52.1 mmol) was added and the mixture was stirred for 1 hour and subsequently 7 hours at room temperature. The solvent was then evaporated and ethyl acetate was added to the residue. The mixture was then washed sequentially with water, 0.1 mol/L hydrochloric acid and brine, followed by drying over magnesium sulfate and evaporation of the solvent. Purification of the residue by silica gel column chromatography (hexane:ethyl acetate=5:1->1:1) gave 9.15 g (85%) of the desired compound as a colorless powder.

$^1$H NMR (400 MHz, DMSO-d$_6$) δ 1.09 (1H, qd, J=12.2, 3.1 Hz), 1.33 (1H, qt, J=11.6, 3.7 Hz), 1.45-1.55 (1H, m), 1.59-1.64 (1H, m), 1.64-1.69 (1H, m), 2.42-2.65 (1H, m), 2.70-2.86 (1H, m), 3.16-3.22 (1H, m), 3.27-3.31 (1H, m), 3.86-

3.93 (1H, m), 4.04 (1H, dd, J=12.8, 2.4 Hz), 4.55 (1H, t, J=5.5 Hz), 5.03-5.10 (2H, m), 7.29-7.39 (5H, m).

Step A2) 1-(Benzyloxycarbonyl)-3-(tert-butyldimethylsilyloxymethyl)piperidine

[Chemical formula 88]

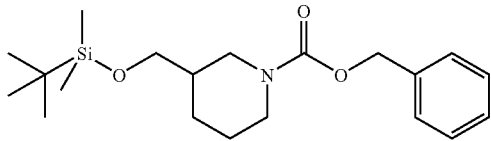

Imidazole (3.00 g, 44.0 mmol) and tert-butyldimethylsilyl chloride (6.63 g, 44.0 mmol) were added to 1-(benzyloxycarbonyl)piperidin-3-yl methanol (9.15 g, 36.7 mmol) in N,N-dimethylformamide (40 mL). The solution was stirred at room temperature for 6 hours. Subsequently, water was added and the mixture was extracted with ethyl acetate. The extract washed with brine and was dried over magnesium sulfate, followed by evaporation of the solvent. Purification of the residue by silica gel column chromatography (hexane:ethyl acetate=20:1->5:1) gave 13.2 g (99%) of the desired compound as a colorless oil.

$^1$H NMR (400 MHz, CDCl$_3$) δ 0.02 (6H, s), 0.88 (9H, s), 1.11-1.25 (1H, m), 1.40-1.53 (1H, m), 1.61-1.71 (2H, m), 1.72-1.80 (1H, m), 2.54-2.66 (1H, m), 2.79 (1H, td, J=11.6, 3.1 Hz), 3.34-3.51 (2H, m), 3.99-4.09 (1H, m), 4.12-4.19 (1H, m), 5.12 (2H, s), 7.29-7.39 (5H, m).

Step A3) 3-(tert-Butyldimethylsilyloxymethyl)piperidine

[Chemical formula 89]

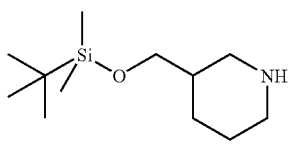

10% palladium on activated carbon (1.32 g) was added to 1-(benzyloxycarbonyl)-3-(tert-butyldimethylsilyloxymethyl)piperidine (13.2 g, 36.3 mmol) in methanol (130 mL). The mixture was stirred at room temperature for 1 hour in a hydrogen atmosphere. Subsequently, the mixture was filtered through Celite, followed by evaporation of the solvent to give 7.96 g (96%) of the desired compound as a colorless oil.

$^1$H NMR (400 MHz, CDCl$_3$) δ 0.03 (6H, s), 0.89 (9H, s), 1.07 (1H, qd, J=12.2, 3.7 Hz), 1.44 (1H, qt, J=12.2, 3.7 Hz), 1.59-1.69 (2H, m), 1.73-1.78 (2H, m), 2.30 (1H, dd, J=12.2, 10.4 Hz), 2.53 (1H, td, J=12.2, 3.1 Hz), 3.00 (1H, dt, J=12.2, 3.1 Hz), 3.11-3.15 (1H, m), 3.39 (1H, dd, J=9.8, 7.3 Hz), 3.44 (1H, dd, J=9.8, 5.5 Hz).

Reference Example 8

1-(tert-Butoxycarbonyl)nipecotic acid

[Chemical formula 90]

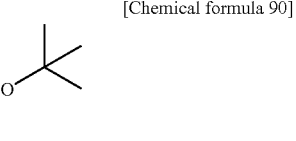

A dichloromethane solution (5 mL) of ditert-butyl dicarbonate (10.9 g, 50.0 mmol) was added to nipecotic acid (6.46 g, 50.0 mmol) in a saturated sodium bicarbonate solution (20 mL). The mixture was stirred at room temperature for 18 hours. Subsequently, the reaction mixture was poured into ice water. This mixture was made acidic by addition of diluted hydrochloric acid and was then extracted with ethyl acetate. The organic layer washed with brine and dried over sodium sulfate, followed by evaporation of the solvent. The resulting residue washed with hexane and was dried to give 5.30 g (46%) of the desired compound as a colorless solid.

$^1$H NMR (400 MHz, DMSO-d$_6$) δ1.25-1.35 (1H, m), 1.39 (9H, s), 1.45-1.55 (1H, m), 1.55-1.65 (1H, m), 1.87-1.93 (1H, m), 2.27-2.32 (1H, m), 2.82 (1H, dt, J=13.4, 3.0 Hz), 2.90-3.15 (1H, m), 3.60-3.75 (1H, m), 3.77-4.10 (1H, m), 12.37 (1H, brs).

FAB$^+$ (m/z): 230 (M+H).

Reference Example 9

Benzyl nipecotate

Step B1) Benzyl 1-(tert-butoxycarbonyl)nipecotate

[Chemical formula 91]

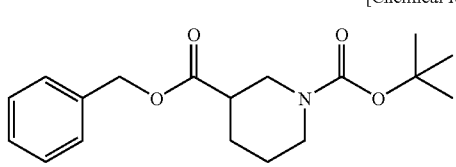

Benzyl bromide (4.34 g, 25.4 mmol) and potassium carbonate (4.80 g, 34.7 mmol) were added to 1-(tert-butoxycarbonyl)nipecotic acid (5.30 g, 23.1 mmol) in N,N-dimethylformamide (20 mL). The mixture was stirred at room temperature for 6 hours. Subsequently, water was added and the mixture was extracted with ethyl acetate. The organic layer washed sequentially with water and brine and was dried over sodium sulfate. The solvent was then evaporated to give 7.11 g (96%) of the desired compound as a pale yellow oil.

$^1$H NMR (400 MHz, DMSO-d$_6$) δ1.30-1.50 (2H, m), 1.38 (9H, s), 1.53-1.64 (2H, m), 1.90-1.93 (1H, m), 2.80-2.90 (2H, m), 3.55-3.70 (1H, m), 3.75-3.90 (1H, m), 5.10 (2H, s), 7.31-7.39 (5H, m).

Step B2) Benzyl nipecotate

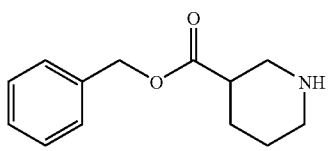

[Chemical formula 92]

Trifluoroacetic acid (43 mL, 558 mmol) was added to benzyl 1-(tert-butoxycarbonyl)nipecotate (7.11 g, 22.3 mmol) in dichloromethane (20 mL). The mixture was stirred for 3 hours. Subsequently, the reaction mixture was concentrated and water was added to the residue, followed by addition of 1 mol/L aqueous sodium hydroxide solution to make the mixture basic. The mixture was then extracted with ethyl acetate. The organic layer washed with brine and was dried over sodium sulfate. The solvent was evaporated to give 5.97 g (quant.) of the desired compound as a yellow oil.

$^1$H NMR (400 MHz, DMSO-d$_6$) δ 1.45-1.70 (3H, m), 1.92-1.96 (1H, m), 2.59-2.69 (2H, m), 2.81 (1H, t, J=9.8 Hz), 2.94-3.02 (1H, m), 3.21 (1H, dd, J=12.6, 3.3 Hz), 5.10 (2H, d, J=3.1 Hz), 7.27-7.38 (5H, m).

EI$^+$ (m/z): 219 (M+).

Reference Example 10

1-Trifluoroacetyl-3-hydroxypiperidine

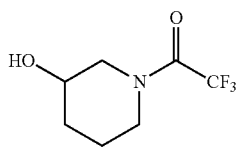

[Chemical formula 93]

Ethyl trifluoroacetate (1.31 mL, 11.0 mmol) and triethylamine (1.68 mL, 12.0 mmol) were added to 3-hydroxypiperidine (1.01 g, 10.0 mmol) in ethanol (10 mL). The mixture was stirred at room temperature for 8 hours. Subsequently, the reaction mixture was concentrated and water was added. The mixture was then extracted with ethyl acetate and the extract washed with brine and dried over magnesium sulfate. Purification of the residue by silica gel column chromatography (hexane:ethyl acetate=10:1->2:1) gave 1.68 g (85%) of the desired compound as a colorless oil.

$^1$H NMR (400 MHz, CDCl$_3$) δ 1.53-1.72 (2H, m), 1.82-2.04 (3H, m), 3.25-3.37 (1H, m), 3.40-3.48 (1H, m), 3.57-3.62 (1H, m), 3.78-3.92 (2H, m).

FAB$^+$ (m/z): 198 (M+H).

Reference Example 11

1-Trifluoroacetylpiperidin-3-yl methanol

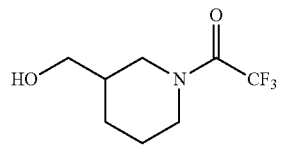

[Chemical formula 94]

Using 3-piperidinemethanol (1.15 g, 10.0 mmol), the same procedure was followed as in Reference Example 10 to give 1.91 g (90%) of the desired compound as a colorless oil.

FAB$^+$ (m/z): 212 (M+H).

Reference Example 12

1-(tert-Butoxycarbonyl)-3-(iodomethyl)piperidine

[Chemical formula 95]

Imidazole (1.58 g, 23.2 mmol), triphenylphosphine (6.09 g, 23.2 mmol) and iodine (4.72 g, 18.6 mmol) were added to 1-(tert-butoxycarbonyl)piperidin-3-yl methanol (2.00 g, 9.29 mmol) in benzene (50 mL). The mixture was stirred at room temperature for 3 hours. Subsequently, the reaction mixture was filtered through Celite and the solvent was evaporated. Water was added to the residue and the mixture was extracted with ethyl acetate. The extract was washed with brine and was dried over magnesium sulfate, followed by evaporation of the solvent. Purification of the residue by silica gel column chromatography (hexane:ethyl acetate=20:1->5:1) gave 2.91 g (96%) of the desired compound as a pale yellow oil.

$^1$H NMR (400 MHz, CDCl$_3$) δ 1.19-1.28 (1H, m), 1.40-1.52 (10H, m), 1.61-1.68 (2H, m), 1.91-1.95 (1H, m), 2.54-2.69 (1H, m), 2.79-2.84 (1H, m), 3.08 (2H, d, J=6.7 Hz), 3.84 (1H, td, J=13.4, 3.7 Hz), 3.97-4.13 (1H, m).

FAB$^+$ (m/z): 326 (M+H).

Reference Example 13

1-Benzyloxycarbonyl-3-formyl piperidine

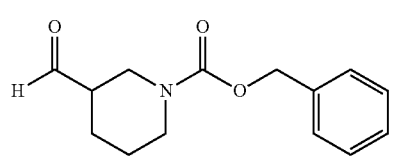

[Chemical formula 96]

An aqueous solution (2 mL) of potassium bromide (983 mg, 8.26 mmol) was added to 1-benzyloxycarbonyl-3-piperidinyl methanol (2.00 g, 8.02 mmol) and 2,2,6,6-tetramethyl piperidine-N-oxyl (12.5 mg, 0.0802 mmol) in dichloromethane (20 mL). The mixture was stirred for 5 min while chilled in an ice bath. A 0.35 mol/L aqueous sodium hypochlorite solution (25.2 mL, 8.82 mmol) and sodium bicarbonate (1.96 g, 23.3 mmol) were added and the mixture was stirred for 10 min. Subsequently, the reaction mixture was extracted with ethyl acetate and the extract washed with brine, followed by drying over magnesium sulfate and evaporation of the solvent. Purification of the residue by silica gel column chromatography (hexane:ethyl acetate=10:1->2:1) gave 1.78 g (90%) of the desired compound as a colorless oil.

$^1$H NMR (400 MHz, DMSO-d$_6$) δ 1.36-1.47 (1H, m), 1.52-1.65 (2H, m), 1.86-1.95 (1H, m), 3.10-3.16 (1H, m), 3.27-3.33 (2H, m), 3.51-3.62 (1H, m), 3.83 (1H, dd, J=13.4, 3.7 Hz), 5.07 (2H, m), 7.30-7.40 (5H, m), 9.59 (1H, s).

FAB$^+$ (M/Z): 248 (M+H).

Reference Example 14

4-(tert-Butoxycarbonyl)morpholin-2-yl methanol

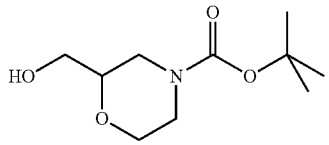

[Chemical formula 97]

Ammonium formate (3.04 g, 48.2 mmol) and 10% palladium on activated carbon (500 mg) were added to (4-benzyl-morpholin-2-yl)methanol (1.00 g, 4.82 mmol) in methanol (50 mL). The mixture was stirred at room temperature for 4 hours. Subsequently, the reaction mixture was filtered through Celite and the solvent was evaporated. The resulting residue was dissolved in acetonitrile (20 mL). While this solution was chilled in an ice bath, ditert-butyldicarbonate (1.58 g, 7.23 mmol) and triethylamine (1.35 mL, 9.64 mmol) were added and the mixture was stirred at room temperature for 3 hours. The solvent was evaporated and water was added to the residue. The mixture was then extracted with ethyl acetate and the extract washed with brine, followed by drying over magnesium sulfate and evaporation of the solvent. Purification of the residue by silica gel column chromatography (hexane:ethyl acetate=5:1->1:1) gave 907 mg (87%) of the desired compound as a colorless oil.

$^1$H NMR (400 MHz, DMSO-d$_6$) δ1.40 (9H, s), 2.47-2.66 (1H, m), 2.73-2.92 (1H, m), 3.25-3.45 (4H, m), 3.70 (1H, d, J=13.4 Hz), 3.79 (1H, dd, J=11.6, 2.4 Hz), 3.85 (1H, d, J=12.8 Hz), 4.77 (1H, t, J=5.5 Hz).

Reference Example 15

4-(tert-Butoxycarbonyl)morpholin-2-yl methylamine

Step C1) N-[[4-(tert-Butoxycarbonyl)morpholin-2-yl]methyl]phthalimide

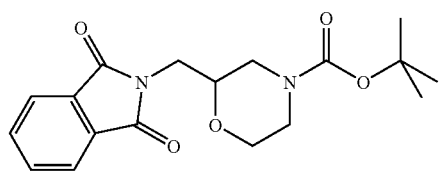

[Chemical formula 98]

Triphenylphosphine (506 mg, 1.87 mmol) and phthalimide (275 mg, 1.87 mmol) were added to 4-(tert-butoxycarbonyl)morpholin-2-yl methanol (340 mg, 1.56 mmol) in tetrahydrofuran (3 mL). The mixture was stirred at room temperature for 5 min, followed by addition of a 40% diethyl azodicarboxylate/toluene solution (1.06 mL, 2.34 mmol) and stirring at room temperature for 4 hours. Subsequently, ethyl acetate was added and the mixture washed sequentially with tap water and brine. The mixture was then dried over magnesium sulfate and the solvent was evaporated. Purification of the residue by silica gel column chromatography (hexane:ethyl acetate=10:1->3:1) gave 524 mg (97%) of the desired compound as a colorless powder.

$^1$H NMR (400 MHz, CDCl$_3$) δ 1.46 (9H, s), 2.70-2.84 (1H, m), 2.93-3.05 (1H, m), 3.45 (1H, td, J=11.6, 3.1 Hz), 3.67 (1H, dd, J=13.4, 4.9 Hz), 3.72-3.79 (2H, m), 3.86-4.04 (3H, m), 7.72-7.74 (2H, m), 7.86-7.88 (2H, m).

Step C2) 4-(tert-Butoxycarbonyl)morpholin-2-yl methylamine

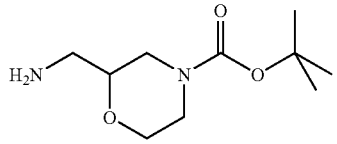

[Chemical formula 99]

Hydrazine monohydrate (0.146 mL, 3.02 mmol) was added to N-[[4-(tert-butoxycarbonyl)morpholin-2-yl]methyl]phthalimide (524 mg, 1.51 mmol) suspended in methanol (15 mL). The mixture was refluxed and stirred for 4 hours. Subsequently, the reaction mixture was allowed to cool and the crystallized product was removed by filtration. The solvent was evaporated and a 1 mol/L aqueous potassium hydroxide solution was added to the residue. The mixture was then extracted with dichloro methane and the extract was dried over sodium sulfate, followed by evaporation of the solvent. The residue was air-dried to give 272 mg (83%) of the desired compound as a colorless oil.

$^1$H NMR (400 MHz, CDCl$_3$) δ 1.47 (9H, s), 2.10 (2H, brs), 2.64 (1H, m), 2.71-2.81 (2H, m), 2.93 (1H, m), 3.35-3.41 (1H, m), 3.53 (1H, td, J=11.6, J=2.4 Hz), 3.75-4.00 (3H, m).

Reference Example 16

4-(tert-Butoxycarbonyl)morpholine-2-carboxylic acid

Step D1) Methyl 4-benzylmorpholine-2-carboxylate

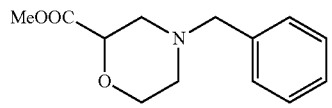

[Chemical formula 100]

4-Benzylmorpholine-2-carboxylic acid hydrochloride (1.00 g, 3.88 mmol) in a 10 (w/w) % hydrochloric acid/methanol solution (20 mL) was stirred at room temperature for 2 hours. The solvent was evaporated and a saturated aqueous sodium bicarbonate solution was added to the residue to make the mixture basic. The mixture was then extracted with ethyl acetate and the extract washed with brine and was dried over magnesium sulfate. Evaporation of the solvent gave 730 mg (80%) of the desired compound as a colorless oil.

$^1$H NMR (400 MHz, DMSO-d$_6$) δ 2.24 (2H, m), 2.47-2.54 (1H, m), 2.68 (1H, dd, J=11.6, 2.4 Hz), 3.45-3.53 (2H, m), 3.53-3.59 (1H, m), 3.63 (3H, s), 3.85-3.90 (1H, m), 4.22 (1H, dd, J=7.3, 3.1 Hz), 7.24-7.35 (5H, m).

Step D2) Methyl 4-(tert-butoxycarbonyl)morpholine-2-carboxylate

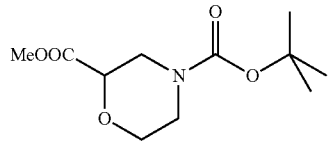

[Chemical formula 101]

Ammonium formate (381 mg, 6.04 mmol) and 10% palladium on activated carbon (180 mg) were added to methyl 4-benzylmorpholine-2-carboxylate (355 mg, 1.51 mmol) in methanol (10 mL). The mixture was stirred at room temperature for 1 hour. Subsequently, the reaction mixture was filtered through Celite. The solvent was evaporated and the resulting residue was suspended in acetonitrile (10 mL). This suspension was chilled in an ice bath and di t-butyl dicarbonate (395 mg, 1.81 mmol) and triethylamine (0.253 mL, 1.81 mmol) were added. This mixture was stirred at room temperature for 2 hours. Subsequently, water was added and the mixture was extracted with ethyl acetate. The extract washed sequentially with a 5% aqueous citric acid and brine and was dried over magnesium sulfate. The solvent was then evaporated. Purification of the residue by silica gel column chromatography (hexane:ethyl acetate=10:1->2:1) gave 251 mg (68%) of the desired compound as a colorless oil.

$^1$H NMR (400 MHz, DMSO-d$_6$) δ1.40 (9H, s), 3.06-3.13 (1H, m), 3.29-3.38 (1H, m), 3.46-3.55 (2H, m), 3.68 (3H, s), 3.74-3.86 (2H, m), 4.19 (1H, dd, J=8.6, 3.7 Hz).

Step 3 D3) 4-(tert-Butoxycarbonyl)morpholine-2-carboxylic acid

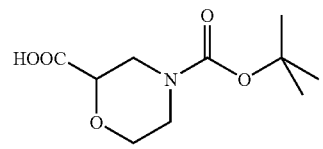

[Chemical formula 101]

A 1 mol/L aqueous potassium hydroxide solution (3 mL) was added to methyl 4-(tert-butoxycarbonyl)morpholine-2-carboxylate (251 mg, 1.02 mmol) in methanol (15 mL). The mixture was stirred at room temperature for 8 hours. Subsequently, water was added to the mixture, followed by addition of a 5% aqueous citric acid solution to make the mixture acidic. The mixture was then extracted with ethyl acetate. The extract was washed with brine and was dried over magnesium sulfate. Evaporation of the solvent gave 219 mg (93%) of the desired compound as a colorless powder.

$^1$H NMR (400 MHz, DMSO-d$_6$) δ 1.40 (9H, s), 2.70 (1H, dd, J=41.6, 15.3 Hz), 3.03-3.09 (1H, m), 3.43-3.54 (2H, m), 3.78 (1H, m), 3.85 (1H, dt, J=11.6, 3.7 Hz), 4.04 (1H, dd, J=8.6, 3.7 Hz), 12.73 (1H, brs).

Example 1

Methyl 2-[3-[[2-(4-Chlorophenyl)-4-methylthiazol-5-yl]carbonylaminomethyl]piperidin-1-yl]benzoate Step 1a) N-[(1-tert-Butoxycarbonyl)piperidin-3-yl methyl]-2-(4-chlorophenyl)-4-methylthiazole-5-carboxamide

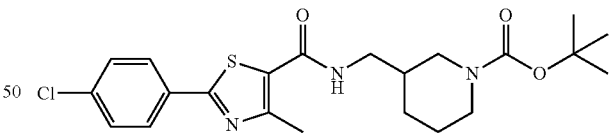

[Chemical formula 102]

2-(4-Chlorophenyl)-4-methylthiazole-5-carboxylic acid (507 mg, 2.00 mmol), 1-(tert-butoxycarbonyl)piperidin-3-yl methylamine (429 mg, 2.00 mmol) and 1-hydroxybenzotriazole monohydrate (368 mg, 2.40 mmol) were dissolved in N,N-dimethylformamide (10 mL). The mixture was chilled in an ice bath and 3-(3-dimethylaminopropyl)-1-ethylcarbodiimide hydrochloride (460 mg, 2.40 mmol) and N-methylmorpholine (0.528 mL, 4.80 mmol) were added. The mixture was then stirred at room temperature for 4 hours and a 5% aqueous citric acid was added. This mixture was extracted with ethyl acetate and the extract washed sequentially with a saturated aqueous sodium bicarbonate solution and brine, followed by drying over magnesium sulfate and evaporation of the solvent. Purification of the resulting residue by silica gel column chromatography (hexane:ethyl acetate=10:1->2:1) gave 851 mg (95%) of the desired compound as a colorless amorphous product.

$^1$H NMR (400 MHz, CDCl$_3$) δ 1.42-1.51 (11H, m), 1.60-1.72 (1H, m), 1.78-1.96 (2H, m), 2.75 (3H, s), 3.05-3.86 (6H, m), 6.59 (1H, brs), 7.42 (2H, d, J=8.6 Hz), 7.87 (2H, d, J=8.6 Hz).

Step 1b) N-(Piperidin-3-yl methyl)-2-(4-chlorophenyl)-4-methylthiazole-5-carboxamide

[Chemical formula 103]

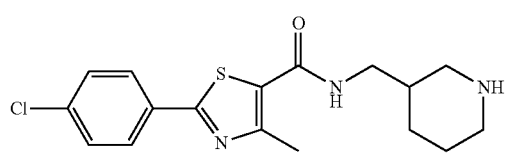

N-[[(1-tert-Butoxycarbonyl)piperidin-3-yl]methyl]-2-(4-chlorophenyl)-4-methylthiazole-5-carboxamide (2.78 g, 6.18 mmol) was dissolved in methanol (30 mL). While this mixture was ice-chilled and stirred, 5.7 mol/L hydrogen chloride/methanol solution (50 mL) was added. The mixture was continuously chilled and stirred for 10 min. The mixture was then allowed to warm to room temperature and was stirred for the subsequent 3 hours. Subsequently, the reaction mixture was concentrated. To the resulting residue, water was added and the mixture was neutralized with a 1 mol/L aqueous sodium hydroxide solution. Sodium chloride was then added to saturation and the mixture was extracted with ethyl acetate. The extract washed with brine and was dried over magnesium sulfate. Evaporation of the solvent gave 2.09 mg (97%) of the desired compound as a colorless powder.

$^1$H NMR (400 MHz, DMSO-d$_6$) δ 1.00-1.10 (1H, m), 1.26-1.37 (1H, m), 1.53-1.74 (3H, m), 2.18 (1H, dd, J=9.8, 11.6 Hz), 2.40 (1H, dt, J=2.4, 11.6 Hz), 2.59 (3H, s), 2.77-2.83 (1H, m), 2.91 (1H, dd, J=2.4, 11.6 Hz), 3.68 (2H, t, J=6.1 Hz), 7.42 (2H, d, J=8.6 Hz), 7.87 (2H, d, J=8.6 Hz), 8.30 (1H, t, J=5.5 Hz).

Step 1c) Methyl 2-[3-[[2-(4-chlorophenyl)-4-methylthiazol-5-yl]carbonylaminomethyl]piperidin-1-yl]benzoate

[Chemical formula 104]

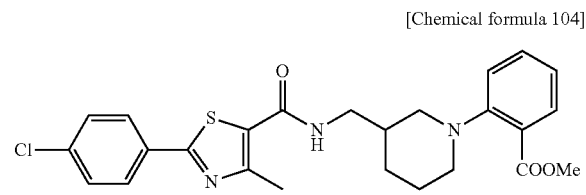

N-(Piperidin-3-yl methyl)-2-(4-chlorophenyl)-4-methylthiazole-5-carboxamide (105 mg, 0.300 mmol) and methyl 2-fluorobenzoate (0.0382 mL, 0.300 mmol) were added to dimethylsulfoxide (5 mL). To this mixture, potassium carbonate (82.9 mg, 0.600 mmol) was added and the mixture was stirred for 6 hours at 130° C. Subsequently, water was added and the mixture was extracted with ethyl acetate. The extract was washed with brine, followed by drying over magnesium sulfate and evaporation of the solvent. Purification of the residue by silica gel column chromatography (hexane:ethyl acetate=10:1->2:1) gave 29.5 mg (20%) of the desired compound as a colorless oil.

$^1$H NMR (400 MHz, CDCl$_3$) δ 1.23-1.90 (3H, m), 2.08-2.19 (1H, m), 2.28-2.38 (1H, m), 2.73-2.79 (4H, m), 2.83-2.88 (1H, m), 3.09-3.24 (2H, m), 3.42-3.54 (2H, m), 3.85 (3H, s), 6.37-6.44 (1H, m), 7.02 (1H, t, J=8.6 Hz), 7.11 (1H, d, J=7.9 Hz), 7.38-7.44 (3H, m), 7.72 (1H, dd, J=1.8, 7.9 Hz), 7.86 (2H, d, J=8.6 Hz).

Example 2

Methyl 3-[3-[[2-(4-Chlorophenyl)-4-methylthiazol-5-yl]carbonylaminomethyl]piperidin-1-yl]benzoate

[Chemical formula 105]

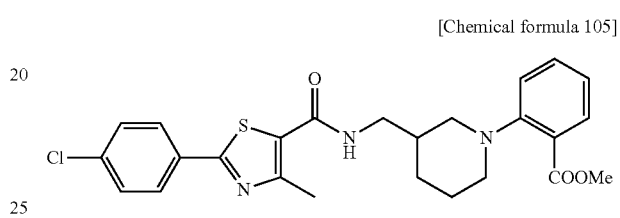

N-(Piperidin-3-yl methyl)-2-(4-chlorophenyl)-4-methylthiazole-5-carboxamide (172 mg, 0.492 mmol), 3-(methoxycarbonyl)phenylboric acid (177 mg, 0.984 mmol) and molecular sieves 4 Å (400 mg) were suspended in dichloromethane (10 mL). To this suspension, copper (II) acetate (188 mg, 0.984 mmol) and triethylamine (0.344 mL, 2.46 mmol) were added and the mixture was stirred at room temperature for 8 hours. Subsequently, the reaction mixture was filtered through Celite, followed by addition of a saturated aqueous sodium bicarbonate solution. The mixture was then extracted with ethyl acetate and the extract washed with brine, followed by drying over magnesium sulfate and evaporation of the solvent. Purification of the residue by silica gel column chromatography (hexane:ethyl acetate=20:1->2:1) gave 88.2 mg (37%) of the desired compound as a colorless powder.

$^1$H NMR (400 MHz, DMSO-d$_6$) δ 1.14-1.23 (1H, m), 1.52-1.61 (1H, m), 1.75-1.82 (2H, m), 1.85-1.94 (1H, m), 2.53-2.58 (1H, m), 2.62 (3H, s), 2.72-2.79 (1H, m), 3.19-3.27 (1H, m), 3.30-3.38 (1H, m), 3.60-3.69 (2H, m), 3.81 (3H, s), 7.19-7.24 (1H, m), 7.33-7.35 (2H, m), 7.46 (1H, m), 7.59 (2H, d, J=8.6 Hz), 7.97 (2H, d, J=8.6 Hz), 8.45 (1H, t, J=5.5 Hz).

Example 3

Methyl 2-[3-[N-[[2-(4-Chlorophenyl)-4-methylthiazol-5-yl]methyl]carbamoyl]piperidin-1-yl]benzoate Step 3a) 1-(tert-Butoxycarbonyl)-N-[[2-(4-chlorophenyl)-4-methylthiazol-5-yl]methyl]piperidine-3-carboxamide

[Chemical formula 106]

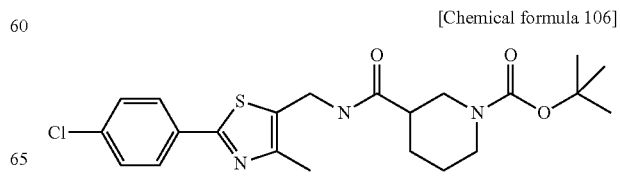

2-(4-Chlorophenyl)-4-methylthiazol-5-yl methylamine (477 mg, 2.00 mmol), 1-tert-butoxycarbonyl nipecotic acid (459 mg, 2.00 mmol) and 1-hydroxybenzotriazole monohydrate (368 mg, 2.40 mmol) were dissolved in N,N-dimethylformamide (10 mL). While this mixture was chilled in an ice bath, 3-(3-dimethylaminopropyl)-1-ethylcarbodiimide hydrochloride (460 mg, 2.40 mmol) and N-methylmorpholine (0.484 mL, 4.40 mmol) were added. The mixture was then stirred at room temperature for 6 hours. Subsequently, 5% aqueous citric acid was added and the mixture was extracted with ethyl acetate. The extract washed sequentially with a saturated aqueous sodium bicarbonate solution and brine, followed by drying over magnesium sulfate and evaporation of the solvent. Purification of the residue by silica gel column chromatography (hexane:ethyl acetate=5:1->1:1) gave 916 mg (100%) of the desired compound as a colorless powder.

$^1$H NMR (400 MHz, CDCl$_3$) δ 1.36-1.51 (10H, m), 1.56-1.62 (1H, m), 1.67-1.85 (1H, m), 2.28-2.40 (1H, m), 2.45 (3H, s), 2.93-3.95 (5H, m), 4.56-4.60 (2H, m), 7.38 (2H, d, J=8.6 Hz), 7.81 (2H, d, J=8.6 Hz).

Step 3b) N-[[2-(4-Chlorophenyl)-4-methylthiazol-5-yl]methyl]piperidine-3-carboxamide hydrochloride

[Chemical formula 107]

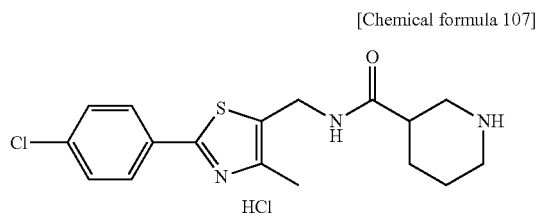

HCl 1-tert-Butoxycarbonyl-N-[[2-(4-chlorophenyl)-4-methylthiazol-5-yl]methyl]piperidine-3-carboxamide (916 mg, 2.04 mmol) was dissolved in a 10% hydrogen chloride/methanol solution (20 mL) and the mixture was stirred at room temperature for 1 hour. Subsequently, the reaction mixture was concentrated and the residue was air-dried to give 769 mg (98%) of the desired compound as a colorless amorphous product.

$^1$H NMR (400 MHz, DMSO-d$_6$) δ 1.49-1.59 (1H, m), 1.64-1.80 (2H, m), 1.88-1.93 (1H, m), 2.39 (3H, s), 2.68-2.75 (1H, m), 2.78-2.86 (1H, m), 2.88-2.97 (1H, m), 4.35-4.47 (2H, m), 7.54 (2H, d, J=8.6 Hz), 7.87 (2H, d, J=8.6 Hz), 8.93 (1H, t, J=5.5 Hz), 8.96-9.09 (1H, m), 9.15-9.35 (1H, m).

Step 3c) Methyl 2-[3-[N-[[2-(4-chlorophenyl)-4-methylthiazol-5-yl]methyl]carbamoyl]piperidin-1-yl]benzoate

[Chemical formula 108]

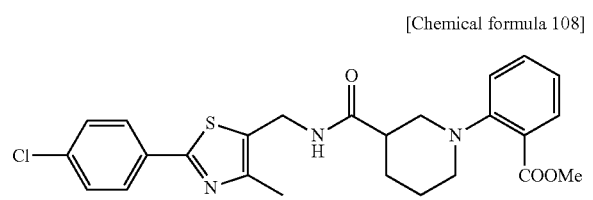

COOMe

N-[[2-(4-Chlorophenyl)-4-methylthiazol-5-yl]methyl]piperidine-3-carboxamide hydrochloride (198 mg, 0.513 mmol) and methyl 2-fluorobenzoate (0.0653 mL, 0.513 mmol) were dissolved in dimethylsulfoxide (5 mL). To this solution, potassium carbonate (142 mg, 1.03 mmol) was added and the mixture was stirred for 6 hours at 160° C. Subsequently, the mixture was allowed to cool and water was added. The mixture was then extracted with ethyl acetate and the extract washed with brine, followed by drying over magnesium sulfate and evaporation of the solvent. Purification of the residue by silica gel column chromatography (hexane:ethyl acetate=5:1->1:1) gave 9.80 mg (4%) of the desired compound as a colorless oil.

$^1$H NMR (400 MHz, CDCl$_3$) δ 1.63-1.69 (1H, m), 1.93-2.17 (2H, m), 2.29-2.36 (1H, m), 2.44-2.45 (3H, m), 2.55-2.65 (1H, m), 2.73-2.80 (1H, m), 3.09-3.12 (2H, m), 3.34-3.37 (1H, m), 3.84 (3H, s), 4.59 (2H, d, J=5.5 Hz), 7.08-7.12 (2H, m), 7.34 (2H, d, J=8.6 Hz), 7.46-7.50 (1H, m), 7.75-7.82 (4H, m).

Example 4

Methyl 3-[3-[N-[[2-(4-Chlorophenyl)-4-methylthiazol-5-yl]methyl]carbamoyl]piperidin-1-yl]benzoate

[Chemical formula 109]

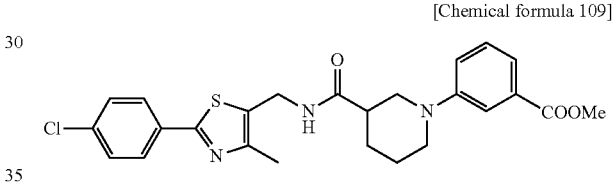

N-[[2-(4-chlorophenyl)-4-methylthiazol-5-yl]methyl]piperidine-3-carboxamide hydrochloride (123 mg, 0.318 mmol) was suspended in diethyl ether. The suspension washed sequentially with a 0.1 mol/L aqueous sodium hydroxide solution and brine and was dried over magnesium sulfate. The solvent was then evaporated and the resulting residue was dissolved in dichloromethane (10 mL). To this solution, 3-(methoxycarbonyl)phenylboric acid (114 mg, 0.636 mmol), molecular sieves 4 Å (300 mg), copper (II) acetate (122 mg, 0.636 mmol) and triethylamine (0.222 mL, 1.59 mmol) were added and the mixture was stirred at room temperature for 16 hours. Subsequently, the reaction mixture was filtered through Celite and a saturated aqueous sodium bicarbonate solution was added to the filtrate. The mixture was extracted with ethyl acetate. The extract washed with brine, followed by drying over magnesium sulfate and evaporation of the solvent. Purification of the resulting residue by silica gel column chromatography (hexane:ethyl acetate=2:1->0:1) gave 20.1 mg (13%) of the desired compound as a colorless powder.

$^1$H NMR (400 MHz, CDCl$_3$) δ 1.68-1.97 (4H, m), 2.43 (3H, s), 2.53-2.65 (1H, m), 3.14-3.24 (2H, m), 3.32-3.41 (2H, m), 3.88 (3H, s), 4.55-4.65 (2H, m), 6.96-6.99 (1H, m), 7.13

(1H, dd, J=2.4, 8.6 Hz), 7.31 (1H, t, J=7.9 Hz), 7.38 (2H, d, J=8.6 Hz), 7.57 (1H, d, J=7.3 Hz), 7.63-7.64 (1H, m), 7.80 (2H, d, J=8.6 Hz).

Example 5

Methyl 2-[3-[[2-(4-Chlorophenyl)-4-methylthiazol-5-yl]methoxymethyl]piperidin-1-yl]benzoate Step 5a) 1-(tert-Butoxycarbonyl)-3-[[2-(4-chlorophenyl)-4-methylthiazol-5-yl]methoxymethyl]piperidine

[Chemical formula 110]

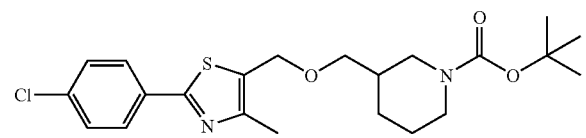

1-(tert-Butoxycarbonyl)piperidin-3-ylmethanol (215 mg, 1.00 mmol) was dissolved in tetrahydrofuran (5 mL). While this solution was chilled in an ice bath, 60% sodium hydride in oil (44.0 mg, 1.10 mmol) was added and the mixture was stirred for 20 min. Subsequently, 5-chloromethyl-2-(4-chlorophenyl)-4-methylthiazole (258 mg, 1.00 mmol) in tetrahydrofuran (5 mL) and sodium iodide (15.0 mg, 0.100 mmol) were added. The mixture was stirred for 2 hours while chilled in an ice bath and was further stirred for 6 hours at room temperature. Subsequently, ethyl acetate was added and the mixture washed sequentially with 5% aqueous citric acid and brine, followed by drying over magnesium sulfate and evaporation of the solvent. Purification of the resulting residue by silica gel column chromatography (hexane:ethyl acetate=20:1->5:1) gave 258 mg (59%) of the desired compound as a colorless oil.

$^1$H NMR (400 MHz, CDCl$_3$) δ 1.17-1.29 (1H, m), 1.40-1.49 (10H, m), 1.60-1.67 (1H, m), 1.74-1.86 (2H, m), 2.44 (3H, s), 2.64 (1H, m), 2.77-2.84 (1H, m), 3.32-3.39 (2H, m), 3.87-3.90 (1H, m), 4.01 (1H, m), 4.62 (2H, s), 7.39 (2H, d, J=8.6 Hz), 7.84 (2H, d, J=8.6 Hz).

Step 5b) 3-[[2-(4-Chlorophenyl)-4-methylthiazol-5-yl]methoxymethyl]piperidine

[Chemical formula 111]

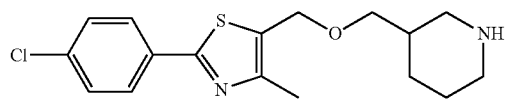

Using 1-(tert-butoxycarbonyl)-3-[[2-(4-chlorophenyl)-4-methylthiazol-5-yl]methoxymethyl]piperidine (258 mg, 0.590 mmol), the same procedure was followed as in Step 1b of Example 1 to give 169 mg (85%) of the desired compound as a colorless oil.

$^1$H NMR (400 MHz, CDCl$_3$) δ 1.08-1.18 (1H, m), 1.40-1.51 (1H, m), 1.62-1.69 (1H, m), 1.75-1.86 (2H, m), 2.35 (1H, dd, J=9.8, 12.2 Hz), 2.44 (3H, s), 2.55 (1H, dt, J=3.1, J=11.6 Hz), 2.97-3.02 (1H, m), 3.12-3.16 (1H, m), 3.30-3.36 (2H, m), 4.62 (2H, s), 7.39 (2H, d, J=8.6 Hz), 7.84 (2H, d, J=8.6 Hz).

Step 5c) 2-[3-[[2-(4-Chlorophenyl)-4-methylthiazol-5-yl]methoxymethyl]piperidin-1-yl]benzaldehyde

[Chemical formula 112]

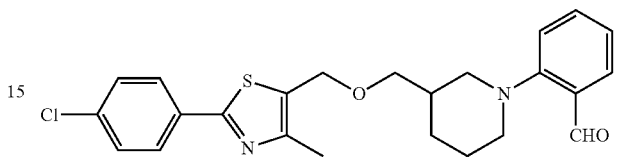

Using 3-[[2-(4-chlorophenyl)-4-methylthiazol-5-yl]methoxymethyl]piperidine (106 mg, 0.315 mmol) and 2-fluorobenzaldehyde (0.0329 mL, 0.315 mmol), the same procedure was followed as in Step 1c of Example 1 to give 45.2 mg (32%) of the desired compound as a colorless oil.

$^1$H NMR (400 MHz, CDCl$_3$) δ1.19-1.28 (1H, m), 1.73-1.87 (3H, m), 2.11-2.21 (1H, m), 2.43 (3H, s), 2.68-2.73 (1H, m), 2.82-2.89 (1H, m), 3.19-3.21 (1H, m), 3.33-3.37 (1H, m), 3.41-3.48 (2H, m), 4.63 (2H, m), 7.06-7.11 (2H, m), 7.38 (2H, d, J=8.6 Hz), 7.47-7.51 (1H, m), 7.77-7.84 (3H, m), 10.29 (1H, s).

Step 5d) Methyl 2-[3-[[2-(4-chlorophenyl)-4-methylthiazol-5-yl]methoxymethyl]piperidin-1-yl]benzoate

[Chemical formula 113]

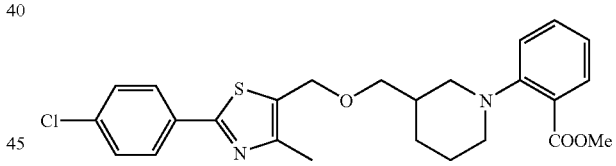

2-[3-[[2-(4-Chlorophenyl)-4-methylthiazol-5-yl]methoxymethyl]piperidin-1-yl]benzaldehyde (45.2 mg, 0.102 mmol) was dissolved in methanol (5 mL). To this solution, sodium cyamide (25.8 mg, 0.510 mmol) and manganese dioxide (88.7 mg, 1.02 mmol) were added and the mixture was stirred at room temperature for 3 hours. Subsequently, a saturated aqueous sodium bicarbonate solution was added and the mixture was filtered through Celite. The filtrate was extracted with ethyl acetate and the extract washed with brine, followed by drying over magnesium sulfate and evaporation of the solvent. Purification of the resulting residue by silica gel column chromatography (Chromatorex NH-DM2035, Fuji Silysia Chemical Co., Ltd.) (hexane:ethyl acetate=50:1->10:1) gave 27.9 mg (58%) of the desired compound as a colorless oil.

$^1$H NMR (400 MHz, CDCl$_3$) δ 1.13-1.23 (1H, m), 1.69-1.82 (3H, m), 2.08-2.19 (1H, m), 2.43 (3H, s), 2.55 (1H, dd, J=9.8, 11.6 Hz), 2.70-2.76 (1H, m), 3.22-3.25 (1H, m), 3.37-3.47 (3H, m), 3.85 (3H, s), 4.59-4.66 (2H, m), 6.94 (1H, t,

J=7.3 Hz), 7.01 (1H, d, J=7.9 Hz), 7.35-7.40 (3H, m), 7.67 (1H, dd, J=1.8, 7.9 Hz), 7.82 (2H, d J=8.6 Hz).

Example 6

Methyl 2-[3-[[2-(4-chlorophenyl)-4-methylthiazol-5-yl]methoxymethyl]piperidin-1-yl]benzoate Step 6a) 1-(tert-Butoxycarbonyl)-3-[[2-(4-chlorophenyl)-4-methylthiazol-5-yl]methoxy]piperidine

[Chemical formula 114]

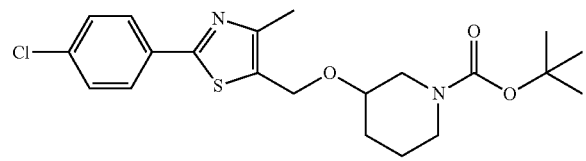

Using 1-(tert-butoxycarbonyl)-3-hydroxypiperidine (201 mg, 1.00 mmol) and 5-chloromethyl-2-(4-chlorophenyl)-4-methylthiazole (258 mg, 1.00 mmol), the same procedure was followed as in Step 5a of Example 5 to give 187 mg (44%) of the desired compound as a colorless oil.

$^1$H NMR (400 MHz, CDCl$_3$) δ 1.41-1.62 (11H, m), 1.71-1.82 (1H, m), 1.88-1.97 (1H, m), 2.44 (3H, s), 3.12-3.22 (2H, m), 3.46 (1H, m), 3.53-3.56 (1H, m), 3.79 (1H, m), 4.64-4.81 (2H, m), 7.38 (2H, d, J=8.6 Hz), 7.83 (2H, d, J=8.6 Hz).

Step 6b) 3-[[2-(4-Chlorophenyl)-4-methylthiazol-5-yl]methoxy]piperidine

[Chemical formula 115]

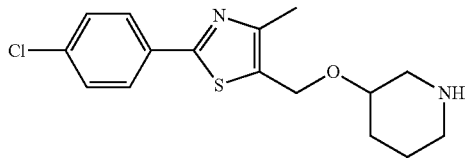

Using 1-(tert-butoxycarbonyl)-3-[[2-(4-chlorophenyl)-4-methylthiazol-5-yl]methoxy]piperidine (187 mg, 0.442 mmol), the same procedure was followed as in Step 1b of Example 1 to give 119 mg (83%) of the desired compound as a colorless oil.

$^1$H NMR (400 MHz, CDCl$_3$) δ 1.39-1.49 (1H, m), 1.53-1.61 (1H, m), 1.72-1.80 (1H, m), 1.91-2.00 (1H, m), 2.44 (3H, s), 2.64-2.70 (2H, m), 2.81-2.86 (1H, m), 3.10 (1H, dd, J=2.4, J=12.2 Hz), 3.41-3.46 (1H, m), 4.65-4.72 (2H, m), 7.39 (2H, d, J=8.6 Hz), 7.83 (2H, d, J=8.6 Hz).

Step 6c) 2-[3-[[2-(4-Chlorophenyl)-4-methylthiazol-5-yl]methoxy]piperidin-1-yl]benzaldehyde

[Chemical formula 116]

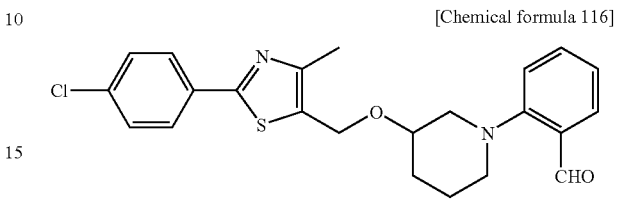

3-[[2-(4-Chlorophenyl)-4-methylthiazol-5-yl]methoxy]piperidine (59.1 mg, 0.183 mmol) and 2-fluorobenzaldehyde (0.0984 mL, 0.915 mmol) were dissolved in dimethylsulfoxide (2 mL). To this solution, cesium carbonate (119 mg, 0.366 mmol) was added and the mixture was stirred at 130° C. for 3 hours. Subsequently, water was added and the mixture was extracted with ethyl acetate and the extracted washed with brine, followed by drying over magnesium sulfate and evaporation of the solvent. Purification of the resulting residue by silica gel column chromatography (hexane:ethyl acetate=20:1->5:1) gave 47.8 mg (61%) of the desired compound as a colorless oil.

$^1$H NMR (400 MHz, CDCl$_3$) δ 1.47-1.54 (1H, m), 1.71-1.82 (1H, m), 1.89-1.97 (1H, m), 2.11-2.15 (1H, m), 2.44 (3H, s), 2.84-2.92 (2H, m), 3.14-3.18 (1H, m), 3.43-3.47 (1H, m), 3.73-3.79 (1H, m), 4.69-4.77 (2H, m), 7.10-7.12 (2H, m), 7.39 (2H, d, J=8.6 Hz), 7.51 (1H, dt, J=1.8, 7.9 Hz), 7.79-7.85 (3H, m), 10.32 (1H, s).

Step 6d) Methyl 2-[3-[[2-(4-chlorophenyl)-4-methylthiazol-5-yl]methoxy]piperidin-1-yl]benzoate

[Chemical formula 117]

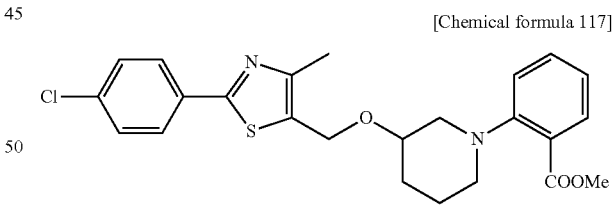

Using 2-[3-[[2-(4-Chlorophenyl)-4-methylthiazol-5-yl]methoxy]piperidin-1-yl]benzaldehyde (47.8 mg, 0.112 mmol), the same procedure was followed as in Step 5d of Example 5 to give 19.7 mg (38%) of the desired compound as a colorless oil.

$^1$H NMR (400 MHz, CDCl$_3$) δ 1.34-1.43 (1H, m), 1.68-1.87 (2H, m), 2.15-2.19 (1H, m), 2.44 (3H, s), 2.63 (1H, dd, J=9.8, 11.6 Hz), 2.70 (1H, dt, J=3.1, 11.6 Hz), 3.21-3.24 (1H, m), 3.54-3.58 (1H, m), 3.70-3.77 (1H, m), 3.87 (3H, s), 4.69-

4.76 (2H, m), 6.97-7.01 (1H, m), 7.04-7.06 (1H, m), 7.37-7.43 (3H, m), 7.73 (1H, dd, J=1.8, 7.9 Hz), 7.83 (2H, d, J=8.6 Hz).

Example 7

Methyl 3-[3-[[2-(4-Chlorophenyl)-4-methylthiazol-5-yl]methoxymethyl]piperidin-1-yl]benzoate

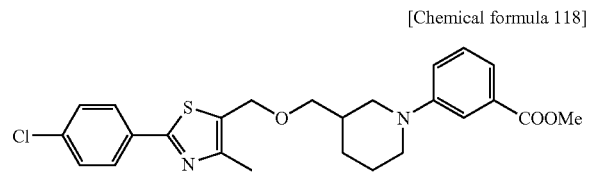

[Chemical formula 118]

Using 3-[[2-(4-chlorophenyl)-4-methylthiazol-5-yl]methoxymethyl]piperidine (62.2 mg, 0.185 mmol) and 3-(methoxycarbonyl)phenylboric acid (66.6 mg, 0.370 mmol), the same procedure was followed as in Example 2 to obtain 69.2 mg (79%) of the desired compound as a colorless oil.

$^1$H NMR (400 MHz, CDCl$_3$) δ 1.17-1.26 (1H, m), 1.63-1.83 (3H, m), 1.99-2.10 (1H, m), 2.45 (3H, s), 2.64 (1H, dd, J=9.8, 11.6 Hz), 2.78-2.84 (1H, m), 3.41-3.48 (2H, m), 3.56-3.59 (1H, m), 3.68-3.72 (1H, m), 3.89 (3H, s), 4.62-4.69 (2H, m), 7.12 (1H, dd, J=1.8, 7.9 Hz), 7.26-7.31 (1H, m), 7.39 (2H, d, J=8.6 Hz), 7.46-7.50 (1H, m), 7.60-7.61 (1H, m), 7.84 (2H, d J=8.6 Hz).

Example 8

Methyl 3-[3-[[2-(4-chlorophenyl)-4-methylthiazol-5-yl]methoxy]piperidin-1-yl]benzoate

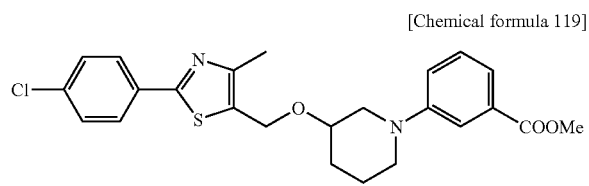

[Chemical formula 119]

Using 3-[[2-(4-chlorophenyl)-4-methylthiazol-5-yl]methoxy]piperidine (60.2 mg, 0.186 mmol) and 3-(methoxycarbonyl)phenylboric acid (66.9 mg, 0.372 mmol), the same procedure was followed as in Example 2 to give 61.0 mg (72%) of the desired compound as a colorless oil.

$^1$H NMR (400 MHz, CDCl$_3$) δ 1.48-1.72 (2H, m), 1.88-1.96 (1H, m), 2.05-2.14 (1H, m), 2.46 (3H, s), 2.85-2.93 (2H, m), 3.47 (1H, td, J=4.3, 12.2 Hz), 3.62-3.72 (2H, m), 3.90 (3H, s), 4.72-4.79 (2H, m), 7.10-7.12 (1H, m), 7.30 (1H, t, J=7.9 Hz), 7.39 (2H, d, J=8.6 Hz), 7.49-7.51 (1H, m), 7.61 (1H, m), 7.84 (2H, d, J=8.6 Hz).

Example 9

Methyl 2-[3-[[2-(4-Chlorophenyl)-4-methylthiazol-5-yl]carbonylaminomethyl]pyrrolidin-1-yl]benzoate Step 9a) N-[[(1-tert-Butoxycarbonyl)pyrrolidin-3-yl]methyl]-2-(4-chlorophenyl)-4-methylthiazole-5-carboxamide

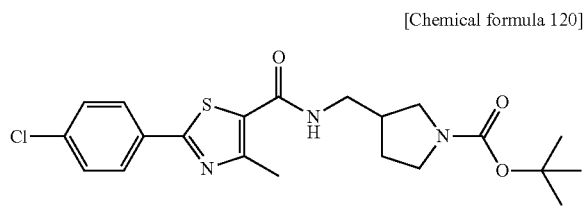

[Chemical formula 120]

Using 2-(4-chlorophenyl)-4-methylthiazolyl-5-carboxylic acid (804 mg, 3.17 mmol) and 1-(tert-butoxycarbonyl)pyrrolidine-3-yl methylamine (635 mg, 3.17 mmol), the same procedure was followed as in Step 1a of Example 1 to give 1.22 g (88%) of the desired compound as a colorless powder.

$^1$H NMR (400 MHz, CDCl$_3$) δ 1.46 (9H, s), 1.61-1.76 (1H, m), 2.01-2.07 (1H, m), 2.48-2.57 (1H, m), 2.73 (3H, s), 3.01-3.18 (1H, m), 3.34-3.56 (5H, m), 5.90 (1H, m), 7.43 (2H, d, J=8.6 Hz), 7.87 (2H, d, J=8.6 Hz).

FAB$^+$ (m/z): 436 (M+H).

Step 9b) N-(Pyrrolidin-3-yl methyl)-2-(4-chlorophenyl)-4-methylthiazole-5-carboxamide

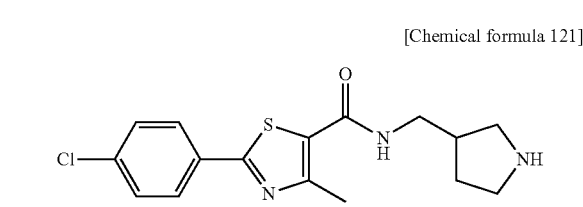

[Chemical formula 121]

Using N-[[(1-tert-butoxycarbonyl)pyrrolidin-3-yl]methyl]-2-(4-chloro phenyl)-4-methylthiazole-5-carboxamide (1.22 g, 2.80 mmol), the same procedure was followed as in Step 1b of Example 1 to give 598 mg (64%) of the desired compound as a colorless powder.

$^1$H NMR (400 MHz, DMSO-d$_6$) δ 1.37-1.46 (1H, m), 1.76-1.85 (1H, m), 2.28-2.35 (1H, m), 2.57-2.61 (4H, m), 2.75-2.81 (1H, m), 2.86-2.93 (2H, m), 3.18-3.22 (3H, m), 7.57 (2H, d, J=8.6 Hz), 7.94 (2H, d, J=8.6 Hz), 8.41 (1H, t, J=5.5 Hz).

FAB⁺ (m/z): 336 (M+H).

Step 9c) Methyl 2-[3-[[2-(4-chlorophenyl)-4-methylthiazol-5-yl]carbonylaminomethyl]pyrrolidin-1-yl]benzoate

[Chemical formula 122]

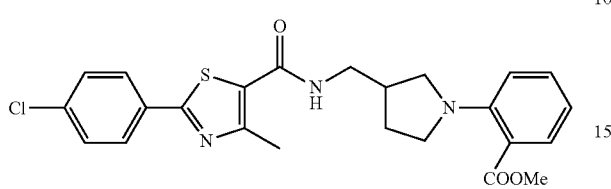

N-(Pyrrolidin-3-yl methyl)-2-(4-chlorophenyl)-4-methylthiazole-5-carboxamide (168 mg, 0.500 mmol) and methyl 2-fluorobenzoate (0.127 mL, 1.00 mmol) were dissolved in dimethylsulfoxide (4 mL). To this solution, potassium carbonate (138 mg, 1.00 mmol) and tetrabutylammonium iodide (18.5 mg, 0.0500 mmol) were added and the mixture was stirred at 140° C. for 6 hours. Subsequently, the reaction mixture was allowed to cool and water was added. The mixture was then extracted with ethyl acetate and the extract washed with brine, followed by drying over magnesium sulfate and evaporation of the solvent. Purification of the resulting residue by silica gel column chromatography (hexane:ethyl acetate=4:1->2:1) gave 136 mg (58%) of the desired compound as a colorless amorphous product.

¹H NMR (400 MHz, CDCl₃) δ 1.77-1.86 (1H, m), 2.11-2.19 (1H, m), 2.60-2.67 (1H, m), 2.71 (3H, s), 3.21-3.38 (4H, m), 3.54 (2H, t, J=6.1 Hz), 3.87 (3H, s), 6.26 (1H, t, J=6.1 Hz), 6.78 (1H, t, J=7.9 Hz), 6.82 (1H, d, J=8.6 Hz), 7.32-7.36 (1H, m), 7.41 (2H, d, J=8.6 Hz), 7.63 (1H, dd, J=1.8, 7.3 Hz), 7.85 (2H, d, J=8.6 Hz).

FAB⁺ (m/z): 470 (M+H).

Example 10

Methyl 3-[3-[[2-(4-chlorophenyl)-4-methylthiazol-5-yl]carbonylaminomethyl]pyrrolidin-1-yl]benzoate

[Chemical formula 123]

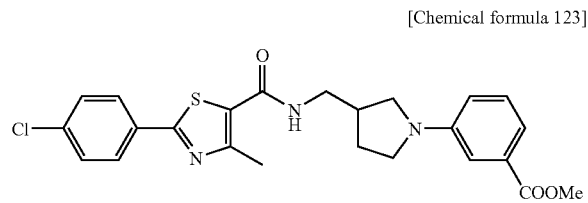

Using N-(pyrrolidin-3-yl methyl)-2-(4-chlorophenyl)-4-methylthiazole-5-carboxamide (168 mg, 0.500 mmol) and 3-(methoxycarbonyl)phenylboric acid (180 mg, 1.00 mmol), the same procedure was followed as in Example 2 to give 73.7 mg (31%) of the desired compound as a colorless powder.

¹H NMR (400 MHz, CDCl₃) δ 1.84-1.93 (1H, m), 2.21-2.29 (1H, m), 2.70-2.77 (4H, m), 3.20 (1H, dd, J=6.1, 9.2 Hz), 3.33-3.40 (1H, m), 3.49-3.63 (4H, m), 3.90 (3H, s), 6.04 (1H, t, J=6.1 Hz), 6.78 (1H, dd, J=1.2, 8.6 Hz), 7.26-7.31 (2H, m), 7.37-7.43 (3H, m), 7.86 (2H, d, J=8.6 Hz).

Example 11

Methyl 2-[3-[[2-(4-chlorophenyl)-4-methylthiazol-5-yl]carbonylaminomethyl]perhydroazepin-1-yl]benzoate Step 11a) N-[[(1-tert-Butoxycarbonyl)perhydroazepin-3-yl]methyl]-2-(4-chlorophenyl)-4-methylthiazole-5-carboxamide

[Chemical formula 124]

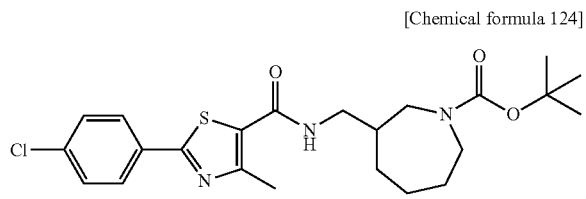

Using 2-(4-chlorophenyl)-4-methylthiazolyl-5-carboxylic acid (792 mg, 3.12 mmol) and 1-(tert-butoxycarbonyl)perhydroazepin-3-yl methylamine (712 mg, 3.12 mmol), the same procedure was followed as in Step 1a of Example 1 to give 1.26 g (87%) of the desired compound as a colorless amorphous product.

¹H NMR (400 MHz, CDCl₃) δ 1.41-1.49 (10H, m), 2.03-2.12 (1H, m), 2.77 (3H, s), 2.99-3.09 (2H, m), 3.13 (1H, dd, J=3.7, 14.7 Hz), 3.58-3.64 (1H, m), 3.65-3.72 (1H, m), 3.78 (1H, dd, J=4.3, 14.7 Hz), 7.41 (2H, d, J=8.6 Hz), 7.64 (1H, t, J=5.5 Hz), 7.87 (2H, d, J=8.6 Hz).

FAB⁺ (m/z): 464 (M+H).

Step 11b) N-(Perhydroazepin-3-yl methyl)-2-(4-chlorophenyl)-4-methylthiazole-5-carboxamide

[Chemical formula 125]

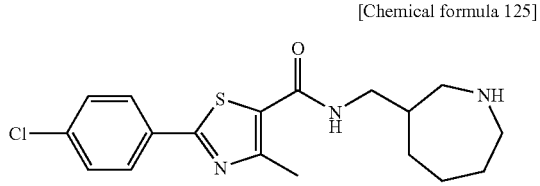

Using N-[[(1-tert-butoxycarbonyl)perhydroazepin-3-yl]methyl]-2-(4-chlorophenyl)-4-methylthiazole-5-carboxamide (1.26 g, 2.72 mmol), the same procedure was followed as in Step 1b of Example 1 to give 896 mg (90%) of the desired compound as a colorless powder.

¹H NMR (400 MHz, CDCl₃) δ 1.43-1.59 (3H, m), 1.76-1.84 (2H, m), 1.90-2.01 (2H, m), 2.62-2.68 (1H, m), 2.75 (3H, s), 2.97 (2H, d, J=4.3 Hz), 3.06 (1H, td, J=4.3, 12.8 Hz), 3.33 (1H, td, J=3.7, 12.8 Hz), 3.53 (1H, td, J=5.2, 12.8 Hz), 7.41 (2H, d, J=8.6 Hz), 7.74 (1H, m), 7.87 (2H, d, J=8.6 Hz).

FAB+ (m/z): 364 (M+H).

Step 11c) Methyl 2-[3-[[2-(4-chlorophenyl)-4-methylthiazol-5-yl]carbonylaminomethyl]perhydroazepin-1-yl]benzoate

[Chemical formula 126]

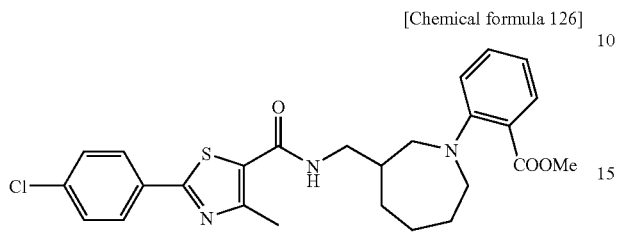

Using N-(perhydroazepin-3-yl methyl)-2-(4-chlorophenyl)-4-methylthiazole-5-carboxamide (200 mg, 0.550 mmol) and methyl 2-fluorobenzoate (0.140 mL, 1.10 mmol), the same procedure was followed as in Step 9c of Example 9 to give 52.7 mg (19%) of the desired compound as a colorless oil.

$^1$H NMR (400 MHz, CDCl$_3$) δ 1.52-1.58 (1H, m), 1.66-1.79 (5H, m), 2.28-2.38 (1H, m), 2.56 (3H, s), 3.10-3.16 (1H, m), 3.21-3.30 (2H, m), 3.36-3.42 (1H, m), 3.46 (1H, dd, J=2.4, 13.4 Hz), 3.54-3.60 (1H, m), 3.88 (3H, s), 6.51 (1H, t, J=5.5 Hz), 6.90 (1H, t, J=7.3 Hz), 7.06 (1H, d, J=7.9 Hz), 7.34 (1H, dt, J=1.2, 7.3 Hz), 7.40 (2H, d, J=8.6 Hz), 7.54 (1H, dd, J=1.2, 7.3 Hz), 7.78 (2H, d, J=8.6 Hz).

FAB+ (m/z): 498 (M+H).

Example 12

Methyl 3-[3-[[2-(4-chlorophenyl)-4-methylthiazol-5-yl]carbonylaminomethyl]perhydroazepin-1-yl]benzoate

[Chemical formula 127]

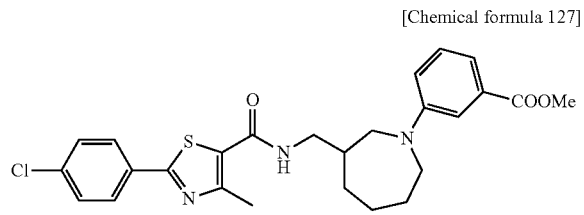

Using N-(perhydroazepin-3-yl methyl)-2-(4-chlorophenyl)-4-methylthiazole-5-carboxamide (200 mg, 0.550 mmol) and 3-(methoxycarbonyl)phenylboric acid (198 mg, 1.10 mmol), the same procedure was followed as in Example 2 to give 126 mg (46%) of the desired compound as a colorless powder.

$^1$H NMR (400 MHz, CDCl$_3$) δ 1.30-1.46 (2H, m), 1.66-1.84 (3H, m), 1.97-2.06 (1H, m), 2.16-2.26 (1H, m), 2.75 (3H, s), 3.10 (1H, dd, J=10.4, 15.3 Hz), 3.30-3.37 (1H, m), 3.38-3.46 (2H, m), 3.63-3.70 (1H, m), 3.81 (1H, dd, J=4.3, 14.7 Hz), 3.86 (3H, s), 5.96 (1H, t, J=5.5 Hz), 6.87 (1H, dd, J=1.8, 7.9 Hz), 7.24 (1H, t, J=7.9 Hz), 7.29 (1H, d, J=7.9 Hz), 7.35-7.36 (1H, m), 7.42 (2H, d, J=8.6 Hz), 7.88 (2H, d, J=8.6 Hz).

FAB+ (m/z): 498 (M+H).

Example 13

Methyl 3-[3-[2-[2-(4-chlorophenyl)-4-methylthiazol-5-yl]acetylamino]piperidin-1-yl]benzoate Step 13a) N-[1-(tert-Butoxycarbonyl)piperidin-3-yl]-2-[2-(4-chlorophenyl)-4-methylthiazol-5-yl]acetamide

[Chemical formula 128]

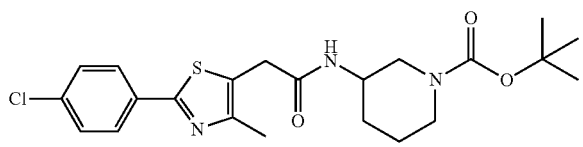

Using 2-[2-(4-chlorophenyl)-4-methylthiazol-5-yl]acetic acid (1.60 g, 5.99 mmol) and 1-(tert-butoxycarbonyl)-3-aminopiperidine (1.20 g, 5.99 mmol), the same procedure was followed as in Step 1a of Example 1 to give 1.59 g (59%) of the desired compound as a colorless powder.

$^1$H NMR (400 MHz, CDCl$_3$) δ 1.41 (9H, s), 1.49-1.57 (2H, m), 1.59-1.68 (1H, m), 1.73-1.81 (1H, m), 2.42 (3H, s), 3.19-3.54 (4H, m), 3.69 (2H, s), 3.98 (1H, m), 5.70 (1H, m), 7.39 (2H, d, J=8.6 Hz), 7.83 (2H, d, J=8.6 Hz).

FAB+ (m/z): 450 (M+H).

Step 13b) N-(Piperidin-3-yl)-2-[2-(4-chlorophenyl)-4-methylthiazol-5-yl]acetamide

[Chemical formula 129]

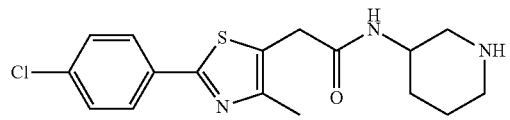

Using N-[1-(tert-butoxycarbonyl)piperidin-3-yl]-2-[2-(4-chlorophenyl)-4-methylthiazol-5-yl]acetamide (1.59 g, 3.53 mmol), the same procedure was followed as in Step 1b of Example 1 to give 1.06 g (86%) of the desired compound as a colorless powder.

$^1$H NMR (400 MHz, CDCl$_3$) δ 1.46-1.53 (1H, m), 1.56-1.64 (1H, m), 1.66-1.80 (2H, m), 2.43 (3H, s), 2.60-2.64 (1H, m), 2.70-2.79 (2H, m), 2.96 (1H, dd, J=3.1, 11.6 Hz), 3.70 (2H, s), 3.94-4.03 (1H, m), 6.18 (1H, m), 7.39 (2H, d, J=8.6 Hz), 7.84 (2H, d, J=8.6 Hz).

FAB⁺ (m/z): 350 (M+H).

Step 13c) Methyl 3-[3-[2-[2-(4-chlorophenyl)-4-methylthiazol-5-yl]acetylamino]piperidin-1-yl]benzoate

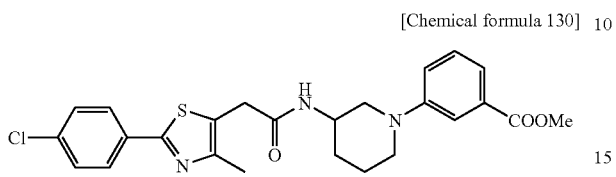

[Chemical formula 130]

Using N-(piperidin-3-yl)-2-[2-(4-chlorophenyl)-4-methylthiazol-5-yl]acetamide (200 mg, 0.572 mmol) and 3-(methoxycarbonyl)phenylboric acid (205 mg, 1.14 mmol), the same procedure was followed as in Example 2 to give 162 mg (59%) of the desired compound as a colorless powder.

¹H NMR (400 MHz, CDCl₃) δ 1.65-1.76 (4H, m), 2.41 (3H, s), 3.01-3.06 (1H, m), 3.12 (1H, dd, J=5.5, 12.2 Hz), 3.22-3.29 (2H, m), 3.72 (2H, s), 3.89 (3H, s), 4.19-4.26 (1H, m), 6.02 (1H, d, J=7.9 Hz), 7.03-7.06 (1H, m), 7.25 (1H, t, J=7.9 Hz), 7.38 (2H, d, J=8.6 Hz), 7.49-7.52 (1H, m), 7.53-7.54 (1H, m), 7.78 (2H, d, J=8.6 Hz).

FAB⁺ (m/z): 484 (M+H).

Example 14

Methyl 2-[3-[[2-(4-chlorophenyl)-4-methylthiazol-5-yl]carbonylamino]piperidin-1-yl]benzoate Step 14a) N-[(1-tert-Butoxycarbonyl)piperidin-3-yl]-2-(4-chlorophenyl)-4-methylthiazole-5-carboxamide

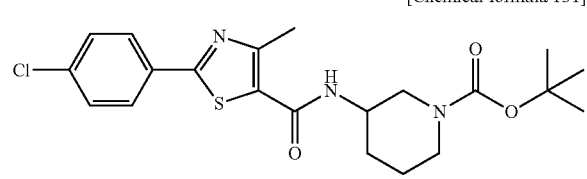

[Chemical formula 131]

Using 2-(4-chlorophenyl)-4-methylthiazole-5-carboxylic acid (1.52 g, 5.99 mmol) and 1-(tert-butoxycarbonyl)-3-aminopiperidine (1.20 g, 5.99 mmol), the same procedure was followed as in Step 1a of Example 1 to give 2.30 g (88%) of the desired compound as a colorless powder.

¹H NMR (400 MHz, CDCl₃) δ 1.47 (9H, s), 1.56-1.74 (2H, m), 1.78-2.03 (2H, m), 2.73 (3H, s), 3.12-3.24 (1H, m), 3.34-3.50 (1H, m), 3.68-3.71 (2H, m), 4.13-4.19 (1H, m), 6.04 (1H, m), 7.42 (2H, d, J=8.6 Hz), 7.86 (2H, d, J=8.6 Hz).

FAB⁺ (m/z): 436 (M+H).

Step 14b) N-(Piperidin-3-yl)-2-(4-chlorophenyl)-4-methylthiazole-5-carboxamide

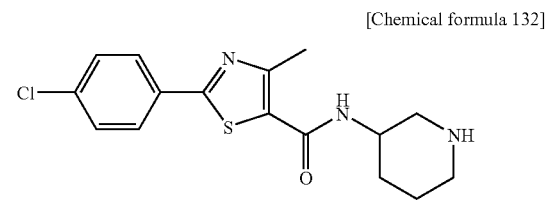

[Chemical formula 132]

Using N-[(1-tert-butoxycarbonyl)piperidin-3-yl]-2-(4-chlorophenyl)-4-methylthiazole-5-carboxamide (2.30 g, 5.28 mmol), the same procedure was followed as in Step 1b of Example 1 to give 1.75 g (99%) of the desired compound as a colorless powder.

¹H NMR (400 MHz, DMSO-d₆) δ 1.33-1.49 (2H, m), 1.57-1.61 (1H, m), 1.80-1.84 (1H, m), 2.37-2.42 (2H, m), 2.57 (3H, s), 2.72-2.77 (1H, m), 2.93 (1H, dd, J=3.1, 11.6 Hz), 3.70-3.79 (1H, m), 7.57 (2H, d, J=8.6 Hz), 7.94 (2H, d, J=8.6 Hz), 8.05 (1H, d, J=7.9 Hz).

Step 14c) 2-[3-[[2-(4-Chlorophenyl)-4-methylthiazol-5-yl]carbonylamino]piperidin-1-yl]benzaldehyde

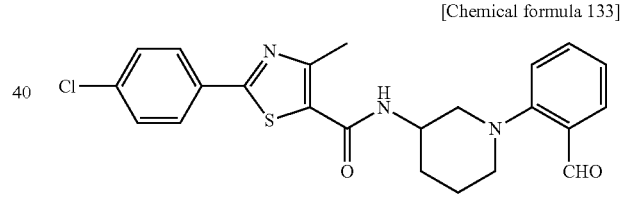

[Chemical formula 133]

Using N-(piperidin-3-yl)-2-(4-chlorophenyl)-4-methylthiazole-5-carboxamide (67.2 mg, 0.200 mmol) and 2-fluorobenzaldehyde (0.211 mL, 2.00 mmol), the same procedure was followed as in Step 6c of Example 6 to give 14.9 mg (17%) of the desired compound as a colorless powder.

¹H NMR (400 MHz, CDCl₃) δ 1.68-1.81 (2H, m), 2.01-2.11 (2H, m), 2.76 (3H, s), 2.92-2.99 (1H, m), 3.13 (1H, dd, J=2.4, 12.2 Hz), 3.24-3.30 (2H, m), 4.36-4.43 (1H, m), 7.15 (1H, d, J=8.6 Hz), 7.20 (1H, t, J=7.3 Hz), 7.40-7.46 (3H, m), 7.56 (1H, dt, J=1.8, 7.3 Hz), 7.79 (1H, dd, J=1.8, 7.9 Hz), 7.88 (2H, d, J=8.6 Hz), 10.14 (1H, s).

Step 14d) Methyl 2-[3-[[2-(4-chlorophenyl)-4-methylthiazol-5-yl]carbonylamino]piperidin-1-yl]benzoate

[Chemical formula 134]

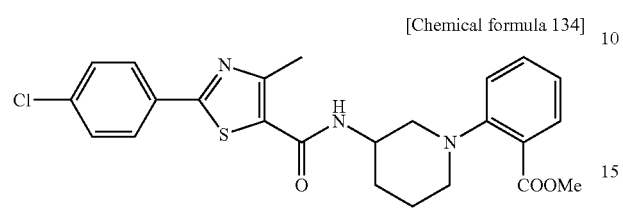

Using 2-[3-[[2-(4-chlorophenyl)-4-methylthiazol-5-yl]carbonylamino]piperidin-1-yl]benzaldehyde (14.9 mg, 0.0339 mmol), the same procedure was followed as in Step 5d of Example 5 to give 2.60 mg (16%) of the desired compound as a colorless oil.

$^1$H NMR (400 MHz, CDCl$_3$) δ 1.58-1.64 (1H, m), 1.68-1.73 (1H, m), 1.97-2.09 (1H, m), 2.14-2.17 (1H, m), 2.79 (3H, s), 2.86 (1H, dt, J=2.4, 11.6 Hz), 2.98 (1H, dd, J=2.4, 12.2 Hz), 3.20-3.29 (2H, m), 3.84 (3H, s), 4.34-4.39 (1H, m), 7.07 (1H, dt, J=1.2, 7.3 Hz), 7.13 (1H, dd, J=1.2, 7.9 Hz), 7.41 (2H, d, J=8.6 Hz), 7.48 (1H, dt, J=1.8, 7.3 Hz), 7.77 (1H, d, J=6.7 Hz), 7.83 (1H, dd, J=1.8, 7.9 Hz), 7.88 (2H, d, J=8.6 Hz).

Example 15

Methyl 3-[3-[[2-(4-Chlorophenyl)-4-methylthiazol-5-yl]carbonylamino]piperidin-1-yl]benzoate Step 15a) Methyl 3-[3-(tert-butoxycarbonylamino)piperidin-1-yl]benzoate

[Chemical formula 135]

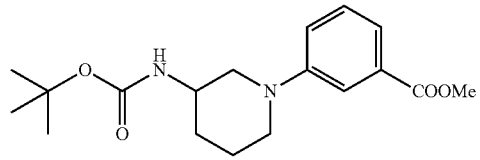

3-(tert-Butoxycarbonylamino)piperidine (200 mg, 1.00 mmol), 3-(methoxycarbonyl)phenylboric acid (360 mg, 2.00 mmol) and molecular sieves 4 Å (100 mg) were suspended in dichloromethane (10 mL). To this suspension, copper (II) acetate (182 mg, 1.00 mmol) and triethylamine (0.280 mL, 2.00 mmol) were added and the mixture was stirred at room temperature for 15 hours. Subsequently, the reaction mixture was filtered through Celite and a saturated aqueous sodium bicarbonate solution was added to the filtrate. This mixture was extracted with ethyl acetate and the extract washed with brine, followed by drying over magnesium sulfate and evaporation of the solvent. The resulting residue was purified by silica gel column chromatography (hexane:ethyl acetate=10:1->5:1) to give a colorless oil. This product was further purified by silica gel column chromatography (Chromatorex NH-DM2035 (Fuji Sylysia Chemical Co., Ltd.) hexane:ethyl acetate=10:1) to give 154 mg (46%) of the desired compound as a colorless powder.

$^1$H NMR (400 MHz, CDCl$_3$) δ1.46 (9H, s), 1.55-1.59 (1H, m), 1.68-1.76 (1H, m), 1.78-1.89 (2H, m), 3.01-3.05 (1H, m), 3.16 (2H, m), 3.37-3.40 (1H, m), 3.82-3.90 (4H, m), 4.87 (1H, m), 7.12-7.14 (1H, m), 7.31 (1H, t, J=7.9 Hz), 7.52 (1H, d, J=7.3 Hz), 7.59 (1H, m).

EI$^+$ (m/z): 334 (M+).

Step 15b) Methyl 3-[3-[[2-(4-chlorophenyl)-4-methylthiazol-5-yl]carbonylamino]piperidin-1-yl]benzoate

[Chemical formula 136]

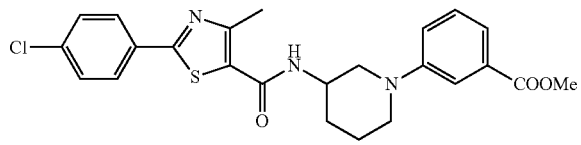

Methyl 3-[3-(tert-butoxycarbonylamino)piperidin-1-yl]benzoate (154 mg, 0.461 mmol) was dissolved in a 10% hydrogen chloride/methanol solution (10 mL) and the solution was stirred at room temperature for 1 hour. Concentration of the reaction mixture resulted in 135 mg of a brown amorphous product. This product (118 mg), along with 2-(4-chlorophenyl)-4-methylthiazole-5-carboxylic acid (111 mg, 0.436 mmol) and 1-hydroxybenzotriazole monohydrate (80.1 mg, 0.523 mmol), was dissolved in N,N-dimethylformamide (5 mL). While this solution was chilled in an ice bath, 3-(3-dimethylaminopropyl)-1-ethylcarbodiimide hydrochloride (100 mg, 0.523 mmol) and N-methylmorpholine (0.115 mL, 1.05 mmol) were added. The mixture was stirred at room temperature for 6 hours and 5% aqueous citric acid was added. The resulting mixture was extracted with ethyl acetate and the extract washed sequentially with a saturated aqueous sodium bicarbonate solution and brine. The washed product was dried over magnesium sulfate and the solvent was evaporated. Purification of the resulting residue by silica gel column chromatography (hexane:ethyl acetate=5:1->1:1) gave 112 mg of the desired compound as a pale yellow powder.

$^1$H NMR (400 MHz, CDCl$_3$) δ 1.78-1.95 (4H, m), 2.72 (3H, s), 3.04-3.10 (1H, m), 3.29-3.41 (3H, m), 3.91 (3H, s), 4.41 (1H, m), 6.31 (1H, d, J=7.9 Hz), 7.17 (1H, dd, J=2.4, 8.6 Hz), 7.34 (1H, t, J=7.9 Hz), 7.41 (2H, d, J=8.6 Hz), 7.56-7.58 (1H, m), 7.64 (1H, m), 7.87 (2H, d, J=8.6 Hz).

FAB+ (m/z): 470 (M+H).

Example 16

Methyl (R)-3-[3-[[2-(4-chlorophenyl)-4-methylthiazol-5-yl]carbonylamino]piperidin-1-yl]benzoate

Step 16a) (R)—N-[(1-tert-Butoxycarbonyl)piperidin-3-yl]-2-(4-chlorophenyl)-4-methylthiazole-5-carboxamide

[Chemical formula 137]

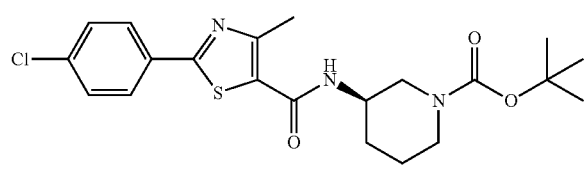

Using 2-(4-chlorophenyl)-4-methylthiazole-5-carboxylic acid (12.4 g, 48.9 mmol) and (R)-1-(tert-butoxycarbonyl)-3-aminopiperidine (9.79 g, 48.9 mmol), the same procedure was followed as in Step 1a of Example 1 to give 18.3 g (86%) of the desired compound as a colorless powder.

$^1$H NMR (400 MHz, CDCl$_3$) δ 1.47 (9H, s), 1.58-1.74 (2H, m), 1.78-2.01 (2H, m), 2.73 (3H, s), 3.11-3.26 (1H, m), 3.34-3.50 (1H, m), 3.57-3.82 (2H, m), 4.13-4.19 (1H, m), 6.01 (1H, m), 7.42 (2H, d, J=8.6 Hz), 7.86 (2H, d, J=8.6 Hz).

FAB+ (m/z): 436 (M+H).

Step 16b) (R)—N-(Piperidin-3-yl)-2-(4-chlorophenyl)-4-methylthiazole-5-carboxamide

[Chemical formula 138]

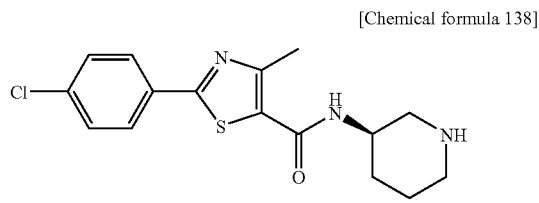

Using (R)—N-[(1-tert-butoxycarbonyl)piperidin-3-yl]-2-(4-chlorophenyl)-4-methylthiazole-5-carboxamide (18.2 g, 41.7 mmol), the same procedure was followed as in Step 1b of Example 1 to give 14.9 g (quant.) of the desired compound as a colorless powder.

$^1$H NMR (400 MHz, DMSO-d$_6$) δ 1.35-1.52 (2H, m), 1.59-1.63 (1H, m), 1.82-1.86 (1H, m), 2.39-2.44 (2H, m), 2.59 (3H, s), 2.75-2.78 (1H, m), 2.95 (1H, dd, J=3.1 Hz, J=11.6 Hz), 3.72-3.80 (1H, m), 7.58-(2H, d, J=8.6 Hz), 7.95 (2H, d, J=8.6 Hz), 8.07 (1H, d, J=7.9 Hz).

FAB+ (m/z): 336 (M+H).

Step 16c) Methyl (R)-3-[3-[[2-(4-chlorophenyl)-4-methylthiazol-5-yl]carbonylamino]piperidin-1-yl]benzoate

[Chemical formula 139]

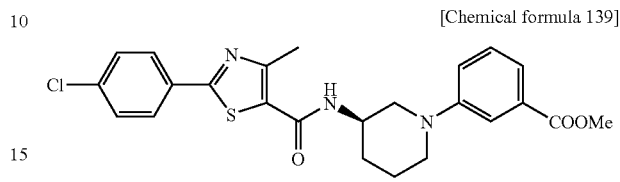

Using (R)—N-(piperidin-3-yl)-2-(4-chlorophenyl)-4-methylthiazole-5-carboxamide (336 mg, 1.00 mmol) and 3-(methoxycarbonyl)phenylboric acid (360 mg, 2.00 mmol), the same procedure was followed as in Example 2 to give 142 mg (30%) of the desired compound as a pale yellow powder.

$^1$H NMR (400 MHz, CDCl$_3$) δ 1.78-1.93 (4H, m), 2.72 (3H, s), 3.04-3.10 (1H, m), 3.29-3.41 (3H, m), 3.91 (3H, s), 4.39-4.44 (1H, m), 6.31 (1H, d, J=7.9 Hz), 7.17 (1H, m), 7.34 (1H, t, J=7.9 Hz), 7.41 (2H, d, J=8.6 Hz), 7.56-7.58 (1H, m), 7.63-7.64 (1H, m), 7.87 (2H, d, J=8.6 Hz).

FAB+ (m/z): 470 (M+H).

[α]$^{27.4°}_D$−110° (C=1.2, CHCl$_3$)

HPLC (CHIRALCEL OJ (Daicel Chemical Industries, Co., Ltd.) φ 0.46×25 cm, mobile phase: hexane/ethanol=80/20, flow rate: 1 mL/min, Temp.: 40° C.): Rt 39.1 min (98% ee)

Example 17

Methyl(S)-3-[3-[[2-(4-chlorophenyl)-4-methylthiazol-5-yl]carbonylamino]piperidin-1-yl]benzoate

Step 17a) (S)—N-[(1-tert-Butoxycarbonyl)piperidin-3-yl]-2-(4-chlorophenyl)-4-methylthiazole-5-carboxamide

[Chemical formula 140]

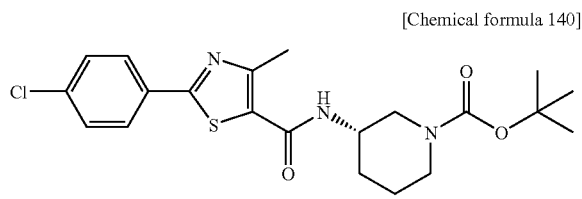

Using 2-(4-chlorophenyl)-4-methylthiazole-5-carboxylic acid (1.27 g, 4.99 mmol) and (S)-1-(tert-butoxycarbonyl)-3-aminopiperidine (1.00 g, 4.99 mmol), the same procedure was followed as in Step 1a of Example 1 to give 1.84 g (85%) of the desired compound as a colorless powder.

$^1$H NMR (400 MHz, CDCl$_3$) δ 1.47 (9H, s), 1.57-1.74 (2H, m), 1.78-2.01 (2H, m), 2.73 (3H, s), 3.13-3.24 (1H, m), 3.35-3.49 (1H, m), 3.64-3.76 (2H, m), 4.13-4.19 (1H, m), 6.04 (1H, m), 7.42 (2H, d, J=8.6 Hz), 7.86 (2H, d, J=8.6 Hz).

FAB⁺ (m/z): 436 (M+H).

Step 17b) (S)—N-(Piperidin-3-yl)-2-(4-chlorophenyl)-4-methylthiazol-5-yl carboxamide

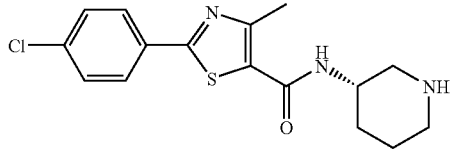
[Chemical formula 141]

Using (S)—N-[(1-tert-butoxycarbonyl)piperidin-3-yl]-2-(4-chlorophenyl)-4-methylthiazole-5-carboxamide (1.74 g, 3.99 mmol), the same procedure was followed as in Step 1b of Example 1 to give 1.23 g (92%) of the desired compound as a colorless powder.

¹H NMR (400 MHz, DMSO-d₆) δ 1.35-1.51 (2H, m), 1.60-1.63 (1H, m), 1.82-1.85 (1H, m), 2.38-2.44 (2H, m), 2.59 (3H, s), 2.75-2.78 (1H, m), 2.93-2.96 (1H, m), 3.70-3.82 (1H, m), 7.58 (2H, d, J=8.6 Hz), 7.95 (2H, d, J=8.6 Hz), 8.05 (1H, d, J=7.3 Hz).

FAB⁺ (m/z): 336 (M+H).

Step 17c) Methyl (S)-3-[3-[[2-(4-chlorophenyl)-4-methylthiazol-5-yl]carbonylamino]piperidin-1-yl]benzoate

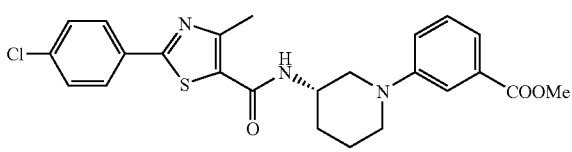
[Chemical formula 142]

Using (S)—N-(piperidin-3-yl)-2-(4-chlorophenyl)-4-methylthiazol-5-carboxamide (336 mg, 1.00 mmol) and 3-(methoxycarbonyl)phenylboric acid (360 mg, 2.00 mmol), the same procedure was followed as in Example 2 to give 233 mg (50%) of the desired compound as a colorless powder.

¹H NMR (400 MHz, CDCl₃) δ 1.78-1.93 (4H, m), 2.72 (3H, s), 3.04-3.10 (1H, m), 3.29-3.41 (3H, m), 3.91 (3H, s), 4.38-4.44 (1H, m), 6.31 (1H, d, J=7.9 Hz), 7.16-7.18 (1H, m), 7.34 (1H, t, J=7.9 Hz), 7.41 (2H, d, J=8.6 Hz), 7.55-7.58 (1H, m), 7.63-7.64 (1H, m), 7.86 (2H, d, J=8.6 Hz).

FAB⁺ (m/z): 470 (M+H).

[α]²⁷·⁶°ᴅ+113° (C=1.0, CHCl₃).

HPLC (CHIRALCEL OJ (Daicel Chemical Industries, Co., Ltd.) φ 0.46×25 cm, mobile phase: hexane/ethanol=80/20, flow rate: 1 mL/min, Temp.: 40° C.): Rt 24.4 min (98% ee)

Example 18

2-[3-[[2-(4-Chlorophenyl)-4-methylthiazol-5-yl]carbonylaminomethyl]piperidin-1-yl]benzoic acid

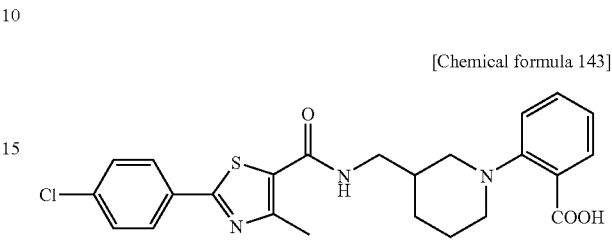
[Chemical formula 143]

Methyl 2-[3-[[2-(4-chlorophenyl)-4-methylthiazol-5-yl]carbonylaminomethyl]piperidin-1-yl]benzoate (29.5 mg, 0.0609 mmol) was dissolved in methanol (3 mL). To this solution, a 1 mol/L aqueous potassium hydroxide solution (0.183 mL, 0.183 mmol) was added and the mixture was stirred for 2 hours while being refluxed. Subsequently, the reaction mixture was concentrated and water was added to the residue, followed by 2 mol/L hydrochloric acid to make the mixture acidic. The crystallized powdery product was collected by filtration and washed with water to give 23.2 mg (81%) of the desired product as a colorless powder.

¹H NMR (400 MHz, DMSO-d₆) δ 1.11-1.34 (2H, m), 1.59-1.72 (1H, m), 1.85-1.95 (2H, m), 1.97-2.10 (1H, m), 2.58 (3H, s), 2.85 (1H, t, J=11.0 Hz), 2.99-3.12 (3H, m), 3.15-3.22 (1H, m), 7.44 (1H, t, J=7.3 Hz), 7.58 (2H, d, J=8.6 Hz), 7.66-7.74 (2H, m), 7.95 (2H, d, J=8.6 Hz), 8.04 (1H, dd, J=1.8, 7.9 Hz), 8.37 (1H, t, J=5.5 Hz), 17.91 (1H, brs).

HR-FAB⁺ (m/z): 470.1291 (−1.4 mmu).

Elemental analysis calcd (%) for $C_{24}H_{24}ClN_3O_3S$·2/5H₂O: C, 60.41; H, 5.24; N, 8.81; found: C, 60.25; H, 5.09; N, 8.62.

Examples 19 Through 32

The compounds obtained in Examples 2 through 17 were reacted in the manner described in Example 18 to obtain compounds given in Table 4 below.

TABLE 4

| Example | Y | Z | Binding position of carboxylic acid |
|---|---|---|---|
| Example 19 | Racemic mixture | CONHCH₂ | CH₂ | Position 3 |
| Example 20 | Racemic mixture | CH₂NHCO | CH₂ | Position 2 |
| Example 21 | Racemic mixture | CH₂NHCO | CH₂ | Position 3 |
| Example 22 | Racemic mixture | CH₂OCH₂ | CH₂ | Position 2 |
| Example 23 | Racemic mixture | CH₂O | CH₂ | Position 2 |
| Example 24 | Racemic mixture | CH₂OCH₂ | CH₂ | Position 3 |
| Example 25 | Racemic mixture | CH₂O | CH₂ | Position 3 |
| Example 26 | Racemic mixture | CONHCH₂ | — | Position 2 |

TABLE 4-continued

| Example | Y | Z | Binding position of carboxylic acid |
|---|---|---|---|
| Example 27 | Racemic mixture | CONHCH$_2$ | — | Position 3 |
| Example 28 | Racemic mixture | CONHCH$_2$ | CH$_2$CH$_2$ | Position 2 |
| Example 29 | Racemic mixture | CONHCH$_2$ | CH$_2$CH$_2$ | Position 3 |
| Example 30 | Racemic mixture | CH$_2$CONH | CH$_2$ | Position 3 |
| Example 31 | Racemic mixture | CONH | CH$_2$ | Position 2 |
| Example 32 | Racemic mixture | CONH | CH$_2$ | Position 3 |
| Example 33 | R | CONH | CH$_2$ | Position 3 |
| Example 34 | S | CONH | CH$_2$ | Position 3 |

<Compound of Example 19>
Colorless Powder
$^1$H NMR (400 MHz, DMSO-d$_6$) δ 1.13-1.23 (1H, m), 1.52-1.62 (1H, m), 1.75-1.95 (3H, m), 2.50-2.57 (1H, m), 2.62 (3H, s), 2.71-2.77 (1H, m), 3.17-3.35 (2H, m), 3.59-3.62 (1H, m), 3.66-3.67 (1H, m), 7.17-7.20 (1H, m), 7.29-7.35 (2H, m), 7.47-7.48 (1H, m), 7.59 (2H, d, J=8.6 Hz), 7.97 (2H, d, J=8.6 Hz), 8.45 (1H, t, J=5.5 Hz), 12.80 (1H, brs).
HR-FAB$^+$ (m/z): 470.1303 (−0.2 mmu).
Elemental analysis calcd (%) for C$_{24}$H$_{24}$ClN$_3$O$_3$S.1/10H$_2$O: C, 61.10; H, 5.17; N, 8.91; found: C, 60.95; H, 5.08; N, 8.84.

<Compound of Example 20>
Colorless Powder
$^1$H NMR (400 MHz, DMSO-d$_6$) δ1.24 (1H, m), 1.60-1.68 (2H, m), 1.87-1.96 (2H, m), 2.37 (3H, s), 2.96-3.04 (2H, m), 3.08-3.15 (2H, m), 4.39-4.41 (2H, m), 7.41 (1H, t, J=7.3 Hz), 7.51 (2H, d, J=8.6 Hz), 7.65 (1H, t, J=7.3 Hz), 7.72 (1H, d, J=7.3 Hz), 7.85 (2H, d, J=8.6 Hz), 8.01 (1H, d, J=7.3 Hz), 8.70 (1H, t, J=5.5 Hz), 17.39 (1H, brs).
HR-FAB$^+$ (m/z): 470.1291 (−1.4 mmu).

<Compound of Example 21>
Colorless Powder
$^1$H NMR (400 MHz, DMSO-d$_6$) δ 1.50-1.62 (2H, m), 1.70-1.79 (1H, m), 1.81-1.89 (1H, m), 2.39 (3H, s), 2.45-2.55 (1H, m), 2.69-2.74 (1H, m), 2.84 (1H, t, J=2.0 Hz), 3.62-3.65 (1H, m), 3.71-3.73 (1H, m), 4.37-4.48 (2H, m), 7.17-7.20 (1H, m), 7.28-7.35 (2H, m), 7.46 (1H, m), 7.53 (2H, d, J=8.6 Hz), 7.87 (2H, d, J=8.6 Hz), 8.62 (1H, t, J=5.5 Hz).
HR-FAB$^+$ (m/z): 470.1343 (+3.8 mmu).

<Compound of Example 22>
Colorless Powder
$^1$H NMR (400 MHz, DMSO-d$_6$) δ 1.24-1.32 (1H, m), 1.62-1.71 (1H, m), 1.80-1.90 (2H, m), 1.99-2.10 (1H, m), 2.36 (3H, s), 2.85 (1H, t, J=11.6 Hz), 2.96-3.11 (3H, m), 3.42-3.48 (2H, m), 4.66 (2H, s), 7.43 (1H, t, J=7.3 Hz), 7.53 (2H, d, J=8.6 Hz), 7.64-7.71 (2H, m), 7.89 (2H, d, J=8.6 Hz), 8.03 (1H, d J=7.9 Hz), 17.86 (1H, brs). HR-FAB$^+$ (m/z) 457.1321 (−3.2 mmu).

<Compound of Example 23>
Colorless Powder
$^1$H NMR (400 MHz, DMSO-d$_6$) δ 1.60-1.78 (2H, m), 1.83-1.99 (2H, m), 2.37 (3H, s), 2.91-3.10 (3H, m), 3.25-3.41 (1H, m), 3.78-3.82 (1H, m), 4.70-4.81 (2H, m), 7.42 (1H, t, J=7.9 Hz), 7.54 (2H, d, J=8.6 Hz), 7.65-7.73 (2H, m), 7.90 (2H, d, J=8.6 Hz), 8.03-8.05 (1H, m), 17.22 (1H, brs).

HR-FAB$^+$ (m/z): 443.1183 (−1.4 mmu).

<Compound of Example 24>
Colorless Powder
$^1$H NMR (400 MHz, DMSO-d$_6$) δ 1.13-1.23 (1H, m), 1.50-1.62 (1H, m), 1.67-1.79 (2H, m), 1.86-1.98 (1H, m), 2.39 (3H, s), 2.58 (1H, dd, J=9.8, 12.2 Hz), 2.70-2.77 (1H, m), 3.40-3.46 (2H, m), 3.56-3.59 (1H, m), 3.64-3.68 (1H, m), 4.66-4.73 (2H, m), 7.15-7.17 (1H, m), 7.28-7.34 (2H, m), 7.45 (1H, m), 7.54 (2H, d, J=8.6 Hz), 7.91 (2H, d, J=8.6 Hz), 12.81 (1H, brs).
HR-FAB$^+$ (m/z): 457.1361 (+0.8 mmu).

<Compound of Example 25>
Colorless Powder
$^1$H NMR (400 MHz, DMSO-d$_6$) δ 1.41-1.59 (2H, m), 1.79-1.82 (1H, m), 1.98-2.03 (1H, m), 2.38 (3H, s), 2.83-2.92 (2H, m), 3.41-3.44 (1H, m), 3.58-3.64 (1H, m), 3.69-3.72 (1H, m), 4.79 (2H, s), 7.20-7.22 (1H, m), 7.28-7.34 (2H, m), 7.46 (1H, m), 7.54 (2H, d, J=8.6 Hz), 7.90 (2H, d, J=8.6 Hz), 12.82 (1H, brs).
HR-FAB$^+$ (m/z): 443.1196 (+0.0 mmu).

<Compound of Example 26>
Colorless Powder
$^1$H NMR (400 MHz, DMSO-d$_6$) δ 1.68-1.77 (1H, m), 2.01-2.09 (1H, m), 2.53-2.56 (1H, m), 2.59 (3H, s), 3.05 (1H, dd, J=6.7, 9.8 Hz), 3.24-3.27 (5H, m), 6.76 (1H, t, J=7.3 Hz), 6.90 (1H, d, J=7.9 Hz), 7.33 (1H, dt, J=1.2, 7.9 Hz), 7.53 (1H, dd, J=1.2, 7.9 Hz), 7.57 (2H, d, J=8.6 Hz), 7.94 (2H, d, J=8.6 Hz), 8.45 (1H, t, J=5.5 Hz), 13.24 (1H, brs).
HR-FAB$^+$ (m/z): 456.1129 (−1.9 mmu).

<Compound of Example 27>
Colorless Powder
$^1$H NMR (400 MHz, DMSO-d$_6$) δ 1.75-1.84 (1H, m), 2.06-2.14 (1H, m), 2.56-2.64 (4H, m), 3.09 (1H, dd, J=6.1, 9.8 Hz), 3.23-3.43 (5H, m), 6.74 (1H, dd, J=1.8, 8.6 Hz), 7.06 (1H, m), 7.16 (1H, d, J=7.9 Hz), 7.26 (1H, t, J=7.9 Hz), 7.57 (2H, d, J=8.6 Hz), 7.95 (2H, d, J=8.6 Hz), 8.48 (1H, t, J=6.1 Hz), 12.68 (1H, brs). HR-FAB$^+$ (m/z): 456.1149 (+0.0 mmu).
Elemental analysis calcd (%) for C$_{23}$H$_{22}$ClN$_3$O$_3$S.1/10H$_2$O: C, 60.35; H, 4.89; N, 9.18; found: C, 60.17; H, 4.78; N, 8.94.

<Compound of Example 28>
Colorless Powder
$^1$H NMR (400 MHz, DMSO-d$_6$) δ 1.38-1.46 (1H, m), 1.56-1.62 (1H, m), 1.77-1.89 (4H, m), 2.16-2.25 (1H, m), 2.51 (3H, s), 3.08-3.27 (6H, m), 7.33-7.37 (1H, m), 7.58 (2H, d, J=8.6 Hz), 7.61-7.66 (2H, m), 7.93 (2H, d, J=8.6 Hz), 7.96 (1H, dd, J=1.2, 7.9 Hz), 8.39 (1H, t, J=5.5 Hz), 17.74 (1H, brs).
HR-FAB$^+$ (m/z): 484.1469 (+0.7 mmu).
Elemental analysis calcd (%) for C$_{25}$H$_{26}$ClN$_3$O$_3$S.1/10H$_2$O: C, 61.81; H, 5.44; N, 8.65; found: C, 61.57; H, 5.36; N, 8.39.

<Compound of Example 29>
Colorless Powder
$^1$H NMR (400 MHz, DMSO-d$_6$) δ 1.20-1.33 (2H, m), 1.54-1.67 (2H, m), 1.68-1.78 (1H, m), 1.86-1.98 (1H, m), 2.06-2.19 (1H, m), 2.63 (3H, s), 3.02 (1H, dd, J=10.4, 15.3 Hz), 3.15-3.30 (3H, m), 3.65 (1H, td, J=5.5, 14.7 Hz), 3.78 (1H, dd, J=3.7, 14.7 Hz), 6.92 (1H, dd, J=1.8, 7.9 Hz), 7.13 (1H, d, J=7.3 Hz), 7.20-7.24 (2H, m), 7.59 (2H, d, J=8.6 Hz), 7.97 (2H, d, J=8.6 Hz), 8.47 (1H, t, J=5.5 Hz), 12.70 (1H, brs).
HR-FAB$^+$ (m/z): 484.1461 (−0.1 mmu).
Elemental analysis calcd (%) for C$_{25}$H$_{26}$ClN$_3$O$_3$S.1/10H$_2$O: C, 61.81; H, 5.44; N, 8.65; found: C, 61.61; H, 5.31; N, 8.37.

<Compound of Example 30>
Colorless Powder

¹H NMR (400 MHz, DMSO-d₆) δ 1.40-1.50 (1H, m), 1.55-1.66 (1H, m), 1.78-1.86 (2H, m), 2.35 (3H, s), 2.71-2.76 (1H, m), 2.86-2.92 (1H, m), 3.46-3.49 (1H, m), 3.58 (1H, dd, J=3.1, 12.2 Hz), 3.71 (2H, s), 3.75-3.84 (1H, m), 7.16-7.19 (1H, m), 7.28-7.35 (2H, m), 7.44 (1H, m), 7.52 (2H, d, J=8.6 Hz), 7.88 (2H, d, J=8.6 Hz), 8.28 (1H, d, J=7.3 Hz), 12.82 (1H, brs).

HR-FAB⁺ (m/z): 470.1303 (−0.2 mmu).

Elemental analysis calcd (%) for $C_{24}H_{24}ClN_3O_3S.1/5H_2O$: C, 60.87; H, 5.19; N, 8.87; found: C, 60.78; H, 5.18; N, 8.67.

<Compound of Example 31>

Colorless Powder

¹H NMR (400 MHz, DMSO-d₆) δ 1.64-1.77 (2H, m), 1.90-2.00 (2H, m), 2.60 (3H, s), 2.97-3.07 (4H, m), 4.02-4.12 (1H, m), 7.37 (1H, t, J=7.3 Hz), 7.58-7.60 (3H, m), 7.65 (1H, dt, J=1.8 Hz, J=7.9 Hz), 7.94-7.99 (3H, m), 8.32 (1H, d, J=6.7 Hz), 16.46 (1H, brs). HR-FAB⁺ (m/z): 456.1165 (+1.6 mmu).

<Compound of Example 32>

Colorless Powder

¹H NMR (400 MHz, DMSO-d₆) δ 1.53-1.68 (2H, m), 1.81-1.85 (1H, m), 1.92-1.95 (1H, m), 2.61 (3H, s), 2.77-2.83 (2H, m), 3.59-3.62 (1H, m), 3.73 (1H, dd, J=3.6, 12.2 Hz), 3.94-4.00 (1H, m), 7.23 (1H, td, J=2.4, 7.3 Hz), 7.31-7.36 (2H, m), 7.47 (1H, m), 7.59 (2H, d, J=8.6 Hz), 7.96 (2H, d, J=8.6 Hz), 8.27 (1H, d, J=7.3 Hz), 12.84 (1H, brs).

HR-FAB⁺ (m/z): 456.1153 (+0.5 mmu).

Elemental analysis calcd (%) for $C_{23}H_{22}ClN_3O_3S$: C, 60.59; H, 4.86; N, 9.22; found: C, 60.41; H, 4.94; N, 9.01.

<Compound of Example 33>

Colorless Powder

¹H NMR (400 MHz, DMSO-d₆) δ 1.53-1.68 (2H, m), 1.81-1.85 (1H, m), 1.92-1.95 (1H, m), 2.60 (3H, s), 2.77-2.83 (2H, m), 3.59-3.62 (1H, m), 3.73 (1H, dd, J=3.6, 11.6 Hz), 3.91-4.01 (1H, m), 7.22 (1H, td, J=2.4, 7.3 Hz), 7.31-7.36 (2H, m), 7.47 (1H, m), 7.59 (2H, d, J=8.6 Hz), 7.96 (2H, d, J=8.6 Hz), 8.27 (2H, d, J=7.3 Hz), 12.83 (1H, brs).

HR-FAB⁺ (m/z): 456.1147 (−0.2 mmu).

Elemental analysis calcd (%) for $C_{23}H_{22}ClN_3O_3S$: C, 60.59; H, 4.86; N, 9.22; found: C, 60.41; H, 4.79; N, 8.93.

$[\alpha]^{27.7°}_D$ −130° (C=1.0, DMF)

HPLC (CHIRALCEL OJ (Daicel Chemical Industries, Co., Ltd.) φ 0.46×25 cm, mobile phase: hexane/ethanol=60/40 (0.1% TFA), flow rate: 1 mL/min, Temp.: 40° C.): Rt 26.6 min (99% ee)

<Compound of Example 34>

¹H NMR (400 MHz, DMSO-d₆) δ 1.53-1.68 (2H, m), 1.81-1.85 (1H, m), 1.92-1.95 (1H, m), 2.60 (3H, s), 2.77-2.83 (2H, m), 3.59-3.62 (1H, m), 3.73 (1H, dd, J=3.6, 11.6 Hz), 3.92-4.02 (1H, m), 7.22 (1H, td, J=2.4, 7.3 Hz), 7.31-7.36 (2H, m), 7.47 (1H, m), 7.59 (2H, d, J=8.6 Hz), 7.96 (2H, d, J=8.6 Hz), 8.27 (2H, d, J=7.3 Hz), 12.84 (1H, brs).

HR-FAB⁺ (m/z): 456.1180 (+3.1 mmu).

Elemental analysis calcd (%) for $C_{23}H_{22}ClN_3O_3S$: C, 60.59; H, 4.86; N, 9.22; found: C, 60.48; H, 4.77; N, 8.93.

$[\alpha]^{27.8°}_D$ +128° (C=1.0, DMF)

HPLC (CHIRALCEL OJ (Daicel Chemical Industries, Co., Ltd.) φ 0.46×25 cm, mobile phase: hexane/ethanol=60/40 (0.1% TFA), flow rate: 1 mL/min, Temp.: 40° C.): Rt 17.2 min (99% ee)

Example 35

Methyl 2-[3-[(4'-chlorobiphenyl-4-yl)carbonylamino]piperidin-1-yl]benzoate

Step 35a) Methyl 2-[3-(tert-butoxycarbonylamino)piperidin-1-yl]benzoate

[Chemical formula 144]

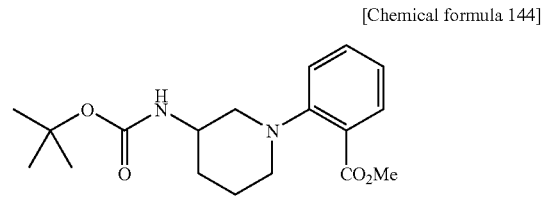

3-(tert-Butoxycarbonylamino)piperidine (7.07 g, 35.3 mmol) was dissolved in N,N-dimethylformamide (120 mL). To this solution, potassium carbonate (9.80 g, 70.9 mmol) and methyl 2-fluorobenzoate (5.0 mL, 39.2 mmol) were added and the mixture was stirred at 130° C. for 8 hours. Subsequently, the mixture was allowed to cool, diluted with ethyl acetate, and washed sequentially with water and brine. The washed product was dried over sodium sulfate and the solvent was evaporated. Purification of the resulting residue by silica gel column chromatography (hexane:ethyl acetate=10:1->5:1) gave 2.34 g (20%) of the desired compound as a yellow oil.

¹H NMR (400 MHz, CDCl₃) δ 1.46 (9H, s), 1.55-1.66 (2H, m), 1.74-1.85 (1H, m), 1.86-1.98 (1H, m), 2.84 (1H, t, J=9.8 Hz), 2.98 (1H, dd, J=11.6, 5.0 Hz), 3.01-3.10 (2H, m), 3.86-3.92 (1H, m), 3.94 (3H, s), 5.62 (1H, brs), 7.01-7.07 (2H, m), 7.41 (1H, t, J=8.6 Hz), 7.69 (1H, d, J=6.1 Hz).

Step 35b) Methyl 2-[3-[(4'-chlorobiphenyl-4-yl)carbonylamino]piperidin-1-yl]benzoate

[Chemical formula 145]

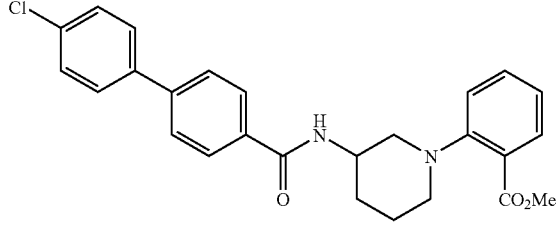

Methyl 2-[3-(tert-butoxycarbonylamino)piperidin-1-yl]benzoate (2.34 g, 7.00 mmol) was dissolved in anhydrous dichloromethane (50 mL). While this solution was ice-chilled and stirred, trifluoroacetic acid (5.2 mL, 6.82 mmol) was added and the mixture was stirred for 3 hours. Subsequently, the reaction mixture was concentrated and a 10% hydrochloric acid/methanol mixture (50 mL) was added to the residue. The mixture was stirred at room temperature for 1 hour and was concentrated. The same process was repeated 3 times and the resulting solid were washed with ethyl acetate. This gave 1.33 g of a colorless powder. This product (113 mg) was dissolved in N,N-dimethylformamide (4 mL). While the solution was chilled to 0° C. and stirred, 4'-chlorobiphenyl-4-carboxylic acid (103 mg, 0.443 mmol), 1-hydroxybenzotriazole monohydrate (63.8 mg, 0.417 mmol), N-methylmorpholine (160 µL, 1.46 mmol) and 3-(3-dimethylaminopropyl)-1-ethylcarbodiimide hydrochloride (78.0 mg, 0.407 mmol) were added. The mixture was stirred at 0° C. for 20 min and at room temperature for the following 6 hours. Subsequently, the reaction mixture was diluted with ethyl acetate. The organic layer washed sequentially with 5% aqueous citric acid, a saturated aqueous sodium bicarbonate solution, water and brine. The washed product was dried over anhydrous sodium sulfate and the solvent was concentrated. Purification of the resulting residue by silica gel column chromatography (hexane:ethyl acetate=3:1) gave 142 mg of the desired compound as colorless crystals.

$^1$H NMR (400 MHz, CDCl$_3$) δ 1.54-1.72 (2H, m), 1.95-2.08 (1H, m), 2.18-2.27 (1H, m), 2.89 (1H, dd, J=11.6, 2.4 Hz), 3.00 (1H, dd, J=11.6, 2.4 Hz), 3.23 (1H, d, J=11.6 Hz), 3.30 (1H, d, J=11.6 Hz), 3.87 (3H, s), 4.36-4.42 (1H, m), 7.08 (1H, t, J=8.6 Hz), 7.15 (1H, d, J=8.6 Hz), 7.42 (2H, d, J=8.6 Hz), 7.47 (1H, td, J=7.3, 1.8 Hz), 7.56 (2H, t, J=8.6 Hz), 7.62 (2H, d, J=8.6 Hz), 7.81 (1H, dd, J=7.3, 1.8 Hz), 8.14-8.23 (3H, m).

FAB$^+$ (m/z): 449 (M+H).

Example 36 Through Example 57

The processes were performed as in Example 15 or Example 35 to obtain compounds given in Table 6 below.

TABLE 6

| | Absolute configuration | Ar | Y | Binding position of carboxylic acid |
|---|---|---|---|---|
| Example 36 | Racemic mixture | 4-F-C$_6$H$_4$-O-C$_6$H$_4$- | CONH | Position 2 |
| Example 37 | Racemic mixture | benzothiazol-2-yl | CONH | Position 2 |
| Example 38 | S | benzothiazol-2-yl | CONH | Position 3 |
| Example 39 | S | 4'-Cl-biphenyl-3-yl | CONH | Position 3 |
| Example 40 | S | 5-(4-Cl-C$_6$H$_4$)-3-methylisoxazol-yl | CONH | Position 3 |
| Example 41 | S | 2-(4-Cl-C$_6$H$_4$)-thiazol-5-yl | CONH | Position 3 |
| Example 42 | S | 2-(4-Cl-C$_6$H$_4$)-4-Me-thiophen-5-yl | CONH | Position 3 |
| Example 43 | S | 2-(4-Cl-C$_6$H$_4$)-4,5-diMe-thiazol-yl | CONH | Position 3 |

TABLE 6-continued

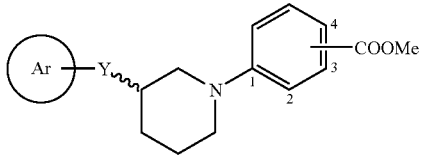

| | Absolute Configuration | Ar | Y | Binding position of COOMe |
|---|---|---|---|---|
| Example 44 | S | 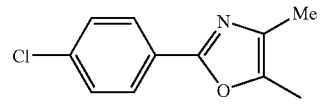 | CONH | Position 3 |
| Example 45 | S | 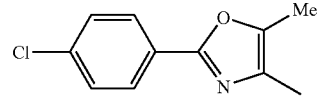 | CONH | Position 3 |
| Example 46 | S | 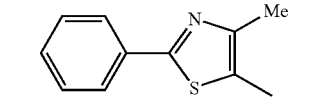 | CONH | Position 3 |
| Example 47 | S | 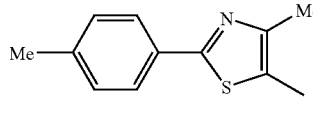 | CONH | Position 3 |
| Example 48 | S | 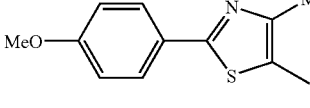 | CONH | Position 3 |
| Example 49 | S | 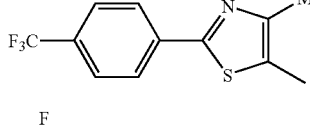 | CONH | Position 3 |
| Example 50 | S | 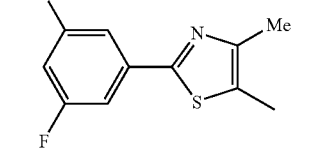 | CONH | Position 3 |

| | Absolute Configuration | Ar | Y | Binding position of COOMe |
|---|---|---|---|---|
| Example 51 | S | 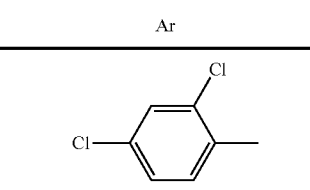 | CONH | Position 3 |
| Example 52 | S | 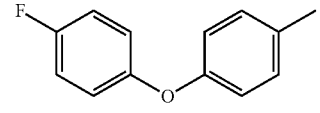 | CONH | Position 3 |
| Example 53 | S | 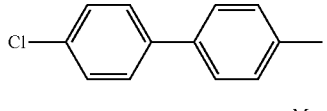 | CONH | Position 3 |
| Example 54 | Racemic mixture | 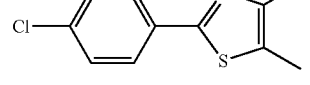 | 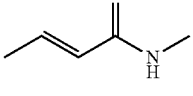 | Position 2 |

<Compound of Example 36>
Colorless Amorphous
$^1$H NMR (400 MHz, CDCl$_3$) δ 1.54-1.73 (2H, m), 1.90-2.09 (1H, m), 2.18-2.26 (1H, m), 2.90 (1H, dd, J=11.6, 2.4 Hz), 3.01 (1H, dd, J=11.6, 2.4 Hz), 3.24 (1H, d, J=11.6 Hz), 3.29 (1H, d, J=11.6 Hz), 3.88 (3H, s), 4.34-4.41 (1H, m), 6.97-7.13 (7H, m), 7.17 (1H, d, J=7.9 Hz), 7.50 (1H, t, J=7.9 Hz), 7.82 (1H, dd, J=7.9, 1.8 Hz), 8.07-8.15 (3H, m).
FAB$^+$ (m/z): 449 (M+H).

<Compound of Example 37>
Yellow Amorphous
$^1$H NMR (400 MHz, CDCl$_3$) δ 1.65-1.82 (2H, m), 1.95-2.06 (2H, m), 2.93 (1H, t, J=9.8 Hz), 3.14-3.21 (1H, m), 3.22-3.28 (2H, m), 4.02 (3H, s), 4.40-4.47 (1H, m), 7.05-7.12 (2H, m), 7.42-7.47 (1H, m), 7.48 (1H, dd, J=7.9, 1.2 Hz), 7.54 (1H, td, J=7.9, 1.2 Hz), 7.78 (1H, dd, J=7.9, 1.8 Hz), 7.98 (1H, d, J=6.1 Hz), 8.07 (1H, d, J=7.9 Hz), 8.39-8.42 (1H, m).
FAB$^+$ (m/z): 396 (M+H).

<Compound of Example 38>
Yellow Oil
$^1$H NMR (400 MHz, CDCl$_3$) δ 1.76-1.86 (2H, m), 1.93-2.02 (2H, m), 3.19 (1H, dd, J=12.2, 6.7 Hz), 3.23-3.31 (2H, m), 3.57 (1H, dd, J=12.2, 3.0 Hz), 3.91 (3H, s), 4.36-4.44 (1H, m), 7.21 (1H, dd, J=7.9, 1.2 Hz), 7.34 (1H, t, J=7.9 Hz), 7.46-7.52 (1H, m), 7.53-7.58 (2H, m), 7.64-7.67 (1H, m), 7.73 (1H, d, J=7.9 Hz), 7.98 (1H, d, J=7.9 Hz), 8.07 (1H, d, J=7.9 Hz).
FAB$^+$ (m/z): 396 (M+H).

<Compound of Example 39>
Colorless Powder
$^1$H NMR (400 MHz, CDCl$_3$) δ 1.75-1.97 (4H, m), 3.10-3.20 (1H, m), 3.29 (1H, dd, J=12.2, 5.5 Hz), 3.30-3.39 (1H, m), 3.44 (1H, dd, J=12.2, 3.1 Hz), 3.90 (3H, s), 4.40-4.50 (1H, m), 6.56 (1H, d, J=7.9 Hz), 7.18 (1H, d, J=7.9 Hz), 7.33 (1H, t, J=7.9 Hz), 7.42 (2H, d, J=8.6 Hz), 7.47-7.58 (4H, m), 7.64 (1H, s), 7.65-7.72 (2H, m), 7.97 (1H, s).
FAB$^+$ (m/z): 449 (M+H).

<Compound of Example 40>
Colorless Powder
$^1$H NMR (400 MHz, CDCl$_3$) δ 1.73-1.86 (2H, m), 1.87-1.98 (2H, m), 3.17 (1H, dd, J=12.2, 6.7 Hz), 3.20-3.29 (2H, m), 3.50 (1H, dd, J=12.2, 3.1 Hz), 3.91 (3H, s), 4.35-4.44 (1H, m), 6.97 (1H, s), 7.14-7.20 (2H, m), 7.33 (1H, t, J=7.9 Hz), 7.47 (2H, d, J=8.6 Hz), 7.55 (1H, d, J=7.9 Hz), 7.61-7.65 (1H, m), 7.73 (2H, d, J=8.6 Hz).
FAB$^+$ (m/z): 440 (M+H).
[α]$^{28.8}_D$ +39.9° (C=0.2, DMF)

<Compound of Example 41>
Pale Yellow Powder
$^1$H NMR (400 MHz, CDCl$_3$) δ 1.75-1.96 (4H, m), 3.10-3.18 (1H, m), 3.26 (1H, dd, J=12.2, 5.5 Hz), 3.30-3.39 (1H, m), 3.42 (1H, dd, J=12.2, 2.4 Hz), 3.91 (3H, s), 4.37-4.45 (1H, m), 6.39 (1H, d, J=7.9 Hz), 7.18 (1H, dd, J=7.9, 2.4 Hz), 7.34 (1H, t, J=7.9 Hz), 7.44 (2H, d, J=8.6 Hz), 7.57 (1H, d, J=7.9 Hz), 7.62-7.66 (1H, m), 7.89 (2H, d, J=8.6 Hz), 8.14 (1H, s).
FAB$^+$ (m/z): 456 (M+H).

<Compound of Example 42>
Colorless Powder
$^1$H NMR (400 MHz, CDCl$_3$) δ 1.75-1.95 (4H, m), 2.51 (3H, s), 3.05-3.14 (1H, m), 3.30 (1H, dd, J=12.2, 5.5 Hz), 3.33-3.42 (2H, m), 3.91 (3H, s), 4.35-4.45 (1H, m), 6.25-6.35 (1H, m), 7.07 (1H, s), 7.18 (1H, d, J=7.9 Hz), 7.28-7.37 (3H, m), 7.51 (2H, d, J=8.6 Hz), 7.56 (1H, d, J=7.9 Hz), 7.64 (1H, s).
FAB$^+$ (m/z): 469 (M+H).

<Compound of Example 43>
Pale Yellow Powder
$^1$H NMR (400 MHz, CDCl$_3$) δ 1.69-1.1.86 (2H, m), 1.88-2.02 (2H, m), 2.89 (3H, s), 3.08-3.24 (2H, m), 3.28-3.36 (1H, m), 3.60 (1H, dd, J=11.2, 3.1 Hz), 3.90 (3H, s), 4.27-4.37 (1H, m), 7.16-7.24 (1H, m), 7.31 (1H, t, J=8.0 Hz), 7.39 (2H, dd, J=6.7, 1.8 Hz), 7.52 (1H, d, J=7.3 Hz), 7.64-7.66 (1H, m), 7.76 (2H, dd, J=6.7, 1.8 Hz).
FAB$^+$ (m/z): 470 (M+H).

<Compound of Example 44>
Reddish Brown Solid
$^1$H NMR (400 MHz, CDCl$_3$) δ 1.75-1.85 (2H, m), 1.90-1.95 (2H, m), 2.58 (3H, s), 3.20-3.25 (2H, m), 3.25-3.35 (1H, m), 3.49 (1H, dd, J=12.2, 3.1 Hz), 3.92 (3H, s), 4.38 (1H, s), 6.57 (1H, d, J=8.0 Hz), 7.18 (1H, dd, J=8.4, 2.4 Hz), 7.33 (1H, t, J=7.9 Hz), 7.43 (2H, d, J=8.3 Hz), 7.55 (1H, d, J=7.4 Hz), 7.65 (1H, s), 7.94 (2H, d, J=8.6 Hz).
FAB$^+$ (m/z): 454 (M+H).

<Compound of Example 45>
Pale Yellow Powder
$^1$H NMR (400 MHz, CDCl$_3$) δ 1.66-1.84 (2H, m), 1.86-2.01 (2H, m), 2.74 (3H, s), 3.10 (1H, dd, J=12.9, 7.6 Hz), 3.16-3.22 (1H, m), 3.28-3.36 (1H, m), 3.90 (3H, s), 4.31 (1H, s), 7.20 (1H, d, J=8.0 Hz), 7.32 (1H, t, J=8.0 Hz), 7.43 (2H, dd, J=6.7, 1.8 Hz), 7.53 (1H, d, J=7.9 Hz), 7.63-7.65 (1H, m), 7.93 (2H, dd, J=6.8, 2.4 Hz)
FAB$^+$ (m/z): 453 (M+H).

<Compound of Example 46>
Colorless Powder
$^1$H NMR (400 MHz, CDCl$_3$) δ 1.75-1.94 (4H, m), 2.74 (3H, s), 3.04-3.14 (1H, m), 3.27-3.43 (3H, m), 3.91 (3H, s), 4.37-4.46 (1H, m), 6.25-6.36 (1H, m), 7.15-7.21 (1H, m), 7.34 (1H, t, J=8.0 Hz), 7.43-7.47 (3H, m), 7.57 (1H, d, J=7.3 Hz), 7.64 (1H, s), 7.91-7.95 (2H, m).
FAB$^+$ (m/z): 436 (M+H).

<Compound of Example 47>
Colorless Powder
$^1$H NMR (400 MHz, CDCl$_3$) δ 1.78-1.86 (4H, m), 2.40 (3H, s), 2.73 (3H, s), 3.07-3.12 (1H, m), 3.26-3.42 (3H, m), 3.91 (3H, s), 4.37-4.43 (1H, m), 6.27 (1H, d, J=8.0 Hz), 7.17 (1H, d, J=7.9 Hz), 7.24 (2H, d, J=8.0 Hz), 7.33 (1H, t, J=8.0 Hz), 7.56 (1H, d, J=7.3 Hz), 7.64 (1H, s), 7.82 (2H, dd, J=6.1, 1.8 Hz).
FAB$^+$ (m/z): 450 (M+H).

<Compound of Example 48>
Colorless Powder
$^1$H NMR (400 MHz, CDCl$_3$) δ 1.80-1.88 (4H, m), 2.71 (3H, s), 3.05-3.13 (1H, m), 3.28-3.42 (3H, m), 3.86 (3H, s), 3.91 (3H, s), 4.36-4.44 (1H, m), 6.95 (2H, dd, J=7.3, 1.8 Hz), 7.15-7.20 (1H, m), 7.34 (1H, t, J=8.0 Hz), 7.56 (1H, d, J=7.9 Hz), 7.64 (1H, s), 7.87 (2H, dd, J=6.7, 1.8 Hz).
FAB$^+$ (m/z): 466 (M+H).

<Compound of Example 49>
Yellow Powder
$^1$H NMR (400 MHz, CDCl$_3$) δ 1.78-1.97 (4H, m), 2.74 (3H, s), 3.34 (2H, d, J=3.6 Hz), 3.38-3.45 (1H, m), 3.91 (3H, s), 4.43-4.46 (1H, m), 6.35 (1H, d, J=7.9 Hz), 7.17 (1H, dd, J=8.5, 1.8 Hz), 7.34 (1H, t, J=8.0 Hz), 7.56 (1H, d, J=7.9 Hz), 7.63-7.67 (1H, m), 7.69 (2H, d, J=8.6 Hz), 8.04 (2H, d, J=8.0 Hz).
FAB$^+$ (m/z): 504 (M+H)

<Compound of Example 50>
Yellow Powder
$^1$H NMR (400 MHz, CDCl$_3$) δ 1.77-1.97 (4H, m), 2.72 (3H, s), 3.03-3.10 (1H, m), 3.34 (2H, d, J=4.3 Hz), 3.38-3.44 (1H, m), 3.91 (3H, s), 4.38-4.46 (1H, m), 6.34 (1H, d, J=7.9 Hz), 6.89 (1H, tt, J=8.6, 2.4 Hz), 7.17 (1H, dd, J=8.0, 1.8 Hz), 7.34 (1H, t, J=8.0 Hz), 7.44-7.48 (2H, m), 7.57 (1H, d, J=7.9 Hz), 7.62-7.65 (1H, m).

FAB+ (m/z): 472 (M+H).

<Compound of Example 51>
Colorless Powder
¹H NMR (400 MHz, CDCl₃) δ 1.74-1.96 (4H, m), 3.05 (1H, t, J=8.5 Hz), 3.32-3.38 (3H, m), 3.91 (3H, s), 4.41-4.46 (1H, m), 6.75 (1H, d, J=8.0 Hz), 7.15 (1H, dd, J=7.9, 1.8 Hz), 7.28-7.34 (2H, m), 7.41 (1H, d, J=1.8 Hz), 7.55 (1H, d, J=7.4 Hz), 7.60-7.63 (1H, m), 7.66 (1H, d, J=8.6 Hz).
FAB+ (m/z): 407 (M+H).

<Compound of Example 52>
Colorless Powder
¹H NMR (400 MHz, CDCl₃) δ 1.75-1.95 (4H, m), 3.06-3.16 (1H, m), 3.24-3.28 (1H, m), 3.31-3.44 (2H, m), 3.90 (3H, s), 4.38-4.46 (1H, m), 6.46 (1H, d, J=8.6 Hz), 6.96 (2H, dd, J=6.7, 2.4 Hz), 6.98-7.09 (4H, m), 7.15-7.19 (1H, m), 7.33 (1H, t, J=8.0 Hz), 7.54 (1H, d, J=8.0 Hz), 7.62-7.64 (1H, m), 7.73 (2H, d, J=9.2 Hz).
FAB+ (m/z): 449 (M+H).

<Compound of Example 53>
Colorless Powder
¹H NMR (400 MHz, CDCl₃) δ 1.78-1.98 (4H, m), 3.08-3.17 (1H, m), 3.23-3.43 (3H, m), 3.90 (3H, s), 4.44-4.50 (1H, m), 6.57 (1H, d, J=8.0 Hz), 7.17-7.21 (1H, m), 7.33 (1H, t, J=8.6 Hz), 7.43 (2H, dd, J=6.7, 1.8 Hz), 7.50-7.65 (3H, m), 7.61 (2H, dd, J=8.6, 1.8 Hz), 7.63-7.66 (1H, m), 7.83 (2H, d, J=8.4 Hz).
FAB+ (m/z): 449 (M+H).

<Compound of Example 54>
Pale Yellow Powder
¹H NMR (400 MHz, CDCl₃) δ 1.52-1.60 (1H, m), 1.64-1.69 (1H, m), 1.93-2.03 (1H, m), 2.09-2.13 (1H, m), 2.57 (3H, s), 2.85-2.91 (1H, m), 2.93-2.97 (1H, m), 3.08-3.15 (1H, m), 3.19-3.22 (1H, m), 3.94 (3H, s), 4.23-4.29 (1H, m), 6.37 (1H, d, J=15.3 Hz), 7.09 (1H, t, J=7.3 Hz), 7.13 (1H, d, J=8.6 Hz), 7.41 (2H, d, J=8.6 Hz), 7.47 (1H, td, J=7.3, 1.2 Hz), 7.70 (1H, d, J=6.7 Hz), 7.77 (1H, dd, J=7.3, 1.2 Hz), 7.79 (1H, d, J=15.3 Hz), 7.86 (2H, d, J=8.6 Hz).
FAB+ (m/z): 496 (M+H).

<Compound of Example 55>
Pale Yellow Powder
¹H NMR (400 MHz, CDCl₃) δ 1.76-1.92 (4H, m), 2.57 (3H, s), 3.07-3.12 (1H, m), 3.21 (1H, dd, J=11.6, 5.5 Hz), 3.30-3.38 (2H, m), 3.91 (3H, s), 4.33-4.41 (1H, m), 6.00 (1H, d, J=7.9 Hz), 6.12 (1H, d, J=15.3 Hz), 7.17 (1H, dd, J=7.9, 1.8 Hz), 7.33 (1H, t, J=7.9 Hz), 7.41 (2H, d, J=8.6 Hz), 7.55 (1H, d, J=7.3 Hz), 7.62-7.63 (1H, m), 7.80 (1H, d, J=15.3 Hz), 7.85 (2H, d, J=8.6 Hz).
FAB+ (m/z): 496 (M+H).

<Compound of Example 56>
Colorless Oil
¹H NMR (400 MHz, CDCl₃) δ 1.42-1.52 (1H, m), 1.53-1.57 (1H, m), 1.73-1.84 (1H, m), 1.96-2.00 (1H, m), 2.43 (3H, s), 2.62 (2H, t, J=7.3 Hz), 2.79 (1H, td, J=11.6, 2.4 Hz), 2.85-2.89 (1H, m), 3.03-3.06 (1H, m), 3.09-3.12 (1H, m), 3.15-3.23 (2H, m), 3.85 (3H, s), 4.10-4.15 (1H, m), 7.03-7.08 (2H, m), 7.35 (2H, d, J=8.6 Hz), 7.42 (1H, td, J=7.3, 1.2 Hz), 7.48 (1H, d, J=6.7 Hz), 7.74 (1H, dd, J=7.9, 1.8 Hz), 7.77 (2H, d, J=8.6 Hz).
FAB+ (m/z): 498 (M+H).

<Compound of Example 57>
Colorless Powder
¹H NMR (400 MHz, CDCl₃) δ 1.62-1.72 (4H, m), 2.41 (3H, s), 2.46-2.55 (2H, m), 2.98-3.04 (1H, m), 3.07 (1H, dd, J=11.6, 5.5 Hz), 3.13-3.17 (1H, m), 3.22-3.26 (2H, m), 3.90 (3H, s), 4.19-4.25 (1H, m), 5.81 (1H, d, J=7.9 Hz), 7.07 (1H, dd, J=7.9, 2.4 Hz), 7.24-7.28 (1H, m), 7.35 (2H, d, J=8.6 Hz), 7.52 (1H, d, J=7.9 Hz), 7.57 (1H, brs), 7.77 (2H, d, J=8.6 Hz).
FAB+ (m/z): 498 (M+H).

Example 58

Methyl 2-[3-[2-[2-(4-chlorophenyl)-4-methylthiazol-5-yl]acetylamino]piperidin-1-yl]benzoate

[Chemical formula 146]

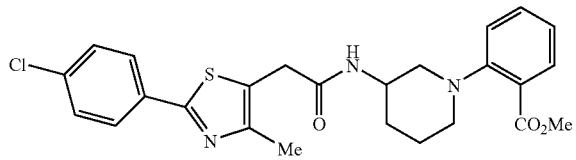

In an argon atmosphere, tri(dibenzylideneacetone)dipalladium (4.85 mg, 0.00530 mmol), 1,1'-bis(diphenylphosphino)ferrocene (9.09 mg, 0.0159 mmol) and cesium carbonate (48.2 mg, 0.148 mmol) were added to a toluene solution (1 mL) containing N-(piperidin-3-yl)-2-[2-(4-chlorophenyl)-4-methylthiazol-5-yl]acetamide (37.2 mg, 0.106 mmol) and methyl 2-iodobenzoate (27.8 mg, 0.106 mmol). This reaction mixture was stirred at 100° C. for 8 hours. Subsequently, the mixture was allowed to cool and was filtered through Celite. The filtrate was purified by silica gel column chromatography (hexane:ethyl acetate=2:1->1:1) to give 23.0 mg (45%) of the desired compound as a colorless oil.
¹H NMR (400 MHz, CDCl₃) δ 1.50 (1H, tt, J=13.5, 4.3 Hz), 1.60-1.65 (1H, m), 1.91 (1H, qt, J=13.5, 4.3 Hz), 2.02-2.05 (1H, m), 2.47 (3H, s), 2.84 (1H, td, J=11.6, 3.1 Hz), 2.90 (1H, dd, J=11.6, 2.4 Hz), 3.09-3.16 (2H, m), 3.79 (2H, s), 3.85 (3H, s), 4.13-4.18 (1H, m), 7.05 (1H, td, J=7.3, 1.2 Hz), 7.09 (1H, dd, J=7.3, 1.2 Hz), 7.37 (2H, d, J=8.6 Hz), 7.44 (1H, td, J=7.3, 1.8 Hz), 7.74 (1H, brs), 7.77 (1H, dd, J=7.9, 1.8 Hz), 7.81 (2H, d, J=8.6 Hz).
FAB+ (m/z): 484 (M+H).

Example 59

Methyl 3-[3-[[2-(4-chlorophenyl)-4-methylthiazol-5-yl]methylamino]piperidin-1-yl]benzoate Step 59a) Methyl 3-(3-aminopiperidin-1-yl)benzoate

[Chemical formula 147]

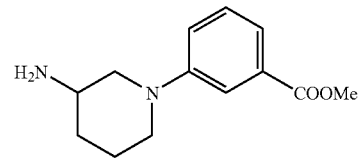

Trifluoroacetic acid (2 mL) was added to methyl 3-[3-(tert-butoxycarbonylamino)piperidin-1-yl]benzoate (451 mg, 1.35 mmol) in dichloromethane (2 mL). The reaction mixture was stirred at room temperature for 1 hour. Subsequently, the mixture was concentrated and a saturated aqueous sodium bicarbonate solution was added to the residue to make it basic. The mixture was extracted with ethyl acetate and the organic layer washed with brine and dried over magnesium sulfate.

Evaporation of the solvent gave 158 mg (50%) of the desired compound as a pale yellow oil.

$^1$H NMR (400 MHz, DMSO-$d_6$) δ 1.32-1.41 (1H, m), 1.53-1.63 (1H, m), 1.75-1.83 (1H, m), 1.86-1.92 (1H, m), 2.73 (1H, dd, J=12.2, 9.1 Hz), 2.78-2.84 (1H, m), 3.01-3.08 (1H, m), 3.47 (1H, td, J=12.2, 4.3 Hz), 3.62 (1H, dd, J=12.2, 3.1 Hz), 3.84 (3H, s), 7.20-7.25 (1H, m), 7.34-7.38 (2H, m), 7.46-7.47 (1H, m).

Step 59b) Methyl 3-[3-[[2-(4-chlorophenyl)-4-methylthiazol-5-yl]methylamino]piperidin-1-yl]benzoate

[Chemical formula 148]

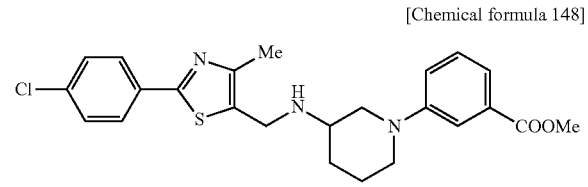

Acetic acid (0.0251 mL, 0.438 mmol) and sodium triacetoxyborohydride (97.7 mg, 0.438 mmol) were added to methyl 3-(3-aminopiperidin-1-yl)benzoate (79.0 mg, 0.337 mmol) and 2-(4-chlorophenyl)-4-methylthiazole-5-carboaldehyde (80.1 mg, 0.337 mmol) in tetrahydrofuran (5 mL). The reaction mixture was stirred at room temperature for 16 hours. Subsequently, a saturated aqueous sodium bicarbonate solution was added to make the mixture basic. The mixture was then extracted with ethyl acetate and the extract washed with brine, followed by drying over magnesium sulfate and evaporation of the solvent. Purification of the resulting residue by silica gel column chromatography (Chromatorex NH-DM2035 (Fuji Sylysia Chemical Co., Ltd.) hexane:ethyl acetate=5:1->2:1) gave 59.4 mg (39%) of the desired compound as a colorless oil.

$^1$H NMR (400 MHz, CDCl$_3$) δ 1.37-1.46 (1H, m), 1.65-1.75 (1H, m), 1.82-1.90 (1H, m), 1.94-2.01 (1H, m), 2.43 (3H, s), 2.79 (1H, dd, J=11.6, 7.9 Hz), 2.86-2.96 (2H, m), 3.43 (1H, td, J=12.2, 4.3 Hz), 3.60-3.64 (1H, m), 3.90 (3H, s), 4.01 (1H, d, J=14.7 Hz), 4.04 (1H, d, J=14.7 Hz), 7.11 (1H, dd, J=8.6, 1.8 Hz), 7.30 (1H, t, J=7.9 Hz), 7.38 (2H, d, J=8.6 Hz), 7.50 (1H, td, J=7.9, 1.2 Hz), 7.60-7.61 (1H, m), 7.83 (2H, d, J=8.6 Hz).

FAB$^+$ (m/z): 456 (M+H).

Example 60

Methyl 2-[3-[[2-(4-chlorophenyl)-4-methylthiazol-5-yl]methylamino]piperidin-1-yl]benzoate Step 60a) Methyl 2-(3-aminopiperidin-1-yl)benzoate

[Chemical formula 149]

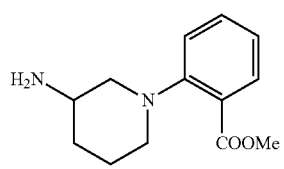

Using methyl 2-[3-(tert-butoxycarbonylamino)piperidin-1-yl]benzoate (246 mg, 0.736 mmol), the same procedure was followed as in Step 59a of Example 59 to give 91.6 mg (53%) of the desired compound as a brown oil.

$^1$H NMR (400 MHz, DMSO-$d_6$) δ 1.22-1.32 (1H, m), 1.52-1.62 (1H, m), 1.72-1.79 (1H, m), 1.85-1.91 (1H, m), 2.56 (1H, dd, J=11.0, 9.1 Hz), 2.69 (1H, td, J=11.6, 2.4 Hz), 2.96-3.02 (1H, m), 3.07 (1H, td, J=11.6, 4.3 Hz), 3.21 (1H, dd, J=11.0, 3.7 Hz), 3.82 (3H, s), 7.01 (1H, td, J=7.3, 1.2 Hz), 7.09 (1H, d, J=7.9 Hz), 7.45 (1H, td, J=7.3, 1.8 Hz), 7.58 (1H, dd, J=7.9, 1.8 Hz).

Step 60b) Methyl 2-[3-[[2-(4-chlorophenyl)-4-methylthiazol-5-yl]methylamino]piperidin-1-yl]benzoate

[Chemical formula 150]

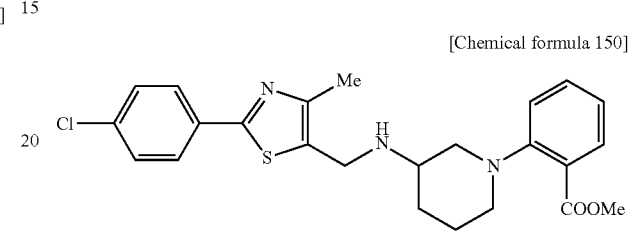

Using methyl 2-(3-aminopiperidin-1-yl)benzoate (45.8 mg, 0.195 mmol), the same procedure was followed as in Step 59b of Example 59 to give 22.2 mg (25%) of the desired compound as a colorless oil.

$^1$H NMR (400 MHz, CDCl$_3$) δ 1.42-1.50 (1H, m), 1.56-1.76 (2H, m), 1.82-1.92 (1H, m), 2.40 (3H, s), 2.71-2.78 (1H, m), 2.82-2.88 (1H, m), 2.91-2.99 (1H, m), 3.06-3.11 (1H, m), 3.30-3.34 (1H, m), 3.86 (3H, s), 3.98 (2H, brs), 6.99 (1H, t, J=7.3 Hz), 7.04 (1H, d, J=8.6 Hz), 7.37 (2H, d, J=8.6 Hz), 7.40-7.42 (1H, m), 7.71 (1H, dd, J=7.3, 1.2 Hz), 7.82 (2H, d, J=8.6 Hz).

FAB$^+$ (m/z): 456 (M+H).

Example 61

Methyl 2-[3-[(4'-chlorobiphenyl-4-yl)carbonylaminomethyl]piperidin-1-yl]benzoate Step 61a)
2-[3-(Hydroxymethyl)piperidin-1-yl]benzaldehyde

[Chemical formula 151]

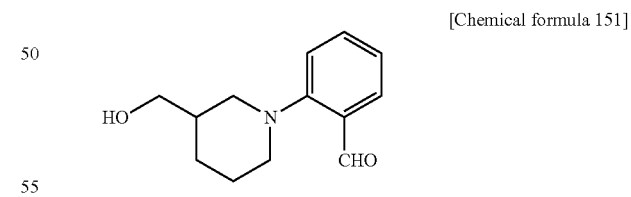

2-Fluorobenzaldehyde (3.26 mL, 30.0 mmol), potassium carbonate (5.64 g, 40.0 mmol) and tetrabutylammonium iodide (739 mg, 2.00 mmol) were added to 3-piperidylmethanol (2.30 g, 20.0 mmol) in N,N-dimethylformamide (20 mL). The reaction mixture was stirred at 130° C. for 8 hours. Subsequently, water was added and the mixture was extracted with ethyl acetate. The extract was washed with brine, followed by drying over magnesium sulfate and evaporation of the solvent. Purification of the resulting residue by silica gel column chromatography (hexane:ethyl acetate=5:1->1:1) gave 1.56 g (36%) of the desired compound as a yellow oil.

$^1$H NMR (400 MHz, CDCl$_3$) δ 1.17-1.27 (1H, m), 1.42 (1H, brs), 1.74-1.90 (3H, m), 1.99-2.09 (1H, m), 2.72 (1H, dd, J=11.6, 9.8 Hz), 2.84-2.90 (1H, m), 3.19-3.24 (1H, m), 3.36-3.40 (1H, m), 3.56-3.67 (2H, m), 7.09 (1H, t, J=7.3 Hz), 7.12 (1H, d, J=8.6 Hz), 7.48-7.53 (1H, m), 7.80 (1H, dd, J=7.3, 1.8 Hz), 10.29 (1H, s).

Step 61b) Methyl 2-[3-(hydroxymethyl)piperidin-1-yl]benzoate

[Chemical formula 152]

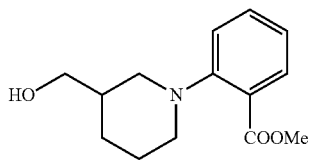

2-[3-(Hydroxymethyl)piperidin-1-yl]benzaldehyde (1.56 g, 7.11 mmol) was reacted as in Step 5d of Example 5 to obtain 1.29 g (73%) of the desired compound as a pale yellow oil.

$^1$H NMR (400 MHz, CDCl$_3$) δ 1.31-1.40 (1H, m), 1.66-1.80 (2H, m), 1.86-2.01 (2H, m), 2.27 (1H, brs), 2.81 (1H, dd, J=11.6, 7.3 Hz), 2.84-2.90 (1H, m), 3.05-3.10 (1H, m), 3.26 (1H, dd, J=11.6, 3.7 Hz), 3.64-3.73 (2H, m), 3.90 (3H, s), 6.99 (1H, td, J=7.9, 1.2 Hz), 7.06 (1H, d, J=7.9 Hz), 7.40 (1H, td, J=7.3, 1.8 Hz), 7.71 (1H, dd, J=7.3, 1.8 Hz).

Step 61c) N-[[1-[2-(Methoxycarbonyl)phenyl]piperidin-3-yl]methyl]phthalimide

[Chemical formula 153]

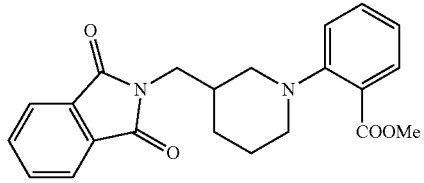

Triphenylphosphine (1.68 g, 6.20 mmol) and phthalimide (799 mg, 5.43 mmol) were added to methyl 2-[3-(hydroxymethyl)piperidin-1-yl]benzoate (1.29 g, 5.17 mmol) in tetrahydrofuran (10 mL). The reaction mixture was stirred at room temperature for 10 min and a 40% diethyl azodicarboxylate/toluene solution (3.52 mL, 7.76 mmol) was added. The mixture was then stirred at room temperature for 8 hours. Subsequently, water was added and the mixture was extracted with ethylacetate. The extract was washed with brine, followed by drying over magnesium sulfate and evaporation of the solvent. Purification of the resulting residue by silica gel column chromatography (hexane:ethyl acetate=20:1->5:1) gave 1.85 g (95%) of the desired compound as a pale yellow oil.

$^1$H NMR (400 MHz, CDCl$_3$) δ 1.14-1.24 (1H, m), 1.67-1.78 (1H, m), 1.80-1.88 (2H, m), 2.21-2.32 (1H, m), 2.59 (1H, dd, J=11.6, 9.8 Hz), 2.72 (1H, td, J=11.6, 2.4 Hz), 3.19-3.26 (2H, m), 3.58 (1H, dd, J=14.1, 7.9 Hz), 3.71 (1H, dd, J=13.4, 6.7 Hz), 3.80 (3H, s), 6.95 (1H, td, J=7.3, 1.2 Hz), 7.01 (1H, d, J=8.6 Hz), 7.37 (1H, td, J=7.3, 1.8 Hz), 7.64 (1H, dd, J=7.3, 1.8 Hz), 7.69-7.74 (2H, m), 7.83-7.87 (2H, m).

Step 61d) Methyl 2-[3-(aminomethyl)piperidin-1-yl]benzoate

[Chemical formula 154]

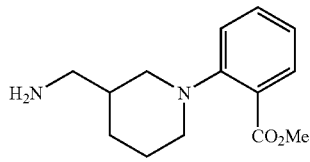

N-[[1-[2-(Methoxycarbonyl)phenyl]piperidin-3-yl]methyl]phthalimide (495 mg, 1.31 mmol) was dissolved in methanol (10 mL). To this solution, hydrazine monohydrate (190 μL) was added and the mixture was refluxed for 3 hours. Subsequently, the reaction mixture was diluted with water and extracted with ethylacetate. The organic layer washed with brine and dried over anhydrous sodium sulfate. Evaporation of the solvent gave 253 mg (78%) of the desired compound as an orange oil.

$^1$H NMR (400 MHz, CDCl$_3$) δ 1.04-1.15 (1H, m), 1.66-1.90 (4H, m), 2.47 (1H, dd, J=11.6, 9.2 Hz), 2.65 (2H, d, J=5.5 Hz), 2.66-2.75 (1H, m), 3.24 (1H, d, J=11.6 Hz), 3.37 (1H, dt, J=11.6, 1.8 Hz), 3.89 (3H, s), 6.96 (1H, td, J=7.3, 1.8 Hz), 7.04 (1H, d, J=7.3 Hz), 7.38 (1H, td, J=7.3, 1.8 Hz), 7.69 (1H, dd, J=7.3, 1.8 Hz).

Step 61e) Methyl 2-[3-[(4'-chlorobiphenyl-4-yl)carbonylaminomethyl]piperidin-1-yl]benzoate

[Chemical formula 155]

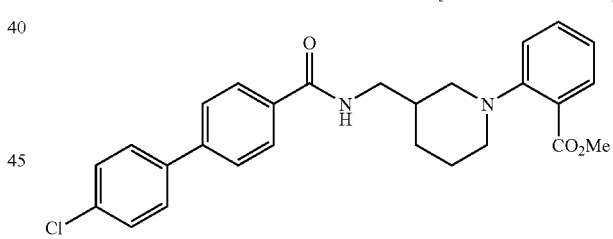

Methyl 2-[3-(aminomethyl)piperidin-1-yl]benzoate (78.2 mg, 0.315 mmol) was dissolved in N,N-dimethylformamide (3 mL) and the solution was chilled to 0° C. While this solution was stirred, 4'-chlorobiphenyl-4-carboxylic acid (81.1 mg, 0.349 mmol), 1-hydroxybenzotriazole monohydrate (54.1 mg, 0.353 mmol), N-methylmorpholine (90 μL, 0.819 mmol) and 3-(3-dimethylaminopropyl)-1-ethylcarbodiimide hydrochloride (64.6 mg, 0.337 mmol) were added and the mixture was stirred for 20 min. The reaction mixture was then stirred at room temperature for 12 hours. Subsequently, the mixture was extracted with ethyl acetate and the organic layer washed sequentially with 5% aqueous citric acid, a saturated aqueous sodium bicarbonate solution, water and brine. The washed product was dried over anhydrous sodium sulfate and the solvent was concentrated. Purification of the resulting residue by silica gel column chromatography (hexane:ethyl acetate=2:1) gave 111 mg (76%) of the desired compound as a colorless powder.

$^1$H NMR (400 MHz, CDCl$_3$) δ 1.34-1.45 (1H, m), 1.67-1.90 (3H, m), 2.08-2.23 (1H, m), 2.75 (1H, t, J=8.6 Hz), 2.86 (1H, t, J=10.4 Hz), 3.12-3.20 (1H, m), 3.24 (1H, d, J=10.4 Hz), 3.48-3.60 (2H, m), 3.84 (3H, s), 6.66-6.80 (1H, m), 7.01 (1H, t, J=7.9 Hz), 7.10 (1H, d, J=7.9 Hz), 7.38-7.45 (3H, m), 7.53 (2H, d, J=8.6 Hz), 7.60 (2H, d, J=8.6 Hz), 7.71 (1H, d, J=6.1 Hz), 7.88 (2H, d, J=8.6 Hz).

FAB$^+$ (m/z): 463 (M+H).

Example 62

Methyl 3-[3-[(4'-chlorobiphenyl-4-yl)carbonylaminomethyl]piperidin-1-yl]benzoate Step 62a) Methyl 3-[3-(hydroxymethyl)piperidin-1-yl]benzoate

[Chemical formula 156]

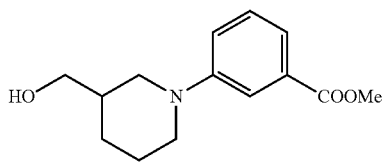

Copper(II) acetate (5.85 g, 30.6 mmol) and triethylamine (4.28 mL, 30.6 mmol) were added to 3-(tert-butyldimethylsilyloxymethyl)piperidine (3.50 g, 15.3 mmol) and 3-(methoxycarbonyl)phenylboric acid (5.51 g, 30.6 mmol) in dichloromethane (150 mL). The reaction mixture was stirred at room temperature for 48 hours. Subsequently, ethyl acetate and a saturated aqueous sodium bicarbonate solution were added and the mixture was stirred for 30 min and was filtered through Celite. The organic layer was collected and washed with brine. The washed product was then dried over magnesium sulfate and the solvent was evaporated. Purification of the resulting residue by silica gel column chromatography (hexane:ethyl acetate=50:1->10:1) gave 4.81 g of a pale yellow oil. This oil product (4.81 g) was dissolved in a 1:1:1 mixture of acetic acid, tetrahydrofuran and water (50 mL) and the solution was stirred for 6 hours while refluxed. The mixture was then allowed to cool and the solvent was evaporated. Water was added to the residue and the mixture was extracted with ethyl acetate. The extract was washed with brine, followed by drying over magnesium sulfate and evaporation of the solvent. Purification of the resulting residue by silica gel column chromatography (hexane:ethyl acetate=10:1->1:1) gave 1.33 g (40%) of the desired compound as a colorless oil.

$^1$H NMR (400 MHz, CDCl$_3$) δ 1.16-1.25 (1H, m), 1.47 (1H, brs), 1.66-1.76 (1H, m), 1.80-1.86 (2H, m), 1.88-1.98 (1H, m), 2.62 (1H, dd, J=11.6, 10.4 Hz), 2.80 (1H, td, J=11.6, 2.4 Hz), 3.57-3.67 (3H, m), 3.72-3.76 (1H, m), 3.90 (3H, s), 7.14 (1H, dd, J=7.9, 2.4 Hz), 7.30 (1H, t, J=7.9 Hz), 7.48 (1H, d, J=7.3 Hz), 7.61-7.62 (1H, m).

Step 62b) N-[[1-[3-(Methoxycarbonyl)phenyl]piperidin-3-yl]methyl]phthalimide

[Chemical formula 157]

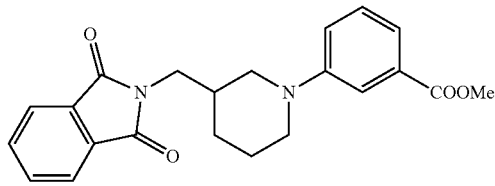

Using methyl 3-[3-(hydroxymethyl)piperidin-1-yl]benzoate (1.33 g, 5.33 mmol), the same procedure was followed as in Step 61c of Example 61 to give 1.91 g (95%) of the desired compound as a colorless powder.

$^1$H NMR (400 MHz, CDCl$_3$) δ 1.20-1.30 (1H, m), 1.61-1.72 (1H, m), 1.80-1.89 (2H, m), 2.16-2.27 (1H, m), 2.67 (1H, dd, J=12.2, 9.8 Hz), 2.81 (1H, td, J=11.6, 2.4 Hz), 3.51-3.58 (2H, m), 3.67 (1H, dd, J=14.1, 7.3 Hz), 3.71 (1H, dd, J=14.1, 7.3 Hz), 3.89 (3H, s), 7.09 (1H, dd, J=7.9, 1.8 Hz), 7.29 (1H, t, J=8.6 Hz), 7.48 (1H, d, J=7.9 Hz), 7.58-7.59 (1H, m), 7.72-7.74 (2H, m), 7.86-7.88 (2H, m).

Step 62c) Methyl 3-[3-(aminomethyl)piperidin-1-yl]benzoate

[Chemical formula 158]

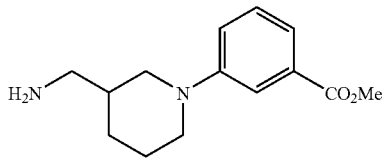

Using N-[[1-[3-(methoxycarbonyl)phenyl]piperidin-3-yl]methyl]phthalimide (533 mg, 1.41 mmol), the same procedure was followed as in Step 61d of Example 61 to give 237 mg (68%) of the desired compound as a colorless oil.

$^1$H NMR (400 MHz, CDCl$_3$) δ 1.05-1.17 (1H, m), 1.63-1.93 (4H, m), 2.49 (1H, dd, J=12.2, 10.4 Hz), 2.68 (2H, d, J=6.7 Hz), 2.75 (1H, td, J=11.6, 3.1 Hz), 3.64 (1H, d, J=12.2 Hz), 3.72 (1H, dd, J=11.6, 1.8 Hz), 3.90 (3H, s), 7.14 (1H, dd, J=7.9, 1.8 Hz), 7.29 (1H, t, J=7.9 Hz), 7.47 (1H, dd, J=6.1, 1.8 Hz), 7.58-7.63 (1H, m).

FAB⁺ (m/z): 249 (M+H).

Step 62d) Methyl 3-[3-[(4'-chlorobiphenyl-4-yl)carbonylaminomethyl]piperidin-1-yl]benzoate

[Chemical formula 159]

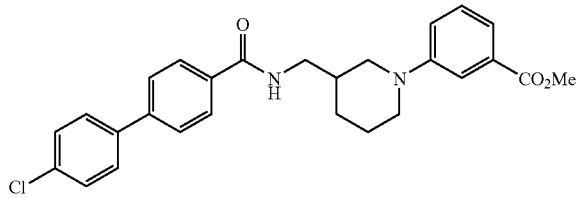

Using methyl 3-[3-(aminomethyl)piperidin-1-yl]benzoate (76.2 mg, 0.307 mmol) and 4'-chlorobiphenyl-4-carboxylic acid (77.2 mg, 0.332 mmol), the same procedure was followed as in Step 61e of Example 61 to give 117 mg (82%) of the desired compound as a pale yellow powder.

$^1$H NMR (400 MHz, CDCl$_3$) δ 1.24-1.35 (1H, m), 1.66-1.78 (1H, m), 1.82-1.97 (2H, m), 2.00-2.13 (1H, m), 2.69 (1H, t, J=12.2 Hz), 2.85 (1H, t, J=12.2 Hz), 3.50 (2H, t, J=6.1 Hz), 3.58 (1H, d, J=12.2 Hz), 3.65 (1H, d, J=12.2 Hz), 3.89 (3H, s), 6.25-6.40 (1H, m), 7.12 (1H, d, J=8.6 Hz), 7.30 (1H, t, J=8.6 Hz), 7.43 (2H, d, J=8.6 Hz), 7.51 (1H, d, J=6.1 Hz), 7.54 (2H, d, J=8.6 Hz), 7.61 (1H, s), 7.63 (2H, d, J=8.6 Hz), 7.86 (2H, d, J=8.6 Hz).

FAB⁺ (m/z): 463 (M+H).

Examples 63 Through 66

The procedures were performed in the same manner as in Example 61 or Example 62 to make compounds given in Table 7 below.

TABLE 7

| | Ar | Binding position of COOMe |
|---|---|---|
| Example 63 | 4-F-C₆H₄-O-C₆H₄-(4-Me) | Position 2 |
| Example 64 | 2-benzothiazolyl | Position 2 |
| Example 65 | 4-F-C₆H₄-O-C₆H₄-(4-Me) | Position 3 |

TABLE 7-continued

| | Ar | Binding position of COOMe |
|---|---|---|
| Example 66 | 2-benzothiazolyl | Position 3 |

<Compound of Example 63>

Colorless Solid $^1$H NMR (400 MHz, CDCl$_3$) δ 1.30-1.45 (1H, m), 1.70-1.95 (3H, m), 2.05-2.19 (1H, m), 2.68-2.76 (1H, m), 2.80-2.88 (1H, m), 3.12-3.25 (2H, m), 3.38-3.56 (2H, m), 3.84 (3H, s), 6.62 (1H, brs), 6.95 (2H, d, J=8.6 Hz), 6.97-7.12 (6H, m), 7.41 (1H, t, J=7.3 Hz), 7.69 (1H, d, J=7.3 Hz), 7.78 (2H, d, J=8.6 Hz).

FAB⁺ (m/z): 463 (M+H).

<Compound of Example 64>

Yellow Amorphous $^1$H NMR (400 MHz, CDCl$_3$) δ 1.26-1.37 (1H, m), 1.74-1.94 (3H, m), 2.13-2.25 (1H, m), 2.67 (1H, t, J=8.6 Hz), 2.81 (1H, t, J=8.6 Hz), 3.18-3.25 (1H, m), 3.30 (1H, d, J=10.4 Hz), 3.52 (2H, t, J=6.8 Hz), 4.11 (3H, s), 6.97 (1H, t, J=7.9 Hz), 7.06 (1H, d, J=8.6 Hz), 7.40 (1H, td, J=7.9, 1.2 Hz), 7.49 (1H, td, J=7.9, 1.2 Hz), 7.55 (1H, td, J=7.9, 1.2 Hz), 7.67 (1H, brs), 7.73 (1H, dd, J=7.9, 1.2 Hz), 7.97 (1H, d, J=7.9 Hz), 8.04 (1H, d, J=7.9 Hz).

FAB⁺ (m/z): 410 (M+H).

<Compound of Example 65>

Colorless Amorphous $^1$H NMR (400 MHz, CDCl$_3$) δ 1.26-1.30 (1H, m), 1.65-1.78 (1H, m), 1.80-1.95 (2H, m), 2.00-2.10 (1H, m), 2.67 (1H, t, J=9.8 Hz), 2.84 (1H, t, J=11.6 Hz), 3.64 (2H, t, J=6.7 Hz), 3.54-3.67 (2H, m), 3.89 (3H, s), 6.15-6.25 (1H, m), 6.98 (2H, d, J=8.6 Hz), 6.95-7.15 (5H, m), 7.29 (1H, t, J=7.9 Hz), 7.49 (1H, d, J=7.9 Hz), 7.60 (1H, s), 7.75 (2H, d, J=8.6 Hz).

FAB⁺ (m/z): 463 (M+H).

<Compound of Example 66>

Colorless Amorphous $^1$H NMR (400 MHz, CDCl$_3$) δ 1.27-1.37 (1H, m), 1.67-1.78 (1H, m), 1.83-1.92 (1H, m), 1.93-2.00 (1H, m), 2.05-2.18 (1H, m), 2.69 (1H, t, J=11.0 Hz), 2.83 (1H, t, J=11.0 Hz), 3.45-3.63 (2H, m), 3.59 (1H, d, J=12.2 Hz), 3.68 (1H, d, J=12.2 Hz), 3.88 (3H, s), 7.13 (1H, d, J=6.1 Hz), 7.30 (1H, t, J=7.3 Hz), 7.46-7.64 (5H, m), 7.99 (1H, d, J=7.3 Hz), 8.08 (1H, d, J=7.3 Hz).

FAB⁺ (m/z): 410 (M+H).

Example 67

Methyl 2-[3-[N-[(4'-chlorobiphenyl-4-yl)methyl]carbamoyl]piperidin-1-yl]benzoate

Step 67a) Benzyl 1-[2-(methoxycarbonyl)phenyl]nipecotate

[Chemical formula 160]

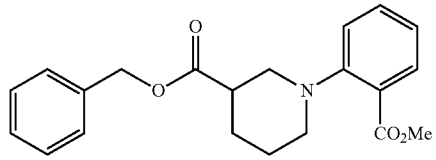

Using benzyl nipecotate (5.90 g, 26.9 mmol) and methyl 2-fluorobenzoate (3.70 mL, 29.0 mmol), the same procedure was followed as in Step 1c of Example 1 to give 1.64 g (17%) of the desired compound as a colorless oil.

¹H NMR (400 MHz, CDCl₃) δ 1.54-1.65 (1H, m), 1.67-1.87 (2H, m), 2.07-2.16 (1H, m), 2.73 (1H, td, J=11.6, 3.1 Hz), 2.80-2.94 (2H, m), 3.25 (1H, d, J=11.6 Hz), 3.52 (1H, d, J=11.6 Hz), 3.84 (3H, s), 5.12 (2H, s), 6.98 (1H, t, J=7.3 Hz), 7.04 (1H, d, J=7.3 Hz), 7.29-7.42 (5H, m), 7.70 (1H, dd, J=7.3, 1.8 Hz).

Step 67b) 1-[2-(Methoxycarbonyl)phenyl]nipecotic acid

[Chemical formula 161]

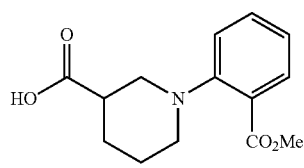

1-[2-(Methoxycarbonyl)phenyl]benzyl nipecotate (1.64 g, 4.64 mmol) was dissolved in methanol (40 mL). To this solution, 10% palladium on activated carbon (169 mg) and 1,4-cyclohexadiene (0.65 mL, 6.98 mmol) were added in an argon atmosphere and the mixture was stirred at room temperature for 8 hours. Subsequently, the mixture was filtered and the solvent evaporated. Purification of the resulting residue by silica gel column chromatography (hexane:ethyl acetate=5:1->1:2) gave 510 mg (42%) of the desired compound as a yellow oil.

¹H NMR (400 MHz, DMSO-d₆) δ 1.40-1.63 (2H, m), 1.70-1.74 (1H, m), 1.90-2.00 (1H, m), 2.48-2.60 (2H, m), 2.65-2.73 (1H, m), 2.77 (1H, t, J=11.6 Hz), 3.11 (1H, d, J=11.6 Hz), 3.79 (3H, s), 7.00 (1H, t, J=7.3 Hz), 7.10 (1H, d, J=7.3 Hz), 7.43 (1H, td, J=7.3, 1.8 Hz), 7.55 (1H, dd, J=7.3, 1.8 Hz), 12.27 (1H, brs).

Step 67c) Methyl 2-[3-[N-[(4'-chlorobiphenyl-4-yl)methyl]carbamoyl]piperidin-1-yl]benzoate

[Chemical formula 162]

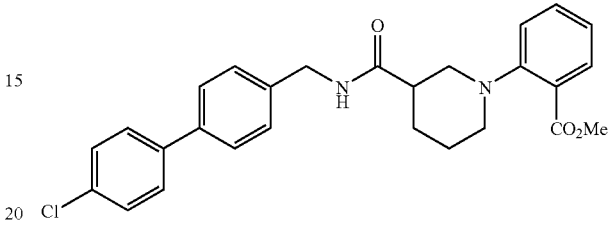

Using 1-[2-(methoxycarbonyl)phenyl]nipecotic acid (77.5 mg, 0.294 mmol) and (4'-chlorobiphenyl-4-yl)methylamine hydrochloride (72.2 mg, 0.284 mmol), the same procedure was followed as in Step 3a of Example 3 to give 114 mg (87%) of the desired compound as a colorless amorphous product.

¹H NMR (400 MHz, CDCl₃) δ 1.57-1.77 (2H, m), 1.85-2.13 (2H, m), 2.67 (1H, t, J=11.6 Hz), 2.75-2.81 (1H, m), 3.08-3.20 (2H, m), 3.36 (1H, d, J=11.6 Hz), 3.74 (3H, s), 4.48 (1H, dd, J=15.3, 5.5 Hz), 4.56 (1H, dd, J=15.3, 5.5 Hz), 7.05-7.15 (2H, m), 7.30-7.50 (9H, m), 7.79 (1H, dd, J=7.9, 1.8 Hz), 8.71 (1H, brs).

FAB⁺ (m/z): 463 (M+H).

Example 68

Methyl 3-[3-[N-[(4'-chlorobiphenyl-4-yl)methyl]carbamoyl]piperidin-1-yl]benzoate

Step 68a) 1-[3-(Methoxycarbonyl)phenyl]benzyl nipecotate

[Chemical formula 163]

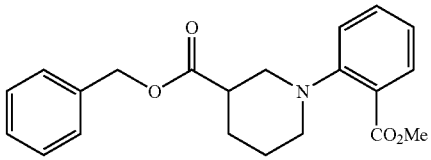

Using benzyl nipecotate (4.39 g, 20.0 mmol) and 3-methoxycarbonylphenylboric acid (7.20 g, 40.0 mmol), the same procedure was followed as in Example 2 to give 2.34 g (33%) of the desired compound as a colorless oil.

¹H NMR (400 MHz, CDCl₃) δ 1.55-1.79 (2H, m), 1.80-1.87 (1H, m), 2.00-2.10 (1H, m), 2.71-2.77 (1H, m), 2.86-2.94 (1H, m), 3.14 (1H, t, J=11.0 Hz), 3.48-3.52 (1H, m), 3.74

(1H, dd, J=12.3, 3.7 Hz), 3.90 (3H, s), 5.16 (2H, s), 7.11 (1H, dd, J=7.3, 1.8 Hz), 7.26-7.37 (6H, m), 7.50 (1H, d, J=7.3 Hz), 7.58-7.62 (1H, m).

Step 68b) 1-[3-(Methoxycarbonyl)phenyl]nipecotic acid

[Chemical formula 164]

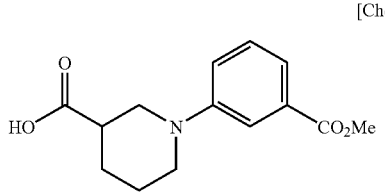

In an argon atmosphere, 10% palladium on activated carbon (234 mg) and ammonium formate (1.66 g, 26.4 mmol) were added to 1-[3-(methoxycarbonyl)phenyl]benzyl nipecotate (2.34 g, 6.60 mmol) in methanol (50 mL). The reaction mixture was stirred at room temperature for 4 hours. Subsequently, the mixture was filtered through Celite and the filtrate was concentrated. 5% aqueous citric acid was added to the residue and the mixture was extracted with ethyl acetate. The organic layer was then washed with brine and was dried over sodium sulfate. The solvent was evaporated to give 1.57 g (90%) of the desired compound as a pale reddish brown powder.

$^1$H NMR (400 MHz, DMSO-$d_6$) δ 1.54-1.62 (2H, m), 1.69-1.75 (1H, m), 1.86-1.96 (1H, m), 2.51-2.60 (1H, m), 2.81-2.90 (1H, m), 3.01 (1H, dd, J=12.2, 9.2 Hz), 3.47 (1H, d, J=11.7 Hz), 3.66 (1H, dd, J=12.8, 3.7 Hz), 3.84 (3H, s) 7.21-7.25 (1H, m), 7.34-7.38 (2H, m), 7.45-7.47 (1H, m), 12.39 (1H, brs).

EI$^+$ (m/z): 263 (M+).

Step 68c) Methyl 3-[3-[N-[(4'-chlorobiphenyl-4-yl)methyl]carbamoyl]piperidin-1-yl]benzoate

[Chemical formula 165]

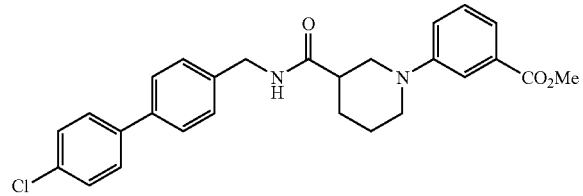

Using 1-[3-(methoxycarbonyl)phenyl]nipecotic acid (108 mg, 0.410 mmol) and (4'-chlorobiphenyl-4-yl)methylamine hydrochloride (95.0 mg, 0.374 mmol), the same procedure was followed as in Step 3a of Example 3 to give 120 mg (69%) of the desired compound as colorless crystals.

$^1$H NMR (400 MHz, CDCl$_3$) δ 1.68-1.78 (1H, m), 1.82-1.96 (3H, m), 2.59-2.65 (1H, m), 3.08-3.15 (1H, m), 3.26-3.35 (2H, m), 3.48 (1H, dd, J=12.2, 3.6 Hz), 3.89 (3H, s), 4.48-4.55 (2H, m), 6.73-6.81 (1H, m), 7.12 (1H, dd, J=7.9, 2.4 Hz), 7.30 (1H, t, J=7.9 Hz), 7.34 (2H, d, J=7.9 Hz), 7.40 (2H, d, J=8.6 Hz), 7.47-7.54 (4H, m), 7.55 (1H, d, J=7.3 Hz), 7.62 (1H, s).

FAB$^+$ (m/z): 463 (M+H).

Example 69

Step 69a) 1-(tert-Butoxycarbonyl)-N-[2-(4-chlorophenyl)-4-methylthiazol-5-yl]piperidine-3-carboxamide

[Chemical formula 166]

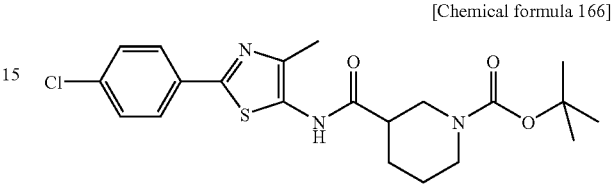

Using 5-amino-2-(4-chlorophenyl)-4-methylthiazole (197 mg, 0.877 mmol) and 1-(tert-butoxycarbonyl)nipecotic acid (205 mg, 0.877 mmol), the same procedure was followed as in Step 3a of Example 3 to give 115 mg (30%) of the desired compound as a yellow powder.

$^1$H NMR (400 MHz, CDCl$_3$) δ 1.45 (9H, s), 1.53-1.61 (2H, m), 1.66-1.76 (1H, m), 1.84-1.92 (1H, m), 2.21-2.33 (1H, m), 2.50 (3H, s), 2.66-2.71 (1H, m), 3.35-3.44 (1H, m), 3.45-3.55 (1H, m), 3.60-3.63 (1H, m), 3.83-3.97 (1H, m), 7.37 (2H, d, J=8.6 Hz), 7.82 (2H, d, J=8.6 Hz).

FAB$^+$ (m/z): 436 (M+H).

Step 69b) N-[2-(4-Chlorophenyl)-4-methylthiazol-5-yl]piperidine-3-carboxamide

[Chemical formula 167]

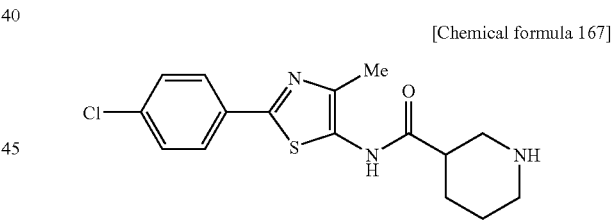

Using 1-(tert-butoxycarbonyl)-N-[2-(4-chlorophenyl)-4-methylthiazol-5-yl]piperidine-3-carboxamide (115 mg, 0.264 mmol), the same procedure was followed as in Step 1b of Example 1 to give 72.3 mg (81%) of the desired compound as a yellow powder.

$^1$H NMR (400 MHz, DMSO-$d_6$) δ 1.36-1.46 (1H, m), 1.56-1.66 (2H, m), 1.83-1.90 (1H, m), 2.40 (3H, s), 2.53-2.59

(1H, m), 2.64-2.74 (2H, m), 2.84 (1H, td, J=12.2, 3.1 Hz), 3.00 (1H, d, J=11.0 Hz), 7.50 (2H, d, J=8.6 Hz), 7.84 (2H, d, J=8.6 Hz), 10.92 (1H, brs).

Step 69c) Methyl 3-[3-[N-[2-(4-chlorophenyl)-4-methylthiazol-5-yl]carbamoyl]piperidin-1-yl]benzoate

[Chemical formula 168]

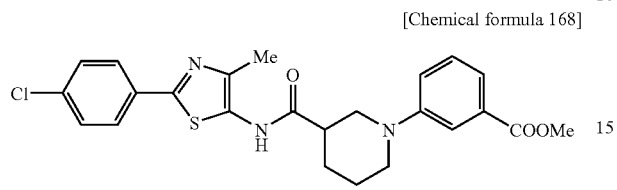

Using N-[2-(4-chlorophenyl)-4-methylthiazole-5-yl]piperidine-3-carboxamide (36.0 mg, 0.107 mmol) and 3-methoxycarbonylphenylboric acid (38.5 mg, 0.214 mmol), the same procedure was followed as in Example 4 to give 21.3 mg (42%) of the desired compound as a pale yellow powder.

¹H NMR (400 MHz, CDCl₃) δ 1.80-1.91 (2H, m), 1.93-2.01 (2H, m), 2.16-2.21 (1H, m), 2.23 (3H, s), 2.92-2.98 (2H, m), 3.15 (1H, dd, J=12.2, 3.1 Hz), 3.64 (1H, td, J=11.0, 3.7 Hz), 3.77-3.81 (1H, m), 3.93 (3H, s), 7.33 (1H, dd, J=7.9, 1.8 Hz), 7.37 (2H, d, J=8.6 Hz), 7.44 (1H, t, J=7.9 Hz), 7.73 (1H, d, J=7.3 Hz), 7.79-7.80 (1H, m), 7.82 (2H, d, J=8.6 Hz), 10.24 (1H, brs).

FAB⁺ (m/z): 470 (M+H).

Example 70 Through 75

The processes were performed as in Example 67, Example 68 or Example 69 to obtain compounds given in Table 8 below.

TABLE 8

| | Ar | Y | Binding position of COOMe |
|---|---|---|---|
| Example 70 | 4-F-C₆H₄-O-C₆H₄- | CH₂NHCO | Position 2 |
| Example 71 | 2-methylbenzothiazol-yl | CH₂NHCO | Position 2 |
| Example 72 | 2-(4-chlorophenyl)-4,5-dimethylthiazol-yl | NHCO | Position 2 |
| Example 73 | 4-F-C₆H₄-O-C₆H₄- | CH₂NHCO | Position 3 |
| Example 74 | 2-methylbenzothiazol-yl | CH₂NHCO | Position 3 |
| Example 75 | 4-F-C₆H₄-O-C₆H₄- | NHCO | Position 3 |

<Compound of Example 70>
Colorless Oil

¹H NMR (400 MHz, CDCl₃) δ 1.55-1.75 (2H, m), 1.94-2.10 (2H, m), 2.67 (1H, t, J=11.6 Hz), 2.73-2.78 (1H, m), 3.06-3.18 (2H, m), 3.33 (1H, d, J=11.6 Hz), 3.77 (3H, s), 4.40

(1H, dd, J=14.7, 5.5 Hz), 4.49 (1H, dd, J=14.7, 5.5 Hz), 6.83 (2H, d, J=8.6 Hz), 6.88-6.95 (2H, m), 6.96-7.03 (2H, m), 7.06-7.14 (2H, m), 7.22 (2H, d, J=6.7 Hz), 7.47 (1H, td, J=7.9, 1.8 Hz), 7.79 (1H, dd, J=7.9, 1.8 Hz), 8.63 (1H, brs).

FAB+ (m/z): 463 (M+H).

<Compound of Example 71>

Colorless Oil

¹H NMR (400 MHz, CDCl₃) δ 1.63-1.78 (2H, m), 2.08-2.22 (2H, m), 2.66 (1H, t, J=11.0 Hz), 2.83-2.88 (1H, m), 3.10-3.22 (2H, m), 3.44 (1H, d, J=11.0 Hz), 3.71 (3H, s), 4.90 (1H, dd, J=16.5, 6.1 Hz), 4.95 (1H, dd, J=16.5, 6.1 Hz), 7.10 (1H, t, J=7.9 Hz), 7.15 (1H, d, J=7.9 Hz), 7.32 (1H, td, J=7.9, 1.2 Hz), 7.42 (1H, td, J=7.9, 1.2 Hz), 7.49 (1H, td, J=7.9, 1.2 Hz), 7.75-7.80 (2H, m), 7.92 (1H, d, J=7.9 Hz), 9.42 (1H, brs).

FAB+ (m/z): 410 (M+H).

<Compound of Example 72>

Yellow Oil

¹H NMR (400 MHz, CDCl₃) δ 1.67-1.74 (1H, m), 1.78-1.83 (1H, m), 1.99-2.06 (1H, m), 2.09 (3H, s), 2.21-2.27 (1H, m), 2.66-2.72 (1H, m), 2.97-3.00 (1H, m), 3.21-3.28 (2H, m), 3.56-3.59 (1H, m), 3.79 (3H, s), 7.14-7.18 (2H, m), 7.35 (2H, d, J=8.6 Hz), 7.54 (1H, dd, J=7.9, 1.2 Hz), 7.81 (2H, d, J=8.6 Hz), 7.93 (1H, dd, J=7.9, 1.2 Hz), 10.37 (1H, brs).

FAB+ (m/z): 470 (M+H).

<Compound of Example 73>

Colorless Oil

¹H NMR (400 MHz, CDCl₃) δ 1.68-1.78 (1H, m), 1.81-1.94 (3H, m), 2.56-2.64 (1H, m), 3.06-3.14 (1H, m), 3.26-3.34 (2H, m), 3.47 (1H, dd, J=12.2, 3.1 Hz), 3.90 (3H, s), 4.38-4.50 (2H, m), 6.66-6.72 (1H, m), 6.89-6.98 (4H, m), 6.99-7.05 (2H, m), 7.09-7.14 (1H, m), 7.23 (2H, d, J=8.6 Hz), 7.31 (1H, t, J=7.9 Hz), 7.56 (1H, d, J=7.9 Hz), 7.60-7.62 (1H, m).

FAB+ (m/z): 463 (M+H).

<Compound of Example 74>

Colorless Powder

¹H NMR (400 MHz, CDCl₃) δ 1.70-1.84 (1H, m), 1.85-2.03 (3H, m), 2.66-2.78 (1H, m), 3.17-3.30 (2H, m), 3.38-3.48 (2H, m), 3.89 (3H, s), 4.91 (2H, d, J=5.5 Hz), 7.20-7.27 (2H, m), 7.29-7.35 (1H, m), 7.38 (1H, td, J=7.9, 1.2 Hz), 7.47 (1H, td, J=7.9, 1.2 Hz), 7.50-7.62 (2H, m), 7.68 (1H, s), 7.86 (1H, d, J=7.9 Hz), 7.93 (1H, d, J=7.9 Hz).

FAB+ (m/z): 410 (M+H).

<Compound of Example 75>

Colorless Amorphous

¹H NMR (CDCl₃-d, 400 MHz) δ 1.77-2.02 (3H, m), 2.04-2.13 (1H, m), 2.73-2.80 (1H, m), 3.12-3.20 (1H, m), 3.30-3.43 (2H, m), 3.56 (1H, d, J=12.8, 5.5 Hz), 3.92 (3H, s), 6.90-6.96 (4H, m), 6.97-7.02 (2H, m), 7.24-7.27 (2H, m), 7.39 (1H, t, J=7.9 Hz), 7.47 (1H, d, J=8.6 Hz), 7.65 (1H, d, J=7.9 Hz), 7.73 (1H, s), 8.90 (1H, s).

FAB+ (m/z): 449 (M+H).

Example 76

Methyl 3-[3-[(benzothiazol-2-yl)oxymethyl]piperidin-1-yl]benzoate

Step 76a) 1-(tert-Butoxycarbonyl)-3-[(benzothiazol-2-yl)oxymethyl]piperidine

[Chemical formula 169]

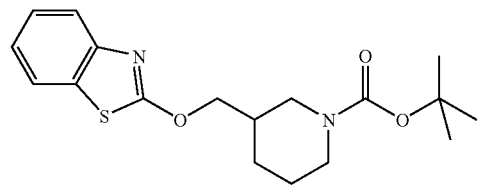

1-(tert-Butoxycarbonyl)piperidin-3-ylmethanol (300 mg, 1.39 mmol) was dissolved in N,N-dimethylformamide (5 mL). While this solution was chilled in an ice bath, 60% sodium hydride in oil (83.6 mg, 2.09 mmol) was added. The reaction mixture was stirred for 10 min while ice-chilled and for another 10 min at room temperature. 2-chlorobenzothiazole (0.344 mL, 2.78 mmol) and sodium iodide (208 mg, 1.39 mmol) were then added and the mixture was stirred at room temperature for 5 hours. Subsequently, water was added and the mixture was extracted with ethyl acetate. The extract washed with brine. The washed product was then dried over magnesium sulfate and the solvent was evaporated. Purification of the resulting residue by silica gel column chromatography (hexane:ethyl acetate=20:1->5:1) gave 460 mg (95%) of the desired compound as a colorless powder.

¹H NMR (400 MHz, DMSO-d₆) δ 1.25-1.45 (1H, m), 1.56-1.67 (1H, m), 1.75-1.85 (1H, m), 1.93-2.06 (1H, m), 2.59-3.11 (2H, m), 3.53-4.07 (2H, m), 4.38-4.48 (2H, m), 7.28 (1H, td, J=7.9, 1.2 Hz), 7.40 (1H, td, J=7.9, 1.2 Hz), 7.66 (1H, d, J=7.3 Hz), 7.88 (1H, dd, J=7.9, 1.2 Hz).

Step 76b) 3-[(Benzothiazol-2-yl)oxymethyl]piperidine

[Chemical formula 170]

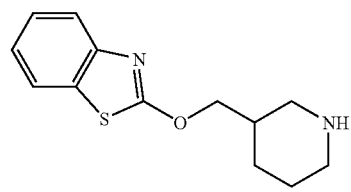

Trifluoroacetic acid (2 mL) was added to 1-tert-butoxycarbonyl-3-[(benzothiazol-2-yl)oxymethyl]piperidine (460 mg, 1.32 mmol) in dichloromethane (2 mL). The mixture was stirred at room temperature for 3 hours. Subsequently, the solvent was evaporated and water was added to the residue, followed by a 1 mol/L aqueous sodium hydroxide solution to make the mixture basic. The mixture was then extracted with ethyl acetate and the extract washed with brine. The washed product was dried over magnesium sulfate and the solvent was evaporated to give 297 mg (91%) of the desired compound as a colorless oil.

$^1$H NMR (400 MHz, DMSO-$d_6$) δ 1.20-1.30 (1H, m), 1.38-1.49 (1H, m), 1.61-1.66 (1H, m), 1.77-1.82 (1H, m), 1.99-2.09 (1H, m), 2.45 (1H, dd, J=11.6, 10.4 Hz), 2.54 (1H, dd, J=11.6, 3.1 Hz), 2.90-2.95 (1H, m), 3.07 (1H, dd, J=11.6, 2.4 Hz), 4.40 (1H, dd, J=10.4, 7.3 Hz), 4.44 (1H, dd, J=10.4, 5.5 Hz), 7.27 (1H, t, J=7.3 Hz), 7.40 (1H, t, J=7.3 Hz), 7.66 (1H, d, J=7.9 Hz), 7.88 (1H, d, J=7.9 Hz).

Methyl 3-[3-[(benzothiazol-2-yl)oxymethyl]piperidin-1-yl]benzoate

[Chemical formula 171]

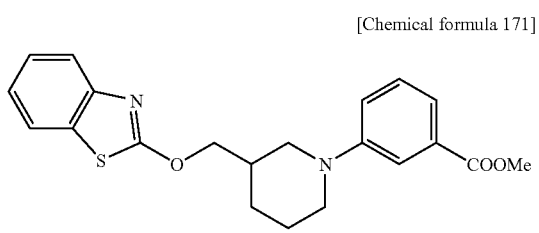

Using 3-[(benzothiazol-2-yl)oxymethyl]piperidine (58.0 mg, 0.234 mmol) and 3-(methoxycarbonyl)phenylboric acid (84.2 mg, 0.468 mmol), the same procedure was followed as in Example 2 to give 17.6 mg (20%) of the desired compound as a colorless oil.

$^1$H NMR (400 MHz, CDCl$_3$) δ 1.32-1.42 (1H, m), 1.71-1.80 (1H, m), 1.85-1.96 (2H, m), 2.29-2.40 (1H, m), 2.75-2.80 (1H, m), 2.83-2.90 (1H, m), 3.58-3.63 (1H, m), 3.75-3.79 (1H, m), 3.90 (3H, s), 4.50 (1H, dd, J=10.4, 7.9 Hz), 4.57 (1H, dd, J=10.4, 5.5 Hz), 7.14-7.16 (1H, m), 7.23 (1H, td, J=7.9, 1.2 Hz), 7.31 (1H, t, J=7.9 Hz), 7.37 (1H, td, J=8.6, 1.2 Hz), 7.50 (1H, d, J=6.7 Hz), 7.62 (1H, brs), 7.65 (1H, d, J=7.9 Hz), 7.68 (1H, d, J=8.6 Hz).

FAB$^+$ (m/z): 383 (M+H).

Example 77

Methyl 3-[3-[(4'-chlorobiphenyl-4-yl)methoxy]piperidin-1-yl]benzoate

Step 77a) 1-(tert-Butoxycarbonyl)-3-[(4'-chlorobiphenyl-4-yl)methoxy]piperidine

[Chemical formula 172]

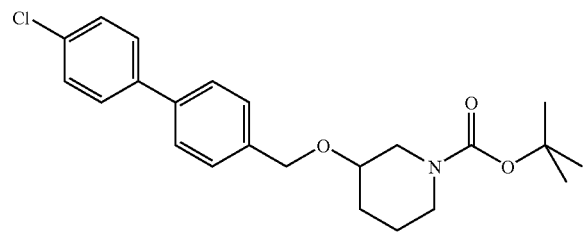

Using 1-(tert-butoxycarbonyl)-3-hydroxypiperidine (403 mg, 2.00 mmol) and 4'-chloro-4-chloromethylbiphenyl (474 mg, 2.00 mmol), the same procedure was followed as in Step 6a of Example 6 to give 672 mg (84%) of the desired compound as a colorless powder.

$^1$H NMR (400 MHz, CDCl$_3$) δ 1.41-1.50 (10H, m), 1.54-1.63 (1H, m), 1.73-1.84 (1H, m), 1.93-2.02 (1H, m), 3.04-3.26 (2H, m), 3.40-3.49 (1H, m), 3.59 (1H, td, J=13.4, 4.9 Hz), 3.68-4.01 (1H, m), 4.55-4.58 (1H, m), 4.66-4.69 (1H, m), 7.39-7.43 (4H, m), 7.49-7.53 (4H, m).

FAB$^+$ (m/z): 402 (M+H).

Step 77b) 3-[(4'-Chlorobiphenyl-4-yl)methoxy]piperidine

[Chemical formula 173]

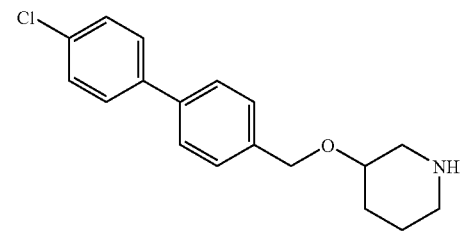

Using 1-(tert-butoxycarbonyl)-3-[(4'-chlorobiphenyl-4-yl)methoxy]piperidine (672 mg, 1.67 mmol), the same procedure was followed as in Step 76b of Example 76 to give 441 mg (87%) of the desired compound as a colorless powder.

$^1$H NMR (400 MHz, DMSO-$d_6$) δ 1.23-1.38 (2H, m), 1.57-1.66 (1H, m), 1.93-2.02 (1H, m), 2.34-2.42 (2H, m), 2.71 (1H, td, J=11.6, 3.1 Hz), 3.05 (1H, dd, J=11.6, 2.4 Hz), 3.27-3.33 (1H, m), 4.55 (2H, s), 7.41 (2H, d, J=8.6 Hz), 7.51 (2H, d, J=8.6 Hz), 7.64 (2H, d, J=8.6 Hz), 7.69 (2H, d, J=8.6 Hz).

Step 77c) Methyl 3-[3-[(4'-chlorobiphenyl-4-yl)methoxy]piperidin-1-yl]benzoate

[Chemical formula 174]

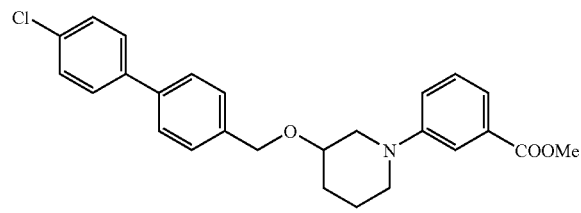

Using 3-[(4'-chlorobiphenyl-4-yl)methoxy]piperidine (220 mg, 0.729 mmol) and 3-(methoxycarbonyl)phenylboric acid (263 mg, 1.46 mmol), the same procedure was followed as in Example 2 to give 107 mg (34%) of the desired compound as a colorless oil.

$^1$H NMR (400 MHz, CDCl$_3$) δ 1.48-1.58 (1H, m), 1.62-1.74 (1H, m), 1.88-1.95 (1H, m), 2.09-2.17 (1H, m), 2.84-2.92 (2H, m), 3.50 (1H, td, J=11.6, 3.6 Hz), 3.61-3.69 (1H, m), 3.72-3.76 (1H, m), 3.90 (3H, s), 4.65 (1H, d, J=12.2 Hz), 4.69 (1H, d, J=12.2 Hz), 7.11 (1H, brs), 7.30 (1H, t, J=7.9 Hz), 7.40 (2H, d, J=8.6 Hz), 7.44 (2H, d, J=8.6 Hz), 7.48-7.52 (3H, m), 7.54 (2H, d, J=8.6 Hz), 7.61 (1H, brs).

FAB⁺ (m/z): 436 (M+H).

Example 78

Methyl 3-[3-[(4'-chlorobiphenyl-4-yl)methoxymethyl]piperidin-1-yl]benzoate

Step 78a) 1-(tert-Butoxycarbonyl)-3-[(4'-chlorobiphenyl-4-yl)methoxymethyl]piperidine

[Chemical formula 175]

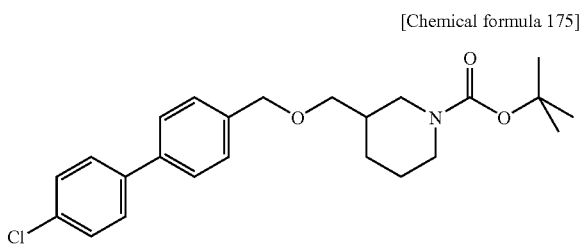

Using 1-(tert-butoxycarbonyl)-piperidin-3-yl methanol (431 mg, 2.00 mmol) and 4'-chloro-4-chloromethylbiphenyl (474 mg, 2.00 mmol), the same procedure was followed as in Step 5a of Example 5 to give 711 mg (86%) of the desired compound as a colorless oil.

$^1$H NMR (400 MHz, CDCl$_3$) δ 1.20-1.30 (1H, m), 1.42-1.50 (10H, m), 1.62-1.67 (1H, m), 1.78-1.90 (2H, m), 2.60-2.73 (1H, m), 2.78-2.85 (1H, m), 3.33-3.40 (2H, m), 3.89 (1H, td, J=13.5, 3.7 Hz), 3.97-4.08 (1H, m), 4.53 (2H, s), 7.39-7.42 (4H, m), 7.49-7.54 (4H, m).

FAB⁺ (m/z): 416 (M+H).

Step 78b) 3-[(4'-Chlorobiphenyl-4-yl)methoxymethyl]piperidine

[Chemical formula 176]

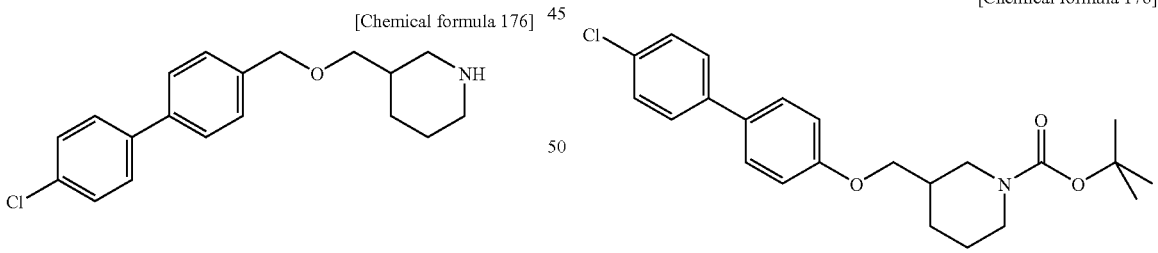

Using 1-(tert-butoxycarbonyl)-3-[(4'-chlorobiphenyl-4-yl)methoxymethyl]piperidine (711 mg, 1.71 mmol), the same procedure was followed as in Step 76b of Example 76 to give 474 mg (88%) of the desired compound as a colorless oil.

$^1$H NMR (400 MHz, DMSO-d$_6$) δ 1.01-1.11 (1H, m), 1.27-1.38 (1H, m), 1.49-1.55 (1H, m), 1.64-1.74 (2H, m), 2.20 (1H, dd, J=11.6, 9.8 Hz), 2.38 (1H, td, J=11.6, 3.1 Hz), 2.81 (1H, td, J=12.2, 3.7 Hz), 2.94-2.99 (1H, m), 3.27 (2H, d, J=6.7 Hz), 4.48 (2H, s), 7.40 (2H, d, J=8.6 Hz), 7.51 (2H, d, J=8.6 Hz), 7.65 (2H, d, J=8.6 Hz), 7.70 (2H, d, J=8.6 Hz).

Step 78c) Methyl 3-[3-[(4'-chlorobiphenyl-4-yl)methoxymethyl]piperidin-1-yl]benzoate

[Chemical formula 177]

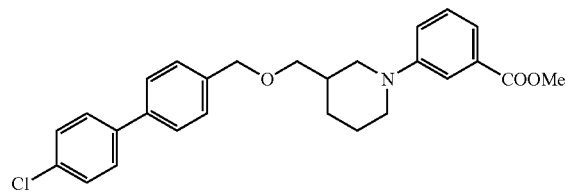

Using 3-[(4'-chlorobiphenyl-4-yl)methoxymethyl]piperidine (237 mg, 0.750 mmol) and 3-(methoxycarbonyl)phenylboric acid (270 mg, 1.50 mmol), the same procedure was followed as in Example 2 to give 168 mg (50%) of the desired compound as a colorless oil.

$^1$H NMR (400 MHz, CDCl$_3$) δ 1.18-1.28 (1H, m), 1.64-1.75 (1H, m), 1.77-1.87 (2H, m), 2.03-2.14 (1H, m), 2.65 (1H, dd, J=12.2, 9.8 Hz), 2.77-2.84 (1H, m), 3.41-3.48 (2H, m), 3.59 (1H, td, J=11.6, 3.7 Hz), 3.74 (1H, dd, J=12.2, 3.7 Hz), 3.89 (3H, s), 4.55 (1H, d, J=12.2 Hz), 4.57 (1H, d, J=12.2 Hz), 7.13 (1H, dd, J=7.9, 2.4 Hz), 7.29 (1H, t, J=7.9 Hz), 7.39-7.43 (4H, m), 7.47 (1H, d, J=7.9 Hz), 7.51 (2H, d, J=8.6 Hz), 7.54 (2H, d, J=8.6 Hz), 7.61 (1H, brs).

FAB⁺ (m/z): 450 (M+H).

Example 79

Methyl 3-[3-[(4'-Chlorobiphenyl-4-yl)oxymethyl]piperidin-1-yl]benzoate

1-(tert-Butoxycarbonyl)-3-[(4'-chlorobiphenyl-4-yl)oxymethyl]piperidine

[Chemical formula 178]

1-(tert-Butoxycarbonyl)piperidin-3-ylmethanol (323 mg, 1.50 mmol) and 4'-chloro-4-hydroxybiphenyl (307 mg, 1.50 mmol) were suspended in tetrahydrofuran (15 mL). To this suspension, triphenylphosphine (608 mg, 2.25 mmol) was added and the mixture was stirred at room temperature for 10 min. A 40% diethylazodicarboxylate/toluene solution (1.36 mL, 3.00 mmol) was then added and the mixture was stirred at room temperature for 16 hours. Subsequently, water was added and the mixture was extracted with ethyl acetate. The extract washed with brine, followed by drying over magnesium sulfate and evaporation of the solvent. Purification of the resulting residue by silica gel column chromatography (hexane:ethyl acetate=50:1->10:1) gave 401 mg (67%) of the desired compound as a colorless powder.

$^1$H NMR (400 MHz, CDCl$_3$) δ 1.34-1.53 (11H, m), 1.67-1.74 (1H, m), 1.86-1.95 (1H, m), 1.98-2.08 (1H, m), 2.62-3.02 (2H, m), 3.80-4.25 (4H, m), 6.95 (2H, d, J=8.6 Hz), 7.37 (2H, d, J=8.6 Hz), 7.44-7.48 (4H, m).

FAB$^+$ (m/z): 401 (M+H).

3-[(4'-Chlorobiphenyl-4-yl)oxymethyl]piperidine

[Chemical formula 179]

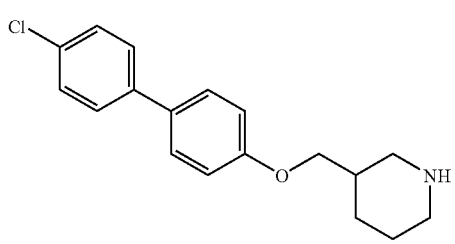

Using 1-(tert-butoxycarbonyl)-3-[(4'-chlorobiphenyl-4-yl)oxymethyl]piperidine (401 mg, 0.998 mmol), the same procedure was followed as in Step 76b of Example 76 to give 250 mg (83%) of the desired compound as a colorless powder.

$^1$H NMR (400 MHz, DMSO-d$_6$) δ 1.14-1.24 (1H, m), 1.31-1.42 (1H, m), 1.55-1.60 (1H, m), 1.78-1.89 (2H, m), 2.32 (1H, dd, J=11.6, 9.2 Hz), 2.44 (1H, td, J=11.6, 3.1 Hz), 2.83 (1H, td, J=12.2, 3.1 Hz), 3.02 (1H, dd, J=11.6, 3.1 Hz), 3.85 (2H, d, J=6.7 Hz), 7.01 (2H, d, J=8.6 Hz), 7.47 (2H, d, J=8.6 Hz), 7.59 (2H, d, J=8.6 Hz), 7.64 (2H, d, J=8.6 Hz).

Methyl 3-[3-[(4'-chlorobiphenyl-4-yl)oxymethyl]piperidin-1-yl]benzoate

[Chemical formula 180]

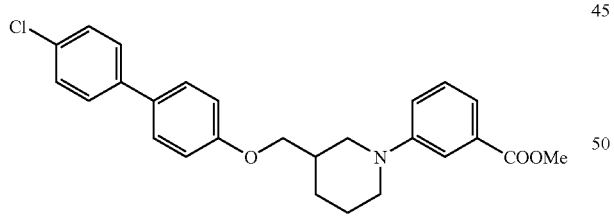

Using 3-[(4'-chlorobiphenyl-4-yl)oxymethyl]piperidine (125 mg, 0.414 mmol) and 3-(methoxycarbonyl)phenylboric acid (149 mg, 0.828 mmol), the same procedure was followed as in Example 2 to give 105 mg (58%) of the desired compound as a colorless powder.

$^1$H NMR (400 MHz, CDCl$_3$) δ 1.32-1.42 (1H, m), 1.71-1.81 (1H, m), 1.84-1.96 (2H, m), 2.23-2.33 (1H, m), 2.74-2.80 (1H, m), 2.84-2.90 (1H, m), 3.62 (1H, td, J=12.2, 3.7 Hz), 3.80 (1H, dd, J=12.2, 3.7 Hz), 3.91 (3H, s), 3.92-4.00 (2H, m), 6.99 (2H, d, J=8.6 Hz), 7.15 (1H, d, J=7.9 Hz), 7.31 (1H, t, J=7.9 Hz), 7.38 (2H, d, J=8.6 Hz), 7.46-7.50 (5H, m), 7.63 (1H, brs).

FAB$^+$ (m/z): 436 (M+H).

Example 80

Methyl 3-[3-[(4-phenylthiazol-2-yl)thiomethyl]piperidin-1-yl]benzoate

Step 80a) 1-(tert-Butoxycarbonyl)-3-[(4-phenylthiazol-2-yl)thiomethyl]piperidine

[Chemical formula 181]

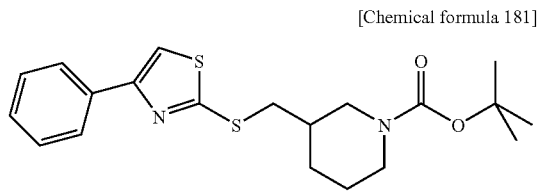

2-Mercapto-4-phenylthiazole (304 mg, 1.54 mmol) and potassium carbonate (261 mg, 1.85 mmol) were added to 1-(tert-butoxycarbonyl)-3-iodomethylpiperidine (500 mg, 1.54 mmol) in N,N-dimethylformamide (5 mL). The mixture was stirred at room temperature for 30 min. Subsequently, water was added and the mixture was extracted with ethyl acetate. The extract was then washed with brine, followed by drying over magnesium sulfate and evaporation of the solvent. Purification of the resulting residue by silica gel column chromatography (hexane:ethyl acetate=40:1->10:1) gave 598 mg (99%) of the desired compound as a colorless oil.

$^1$H NMR (400 MHz, CDCl$_3$) δ 1.31-1.38 (1H, m), 1.41-1.49 (10H, m), 1.65-1.72 (1H, m), 1.92-2.01 (2H, m), 2.67-3.00 (2H, m), 3.19-3.28 (2H, m), 3.77-3.85 (1H, m), 3.91-4.08 (1H, m), 7.30-7.35 (2H, m), 7.39-7.43 (2H, m), 7.87-7.89 (2H, m).

FAB$^+$ (m/z): 391 (M+H).

Step 80b)
3-[(4-Phenylthiazol-2-yl)thiomethyl]piperidine

[Chemical formula 182]

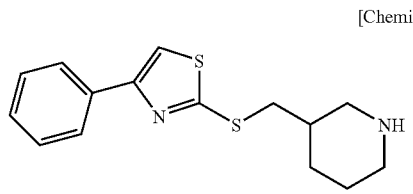

Using 1-(tert-butoxycarbonyl)-3-[(4-phenylthiazol-2-yl)thiomethyl]piperidine (598 mg, 1.53 mmol), the same procedure was followed as in Step 76b of Example 76 to give 420 mg (92%) of the desired compound as a pale yellow oil.

$^1$H NMR (400 MHz, DMSO-d$_6$) δ 1.15-1.24 (1H, m), 1.28-1.38 (10H, m), 1.54-1.61 (1H, m), 1.73-1.83 (1H, m), 1.84-1.91 (1H, m), 2.30 (1H, dd, J=11.6, 9.8 Hz), 2.42 (1H, td, J=11.6, 3.1 Hz), 2.81 (1H, td, J=12.2, 3.7 Hz), 3.00-3.03 (1H, m), 3.17 (1H, dd, J=13.4, 6.7 Hz), 3.21 (1H, dd, J=13.4, 6.7 Hz), 7.35 (1H, td, J=7.3, 1.2 Hz), 7.43-7.46 (2H, m), 7.91-7.94 (2H, m), 8.02 (1H, m).

Step 80c) Methyl 3-[3-[(4-phenylthiazol-2-yl)thiomethyl]piperidin-1-yl]benzoate

[Chemical formula 183]

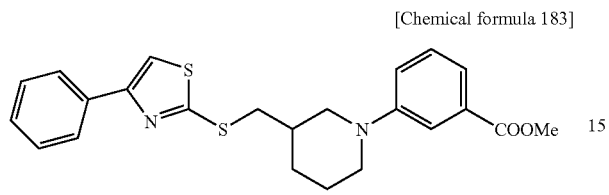

Using 3-[(2-phenylthiazol-4-yl)thiomethyl]piperidine (210 mg, 0.707 mmol) and 3-(methoxycarbonyl)phenylboric acid (254 mg, 1.41 mmol), the same procedure was followed as in Example 2 to give 159 mg (53%) of the desired compound as a colorless oil.

$^1$H NMR (400 MHz, CDCl$_3$) δ 1.29-1.39 (1H, m), 1.65-1.76 (1H, m), 1.80-1.88 (1H, m), 2.00-2.06 (1H, m), 2.14-2.25 (1H, m), 2.73 (1H, dd, J=12.2, 9.8 Hz), 2.85 (1H, td, J=11.6, 3.7 Hz), 3.30 (1H, dd, J=13.4, 7.3 Hz), 3.34 (1H, dd, J=13.4, 6.1 Hz), 3.57 (1H, td, J=12.2, 3.7 Hz), 3.75-3.79 (1H, m), 3.89 (3H, s), 7.12 (1H, dd, J=7.3, 1.8 Hz), 7.25-7.29 (1H, m), 7.31-7.35 (2H, m), 7.39-7.43 (2H, m), 7.47-7.49 (1H, m), 7.59-7.60 (1H, m), 7.86-7.89 (2H, m).

FAB$^+$ (m/z): 425 (M+H).

Example 81

Methyl 3-[3-[[4-(4-fluorophenoxy)phenyl]methoxy]piperidin-1-yl]benzoate

Step 81a) 1-Trifluoroacetyl-3-[[4-(4-fluorophenoxy)phenyl]methoxy]piperidine

[Chemical formula 184]

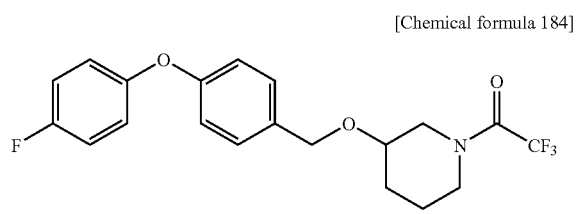

Using 1-trifluoroacetyl-3-hydroxypiperidine (394 mg, 2.00 mmol) and 4-(4-fluorophenoxy)benzylchloride (473 mg, 2.00 mmol), the same procedure was followed as in Step 6a of Example 6 to give 434 mg (55%) of the desired compound as a colorless oil.

$^1$H NMR (400 MHz, CDCl$_3$) δ 1.47-1.61 (1H, m), 1.64-1.79 (1H, m), 1.84-2.06 (2H, m), 3.22-3.31 (1H, m), 3.43-3.50 (1H, m), 3.52-3.62 (2H, m), 3.82-3.95 (1H, m), 4.46-4.63 (2H, m), 6.92-7.05 (5H, m), 7.26-7.29 (3H, m).

FAB$^+$ (m/z): 397 (M+H).

Step 81b) 3-[[4-(4-Fluorophenoxy)phenyl]methoxy]piperidine

[Chemical formula 185]

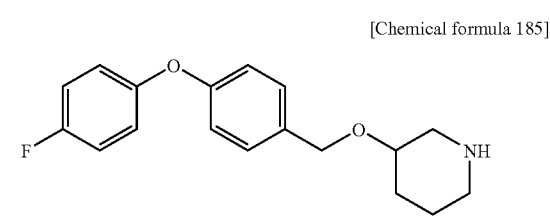

A 1 mol/L aqueous potassium hydroxide solution (2 mL) was added to 1-trifluoroacetyl-3-[4-(4-fluorophenoxy)benzyloxy]piperidine (434 mg, 1.09 mmol) in methanol (4 mL). The mixture was refluxed for 2 hours and was allowed to cool. Water was then added and the mixture was extracted with ethyl acetate. The organic layer was washed with brine and the washed product was dried over magnesium sulfate. The solvent was evaporated to give 314 mg (95%) of the desired compound as a colorless oil.

$^1$H NMR (400 MHz, DMSO-d$_6$) δ 1.23-1.36 (2H, m), 1.56-1.64 (1H, m), 1.92-1.99 (1H, m), 2.32-2.42 (2H, m), 2.69-2.73 (1H, m), 3.01-3.04 (1H, m), 3.24-3.31 (1H, m), 4.47 (2H, s), 6.95 (2H, d, J=8.6 Hz), 7.05 (2H, dd, J=9.2, 4.3 Hz), 7.22 (2H, t, J=8.6 Hz), 7.32 (2H, d, J=8.6 Hz).

Step 81c) Methyl 3-[3-[[4-(4-fluorophenoxy)phenyl]methoxy]piperidin-1-yl]benzoate

[Chemical formula 186]

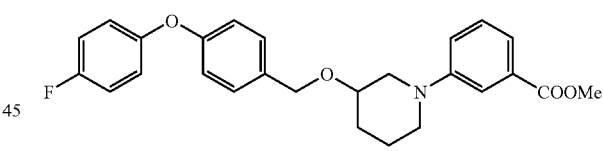

Using 3-[4-(4-fluorophenoxy)benzyloxy]piperidine (157 mg, 0.521 mmol) and 3-(methoxycarbonyl)phenylboric acid (187 mg, 1.04 mmol), the same procedure was followed as in Example 2 to give 94.8 mg (42%) of the desired compound as a colorless oil.

$^1$H NMR (400 MHz, CDCl$_3$) δ 1.46-1.55 (1H, m), 1.59-1.75 (1H, m), 1.87-1.94 (1H, m), 2.07-2.15 (1H, m), 2.81-2.90 (2H, m), 3.50 (1H, td, J=12.2, 4.3 Hz), 3.57-3.66 (1H, m), 3.70-3.74 (1H, m), 3.90 (3H, s), 4.57 (1H, d, J=11.6 Hz), 4.61 (1H, d, J=11.6 Hz), 6.93-7.05 (6H, m), 7.09-7.11 (1H, m), 7.28-7.34 (3H, m), 7.49 (1H, d, J=7.3 Hz), 7.60 (1H, brs).

FAB+ (m/z): 436 (M+H).

Example 82

Methyl 3-[3-[[4-(4-fluorophenoxy)phenyl]methoxymethyl]piperidin-1-yl]benzoate

Step 82a) 1-Trifluoroacetyl-3-[[4-(4-fluorophenoxy)phenyl]methoxymethyl]piperidine

[Chemical formula 187]

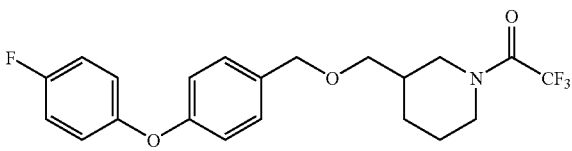

Using 1-trifluoroacetylpiperidin-3-yl methanol (422 mg, 2.00 mmol) and 4-(4-fluorophenoxy)benzylchloride (473 mg, 2.00 mmol), the same procedure was followed as in Step 5a of Example 5 to give 110 mg (13%) of the desired compound as a colorless oil.

$^1$H NMR (400 MHz, DMSO-$d_6$) δ 1.28-1.37 (1H, m), 1.38-1.50 (1H, m), 1.69-1.78 (2H, m), 1.80-1.89 (1H, m), 2.77-3.40 (4H, m), 3.72-3.93 (1H, m), 4.11-4.25 (1H, m), 4.42 (1H, d, J=12.2 Hz), 4.43 (1H, d, J=12.2 Hz), 6.97 (2H, d, J=8.6 Hz), 7.05-7.08 (2H, m), 7.23 (2H, t, J=8.6 Hz), 7.32 (2H, d, J=8.6 Hz).

FAB+ (m/z): 411 (M+H).

Step 82b) 3-[[4-(4-Fluorophenoxy)phenyl]methoxymethyl]piperidine

[Chemical formula 188]

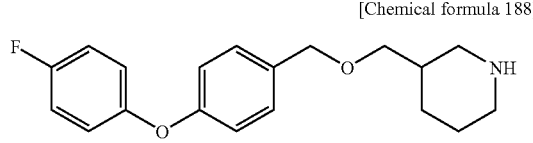

Using 1-trifluoroacetyl-3-[4-(4-fluorophenoxy)benzyloxymethyl]piperidine (110 mg, 0.267 mmol), the same procedure was followed as in Step 81b of Example 81 to give 71.4 mg (85%) of the desired compound as a colorless oil.

$^1$H NMR (400 MHz, DMSO-$d_6$) δ 1.01-1.11 (1H, m), 1.29-1.40 (1H, m), 1.51-1.58 (1H, m), 1.65-1.73 (2H, m), 2.23 (1H, dd, J=11.6, 9.8 Hz), 2.42 (1H, td, J=11.6, 3.1 Hz), 2.85 (1H, td, J=11.6, 3.1 Hz), 2.96-2.99 (1H, m), 3.24-3.26 (2H, m), 4.39 (1H, d, J=12.2 Hz), 4.41 (1H, d, J=12.2 Hz), 6.96 (2H, d, J=8.6 Hz), 7.06 (2H, dd, J=9.2, 4.9 Hz), 7.23 (2H, t, J=8.6 Hz), 7.31 (2H, d, J=8.6 Hz).

Step 82c) Methyl 3-[3-[[4-(4-fluorophenoxy)phenyl]methoxymethyl]piperidin-1-yl]benzoate

[Chemical formula 189]

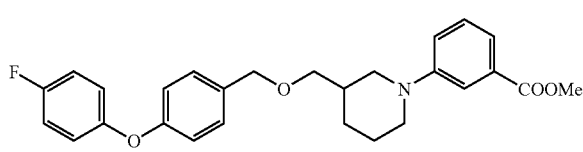

Using 3-[4-(4-fluorophenoxy)benzyloxymethyl]piperidine (35.7 mg, 0.113 mmol) and 3-(methoxycarbonyl)phenylboric acid (40.7 mg, 0.226 mmol), the same procedure was followed as in Example 2 to give 29.1 mg (57%) of the desired compound as a colorless oil.

$^1$H NMR (400 MHz, CDCl$_3$) δ 1.16-1.25 (1H, m), 1.45-1.93 (3H, m), 2.02-2.12 (1H, m), 2.60-2.65 (1H, m), 2.76-2.83 (1H, m), 3.38-3.45 (2H, m), 3.56-3.61 (1H, m), 3.70-3.74 (1H, m), 3.89 (3H, s), 4.47 (1H, d, J=11.6 Hz), 4.49 (1H, d, J=11.6 Hz), 6.93-7.05 (6H, m), 7.11 (1H, dd, J=8.6, 1.2 Hz), 7.29-7.31 (3H, m), 7.47 (1H, d, J=7.3 Hz), 7.60 (1H, brs).

FAB+ (m/z): 450 (M+H).

Example 83

Methyl 3-[3-[[2-(4-chlorophenyl)-4-methylthiazol-5-yl]methoxycarbonylamino]piperidin-1-yl]benzoate

[Chemical formula 190]

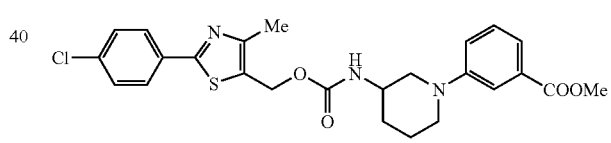

1-[3-(Methoxycarbonyl)phenyl]nipecotic acid (105 mg, 0.400 mmol) was suspended in benzene (8 mL). To this suspension, diphenylphosphoryl azide (0.0948 mL, 0.440 mmol) and triethylamine (0.0615 mL, 0.440 mmol) were added and the mixture was stirred for 2 hours while being refluxed. Subsequently, 2-(4-chlorophenyl)-4-methylthiazol-5-yl methanol (105 mg, 0.440 mmol) and triethylamine (0.0615 mL, 0.440 mmol) were added and the mixture was further stirred for 6 hours while refluxed. Water was then added and the mixture was extracted with ethyl acetate. The extract washed sequentially with a saturated aqueous sodium bicarbonate solution and brine. This was followed by drying over magnesium sulfate and evaporation of the solvent. Purification of the resulting residue by silica gel column chromatography (hexane:ethyl acetate=10:1->2:1) gave 103 mg (52%) of the desired compound as a colorless powder.

$^1$H NMR (400 MHz, CDCl$_3$) δ 1.52-1.95 (4H, m), 2.50 (3H, s), 3.06-3.13 (2H, m), 3.16-3.24 (1H, m), 3.35-3.38 (1H, m), 3.90 (3H, s), 3.93-4.00 (1H, m), 5.16 (1H, d, J=6.7 Hz), 5.24 (2H, s), 7.11 (1H, d, J=7.3 Hz), 7.29 (1H, t, J=7.9 Hz), 7.38 (2H, d, J=8.6 Hz), 7.52 (1H, d, J=7.9 Hz), 7.58 (1H, brs), 7.83 (2H, d, J=8.6 Hz).

FAB+ (m/z): 500 (M+H).

Example 84

Methyl 2-[3-[[2-(4-chlorophenyl)-4-methylthiazol-5-yl]methoxycarbonylamino]piperidin-1-yl]benzoate

[Chemical formula 191]

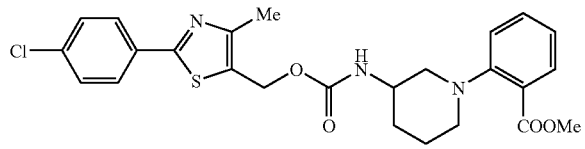

Using 1-[2-(methoxycarbonyl)phenyl]nipecotic acid (79.0 mg, 0.300 mmol) and 2-(4-chlorophenyl)-4-methylthiazol-5-yl methanol (71.9 mg, 0.300 mmol), the same procedure was followed as in Example 83 to give 43.7 mg (29%) of the desired compound as a pale yellow oil.

$^1$H NMR (400 MHz, CDCl$_3$) δ 1.54-1.65 (2H, m), 1.83-1.97 (2H, m), 2.50 (3H, s), 2.83 (1H, td, J=11.0, 1.8 Hz), 2.99-3.10 (3H, m), 3.89 (3H, s), 3.90-3.96 (1H, m), 5.22 (1H, d, J=13.4 Hz), 5.27 (1H, d, J=13.4 Hz), 6.16 (1H, d, J=7.3 Hz), 7.02-7.06 (2H, m), 7.37-7.43 (3H, m), 7.71 (1H, dd, J=7.3, 1.8 Hz), 7.83 (2H, d, J=8.6 Hz).

FAB+ (m/z): 500 (M+H).

Example 85

Methyl 3-[3-[3-[2-(4-chlorophenyl)-4-methylthiazol-5-yl]ureido]piperidin-1-yl]benzoate

[Chemical formula 192]

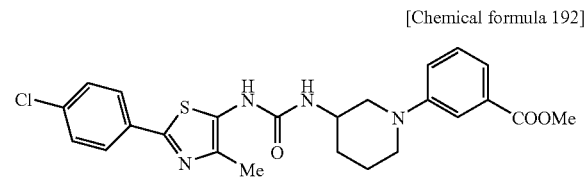

1-[3-(Methoxycarbonyl)phenyl]nipecotic acid (54.0 mg, 0.205 mmol) was suspended in benzene (4 mL). To this suspension, diphenylphosphoryl azide (0.0487 mL, 0.226 mmol) and triethylamine (0.0316 mL, 0.226 mmol) were added and the mixture was stirred for 2 hours while being refluxed. Subsequently, 5-amino-2-(4-chlorophenyl)-4-methylthiazole (46.0 mg, 0.205 mmol) and triethylamine (0.0316 mL, 0.226 mmol) were added and the mixture was further stirred for 6 hours while refluxed. Water was then added and the mixture was extracted with ethyl acetate. The extract was washed sequentially with 0.1 mol/L hydrochloric acid, a saturated aqueous sodium bicarbonate solution and brine. The washed product was dried over magnesium sulfate and the solvent was evaporated. Purification of the resulting residue by silica gel column chromatography (hexane:ethyl acetate=4:1->1:4) gave 43.5 mg (44%) of the desired compound as a yellow powder.

$^1$H NMR (400 MHz, CDCl$_3$) δ 1.68-1.80 (4H, m), 2.33 (3H, s), 3.00-3.05 (1H, m), 3.16 (1H, dd, J=11.6, 5.5 Hz), 3.20-3.25 (1H, m), 3.28 (1H, dd, J=11.6, 3.1 Hz), 3.87 (3H, s), 4.12-4.18 (1H, m), 5.49 (1H, d, J=7.9 Hz), 6.72 (1H, brs), 7.07 (1H, dd, J=7.9, 1.8 Hz), 7.25-7.29 (1H, m), 7.36 (2H, d, J=8.6 Hz), 7.49 (1H, d, J=7.3 Hz), 7.53-7.54 (1H, m), 7.76 (2H, d, J=8.6 Hz).

FAB+ (m/z): 485 (M+H).

Example 86

Methyl 2-[3-[3-[2-(4-chlorophenyl)-4-methylthiazol-5-yl]ureido]piperidin-1-yl]benzoate

[Chemical formula 193]

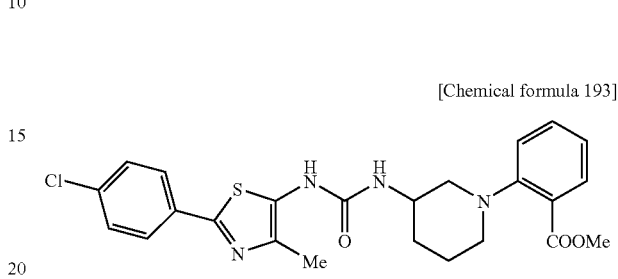

Using 1-(2-methoxycarbonylphenyl)nipecotic acid (79.0 mg, 0.300 mmol) and 5-amino-2-(4-chlorophenyl)-4-methylthiazole (67.4 mg, 0.300 mmol), the same procedure was followed as in Example 85 to give 29.0 mg (20%) of the desired compound as a pale yellow amorphous product.

$^1$H NMR (400 MHz, CDCl$_3$) δ 1.47-1.74 (2H, m), 1.97-2.03 (2H, m), 2.40 (3H, s), 2.84-2.90 (1H, m), 2.95-2.98 (1H, m), 3.05-3.08 (1H, m), 3.13-3.16 (1H, m), 3.85 (3H, s), 4.10-4.13 (1H, m), 6.83 (1H, brs), 6.92 (1H, brs), 7.07 (1H, t, J=7.3 Hz), 7.11 (1H, d, J=7.9 Hz), 7.35 (2H, d, J=8.6 Hz), 7.46 (1H, td, J=7.3, 1.2 Hz), 7.75 (1H, dd, J=7.3, 1.2 Hz), 7.79 (2H, d, J=8.6 Hz).

FAB+ (m/z): 485 (M+H).

Example 87

Methyl 3-[3-[2-[2-(4-chlorophenyl)-4-methylthiazol-5-yl]-2-oxoethyl]piperidin-1-yl]benzoate Step 87a) 2-[2-(4-Chlorophenyl)-4-methylthiazol-5-yl]-2-(trimethylsilyloxy)acetonitrile

[Chemical formula 194]

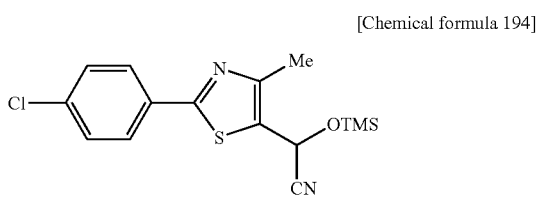

2-(4-Chlorophenyl)-4-methylthiazole-5-carboaldehyde (475 mg, 2.00 mmol) was suspended in acetonitrile (4 mL). To this suspension, trimethylsilyl cyamide (0.529 mL, 4.00 mmol) and zinc iodide (12.8 mg, 0.0400 mmol) were added and the mixture was stirred at room temperature for 2 hours. Subsequently, water was added and the mixture was extracted with ethyl acetate. The extract was washed with brine, followed by drying over magnesium sulfate and evaporation of the solvent. The residue was air-dried to give 669 mg (quant.) of the desired compound as a pale yellow powder.

$^1$H NMR (400 MHz, CDCl$_3$) δ 0.25 (9H, s), 2.49 (3H, s), 5.69 (1H, s), 7.41 (2H, d, J=8.6 Hz), 7.85 (2H, d, J=8.6 Hz).

FAB⁺ (m/z): 337 (M+H).

Step 87b) 1-(tert-Butoxycarbonyl)-3-[2-[2-(4-chlorophenyl)-4-methylthiazol-5-yl]-2-oxoethyl]piperidine

[Chemical formula 195]

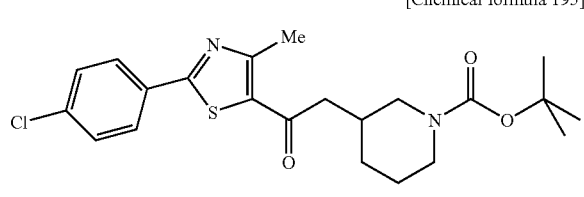

In an argon atmosphere, a solution of 1.8 mol/L lithium diisopropylamide in heptane/tetrahydrofuran/ethylbenzene (1.22 mL, 2.19 mmol), chilled to −78° C., was added to 2-[2-(4-chlorophenyl)-4-methylthiazol-5-yl]-2-(trimethylsilyloxy)acetonitrile (669 mg, 1.99 mmol) in tetrahydrofuran (2 mL). The mixture was stirred for 20 min, followed by addition of 1-(tert-butoxycarbonyl)-3-iodomethylpiperidine (647 mg, 1.99 mmol) in tetrahydrofuran (2 mL). The mixture was further stirred for 1 hour as it warmed from −78° C. to room temperature. 0.5 mol/L ice-chilled hydrochloric acid was then added and the mixture was further stirred for 10 min. Subsequently, the mixture was extracted with ethyl acetate and washed sequentially with a saturated aqueous sodium bicarbonate solution and brine. The washed product was dried over magnesium sulfate and the solvent was evaporated. Purification of the resulting residue by silica gel column chromatography (hexane:ethyl acetate=20:1->5:1) gave 429 mg (50%) of the desired compound as a yellow oil.

¹H NMR (400 MHz, CDCl₃) δ 1.22-1.52 (12H, m), 1.61-1.68 (1H, m), 1.86-1.93 (1H, m), 2.18-2.28 (1H, m), 2.67 (1H, dd, J=7.3, 15.9 Hz), 2.78 (3H, s), 2.82 (1H, dd, J=15.9, 6.1 Hz), 2.87-3.10 (1H, m), 3.67-3.97 (2H, m), 7.44 (2H, d, J=8.6 Hz), 7.92 (2H, d, J=8.6 Hz).

FAB⁺ (m/z): 434 (M+H).

Step 87c) 3-[2-[2-(4-Chlorophenyl)-4-methylthiazol-5-yl]-2-oxoethyl]piperidine

[Chemical formula 196]

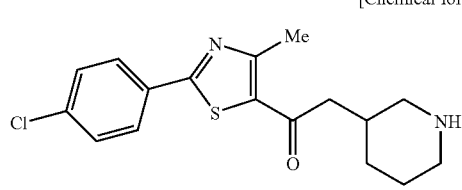

Using 1-(tert-butoxycarbonyl)-3-[2-[2-(4-chlorophenyl)-4-methylthiazol-5-yl]-2-oxoethyl]piperidine (429 mg, 0.986 mmol), the same procedure was followed as in Step 76b of Example 76 to give 281 mg (85%) of the desired compound as a yellow oil.

¹H NMR (400 MHz, DMSO-d₆) δ 1.08-1.18 (1H, m), 1.31-1.42 (1H, m), 1.51-1.58 (1H, m), 1.72-1.78 (1H, m), 1.94-2.04 (1H, m), 2.25 (1H, dd, J=11.6, 9.8 Hz), 2.43 (1H, td, J=11.6, 2.4 Hz), 2.71 (3H, s), 2.75-2.85 (3H, m), 2.90 (1H, dd, J=11.6, 2.4 Hz), 7.60 (2H, d, J=8.6 Hz), 8.03 (2H, d, J=8.6 Hz).

Step 87d) Methyl 3-[3-[2-[2-(4-chlorophenyl)-4-methylthiazol-5-yl]-2-oxoethyl]piperidin-1-yl]benzoate

[Chemical formula 197]

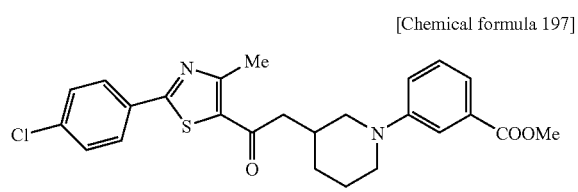

Using 3-[2-[2-(4-chlorophenyl)-4-methylthiazol-5-yl]-2-oxoethyl]piperidine (140 mg, 0.418 mmol) and 3-(methoxycarbonyl)phenylboric acid (150 mg, 0.836 mmol), the same procedure was followed as in Example 2 to give 88.7 mg (45%) of the desired compound as a yellow oil.

¹H NMR (400 MHz, CDCl₃) δ 1.24-1.95 (4H, m), 2.40-2.50 (1H, m), 2.70 (1H, dd, J=11.6, 9.8 Hz), 2.77-2.82 (4H, m), 2.87-2.93 (2H, m), 3.57 (1H, td, J=12.2, 4.3 Hz), 3.65 (1H, dd, J=12.2, 3.7 Hz), 3.90 (3H, s), 7.13 (1H, dd, J=7.9, 1.8 Hz), 7.29 (1H, t, J=7.9 Hz), 7.44 (2H, d, J=8.6 Hz), 7.47 (1H, d, J=7.9 Hz), 7.59 (1H, brs), 8.03 (2H, d, J=8.6 Hz).

FAB⁺ (m/z): 468 (M+H).

Example 88

Methyl 3-[3-[2-[2-(4-chlorophenyl)-4-methylthiazol-5-yl]ethenyl]piperidin-1-yl]benzoate Step 88a) [2-(4-Chlorophenyl)-4-methylthiazol-5-yl]methyltriphenylphosphonium iodide

[Chemical formula 198]

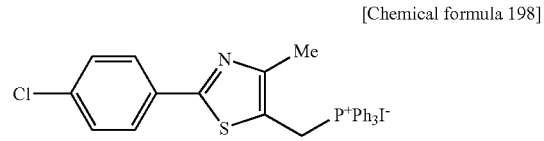

Triphenylphosphine (1.15 g, 4.26 mmol) and sodium iodide (580 mg, 3.87 mmol) were added to 5-chloromethyl-2-(4-chlorophenyl)-4-methylthiazole (1.00 g, 3.87 mmol) in tetrahydrofuran (20 mL). The reaction mixture was stirred for 5 hours while being stirred. Subsequently, the crystallized powdery product was collected by filtration and washed with hexane to give 2.43 g (quant.) of the desired compound as a colorless powder.

¹H NMR (400 MHz, DMSO-d₆) δ 1.80 (3H, d, J=3.1 Hz), 5.45 (2H, d, J=14.1), 7.52 (2H, d, J=8.6 Hz), 7.74-7.82 (14H, m), 7.93-7.98 (3H, m).

Step 88b) 1-Benzyloxycarbonyl-3-[2-[2-(4-chlorophenyl)-4-methylthiazol-5-yl]ethenyl]piperidine

[Chemical formula 199]

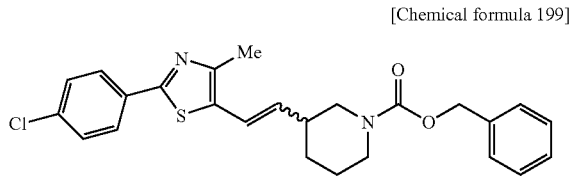

In an argon atmosphere, a solution of 1.59 mol/Ln-butyl lithium in hexane (2.03 mL, 3.23 mmol), chilled to −78° C., was added to a suspension of [2-(4-chlorophenyl)-4-methylthiazol-5-yl]methyltriphenylphosphonium iodide (1.80 g, 2.94 mmol) in tetrahydrofuran (20 mL). The reaction mixture was stirred for 1 hour as it warmed from −78° C. to room temperature. Subsequently, the mixture was chilled again to −78° C. and 1-benzyloxycarbonyl-3-formylpiperidine (727 mg, 2.94 mmol) in tetrahydrofuran (5 mL) was added. The mixture was stirred at −78° C. for 1 hour and at room temperature for the subsequent 6 hours. Subsequently, water was added and the mixture was extracted with ethyl acetate and washed with brine. The washed product was dried over magnesium sulfate and the solvent was evaporated. Purification of the resulting residue by silica gel column chromatography (hexane:ethyl acetate=20:1->5:1) gave 1.16 g (87%) of the desired compound as a yellow oil.

FAB⁺ (m/z): 453 (M+H).

Step 88c) 3-[2-[2-(4-Chlorophenyl)-4-methylthiazol-5-yl]ethenyl]piperidine

[Chemical formula 200]

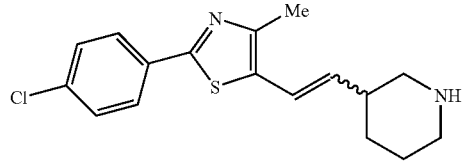

1-Benzyloxycarbonyl-3-[2-[2-(4-chlorophenyl)-4-methylthiazol-5-yl]ethenyl]piperidine (1.16 g, 2.56 mmol) in 6 mol/L hydrochloric acid (25 mL) was stirred for 1 hour while being refluxed. Subsequently, the reaction mixture washed with ethyl acetate. A 10 mol/L aqueous sodium hydroxide solution was then added to make the mixture basic and the mixture was extracted with ethyl acetate. The extract washed with brine, followed by drying over magnesium sulfate and evaporation of the solvent. The residue was air-dried to give 749 mg (92%) of the desired compound as a yellow powder.

FAB⁺ (m/z): 319 (M+H).

Step 88d) Methyl (E)-3-[(3-[2-[2-(4-chlorophenyl)-4-methylthiazol-5-yl]ethenyl]piperidin-1-yl]benzoate

[Chemical formula 201]

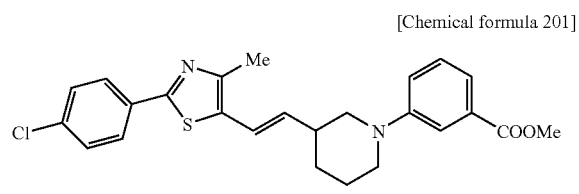

Using 3-[2-[2-(4-chlorophenyl)-4-methylthiazol-5-yl]ethenyl]piperidine (153 mg, 0.480 mmol) and 3-(methoxycarbonyl)phenylboric acid (173 mg, 0.960 mmol), the same procedure was followed as in Example 2 to give 77.7 mg (36%) of the desired compound as a yellow powder.

¹H NMR (400 MHz, CDCl₃) δ 1.35-1.45 (1H, m), 1.70-1.81 (1H, m), 1.83-1.90 (1H, m), 1.95-2.01 (1H, m), 2.46 (3H, s), 2.52-2.62 (1H, m), 2.67-2.72 (1H, m), 2.80 (1H, td, J=12.2, 3.1 Hz), 3.65-3.68 (1H, m), 3.70-3.74 (1H, m), 3.91 (3H, s), 5.94 (1H, dd, J=15.9, 7.3 Hz), 6.57 (1H, dd, J=15.9, 1.2 Hz), 7.14 (1H, dd, J=7.9, 2.4 Hz), 7.31 (1H, t, J=7.9 Hz), 7.39 (2H, d, J=8.6 Hz), 7.49 (1H, d, J=7.3 Hz), 7.62-7.63 (1H, m), 7.83 (2H, d, J=8.6 Hz).

FAB⁺ (m/z): 453 (M+H).

Example 89

Methyl 3-[2-[[2-(4-chlorophenyl)-4-methylthiazol-5-yl]carbonylaminomethyl]morpholine-4-yl]benzoate Step 89a) N-[[4-(tert-Butoxycarbonyl)morpholin-2-yl]methyl]-2-(4-chlorophenyl)-4-methylthiazole-5-carboxamide

[Chemical formula 202]

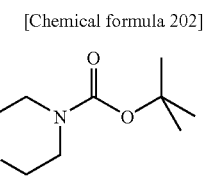

Using 2-(4-chlorophenyl)-4-methylthiazole-5-carboxylic acid (307 mg, 1.21 mmol) and 4-(tert-butoxycarbonyl)morpholine-2-yl methylamine (262 mg, 1.21 mmol), the same procedure was followed as in Step 1a of Example 1 to give 483 mg (88%) of the desired compound as a colorless powder.

¹HMR (400 MHz, CDCl₃) δ 1.47 (9H, s), 2.66-2.76 (4H, m), 2.93 (1H, m), 3.25-3.36 (1H, m), 3.53-3.62 (2H, m), 3.74-3.79 (1H, m), 3.83-4.04 (3H, m), 6.20 (1H, m), 7.42 (2H, d, J=8.6 Hz), 7.87 (2H, d, J=8.6 Hz).

Step 89b) N-(Morpholin-2-yl methyl)-2-(4-chlorophenyl)-4-methylthiazole-5-carboxamide

[Chemical formula 203]

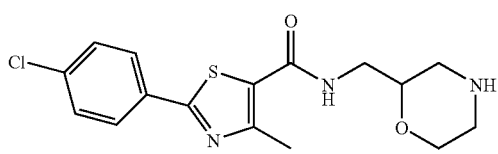

Using N-[[4-(tert-butoxycarbonyl)morpholin-2-yl]methyl]-2-(4-chlorophenyl)-4-methylthiazole-5-carboxamide (483 mg, 1.07 mmol), the same procedure was followed as in Step 76b of Example 76 to give 366 mg (97%) of the desired compound as a colorless powder.

$^1$H NMR (400 MHz, DMSO-d$_6$) δ 2.36 (1H, dd, J=12.2, 9.8 Hz), 2.58-2.67 (5H, m), 2.80 (1H, dd, J=12.2, 1.8 Hz), 3.23 (2H, td, J=5.5, 1.8 Hz), 3.42 (1H, td, J=11.0, 3.7 Hz), 3.46-3.52 (1H, m), 3.72-3.74 (1H, m), 7.58 (2H, d, J=8.6 Hz), 7.95 (2H, d, J=8.6 Hz), 8.33 (1H, t, J=5.5 Hz).

Step 89c) Methyl 3-[2-[[2-(4-chlorophenyl)-4-methylthiazol-5-yl]carbonylaminomethyl]morpholin-4-yl]benzoate

[Chemical formula 204]

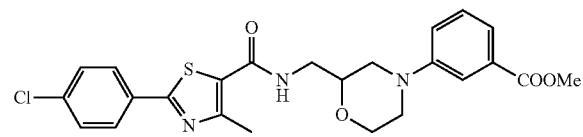

Using N-(morpholin-2-yl methyl)-2-(4-chlorophenyl)-4-methylthiazole-5-carboxamide (120 mg, 0.341 mmol) and 3-(methoxycarbonyl)phenylboric acid (123 mg, 0.682 mmol), the same procedure was followed as in Example 2 to give 102 mg (62%) of the desired compound as a colorless powder.

$^1$H NMR (400 MHz, CDCl$_3$) δ 2.64-2.69 (1H, m), 2.75 (3H, s), 2.90 (1H, td, J=11.6, 3.1 Hz), 3.42-3.51 (2H, m), 3.58-3.62 (1H, m), 3.80-3.92 (6H, m), 4.07-4.11 (1H, m), 6.26 (1H, t, J=5.5 Hz), 7.11 (1H, dd, J=7.9, 2.4 Hz), 7.35 (1H, d, J=7.9 Hz), 7.42 (2H, d, J=8.6 Hz), 7.55-7.59 (2H, m), 7.88 (2H, d, J=8.6 Hz).

Example 90

Methyl 3-[2-[N-[[2-(4-chlorophenyl)-4-methylthiazol-5-yl]methyl]carbamoyl]morpholin-4-yl]benzoate Step 90a) N-[[2-(4-Chlorophenyl)-4-methylthiazol-5-yl]methyl]-4-(tert-butoxycarbonyl)morpholine-2-carboxamide

[Chemical formula 205]

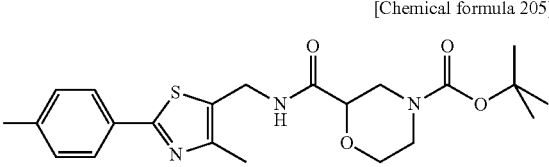

Using 2-(4-chlorophenyl)-4-methylthiazol-5-yl methylamine (39.4 mg, 0.165 mmol) and 4-(tert-butoxycarbonyl)morpholine-2-carboxylic acid (38.3 mg, 0.165 mmol), the same procedure was followed as in Step 3a of Example 3 to give 49.5 mg (67%) of the desired compound as a colorless amorphous product.

$^1$H NMR (400 MHz, CDCl$_3$) δ 1.47 (9H, s), 2.46 (3H, s), 2.76 (1H, t, J=12.2 Hz), 2.88 (1H, t, J=12.2 Hz), 3.57 (1H, td, J=11.6, 3.1 Hz), 3.92-3.96 (3H, m), 4.32-4.43 (1H, m), 4.60 (2H, d, J=6.1 Hz), 6.90 (1H, m), 7.39 (2H, d, J=8.6 Hz), 7.82 (2H, d, J=8.6 Hz).

Step 90b) N-[[2-(4-Chlorophenyl)-4-methylthiazol-5-yl]methyl]morpholine-2-carboxamide

[Chemical formula 206]

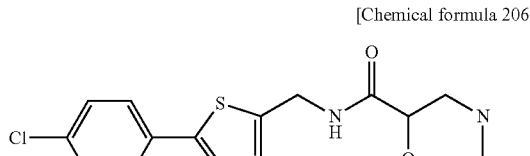

Using N-[[2-(4-chlorophenyl)-4-methylthiazol-5-yl]methyl]-4-(tert-butoxycarbonyl)morpholine-2-carboxamide (49.5 mg, 0.110 mmol), the same procedure was followed as in Step 76b of Example 76 to give 29.5 mg (76%) of the desired compound as a colorless powder.

$^1$H NMR (400 MHz, DMSO-d$_6$) δ 2.39 (3H, s), 2.46 (1H, dd, J=12.2 10.4 Hz), 2.58-2.70 (3H, m), 3.00 (1H, dd, J=12.2

3.1 Hz), 3.49 (1H, td, J=11.0 3.1 Hz), 3.77-3.83 (2H, m), 4.39 (2H, d, J=6.1 Hz), 7.52 (2H, d, J=8.6 Hz), 7.87 (2H, d, J=8.6 Hz), 8.43 (1H, t, J=6.1 Hz).

Step 90c) Methyl 3-[2-[N-[[2-(4-chlorophenyl)-4-methylthiazol-5-yl]methyl]carbamoyl]morpholin-4-yl]benzoate

[Chemical formula 207]

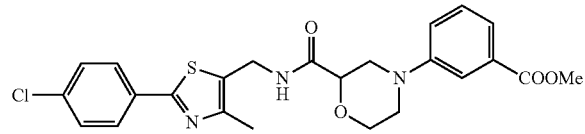

Using N-[[2-(4-chlorophenyl)-4-methylthiazol-5-yl]methyl]morpholine-2-carboxamide (29.5 mg, 0.0838 mmol) and 3-(methoxycarbonyl)phenylboric acid (30.2 mg, 0.168 mmol), the same procedure was followed as in Example 2 to give 28.9 mg (71%) of the desired compound as a colorless oil.

$^1$H NMR (400 MHz, CDCl$_3$) δ 2.47 (3H, s), 2.71 (1H, dd, J=12.2, 11.0 Hz), 2.89 (1H, td, J=12.2 3.1 Hz), 3.47-3.50 (1H, m), 3.83 (1H, dd, J=8.6, 2.4 Hz), 3.91 (3H, s), 4.04-4.11 (2H, m), 4.22 (1H, dd, J=11.4 Hz, J=3.1 Hz), 4.63 (2H, d, J=6.1 Hz), 6.96 (1H, t, J=5.5 Hz), 7.15 (1H, dd, J=7.9, 2.4 Hz), 7.35 (1H, t, J=7.9 Hz), 7.38 (2H, d, J=8.6 Hz), 7.58 (1H, d, J=7.3 Hz), 7.60-7.61 (1H, m), 7.82 (2H, d, J=8.6 Hz).

Example 91

Methyl 2-[2-[N-[[2-(4-chlorophenyl)-4-methylthiazol-5-yl]methyl]carbamoyl]morpholin-4-yl]benzoate

[Chemical formula 208]

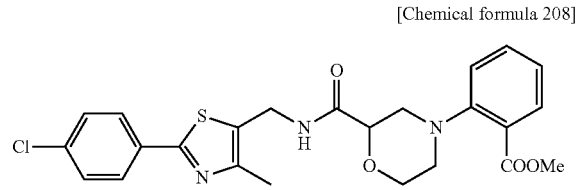

Using N-[[2-(4-chlorophenyl)-4-methylthiazol-5-yl]methyl]morpholine-2-carboxamide (54.4 mg, 0.155 mmol) and methyl 2-iodobenzoate (40.6 mg, 0.155 mmol), the same procedure was followed as in Example 58 to give 64.5 mg (86%) of the desired compound as a colorless powder.

$^1$H NMR (400 MHz, CDCl$_3$) δ 2.47 (3H, s), 2.76 (1H, dd, J=11.6, 10.4 Hz), 2.89 (1H, td, J=11.0 Hz, J=3.1 Hz), 3.15-3.20 (1H, m), 3.69 (1H, dt, J=12.2 Hz, J=2.4 Hz), 3.87-3.93 (4H, m), 3.99-4.03 (1H, m), 4.28 (1H, dd, J=10.4, 2.4 Hz), 4.55-4.66 (2H, m), 6.97 (1H, t, J=6.1 Hz), 7.03-7.08 (2H, m), 7.39 (2H, d, J=8.6 Hz), 7.43 (1H, td, J=7.9, 1.8 Hz), 7.79 (1H, dd, J=7.9, 1.8 Hz), 7.83 (2H, d, J=8.6 Hz).

Example 92

Methyl 3-[2-[[2-(4-chlorophenyl)-4-methylthiazol-5-yl]methoxymethyl]morpholin-4-yl]benzoate Step 92a) 4-(tert-Butoxycarbonyl)-2-[[2-(4-chlorophenyl)-4-methylthiazol-5-yl]methoxymethyl]morpholine

[Chemical formula 209]

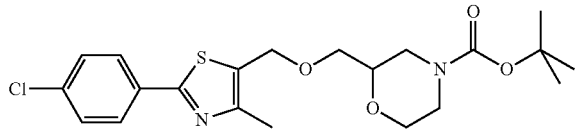

Using 4-(tert-butoxycarbonyl)morpholin-2-ylmethanol (217 mg, 1.00 mmol) and 5-chloromethyl-2-(4-chlorophenyl)-4-methylthiazole (258 mg, 1.00 mmol), the same procedure was followed as in Step 5a of Example 5 to give 303 mg (69%) of the desired compound as a yellow oil.

$^1$H NMR (400 MHz, CDCl$_3$) δ 1.46 (9H, s), 2.45 (3H, s), 2.74 (1H, t, J=11.6 Hz), 2.88-3.00 (1H, m), 3.49-3.63 (4H, m), 3.78-4.00 (3H, m), 4.71 (2H, s), 7.39 (2H, d, J=8.6 Hz), 7.83 (2H, d, J=8.6 Hz).

Step 92b) 2-[[2-(4-Chlorophenyl)-4-methylthiazol-5-yl]methoxymethyl]morpholine

[Chemical formula 210]

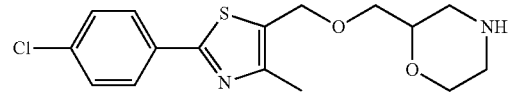

Using 4-tert-butoxycarbonyl-2-[[2-(4-chlorophenyl)-4-methylthiazol-5-yl]methoxymethyl]morpholine (303 mg, 0.690 mmol), the same procedure was followed as in Step 76b of Example 76 to give 220 mg (94%) of the desired compound as a yellow oil.

$^1$H NMR (400 MHz, DMSO-d$_6$) δ 2.33-2.42 (4H, m), 2.57-2.68 (2H, m), 2.76 (1H, dd, J=12.2, J=2.4 Hz), 3.36-3.45

(4H, m), 3.48-3.53 (1H, m), 3.68-3.72 (1H, m), 4.67 (2H, s), 7.54 (2H, d, J=8.6 Hz), 7.91 (2H, d, J=8.6 Hz).

Step 92c) Methyl 3-[2-[[2-(4-chlorophenyl)-4-methylthiazol-5-yl]methoxymethyl]morpholin-4-yl]benzoate

[Chemical formula 211]

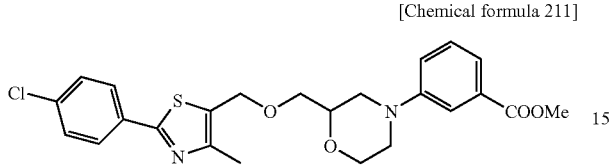

Using 2-[2-(4-chlorophenyl)-4-methylthiazol-5-yl]methoxymethyl]morpholine (49.0 mg, 0.145 mmol) and 3-(methoxycarbonyl)phenylboric acid (52.2 mg, 0.290 mmol), the same procedure was followed as in Example 2 to give 50.5 mg (74%) of the desired compound as a pale yellow oil.

$^1$H NMR (400 MHz, CDCl$_3$) δ 2.47 (3H, s), 2.68 (1H, dd, J=11.6, 10.4 Hz), 2.90 (1H, dd, J=11.6, 3.1 Hz), 3.47 (1H, d, J=12.2 Hz), 3.56-3.66 (3H, m), 3.82 (1H, td, J=11.6 Hz, J=2.4 Hz), 3.89-3.90 (4H, m), 4.06-4.10 (1H, m), 4.75 (2H, s), 7.10 (1H, dd, J=7.9, 2.4 Hz), 7.33 (1H, t, J=7.9 Hz), 7.39 (2H, d, J=8.6 Hz), 7.54 (1H, dt, J=7.3, 1.2 Hz), 7.58-7.59 (1H, m), 7.85 (2H, d, J=8.6 Hz).

Example 93

Methyl 2-[2-[[2-(4-chlorophenyl)-4-methylthiazol-5-yl]methoxymethyl]morpholin-4-yl]benzoate

[Chemical formula 212]

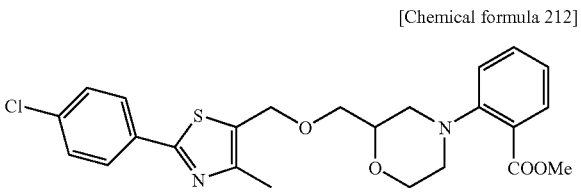

Using 2-[2-(4-chlorophenyl)-4-methylthiazol-5-yl]methoxymethyl]morpholine (110 mg, 0.325 mmol) and a solution of methyl 2-iodobenzoate (85.2 mg, 0.325 mmol) in toluene (1 mL), the same procedure was followed as in Example 58 to give 81.4 mg (53%) of the desired compound as a pale yellow oil.

$^1$H NMR (400 MHz, CDCl$_3$) δ 2.45 (3H, s), 2.73 (1H, dd, J=11.6, 10.4 Hz), 2.94 (1H, td, J=11.6, 3.1 Hz), 3.11-3.15 (1H, m), 3.23 (1H, dt, J=11.6, 1.8 Hz), 3.53-3.63 (2H, m), 3.86-3.91 (4H, m), 3.93-3.97 (1H, m), 4.00 (1H, dt, J=12.2, 2.4 Hz), 4.72 (2H, s), 7.01-7.05 (2H, m), 7.38-7.44 (3H, m), 7.75 (1H, dd, J=7.9 Hz, J=1.2 Hz), 7.83 (2H, d, J=8.6 Hz).

Example 94

Methyl 5-[3-[[2-(4-chlorophenyl)-4-methylthiazol-5-yl]carbonylamino]piperidin-1-yl]-2-methoxybenzoate Step 94a) 5-[3-[[2-(4-Chlorophenyl)-4-methylthiazol-5-yl]carbonylamino]piperidin-1-yl]-2-methoxybenzaldehyde

[Chemical formula 213]

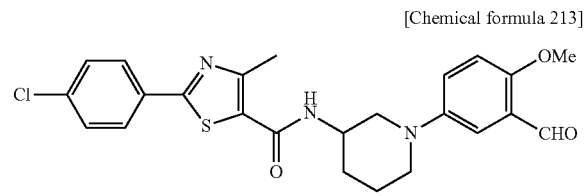

Using N-(piperidin-3-yl)-2-(4-chlorophenyl)-4-methylthiazole-5-carboxamide (254 mg, 0.756 mmol) and 3-formyl-4-methoxyphenylboric acid (273 mg, 1.52 mmol), the same procedure was followed as in Example 2 to give 49.8 mg (14%) of the desired compound as a yellow powder.

$^1$H NMR (400 MHz, CDCl$_3$) δ 1.73-1.94 (4H, m), 2.74 (3H, s), 2.92-2.98 (1H, m), 3.13-3.30 (3H, m), 3.90 (3H, s), 4.37-4.44 (1H, m), 6.39 (1H, d, J=7.9 Hz), 6.95 (1H, d, J=9.1 Hz), 7.20-7.25 (1H, m), 7.39-7.44 (3H, m), 7.87 (2H, d, J=8.6 Hz), 10.45 (1H, s).

FAB$^+$ (m/z): 470 (M+H).

Step 94b) Methyl 5-[3-[[2-(4-chlorophenyl)-4-methylthiazol-5-yl]carbonylamino]piperidin-1-yl]-2-methoxybenzoate

[Chemical formula 214]

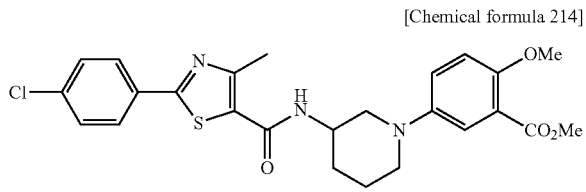

Using 5-[3-[[2-(4-chlorophenyl)-4-methylthiazol-5-yl]carbonylamino]piperidin-1-yl]-2-methoxybenzaldehyde (45.2 mg, 0.0962 mmol), the same procedure was followed as in Step 5d of Example 5 to give 31.8 mg (66%) of the desired compound as a cream-colored powder.

$^1$H NMR (400 MHz, CDCl$_3$) δ 1.72-1.93 (4H, m), 2.74 (3H, s), 2.88-2.98 (1H, m), 3.18 (2H, d, J=3.4 Hz), 3.24-3.30 (1H, m), 3.87 (3H, s), 3.90 (3H, s), 4.37-4.44 (1H, m), 6.45 (1H, d, J=8.6 Hz), 6.93 (1H, d, J=8.6 Hz), 7.12 (1H, dd, J=8.6, 5.4 Hz), 7.40-7.45 (3H, m), 7.88 (2H, d, J=8.6 Hz).

FAB+ (m/z): 500 (M+H).

Example 95

Methyl 5-[3-[[2-(4-chlorophenyl)-4-methylthiazol-5-yl]carbonylamino]piperidin-1-yl]-2-fluorobenzoate Step 95a) 5-[3-[[2-(4-Chlorophenyl)-4-methylthiazol-5-yl]carbonylamino]piperidin-1-yl]-2-fluorobenzaldehyde

[Chemical formula 215]

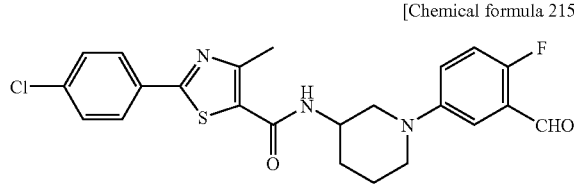

Using N-(piperidin-3-yl)-2-(4-chlorophenyl)-4-methylthiazole-5-carboxamide (238 mg, 0.709 mmol) and 3-formyl-4-fluorophenylboric acid (238 mg, 1.42 mmol), the same procedure was followed as in Example 2 to give 55.0 mg (17%) of the desired compound as a pale yellow powder.

$^1$H NMR (400 MHz, CDCl$_3$) δ 1.76-1.93 (4H, m), 2.73 (3H, s), 3.02-3.09 (1H, m), 3.16 (1H, dd, J=11.6, 5.5 Hz), 3.22-3.30 (1H, m), 3.34 (1H, dd, J=11.6, 3.0 Hz), 4.36-4.43 (1H, m), 6.24 (1H, d, J=7.9 Hz), 7.10 (1H, t, J=9.1 Hz), 7.20-7.25 (1H, m), 7.38 (1H, dd, J=5.5, 3.0 Hz), 7.42 (2H, d, J=8.6 Hz), 7.87 (2H, d, J=8.6 Hz), 10.34 (1H, s).

FAB+ (m/z): 458 (M+H).

Step 95b) Methyl 5-[3-[[2-(4-chlorophenyl)-4-methylthiazol-5-yl]carbonylamino]piperidin-1-yl]-2-fluorobenzoate

[Chemical formula 216]

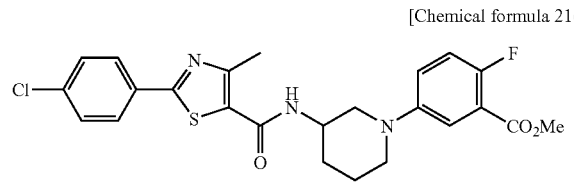

Using 5-[3-[[2-(4-chlorophenyl)-4-methylthiazol-5-yl]carbonylamino]piperidin-1-yl]-2-fluorobenzaldehyde (52.7 mg, 0.115 mmol), the same procedure was followed as in Step 5d of Example 5 to give 30.7 mg (55%) of the desired compound as a colorless powder.

$^1$H NMR (400 MHz, CDCl$_3$) δ 1.76-1.94 (4H, m), 2.74 (3H, s), 2.97-3.05 (1H, m), 3.16-3.22 (1H, m), 3.25-3.33 (2H, m), 3.93 (3H, s), 4.37-4.44 (1H, m), 6.31 (1H, d, J=7.9 Hz), 7.04-7.08 (1H, m), 7.09-7.15 (1H, m), 7.42 (2H, d, J=8.6 Hz), 7.48 (1H, dd, J=5.5, 3.1 Hz), 7.87 (2H, d, J=8.6 Hz).

EI+ (m/z): 487 (M+).

Example 96

Methyl 3-benzyloxy-5-[3-[[2-(4-chlorophenyl)-4-methylthiazol-5-yl]carbonylamino]piperidin-1-yl]benzoate Step 96a) Methyl 3-benzyloxy-5-[3-(tert-butoxycarbonylamino)piperidin-1-yl]benzoate

[Chemical formula 217]

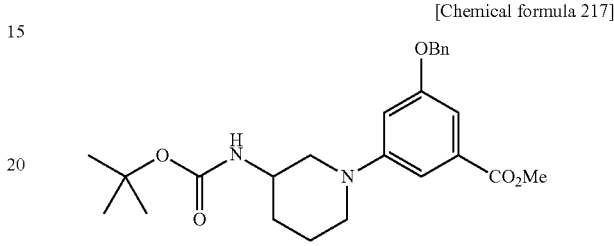

Using 3-(tert-butoxycarbonylamino)piperidine (301 mg, 1.50 mmol) and methyl 3-benzyloxy-5-(trifluoromethanesulfonyloxy)benzoate (595 mg, 1.52 mmol), the same procedure was followed as in Example 58 to give 39.7 mg (6.0%) of the desired compound as a brown oil.

$^1$H NMR (400 MHz, CDCl$_3$) δ 1.38-1.54 (10H, m), 1.63-1.73 (1H, m), 1.75-1.87 (2H, m), 2.97-3.05 (1H, m), 3.10-3.18 (2H, m), 3.32-3.38 (1H, m), 3.80-3.93 (4H, m), 4.81-4.89 (1H, m), 5.08 (2H, s), 6.74 (1H, s), 7.13-7.17 (1H, m), 7.23-7.27 (1H, m), 7.30-7.47 (5H, m).

FAB+ (m/z): 441 (M+H).

Step 96b) Methyl 3-benzyloxy-5-[3-[[2-(4-chlorophenyl)-4-methylthiazol-5-yl]carbonylamino]piperidin-1-yl]benzoate

[Chemical formula 218]

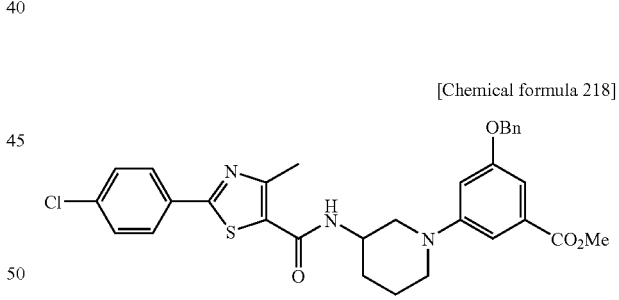

Methyl 3-benzyloxy-5-(3-tert-butoxycarbonylaminopiperidin-1-yl)benzoate (23.0 mg, 0.0522 mmol) was dissolved in anhydrous dichloromethane (0.5 mL). While this solution is chilled in an ice bath and stirred, trifluoroacetic acid (80 μL, 6.82 mmol) was added and the reaction mixture was stirred for 2 hours. Subsequently, the mixture was concentrated and a 10% hydrochloric acid/methanol solution (1.5 mL) was added to the residue. The mixture was then stirred at room temperature for 1 hour and was concentrated. The same process was repeated 3 times and the resulting solid were washed with ethyl acetate. This gave 20.9 mg of a blown powder. This product (19.8 mg) was dissolved in N,N-dimethylformamide (1 mL). While the solution was chilled to 0° C. and stirred, 2-(4-chlorophenyl)-4-methylthiazole-5-carboxylic acid (15.5 mg, 0.0611 mmol), 1-hydroxybenzotriazole monohydrate (8.8 mg, 0.0575 mmol), N-methylmorpholine (17 μL, 0.155 mmol) and 3-(3-dimethylaminopropyl)-1-ethylcarbodiimide hydrochloride (11.7 mg, 0.0610 mmol) were added and the mixture was stirred for 20 min. The reaction mixture was further stirred at room temperature for the subsequent 6 hours. Subsequently, the mixture was diluted with ethyl acetate and the organic layer washed sequentially with 5% aqueous citric acid, a saturated aqueous sodium bicarbonate solution, water and brine. The washed product was then dried over anhydrous sodium sulfate and was concentrated. Purification of the resulting residue by silica gel column chromatography (hexane:ethyl acetate=4:1) gave 22.8 mg (75%) of the desired compound as a colorless powder.

$^1$H NMR (400 MHz, CDCl$_3$) δ 1.74-1.92 (4H, m), 2.71 (3H, s), 3.01-3.08 (1H, m), 3.32 (2H, d, J=3.6 Hz), 3.35-3.43 (1H, m), 3.90 (3H, s), 4.36-4.42 (1H, m), 5.08 (2H, s), 6.27 (1H, d, J=7.9 Hz), 6.75-6.79 (1H, m), 7.19 (1H, s), 7.28-7.43 (8H, m), 7.86 (2H, d, J=8.6 Hz).

FAB$^+$ (m/z): 576 (M+H).

Example 97

Methyl 5-[3-[[2-(4-chlorophenyl)-4-methylthiazole-5-carbonyl]amino]piperidin-1-yl]-2-nitrobenzoate

[Chemical formula 219]

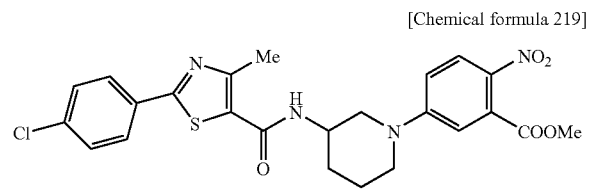

Potassium carbonate (5.08 g, 36.0 mmol) was added to a solution of N-(piperidin-3-yl)-2-(4-chlorophenyl)-4-methylthiazole-5-carboxamide (10.1 g, 30.0 mmol) and methyl 5-fluoro-2-nitrobenzoate (5.97 g, 30.0 mmol) in N,N-dimethylformamide (60 mL). The reaction mixture was stirred at room temperature for 2 hours. Subsequently, the solvent was evaporated and water was added to the residue. The precipitates were collected by filtration and were washed sequentially with 0.1 mol/L hydrochloric acid, a saturated aqueous sodium bicarbonate solution, water and ethanol to give 14.6 g (95%) of the desired compound as a yellow powder.

$^1$H NMR (400 MHz, DMSO-d$_6$) δ 1.51-1.61 (1H, m), 1.67-1.76 (1H, m), 1.80-1.87 (1H, m), 1.95-1.99 (1H, m), 2.57 (3H, s), 3.16-3.24 (2H, m), 3.82 (3H, s), 3.85-3.92 (2H, m), 3.98-4.02 (1H, m), 7.07-7.11 (2H, m), 7.58 (2H, d, J=8.6 Hz), 7.95 (2H, d, J=8.6 Hz), 8.01 (1H, d, J=9.1 Hz), 8.33 (1H, d, J=6.7 Hz).

Example 98

Methyl 2-amino-5-[3-[[2-(4-chlorophenyl)-4-methylthiazole-5-carbonyl]amino]piperidin-1-yl]benzoate

[Chemical formula 220]

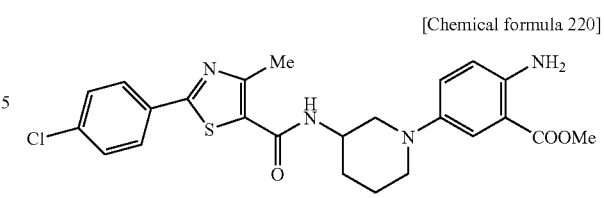

Methyl 5-[3-[[2-(4-chlorophenyl)-4-methylthiazole-5-carbonyl]amino]piperidin-1-yl]-2-nitrobenzoate (14.6 g, 28.4 mmol) was suspended in acetic acid (140 mL). To this suspension, reduced iron (9.49 g, 170 mmol) was added and the mixture was stirred at 80° C. for 3 hours. The mixture was then allowed to cool and was filtered through Celite. The solvent was removed and a saturated aqueous sodium bicarbonate solution was added to the residue to make it basic. The crystallized powdery product was collected by filtration and washed with water. The resulting powder was dissolved in ethyl acetate and was filtered through Celite. The solvent was then removed to give 12.7 g (26.2 mmol, 92%) of the desired compound as a pale yellow powder.

$^1$H NMR (400 MHz, DMSO-d$_6$) δ 1.46 (1H, qd, J=11.0, 3.7 Hz), 1.60-1.69 (1H, m), 1.79-1.84 (1H, m), 1.86-1.91 (1H, m), 2.52-2.57 (2H, m), 2.61 (3H, s), 3.19-3.24 (1H, m), 3.29-3.41 (1H, m), 3.78 (3H, s), 3.95-4.04 (1H, m), 6.29 (2H, s), 6.73 (1H, d, J=8.6 Hz), 7.10 (1H, dd, J=8.6, 3.1 Hz), 7.22 (1H, d, J=3.1 Hz), 7.58 (2H, d, J=8.6 Hz), 7.96 (2H, d, J=8.6 Hz), 8.21 (1H, d, J=7.3 Hz).

Example 99

Methyl (R)-3-[3-[[2-(4-chlorophenyl)-4-methylthiazol-5-yl]methoxy]piperidin-1-yl]benzoate Step 99a) (R)-1-(tert-Butoxycarbonyl)-3-[[2-(4-chlorophenyl)-4-methylthiazol-5-yl]methoxy]piperidine

[Chemical formula 221]

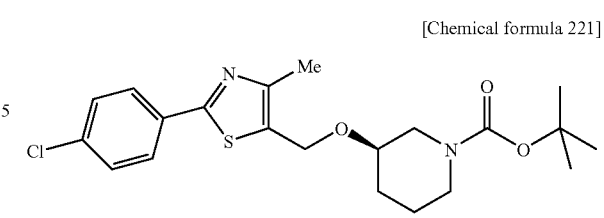

In an argon atmosphere, (R)-1-(tert-butoxycarbonyl)-3-hydroxypiperidine (604 mg, 3.00 mmol) and 5-chloromethyl-2-(4-chlorophenyl)-4-methylthiazole (775 mg, 3.00 mmol) were reacted in the same manner as in Step 6a of Example 6 to give 996 mg (78%) of the desired compound as a yellow oil.

$^1$H NMR (400 MHz, CDCl$_3$) δ 1.42-1.50 (10H, m), 1.53-1.62 (1H, m), 1.73-1.81 (1H, m), 1.90-1.96 (1H, m), 2.44 (3H, s), 3.12-3.22 (2H, m), 3.42-3.49 (1H, m), 3.52-3.58 (1H, m), 3.67-3.89 (1H, m), 4.64-4.67 (1H, m), 4.73-4.80 (1H, m), 7.38 (2H, d, J=8.6 Hz), 7.83 (2H, d, J=8.6 Hz).

Step 99b) (R)-3-[[2-(4-Chlorophenyl)-4-methylthiazol-5-yl]methoxy]piperidine

[Chemical formula 222]

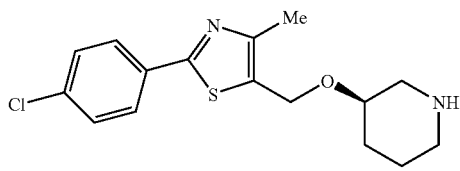

Using (R)-1-(tert-butoxycarbonyl)-3-[[2-(4-chlorophenyl)-4-methylthiazol-5-yl]methoxy]piperidine (946 mg, 2.24 mmol), the same procedure was followed as in Step 76b of Example 76 to give 608 mg (84%) of the desired compound as a pale yellow oil.

$^1$H NMR (400 MHz, DMSO-$d_6$) δ 1.26-1.37 (2H, m), 1.56-1.64 (1H, m), 1.92-2.00 (1H, m), 2.31-2.41 (5H, m), 2.71 (1H, td, J=11.6, J=3.7 Hz), 3.03 (1H, dd, J=11.6 Hz, J=2.4 Hz), 3.30-3.36 (1H, m), 4.69 (2H, s), 7.54 (2H, d, J=8.6 Hz), 7.90 (2H, d, J=8.6 Hz).

Step 99b) Methyl (R)-3-[3-[[2-(4-chlorophenyl)-4-methylthiazol-5-yl]methoxy]piperidin-1-yl]benzoate

[Chemical formula 223]

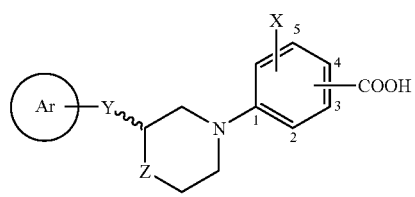

Using (R)-3-[[2-(4-chlorophenyl)-4-methylthiazol-5-yl]methoxy]piperidine (294 mg, 0.911 mmol) and 3-(methoxycarbonyl)phenylboric acid (328 mg, 1.82 mmol), the same procedure was followed as in Example 2 to give 167 mg (40%) of the desired compound as a colorless oil.

$^1$H NMR (400 MHz, CDCl$_3$) δ 1.48-1.57 (1H, m), 1.62-1.73 (1H, m), 1.88-1.96 (1H, m), 2.06-2.12 (1H, m), 2.46 (3H, s), 2.85-2.93 (2H, m), 3.47 (1H, td, J=12.2, 4.3 Hz), 3.63-3.72 (2H, m), 3.90 (3H, s), 4.74 (1H, d, J=12.8 Hz), 4.77 (1H, d, J=12.8 Hz), 7.11 (1H, dd, J=7.9, 2.4 Hz), 7.29 (1H, t, J=7.9 Hz), 7.39 (2H, d, J=8.6 Hz), 7.49 (1H, d, J=7.3 Hz), 7.60-7.61 (1H, m), 7.84 (2H, d, J=8.6 Hz).

Example 100 tert-Butyl 2-[2-[[2-(4-chlorophenyl)-4-methylthiazole-5-carbonyl]aminomethyl]morpholin-4-yl]benzoate

[Chemical formula 224]

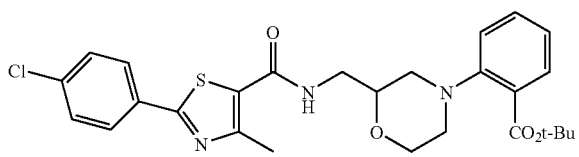

Using N-(morpholin-2-yl methyl)-2-(4-chlorophenyl)-4-methylthiazole-5-carboxamide (120 mg, 0.341 mmol) and tert-butyl 2-iodobenzoate (104 mg, 0.341 mmol), the same procedure was followed as in Example 58 to give 113 mg (63%) of the desired compound as a pale yellow amorphous product.

$^1$H NMR (400 MHz, CDCl$_3$) δ 1.59 (9H, s), 2.70-2.78 (4H, m), 2.94 (1H, td, J=11.6, 3.1 Hz), 3.15-3.19 (1H, m), 3.24 (1H, dt, J=11.6, 1.8 Hz), 3.40-3.47 (1H, m), 3.71-3.77 (1H, m), 3.87-3.96 (2H, m), 4.00 (1H, dt, J=10.4, 2.4 Hz), 6.29 (1H, t, J=5.5 Hz), 7.01-7.05 (2H, m), 7.38 (1H, td, J=7.9, 1.8 Hz), 7.42 (2H, d, J=8.6 Hz), 7.60 (1H, dd, J=7.9, 1.8 Hz), 7.87 (2H, d, J=8.6 Hz).

Examples 101 Through 163

The procedures were performed in the same manner as in Example 18 to make compounds given in Table 9 below.

TABLE 9

| | Absolute configuration | Ar | X | Y | Z | Binding position of carboxylic acid |
|---|---|---|---|---|---|---|
| Example 101 | S | (2-(4-chlorophenyl)-4-methylthiazol-5-yl) | H | CONH | CH$_2$ | Position 3 |

TABLE 9-continued

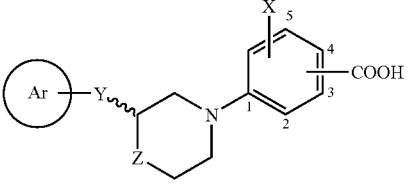

| | Absolute configuration | Ar | X | Y | Z | Binding position of carboxylic acid |
|---|---|---|---|---|---|---|
| Example 102 | S | 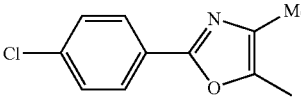 | H | CONH | CH$_2$ | Position 3 |
| Example 103 | S | 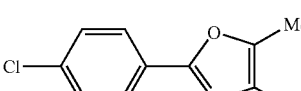 | H | CONH | CH$_2$ | Position 3 |
| Example 104 | S | 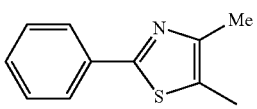 | H | CONH | CH$_2$ | Position 3 |
| Example 105 | S | 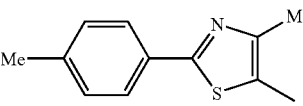 | H | CONH | CH$_2$ | Position 3 |
| Example 106 | S | 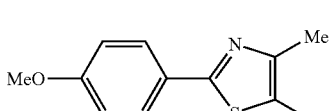 | H | CONH | CH$_2$ | Position 3 |
| Example 107 | S | 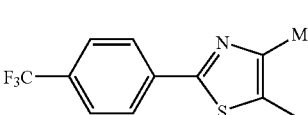 | H | CONH | CH$_2$ | Position 3 |
| Example 108 | S | 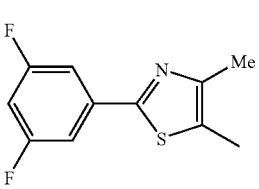 | H | CONH | CH$_2$ | Position 3 |
| Example 109 | S | 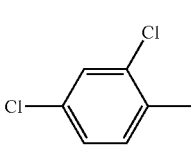 | H | CONH | CH$_2$ | Position 3 |
| Example 110 | S | 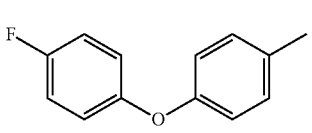 | H | CONH | CH$_2$ | Position 3 |
| Example 111 | S | 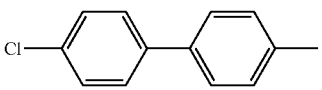 | H | CONH | CH$_2$ | Position 3 |
| Example 112 | Racemic mixture | 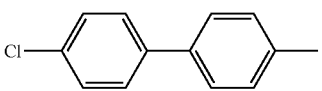 | H | CONH | CH$_2$ | Position 2 |

TABLE 9-continued

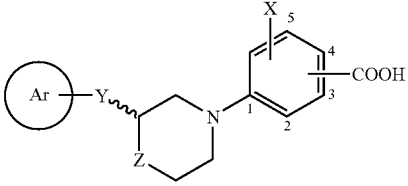

| | Absolute configuration | Ar | X | Y | Z | Binding position of carboxylic acid |
|---|---|---|---|---|---|---|
| Example 113 | Racemic mixture | 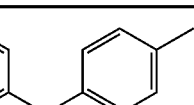 | H | CONH | CH$_2$ | Position 2 |
| Example 114 | Racemic mixture | 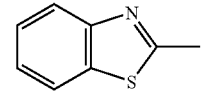 | H | CONH | CH$_2$ | Position 2 |
| Example 115 | S | 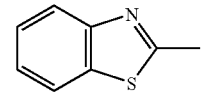 | H | CONH | CH$_2$ | Position 3 |
| Example 116 | S | 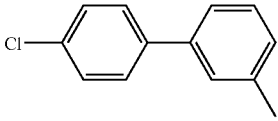 | H | CONH | CH$_2$ | Position 3 |
| Example 117 | S | 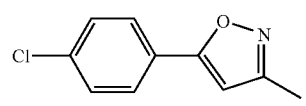 | H | CONH | CH$_2$ | Position 3 |
| Example 118 | S | 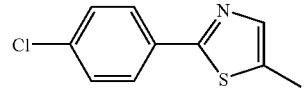 | H | CONH | CH$_2$ | Position 3 |
| Example 119 | S | 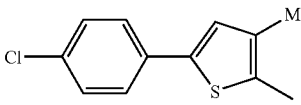 | H | CONH | CH$_2$ | Position 3 |
| Example 120 | Racemic mixture | 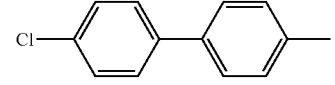 | H | CONHCH$_2$ | CH$_2$ | Position 2 |
| Example 121 | Racemic mixture | 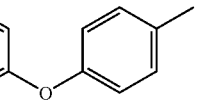 | H | CONHCH$_2$ | CH$_2$ | Position 2 |
| Example 122 | Racemic mixture | 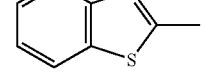 | H | CONHCH$_2$ | CH$_2$ | Position 2 |
| Example 123 | Racemic mixture | 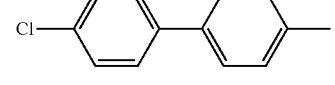 | H | CONHCH$_2$ | CH$_2$ | Position 3 |
| Example 124 | Racemic mixture | 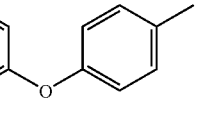 | H | CONHCH$_2$ | CH$_2$ | Position 3 |

TABLE 9-continued

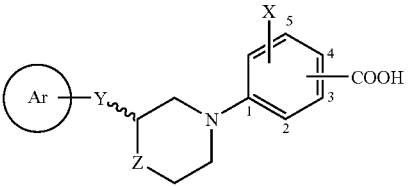

| | Absolute configuration | Ar | X | Y | Z | Binding position of carboxylic acid |
|---|---|---|---|---|---|---|
| Example 125 | Racemic mixture | 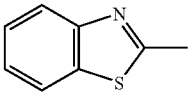 | H | CONHCH$_2$ | CH$_2$ | Position 3 |
| Example 126 | Racemic mixture | 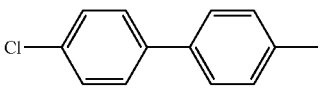 | H | CH$_2$NHCO | CH$_2$ | Position 2 |
| Example 127 | Racemic mixture | 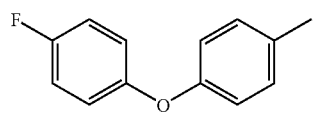 | H | CH$_2$NHCO | CH$_2$ | Position 2 |
| Example 128 | Racemic mixture | 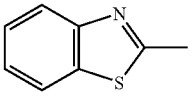 | H | CH$_2$NHCO | CH$_2$ | Position 2 |
| Example 129 | Racemic mixture | 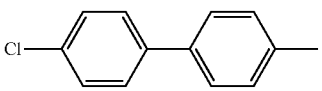 | H | CH$_2$NHCO | CH$_2$ | Position 3 |
| Example 130 | Racemic mixture | 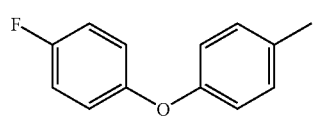 | H | CH$_2$NHCO | CH$_2$ | Position 3 |
| Example 131 | Racemic mixture | 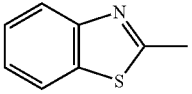 | H | CH$_2$NHCO | CH$_2$ | Position 3 |
| Example 132 | Racemic mixture | 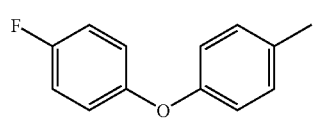 | H | NHCO | CH$_2$ | Position 3 |
| Example 133 | Racemic mixture | 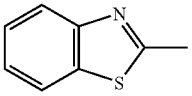 | H | OCH$_2$ | CH$_2$ | Position 3 |
| Example 134 | Racemic mixture | 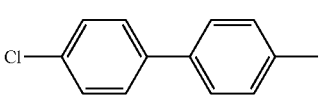 | H | CH$_2$O | CH$_2$ | Position 3 |
| Example 135 | Racemic mixture | 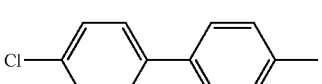 | H | OCH$_2$ | CH$_2$ | Position 3 |
| Example 136 | Racemic mixture | 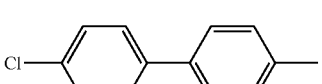 | H | CH$_2$OCH$_2$ | CH$_2$ | Position 3 |

TABLE 9-continued

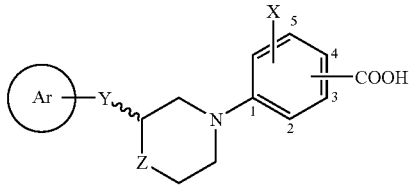

| | Absolute configuration | Ar | X | Y | Z | Binding position of carboxylic acid |
|---|---|---|---|---|---|---|
| Example 137 | Racemic mixture | 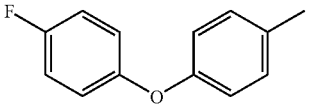 | H | CH$_2$O | CH$_2$ | Position 3 |
| Example 138 | Racemic mixture | 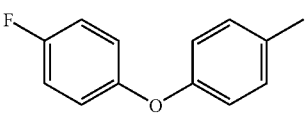 | H | CH$_2$OCH$_2$ | CH$_2$ | Position 3 |
| Example 139 | Racemic mixture | 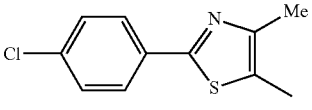 | H | CONH | CH$_2$ | Position 3 |
| Example 140 | Racemic mixture | 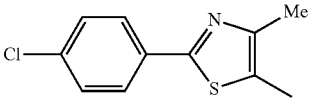 | H | CH$_2$CONH | CH$_2$ | Position 2 |
| Example 141 | Racemic mixture | 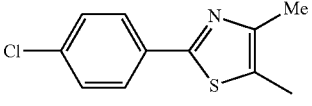 | H | CH$_2$NH | CH$_2$ | Position 3 |
| Example 142 | Racemic mixture | 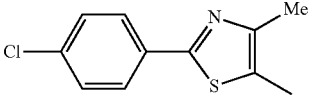 | H | CH$_2$NH | CH$_2$ | Position 2 |
| Example 143 | Racemic mixture | 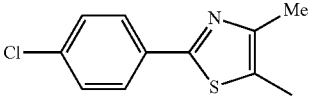 | H | NHCO | CH$_2$ | Position 3 |
| Example 144 | Racemic mixture | 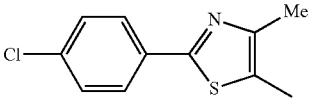 | H | NHCO | CH$_2$ | Position 2 |
| Example 145 | Racemic mixture | 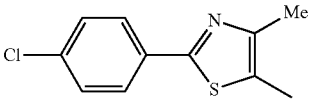 | H | 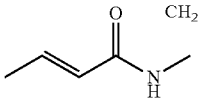 | CH$_2$ | Position 3 |
| Example 146 | Racemic mixture | 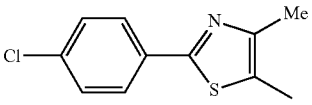 | H | 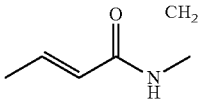 | CH$_2$ | Position 2 |
| Example 147 | Racemic mixture | 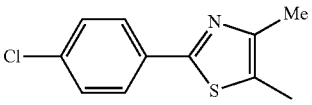 | H | CH$_2$CH$_2$CONH | CH$_2$ | Position 3 |

TABLE 9-continued

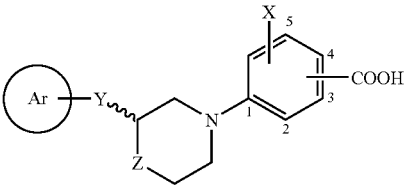

| | Absolute configuration | Ar | X | Y | Z | Binding position of carboxylic acid |
|---|---|---|---|---|---|---|
| Example 148 | Racemic mixture | 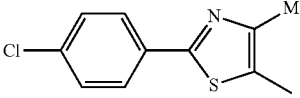 | H | CH$_2$CH$_2$CONH | CH$_2$ | Position 2 |
| Example 149 | Racemic mixture | 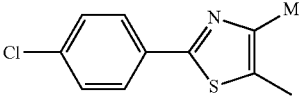 | H | CH$_2$OCONH | CH$_2$ | Position 3 |
| Example 150 | Racemic mixture | 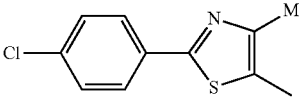 | H | CH$_2$OCONH | CH$_2$ | Position 2 |
| Example 151 | Racemic mixture | 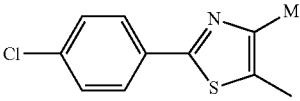 | H | NHCONH | CH$_2$ | Position 3 |
| Example 152 | Racemic mixture | 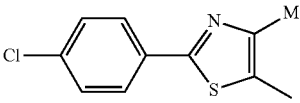 | H | NHCONH | CH$_2$ | Position 2 |
| Example 153 | Racemic mixture | 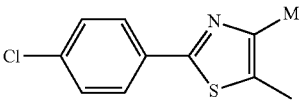 | H | COCH$_2$ | CH$_2$ | Position 3 |
| Example 154 | Racemic mixture | 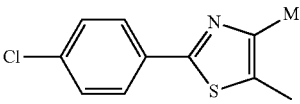 | H | 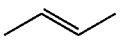 | CH$_2$ | Position 3 |
| Example 155 | Racemic mixture | 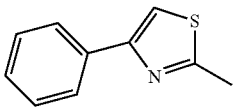 | H | SCH$_2$ | CH$_2$ | Position 3 |
| Example 156 | Racemic mixture | 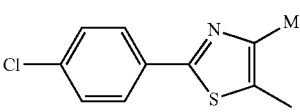 | H | CONHCH$_2$ | O | Position 3 |
| Example 157 | Racemic mixture | 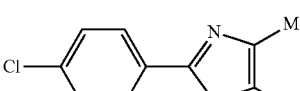 | H | CH2NHCO | O | Position 3 |
| Example 158 | Racemic mixture | 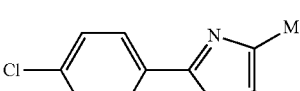 | H | CH2NHCO | O | Position 3 |

TABLE 9-continued

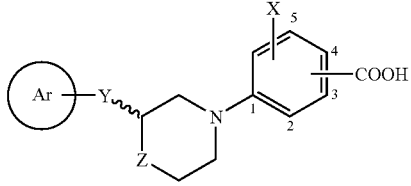

| | Absolute configuration | Ar | X | Y | Z | Binding position of carboxylic acid |
|---|---|---|---|---|---|---|
| Example 159 | Racemic mixture | 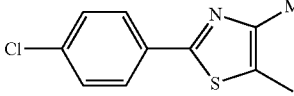 | H | $CH_2OCH_2$ | O | Position 3 |
| Example 160 | Racemic mixture | 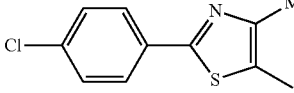 | H | $CH_2OCH_2$ | O | Position 2 |
| Example 161 | Racemic mixture | 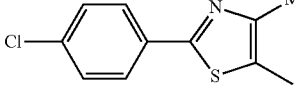 | 4-$NO_2$ | CONH | $CH_2$ | Position 3 |
| Example 162 | Racemic mixture | 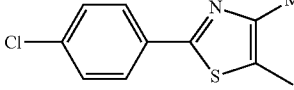 | 4-$NH_2$ | CONH | $CH_2$ | Position 3 |
| Example 163 | R | 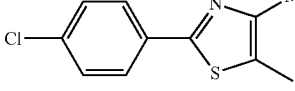 | H | $CH_2O$ | $CH_2$ | Position 3 |
| Example 164 | Racemic mixture | 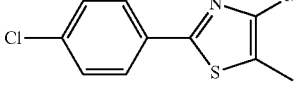 | 4-F | CONH | $CH_2$ | Position 3 |
| Example 165 | Racemic mixture | 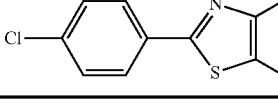 | 5-BnO | CONH | $CH_2$ | Position 3 |

<Compound of Example 101>
Colorless Powder
$^1$H NMR (400 MHz, DMSO-$d_6$) δ 1.62-1.72 (2H, m), 1.75-1.85 (1H, m), 1.88-1.96 (1H, m), 2.80 (3H, s), 2.88-2.94 (2H, m), 3.60 (1H, d, J=12.8 Hz), 3.69 (1H, d, J=8.9 Hz), 3.98-4.06 (1H, m), 7.21-7.25 (1H, m), 7.31-7.36 (2H, m), 7.48 (1H, s), 7.57 (2H, dd, J=6.7, 1.8 Hz), 8.00 (2H, dd, J=6.7, 2.4 Hz), 8.28 (1H, d, J=7.9 Hz), 12.85 (1H, brs).
HR-FAB$^+$ (m/z): 456.1180 (+3.1 mmu).
Elemental analysis calcd (%) for $C_{23}H_{22}ClN_3O_3S·2/10H_2O$: C, 60.11, H, 4.87, N, 9.14; found: C, 60.15; H, 4.72; N, 9.10.
$[α]^{28.3°}_D$+131° (C=1.0, DMF)

<Compound of Example 102>
Colorless Powder
$^1$H NMR (400 MHz, DMSO-$d_6$) δ 1.55-1.73 (2H, m), 1.80-1.90 (1H, m), 1.93-2.02 (1H, m), 2.45 (3H, s), 2.75 (2H, t, J=11.7 Hz), 3.72 (1H, d, J=11.7 Hz), 3.80 (1H, d, J=11.7 Hz), 3.95-4.05 (1H, m), 7.22-7.27 (1H, m), 7.30-7.37 (2H, m), 7.47 (1H, d, J=1.8 Hz), 7.67 (2H, dd, J=6.7, 1.8 Hz), 8.19 (2H, dd, J=6.7, 1.8 Hz), 8.43 (1H, d, J=7.3 Hz), 12.85 (1H, brs).
HR-FAB$^+$ (m/z): 440.1388 (+1.1 mmu).
Elemental analysis calcd (%) for $C_{23}H_{22}ClN_3O_4·3/10H_2O$: C, 62.04; H, 5.05; N, 9.44; found: C, 62.03; H, 4.90; N, 9.40.
$[α]^{27.2°}_D$+178° (C=1.1, DMF)

<Compound of Example 103>
Colorless Powder
$^1$H NMR (400 MHz, DMSO-$d_6$) δ 1.60-1.75 (2H, m), 1.76-1.93 (2H, m), 2.67 (3H, s), 2.80-2.93 (2H, m), 3.56-3.68 (2H, m), 3.96-4.08 (1H, m), 7.23-7.26 (1H, m), 7.30-7.36 (2H, m), 7.47 (1H, m), 7.63 (2H, dd, J=6.7, 1.8 Hz), 7.99 (2H, dd, J=6.7, 2.4 Hz), 8.04 (1H, s), 12.84 (1H, brs).
HR-FAB$^+$ (m/z): 440.1384 (+0.7 mmu).
Elemental analysis calcd (%) for $C_{23}H_{22}ClN_3O_4·3/10H_2O$: C, 62.03; H, 5.05; N, 9.44; found: C, 62.02; H, 4.90; N, 9.43.
$[α]^{27.0°}_D$+110° (C=1.0, DMF)

<Compound of Example 104>
Colorless Powder
$^1$H NMR (400 MHz, DMSO-$d_6$) δ 1.50-1.70 (2H, m), 1.79-1.85 (1H, m), 1.90-1.95 (1H, m), 2.60 (3H, s), 2.75-2.85

(2H, m), 3.60 (1H, d, J=12.2 Hz), 3.73 (1H, d, J=12.2 Hz), 3.90-3.99 (1H, m), 7.20-7.24 (1H, m), 7.31-7.35 (2H, m), 7.47 (1H, s), 7.51-7.54 (3H, m), 7.93-7.97 (2H, m), 8.25 (1H, d, J=7.3 Hz), 12.85 (1H, brs).

HR-FAB$^+$ (m/z): 422.1545 (+0.7 mmu).

Elemental analysis calcd (%) for $C_{23}H_{23}N_3O_3S.1/10H_2O$: C, 65.26; H, 5.50; N, 9.93; found: C, 65.20; H, 5.45; N, 9.81.

$[\alpha]^{27.9°}_D$+117° (C=1.1, DMF)

<Compound of Example 105>

Colorless Powder $^1$H NMR (400 MHz, DMSO-$d_6$) δ 1.51-1.69 (2H, m), 1.78-1.85 (1H, m), 1.88-1.95 (1H, m), 2.36 (3H, s), 2.59 (3H, s), 2.78-2.84 (2H, m), 3.57-3.65 (1H, m), 3.73-3.77 (1H, m), 3.90-4.01 (1H, m), 7.19-7.25 (1H, m), 7.30-7.36 (4H, m), 7.47 (1H, s), 7.83 (2H, d, J=8.6 Hz), 8.21 (1H, d, J=7.3 Hz), 12.83 (1H, brs).

HR-FAB$^+$ (m/z): 436.1715 (+2.0 mmu).

Elemental analysis calcd (%) for $C_{24}H_{25}N_3O_3S$: C, 66.18; H, 5.79; N, 9.65; found: C, 66.08; H, 5.78; N, 9.48.

$[\alpha]^{27.6°}_D$+120° (C=1.1, DMF)

<Compound of Example 106>

Colorless Powder $^1$H NMR (400 MHz, DMSO-$d_6$) δ 1.53-1.69 (2H, m), 1.78-1.87 (1H, m), 1.91-1.97 (1H, m), 2.59 (3H, s), 2.75-2.83 (2H, m), 3.61 (1H, d, J=12.7 Hz), 3.73 (1H, dd, J=11.3, 3.0 Hz), 3.83 (3H, s), 3.90-4.02 (1H, m), 7.06 (2H, dd, J=6.7, 1.8 Hz), 7.19-7.26 (1H, m), 7.30-7.35 (2H, m), 7.45-7.48 (1H, m), 7.88 (2H, dd, J=6.7, 2.5 Hz), 8.17 (1H, d, J=7.3 Hz), 12.83 (1H, brs).

HR-FAB$^+$ (m/z): 452.1613 (−3.1 mmu).

$[\alpha]^{26.5°}_D$+140° (C=1.1, DMF)

<Compound of Example 107>

Pale Reddish Brown Powder $^1$H NMR (400 MHz, DMSO-$d_6$) δ 1.53-1.71 (2H, m), 1.82-1.87 (1H, m), 1.90-1.98 (1H, m), 2.63 (3H, s), 2.76-2.86 (2H, m), 3.62 (1H, d, J=11.6 Hz), 3.71-3.76 (1H, m), 3.91-4.02 (1H, m), 7.24 (1H, s), 7.31-7.36 (2H, m), 7.47 (1H, s), 7.89 (2H, d, J=8.6 Hz), 8.16 (2H, d, J=7.9 Hz), 8.34 (1H, d, J=7.3 Hz), 12.83 (1H, brs). HR-FAB$^+$ (m/z): 490.1456 (+4.4 mmu).

Elemental analysis calcd (%) for $C_{24}H_{22}F_3N_3O_3S$: C, 58.89; H, 4.53; N, 8.58; found: C, 58.96; H, 4.48; N, 8.30.

$[\alpha]^{28.4°}_D$+101° (C=1.1, DMF)

<Compound of Example 108>

Yellow Powder $^1$H NMR (400 MHz, DMSO-$d_6$) δ 1.49-1.68 (2H, m), 1.78-1.86 (1H, m), 1.88-1.96 (1H, m), 2.59 (3H, s), 2.74-2.85 (2H, m), 3.58 (1H, d, J=12.2 Hz), 3.71 (1H, dd, J=12.2, 3.6 Hz), 3.90-4.05 (1H, m), 7.18-7.24 (2H, m), 7.29-7.34 (2H, m), 7.44 (2H, m), 7.64 (2H, dd, J=7.9, 1.8 Hz), 8.34 (1H, d, J=7.3 Hz), 12.85 (1H, brs).

HR-FAB$^+$ (m/z): 458.1371 (+2.2 mmu).

Elemental analysis calcd (%) for $C_{23}H_{21}F_2N_3O_3S$: C, 60.38; H, 4.63; N, 9.18; found: C, 60.15; H, 4.55; N, 8.91.

$[\alpha]^{26.7°}_D$+105° (C=1.1, DMF)

<Compound of Example 109>

Colorless Powder $^1$H NMR (400 MHz, DMSO-$d_6$) δ 1.46-1.54 (1H, m), 1.56-1.69 (1H, m), 1.79-1.87 (1H, m), 1.88-1.96 (1H, m), 2.73-2.89 (2H, m), 3.49-3.58 (1H, m), 3.66-3.72 (1H, m), 3.91-4.00 (1H, m), 7.18-7.24 (1H, m), 7.36 (2H, d, J=6.7 Hz), 7.46-7.48 (3H, m), 7.69 (1H, s), 8.56 (1H, d, J=7.3 Hz), 12.79 (1H, brs).

HR-FAB$^+$ (m/z): 393.0811 (+3.8 mmu).

Elemental analysis calcd (%) for $C_{19}H_{18}Cl_2N_2O_3$.1/10H$_2$O: C, 57.76; H, 4.62; N, 7.09; found: C, 57.58; H, 4.48; N, 7.08.

$[\alpha]^{28.6°}_D$+75.9° (C=1.0, DMF)

<Compound of Example 110>

Colorless Powder $^1$H NMR (400 MHz, DMSO-$d_6$) δ 1.51-1.70 (2H, m), 1.79-1.86 (1H, m), 1.89-1.97 (1H, m), 2.64-2.78 (2H, m), 3.67 (1H, d, J=11.8 Hz), 3.76 (1H, d, J=11.8 Hz), 3.92-4.03 (1H, m), 7.01 (2H, dd, J=6.7, 1.8 Hz), 7.12-7.16 (1H, m), 7.18-7.35 (5H, m), 7.46 (1H, s), 7.89 (2H, dd, J=6.7, 1.8 Hz), 8.29 (1H, d, J=8.0 Hz), 12.75 (1H, brs).

HR-FAB$^+$ (m/z): 435.1718 (−0.2 mmu).

Elemental analysis calcd (%) for $C_{25}H_{23}FN_2O_4.3/10H_2O$: C, 68.26; H, 5.34; N, 6.37; found: C, 68.17; H, 5.25; N, 6.38.

$[\alpha]^{28.5°}_D$+81.7° (C=1.1, DMF)

<Compound of Example 111>

Pale Reddish Brown Powder $^1$H NMR (400 MHz, DMSO-$d_6$) δ 1.55-1.1.69 (2H, m), 1.80-1.87 (1H, m), 1.92-1.98 (1H, m), 2.69-2.79 (2H, m), 3.68 (1H, d, J=12.2 Hz), 3.81 (1H, d, J=12.2 Hz), 3.97-4.07 (1H, m), 7.20-7.25 (1H, m), 7.30-7.36 (2H, m), 7.46-7.48 (1H, m), 7.55 (2H, dd, J=6.8, 2.4 Hz), 7.72-7.79 (4H, m), 7.97 (2H, d, J=8.5 Hz), 8.42 (1H, d, J=7.3 Hz), 12.90 (1H, brs).

HR-FAB$^+$ (m/z): 435.1466 (−1.0 mmu).

$[\alpha]^{27.8°}_D$+95.9° (C=1.0, DMF)

<Compound of Example 112>

Colorless Powder $^1$H NMR (400 MHz, DMSO-$d_6$) δ 1.65-1.80 (2H, m), 1.90-2.06 (2H, m), 2.93-3.13 (3H, m), 3.24 (1H, dd, J=11.0, 3.0 Hz), 4.09-4.25 (1H, m), 7.40 (1H, t, J=7.3 Hz), 7.55 (2H, d, J=8.6 Hz), 7.60-7.70 (2H, m), 7.74-7.88 (4H, m), 7.96 (2H, d, J=8.6 Hz), 8.00 (1H, d, J=7.3 Hz), 8.49 (1H, d, J=7.3 Hz), 16.94 (1H, brs).

HR-FAB$^+$ (m/z): 435.1483 (+0.7 mmu).

Elemental analysis calcd (%) for $C_{25}H_{23}ClN_2O_3.1/5H_2O$: C, 68.47; H, 5.38; N, 6.39; found: C, 68.23; H, 5.33; N, 6.29.

<Compound of Example 113>

Colorless Powder $^1$H NMR (400 MHz, DMSO-$d_6$) δ 1.65-1.77 (2H, m), 1.87-2.03 (2H, m), 2.92-3.10 (2H, m), 3.14-3.27 (2H, m), 4.01-4.15 (1H, m), 7.01 (2H, d, J=8.6 Hz), 7.08-7.17 (2H, m), 7.23-7.30 (2H, m), 7.38 (1H, t, J=7.9 Hz), 7.55-7.68 (2H, m), 7.89 (2H, d, J=8.6 Hz), 7.98 (1H, d, J=7.9 Hz), 8.41 (1H, brs).

HR-FAB$^+$ (m/z): 435.1750 (+2.9 mmu).

Elemental analysis calcd (%) for $C_{25}H_{23}FN_2O_4.3/10H_2O$: C, 68.26; H, 5.41; N, 6.37; found: C, 68.23; H, 5.30; N, 6.33.

<Compound of Example 114>

Pale Yellow Powder $^1$H NMR (400 MHz, DMSO-$d_6$) δ 1.65-1.85 (2H, m), 1.88-2.02 (2H, m), 2.93 (1H, t, J=9.2 Hz), 3.03-3.12 (2H, m), 3.20 (1H, dd, J=11.0, 3.7 Hz), 4.10-4.20 (1H, m), 7.34 (1H, t, J=7.9 Hz), 7.53-7.68 (4H, m), 7.95 (1H, dd, J=7.9, 1.8 Hz), 8.14 (1H, d, J=7.9 Hz), 8.22 (1H, d, J=7.9 Hz), 9.20 (1H, d, J=7.9 Hz), 16.30 (1H, brs).

HR-FAB$^+$ (m/z): 382.1197 (−2.8 mmu).

<Compound of Example 115>

Cream-Colored Powder $^1$H NMR (400 MHz, DMSO-$d_6$) δ 1.58-1.85 (3H, m), 1.88-1.95 (1H, m), 2.78 (1H, t, J=11.6 Hz), 2.88 (1H, t, J=11.6 Hz), 3.64 (1H, d, J=11.6 Hz), 3.75 (1H, d, J=11.6 Hz), 3.97-4.08 (1H, m), 7.20-7.26 (1H, m), 7.28-7.35 (2H, m), 7.47 (1H, s), 7.55-7.65 (2H, m), 8.14 (1H, d, J=7.9 Hz), 8.23 (1H, d, J=7.9 Hz), 9.09 (1H, d, J=7.9 Hz), 12.81 (1H, brs).

HR-FAB$^+$ (m/z): 382.1191 (−3.4 mmu).

Elemental analysis calcd (%) for $C_{20}H_{19}N_3O_3S.3/10H_2O$: C, 62.09; H, 5.11; N, 10.86; found: C, 62.39; H, 5.15; N, 10.58.

$[\alpha]^{27.0°}_D$+180° (C=1.1, DMF)

<Compound of Example 116>

Cream-Colored Powder

¹H NMR (400 MHz, DMSO-d₆) δ 1.54-1.70 (2H, m), 1.78-1.88 (1H, m), 1.93-2.01 (1H, m), 2.63-2.81 (2H, m), 3.68 (1H, d, J=12.2 Hz), 3.82 (1H, d, J=12.2 Hz), 3.97-4.07 (1H, m), 7.18-7.26 (1H, m), 7.28-7.35 (2H, m), 7.47 (1H, s), 7.52-7.68 (3H, m), 7.76 (2H, d, J=8.6 Hz), 7.80-7.90 (2H, m), 8.11 (1H, s), 8.47 (1H, d, J=7.3 Hz), 12.81 (1H, brs).

HR-FAB⁺ (m/z): 435.1512 (+3.6 mmu).

Elemental analysis calcd (%) for $C_{25}H_{23}ClN_2O_3 \cdot 2/5H_2O$: C, 67.92; H, 5.43; N, 6.34; found: C, 67.76; H, 5.23; N, 6.38.

$[\alpha]^{28.7°}_D$ +73.2° (C=1.1, DMF)

<Compound of Example 117>
Colorless Powder

¹H NMR (400 MHz, DMSO-d₆) δ 1.55-1.70 (2H, m), 1.75-1.85 (1H, m), 1.86-1.95 (1H, m), 2.73-2.83 (2H, m), 3.63 (1H, d, J=12.2 Hz), 3.74 (1H, d, J=12.2 Hz), 3.95-4.06 (1H, m), 7.18-7.25 (1H, m), 7.28-7.36 (2H, m), 7.44 (1H, s), 7.46 (1H, s), 7.63 (2H, d, J=8.6 Hz), 7.95 (2H, d, J=8.6 Hz), 8.80 (1H, d, J=7.3 Hz), 12.80 (1H, brs).

HR-FAB⁺ (m/z): 426.1242 (+2.2 mmu).

Elemental analysis calcd (%) for $C_{22}H_{20}ClN_3O_4$: C, 62.05; H, 4.73; N, 9.87; found: C, 61.73; H, 4.69; N, 9.75.

$[\alpha]^{28.7°}_D$ +40.6° (C=1.1, DMF)

<Compound of Example 118>
Cream-Colored Powder

¹H NMR (400 MHz, DMSO-d₆) δ 1.50-1.72 (2H, m), 1.79-1.88 (1H, m), 1.92-2.02 (1H, m), 2.65-2.80 (2H, m), 3.66 (1H, d, J=12.2 Hz), 3.79 (1H, d, J=12.2 Hz), 3.90-4.02 (1H, m), 7.19 (1H, d, J=7.9 Hz), 7.26-7.35 (2H, m), 7.47 (1H, s), 7.59 (2H, d, J=8.6 Hz), 8.00 (2H, d, J=8.6 Hz), 8.51 (1H, s), 8.66 (1H, d, J=7.9 Hz), 12.83 (1H, brs).

HR-FAB⁺ (m/z): 442.1001 (+0.9 mmu).

$[\alpha]^{28.7°}_D$ +53.1° (C=0.5, DMF)

<Compound of Example 119>
Orange Powder

¹H NMR (400 MHz, DMSO-d₆) δ 1.50-1.70 (2H, m), 1.75-1.86 (1H, m), 1.87-1.96 (1H, m), 2.41 (3H, s), 2.81 (2H, t, J=10.4 Hz), 3.58 (1H, d, J=12.2 Hz), 3.71 (1H, d, J=12.2 Hz), 3.90-4.03 (1H, m), 7.24 (1H, d, J=7.3 Hz), 7.30-7.37 (2H, m), 7.41 (1H, s), 7.44-7.74 (3H, m), 7.68 (2H, d, J=8.6 Hz), 7.94 (1H, d, J=7.3 Hz), 12.83 (1H, brs).

HR-FAB⁺ (m/z): 455.1160 (−3.6 mmu).

$[\alpha]^{28.8°}_D$ +118° (C=1.0, DMF)

<Compound of Example 120>
Colorless Powder

¹H NMR (400 MHz, DMSO-d₆) δ 1.20-1.33 (1H, m), 1.56-1.72 (1H, m), 1.89 (2H, t, J=14.0 Hz), 2.00-2.10 (1H, m), 2.86 (1H, t, J=11.0 Hz), 2.96-3.06 (2H, m), 3.10 (1H, d, J=7.9 Hz), 3.18-3.30 (2H, m), 7.42 (1H, t, J=7.9 Hz), 7.53 (2H, d, J=8.6 Hz), 7.66 (1H, t, J=7.9 Hz), 7.70-7.78 (5H, m), 7.91 (2H, d, J=8.6 Hz), 8.02 (1H, d, J=7.9 Hz), 8.54-8.62 (1H, m), 17.99 (1H, brs).

HR-FAB⁺ (m/z): 449.1657 (+2.5 mmu).

Elemental analysis calcd (%) for $C_{26}H_{25}ClN_2O_3$: C, 69.56; H, 5.61; N, 6.24; found: C, 69.46; H, 5.60; N, 6.14.

<Compound of Example 121>
Colorless Powder

¹H NMR (400 MHz, DMSO-d₆) δ 1.18-1.32 (1H, m), 1.55-1.72 (1H, m), 1.74-2.08 (2H, m), 2.84 (1H, t, J=11.0 Hz), 2.95-3.10 (2H, m), 3.15-3.35 (2H, m), 6.98 (2H, d, J=8.6 Hz), 7.07-7.15 (2H, m), 7.20-7.28 (2H, m), 7.42 (1H, t, J=7.9 Hz), 7.66 (1H, td, J=7.9, 1.2 Hz), 7.72 (1H, d, J=7.9 Hz), 7.83 (2H, d, J=8.6 Hz), 8.02 (1H, d, J=6.1 Hz), 8.40-8.48 (1H, m), 17.99 (1H, brs).

HR-FAB⁺ (m/z): 449.1883 (+0.6 mmu).

Elemental analysis calcd (%) for $C_{26}H_{25}FN_2O_4 \cdot 3/10H_2O$: C, 68.80; H, 5.68; N, 6.17; found: C, 68.83; H, 5.76; N, 5.87.

<Compound of Example 122>
Colorless Powder

¹H NMR (400 MHz, DMSO-d₆) δ 1.20-1.35 (1H, m), 1.55-1.70 (1H, m), 1.78-1.98 (2H, m), 2.04-2.17 (1H, m), 2.86 (1H, t, J=11.0 Hz), 3.02 (2H, d, J=6.7 Hz), 3.10 (1H, d, J=7.9 Hz), 7.41 (1H, t, J=7.9 Hz), 7.55 (1H, td, J=7.9, 1.2 Hz), 7.61 (1H, td, J=7.9, 1.2 Hz), 7.66 (1H, td, J=7.9, 1.2 Hz), 7.73 (1H, d, J=7.9 Hz), 8.01 (1H, dd, J=7.9, 1.2 Hz), 8.10 (1H, d, J=7.9 Hz), 8.20 (1H, dd, J=7.9, 1.2 Hz), 9.31 (1H, t, J=6.1 Hz), 17.92 (1H, brs).

HR-FAB⁺ (m/z): 396.1402 (+2.0 mmu).

<Compound of Example 123>
Colorless Powder

¹H NMR (400 MHz, DMSO-d₆) δ 1.10-1.24 (1H, m), 1.48-1.65 (1H, m), 1.70-1.83 (2H, m), 1.83-2.00 (1H, m), 2.70-2.80 (1H, m), 3.59 (1H, d, J=12.2 Hz), 3.67 (1H, d, J=12.2 Hz), 7.12-7.23 (1H, m), 7.25-7.38 (2H, m), 7.47 (1H, s), 7.54 (2H, d, J=8.6 Hz), 7.70-7.83 (4H, m), 7.95 (2H, d, J=8.6 Hz), 8.62 (1H, t, J=5.5 Hz), 12.81 (1H, brs).

HR-FAB⁺ (m/z): 449.1657 (+2.5 mmu).

<Compound of Example 124>
Colorless Powder

¹H NMR (400 MHz, DMSO-d₆) δ 1.10-1.25 (1H, m), 1.48-1.62 (1H, m), 1.70-1.82 (2H, m), 1.83-1.95 (1H, m), 2.72 (1H, t, J=11.0 Hz), 3.15-3.30 (3H, m), 3.54-3.68 (2H, m), 7.01 (2H, d, J=8.6 Hz), 7.08-7.20 (3H, m), 7.21-7.35 (4H, m), 7.45 (1H, s), 7.87 (2H, d, J=8.6 Hz), 8.49 (1H, t, J=5.5 Hz), 12.79 (1H, brs).

HR-FAB⁺ (m/z): 449.1913 (+3.7 mmu).

Elemental analysis calcd (%) for $C_{26}H_{25}FN_2O_4 \cdot 1/5H_2O$: C, 69.07; H, 5.66; N, 6.20; found: C, 68.83; H, 5.56; N, 6.07.

<Compound of Example 125>
Colorless Powder

¹H NMR (400 MHz, DMSO-d₆) δ 1.10-1.23 (1H, m), 1.48-1.62 (1H, m), 1.70-1.83 (2H, m), 1.92-2.05 (1H, m), 2.48-2.60 (1H, m), 2.72 (1H, t, J=12.2 Hz), 3.57 (1H, d, J=12.2 Hz), 3.64 (1H, d, J=12.2 Hz), 7.15-7.20 (1H, m), 7.25-7.34 (2H, m), 7.45 (1H, s), 7.57 (1H, td, J=7.9, 1.2 Hz), 7.63 (1H, td, J=7.9, 1.2 Hz), 8.14 (1H, d, J=7.3 Hz), 8.22 (1H, d, J=7.3 Hz), 9.36 (1H, t, J=6.1 Hz), 12.76 (1H, brs).

HR-FAB⁺ (m/z): 396.1354 (−2.8 mmu).

Elemental analysis calcd (%) for $C_{21}H_2N_3O_3S \cdot 1/10H_2O$: C, 63.49; H, 5.38; N, 10.58; found: C, 63.39; H, 5.27; N, 10.48.

<Compound of Example 126>
Colorless Powder

¹H NMR (400 MHz, DMSO-d₆) δ 1.60-1.74 (2H, m), 1.85-2.00 (2H, m), 2.65-2.75 (1H, m), 2.95-3.07 (2H, m), 3.16 (2H, d, J=7.9 Hz), 4.29 (2H, d, J=5.5 Hz), 7.31 (2H, d, J=7.9 Hz), 7.42 (1H, t, J=7.9 Hz), 7.49 (2H, d, J=8.6 Hz), 7.59 (2H, d, J=8.6 Hz), 7.62-7.69 (3H, m), 7.75 (1H, d, J=7.9 Hz), 8.02 (1H, dd, J=7.9, 1.2 Hz), 8.56 (1H, t, J=5.5 Hz), 17.41 (1H, brs).

HR-FAB⁺ (m/z): 449.1596 (−3.6 mmu).

Elemental analysis calcd (%) for $C_{26}H_{25}ClN_2O_3 \cdot 3/5H_2O$: C, 67.92; H, 5.74; N, 6.09; found: C, 67.75; H, 5.51; N, 6.02.

<Compound of Example 127>
Colorless Powder

¹H NMR (400 MHz, DMSO-d₆) δ 1.57-1.72 (2H, m), 1.85-1.97 (2H, m), 2.55-2.73 (1H, m), 2.95-3.05 (2H, m), 3.08-3.18 (2H, m), 4.23 (2H, d, J=6.1 Hz), 6.91 (2H, d, J=8.6 Hz), 6.96-7.05 (2H, m), 7.15-7.25 (4H, m), 7.41 (1H, t, J=7.3 Hz), 7.65 (1H, t, J=7.3 Hz), 7.72 (1H, d, J=7.9 Hz), 8.01 (1H, dd, J=7.9, 1.8 Hz), 8.50 (1H, t, J=5.5 Hz), 17.51 (1H, brs).

HR-FAB⁺ (m/z): 449.1907 (+3.0 mmu).

Elemental analysis calcd (%) for $C_{26}H_{25}FN_2O_4 \cdot 1/5H_2O$: C, 69.07; H, 5.66; N, 6.20; found: C, 68.81; H, 5.62; N, 5.99.

<Compound of Example 128>
Colorless Powder
$^1$H NMR (400 MHz, DMSO-$d_6$) δ 1.60-1.75 (2H, m), 1.90-2.03 (2H, m), 2.68-2.80 (1H, m), 2.96-3.07 (2H, m), 3.17 (2H, d, J=7.3 Hz), 4.60-4.72 (2H, m), 7.38 (1H, d, J=7.9 Hz), 7.41 (1H, d, J=7.9 Hz), 7.48 (1H, d, J=8.6 Hz), 7.66 (1H, td, J=7.9, 1.8 Hz), 7.73 (1H, d, J=7.9 Hz), 7.91 (1H, d, J=7.9 Hz), 8.02 (2H, td, J=7.9, 1.8 Hz), 9.07 (1H, t, J=6.1 Hz), 17.32 (1H, brs).
HR-FAB$^+$ (m/z): 396.1402 (+2.0 mmu).
Elemental analysis calcd (%) for $C_{21}H_{21}N_3O_3S$: C, 63.78; H, 5.35; N, 10.63; found: C, 63.51; H, 5.29; N, 10.33.

<Compound of Example 129>
Colorless Powder
$^1$H NMR (400 MHz, DMSO-$d_6$) δ 1.51-1.67 (2H, m), 1.72-1.80 (1H, m), 1.84-1.95 (1H, m), 2.48-2.59 (1H, m), 2.73 (1H, t, J=12.2 Hz), 2.87 (1H, t, J=12.2 Hz), 3.66 (1H, d, J=12.2 Hz), 3.76 (1H, d, J=12.2 Hz), 4.30 (1H, dd, J=15.3, 5.5 Hz), 4.37 (1H, dd, J=15.3, 5.5 Hz), 7.18-7.24 (1H, m), 7.28-7.38 (4H, m), 7.47 (1H, s), 7.51 (2H, d, J=8.6 Hz), 7.63 (2H, d, J=7.9 Hz), 7.68 (2H, d, J=8.6 Hz), 8.50 (1H, t, J=6.1 Hz).
HR-FAB$^+$ (m/z): 449.1648 (+1.6 mmu).
Elemental analysis calcd (%) for $C_{26}H_{25}ClN_2O_3$: C, 69.56; H, 5.61; N, 6.24; found: C, 69.39; H, 5.62; N, 6.13.

<Compound of Example 130>
Colorless Powder
$^1$H NMR (400 MHz, DMSO-$d_6$) δ 1.50-1.63 (2H, m), 1.70-1.77 (1H, m), 1.83-1.90 (1H, m), 2.45-2.55 (1H, m), 2.65-2.75 (1H, m), 2.83 (1H, t, J=12.2 Hz), 3.64 (1H, d, J=12.2 Hz), 3.73 (1H, d, J=12.2 Hz), 4.22 (1H, dd, J=15.3, 5.5 Hz), 4.29 (1H, dd, J=15.3, 5.5 Hz), 6.93 (2H, d, J=9.2 Hz), 6.98-7.05 (2H, m), 7.15-7.35 (7H, m), 7.45 (1H, s), 8.42 (1H, t, J=6.1 Hz), 12.78 (1H, brs).
HR-FAB$^+$ (m/z): 449.1869 (−0.7 mmu).
Elemental analysis calcd (%) for $C_{26}H_{25}FN_2O_4$: C, 69.63; H, 5.62; N, 6.25; found: C, 69.58; H, 5.61; N, 6.11.

<Compound of Example 131>
Colorless Powder
$^1$H NMR (400 MHz, DMSO-$d_6$) δ 1.56-1.67 (2H, m), 1.73-1.82 (1H, m), 1.87-1.97 (1H, m), 2.52-2.63 (1H, m), 2.73 (1H, t, J=12.2 Hz), 2.87 (1H, t, J=12.2 Hz), 3.66 (1H, d, J=12.2 Hz), 3.80 (1H, d, J=12.2 Hz), 4.65 (1H, dd, J=16.5, 6.1 Hz), 4.71 (1H, dd, J=16.5, 6.1 Hz), 7.18-7.25 (1H, m), 7.28-7.35 (2H, m), 7.40 (1H, t, J=7.9 Hz), 7.45-7.53 (2H, m), 7.93 (1H, d, J=7.9 Hz), 8.05 (1H, d, J=7.3 Hz), 8.98 (1H, t, J=6.1 Hz), 12.83 (1H, brs).
HR-FAB$^+$ (m/z): 396.1373 (−0.9 mmu).
Elemental analysis calcd (%) for $C_{21}H_{21}N_3O_3S \cdot 1/5H_2O$: C, 63.20; H, 5.41; N, 10.53; found: C, 63.04; H, 5.33; N, 10.50.

<Compound of Example 132>
Colorless Powder
$^1$H NMR (400 MHz, DMSO-$d_6$) δ 1.53-1.68 (2H, m), 1.74-1.83 (1H, m), 1.90-2.00 (1H, m), 2.60-2.78 (2H, m), 2.87 (1H, t, J=12.2 Hz), 3.70 (1H, d, J=12.2 Hz), 3.84 (1H, d, J=12.2 Hz), 6.92-7.02 (4H, m), 7.14-7.26 (3H, m), 7.28-7.36 (2H, m), 7.48 (1H, s), 7.61 (2H, d, J=8.6 Hz), 10.00 (1H, s), 12.81 (1H, brs).
HR-FAB$^+$ (m/z): 435.1703 (−1.8 mmu).
Elemental analysis calcd (%) for $C_{25}H_{23}FN_2O_4 \cdot 1/10H_2O$: C, 68.83; H, 5.36; N, 6.42; found: C, 68.77; H, 5.31; N, 6.34.

<Compound of Example 133>
Colorless Powder
$^1$H NMR (400 MHz, DMSO-$d_6$) δ 1.30-1.40 (1H, m), 1.57-1.67 (1H, m), 1.76-1.82 (1H, m), 1.84-1.90 (1H, m), 2.17-2.27 (1H, m), 2.75 (1H, dd, J=11.6, 10.4 Hz), 2.81 (1H, dd, J=12.2, 3.1 Hz), 3.58 (1H, td, J=12.2, 3.1 Hz), 3.71 (1H, dd, J=12.2, 3.1 Hz), 4.54 (2H, d, J=6.7 Hz), 7.20 (1H, td, J=8.6, 2.4 Hz), 7.26-7.35 (3H, m), 7.40 (1H, td, J=7.9, 1.2 Hz), 7.48 (1H, brs), 7.67 (1H, d, J=7.3 Hz), 7.88 (1H, d, J=7.3 Hz).
HR-FAB$^+$ (m/z): 369.1258 (−1.5 mmu).

<Compound of Example 134>
Colorless Powder
$^1$H NMR (400 MHz, DMSO-$d_6$) δ 1.42-1.59 (2H, m), 1.78-1.85 (1H, m), 1.99-2.06 (1H, m), 2.83-2.91 (2H, m), 3.45 (1H, td, J=12.2, 3.6 Hz), 3.54-3.60 (1H, m), 3.71 (1H, dd, J=12.2, 3.6 Hz), 4.64 (2H, s), 7.20 (1H, td, J=7.9, 2.4 Hz), 7.28-7.34 (2H, m), 7.43-7.45 (3H, m), 7.51 (2H, d, J=8.6 Hz), 7.64 (2H, d, J=8.6 Hz), 7.69 (2H, d, J=8.6 Hz), 12.82 (1H, brs).
HR-FAB$^+$ (m/z): 422.1514 (−0.9 mmu).
Elemental analysis calcd (%) for $C_{25}H_{24}ClNO_3$: C, 71.17; H, 5.73; N, 3.32; found: C, 71.30; H, 5.70; N, 3.26.

<Compound of Example 135>
Colorless Powder
$^1$H NMR (400 MHz, DMSO-$d_6$) δ 1.28-1.38 (1H, m), 1.57-1.68 (1H, m), 1.76-1.83 (1H, m), 1.85-1.92 (1H, m), 2.09-2.17 (1H, m), 2.72 (1H, dd, J=11.6, 10.4 Hz), 2.80 (1H, td, J=11.6, 2.4 Hz), 3.61 (1H, td, J=12.8, 3.1 Hz), 3.75 (1H, dd, J=11.6, 3.1 Hz), 3.97-4.04 (2H, m), 7.07 (2H, d, J=8.6 Hz), 7.20 (1H, td, J=7.3, 2.4 Hz), 7.29-7.36 (2H, m), 7.46-7.48 (3H, m), 7.61 (2H, d, J=8.6 Hz), 7.64 (2H, d, J=8.6 Hz), 12.87 (1H, brs).
HR-FAB$^+$ (m/z): 422.1552 (+2.9 mmu).

<Compound of Example 136>
Colorless Powder
$^1$H NMR (400 MHz, DMSO-$d_6$) δ 1.15-1.25 (1H, m), 1.52-1.63 (1H, m), 1.69-1.80 (2H, m), 1.91-2.01 (1H, m), 2.61 (1H, dd, J=12.2, 10.4 Hz), 2.72-2.79 (1H, m), 3.41 (2H, d, J=6.7 Hz), 3.56-3.62 (1H, m), 3.68-3.72 (1H, m), 4.52 (1H, d, J=12.8 Hz), 4.55 (1H, d, J=12.8 Hz), 7.16 (1H, td, J=7.3, 2.4 Hz), 7.29-7.34 (2H, m), 7.43-7.46 (3H, m), 7.52 (2H, d, J=8.6 Hz), 7.66 (2H, d, J=8.6 Hz), 7.70 (2H, d, J=8.6 Hz), 12.82 (1H, brs).
HR-FAB$^+$ (m/z): 436.1701 (+2.2 mmu).
Elemental analysis calcd (%) for $C_{26}H_{26}ClNO_3$: C, 71.63; H, 6.01; N, 3.21; found: C, 71.61; H, 5.96; N, 3.13.

<Compound of Example 137>
Colorless Powder
$^1$H NMR (400 MHz, DMSO-$d_6$) δ 1.37-1.56 (2H, m), 1.74-1.81 (1H, m), 1.95-2.01 (1H, m), 2.77-2.87 (2H, m), 3.41 (1H, td, J=12.2, 4.3 Hz), 3.49-3.54 (1H, m), 3.64-3.68 (1H, m), 4.54 (2H, s), 6.92 (2H, d, J=8.6 Hz), 6.99-7.05 (2H, m), 7.15-7.22 (3H, m), 7.25-7.33 (4H, m), 7.41 (1H, brs), 12.78 (1H, brs).
HR-FAB$^+$ (m/z): 422.1748 (−1.9 mmu).
Elemental analysis calcd (%) for $C_{25}H_{24}FNO_4$: C, 71.24; H, 5.74; N, 3.32; found: C, 71.05; H, 5.79; N, 3.19.

<Compound of Example 138>
Colorless Oil
$^1$H NMR (400 MHz, DMSO-$d_6$) δ 1.13-1.23 (1H, m), 1.51-1.62 (1H, m), 1.69-1.77 (2H, m), 1.88-1.98 (1H, m), 2.58 (1H, dd, J=12.2, 9.8 Hz), 2.71-2.78 (1H, m), 3.38 (2H, d, J=6.7 Hz), 3.56-3.61 (1H, m), 3.65-3.69 (1H, m), 4.46 (2H, s), 6.97 (2H, d, J=8.6 Hz), 7.05 (2H, dd, J=9.2, 4.3 Hz), 7.15 (1H, td, J=7.3, 1.8 Hz), 7.22 (2H, t, J=8.6 Hz), 7.28-7.36 (4H, m), 7.44 (1H, brs), 12.80 (1H, brs).
HR-FAB$^+$ (m/z): 436.1947 (+2.3 mmu).

<Compound of Example 139>
Colorless Powder
$^1$H NMR (400 MHz, DMSO-$d_6$) δ 1.48-1.62 (1H, m), 1.63-1.77 (1H, m), 1.78-1.97 (2H, m), 2.61 (3H, s), 2.66-2.88

(2H, m), 3.77 (3H, s), 4.97-4.12 (1H, m), 7.07 (1H, d, J=9.1 Hz), 7.20-7.43 (2H, m), 7.59 (2H, d, J=8.6 Hz), 7.96 (2H, d, J=8.6 Hz).

HR-FAB$^+$ (m/z): 486.1274 (+2.0 mmu).

<Compound of Example 140>

Colorless Powder $^1$H NMR (400 MHz, DMSO-d$_6$) δ 1.48-1.57 (1H, m), 1.63-1.73 (1H, m), 1.85-1.99 (2H, m), 2.33 (3H, s), 2.83-2.88 (1H, m), 2.92-2.97 (1H, m), 3.00-3.05 (1H, m), 3.11-3.14 (1H, m), 3.66 (1H, d, J=6.5 Hz), 3.70 (1H, d, J=6.5 Hz), 3.81-3.89 (1H, m), 7.34-7.38 (1H, m), 7.50 (2H, d, J=8.6 Hz), 7.59-7.64 (2H, m), 7.84 (2H, d, J=8.6 Hz), 7.95 (1H, d, J=7.3 Hz), 8.36-8.37 (1H, m), 16.78 (1H, brs).

HR-FAB$^+$ (m/z): 470.1315 (+1.0 mmu).

<Compound of Example 141>

Pale Yellow Powder $^1$H NMR (400 MHz, DMSO-d$_6$) δ 1.20-1.30 (1H, m), 1.49-1.58 (1H, m), 1.72-1.80 (1H, m), 1.93-2.00 (1H, m), 2.36 (3H, s), 2.54-2.59 (1H, m), 2.65-2.77 (2H, m), 3.52-3.55 (1H, m), 3.73-3.75 (1H, m), 3.95 (1H, d, J=15.9 Hz), 3.97 (1H, d, J=15.9 Hz), 7.17 (1H, td, J=7.3, 2.4 Hz), 7.27-7.32 (2H, m), 7.45 (1H, brs), 7.52 (2H, d, J=8.6 Hz), 7.88 (2H, d, J=8.6 Hz).

HR-FAB$^+$ (m/z): 442.1395 (+3.9 mmu).

<Compound of Example 142>

Pale Yellow Powder $^1$H NMR (400 MHz, DMSO-d$_6$) δ 1.45-1.57 (1H, m), 1.60-1.70 (1H, m), 1.93-1.99 (1H, m), 2.05-2.15 (1H, m), 2.39 (3H, s), 2.89-2.95 (2H, m), 3.05-3.08 (1H, m), 3.09-4.00 (2H, m), 4.08-4.40 (2H, m), 7.37 (1H, t, J=7.3 Hz), 7.51-7.60 (3H, m), 7.66 (1H, t, J=7.3 Hz), 7.90 (2H, d, J=8.6 Hz), 7.97 (1H, d, J=7.3 Hz).

HR-FAB$^+$ (m/z): 442.1399 (+4.3 mmu).

<Compound of Example 143>

Pale Yellow Powder $^1$H NMR (400 MHz, DMSO-d$_6$) δ 1.57-1.70 (2H, m), 1.76-1.85 (1H, m), 1.93-2.02 (1H, m), 2.43 (3H, s), 2.75-2.80 (1H, m), 2.88-2.95 (2H, m), 3.70-3.73 (1H, m), 3.85-3.92 (1H, m), 7.25 (1H, td, J=7.3, 1.8 Hz), 7.31-7.37 (2H, m), 7.49-7.53 (3H, m), 7.85 (2H, d, J=8.6 Hz), 10.67 (1H, s), 12.83 (1H, brs).

HR-FAB$^+$ (m/z): 456.1153 (+0.5 mmu).

<Compound of Example 144>

Colorless Powder $^1$H NMR (400 MHz, DMSO-d$_6$) δ 1.64-1.75 (2H, m), 1.93-2.04 (2H, m), 2.38 (3H, s), 2.97-3.09 (3H, m), 3.17-3.26 (2H, m), 7.39 (1H, td, J=7.3, 1.2 Hz), 7.47 (2H, d, J=8.6 Hz), 7.64 (1H, td, J=7.3, 1.2 Hz), 7.72 (1H, d, J=7.9 Hz), 7.82 (2H, d, J=8.6 Hz), 7.99 (1H, dd, J=7.3, 1.2 Hz), 10.71 (1H, brs), 17.26 (1H, brs).

HR-FAB$^+$ (m/z): 456.1151 (+0.2 mmu).

<Compound of Example 145>

Colorless Powder $^1$H NMR (400 MHz, DMSO-d$_6$) δ 1.43-1.52 (1H, m), 1.58-1.68 (1H, m), 1.78-1.92 (2H, m), 2.51 (3H, s), 2.73 (1H, dd, J=11.6, 8.6 Hz), 2.87-2.93 (1H, m), 3.51 (1H, td, J=12.2, 3.7 Hz), 3.66 (1H, dd, J=12.2, 3.7 Hz), 3.86-3.95 (1H, m), 6.42 (1H, d, J=15.3 Hz), 7.20 (1H, td, J=7.3, 2.4 Hz), 7.30-7.35 (2H, m), 7.45 (1H, brs), 7.59 (2H, d, J=8.6 Hz), 7.60 (1H, d, J=15.3 Hz), 7.96 (2H, d, J=8.6 Hz), 8.27 (1H, d, J=7.3 Hz), 12.81 (1H, brs).

HR-FAB$^+$ (m/z): 482.1319 (+1.4 mmu).

Elemental analysis calcd (%) for C$_{25}$H$_{24}$ClN$_3$O$_3$S.1/10H$_2$O: C, 62.06; H, 5.04; N, 8.69; found: C, 61.98; H, 5.01; N, 8.46.

<Compound of Example 146>

Colorless Powder $^1$H NMR (400 MHz, DMSO-d$_6$) δ 1.50-1.60 (1H, m), 1.67-1.77 (1H, m), 1.90-2.02 (2H, m), 2.47 (3H, s), 2.87-2.92 (1H, m), 2.94-2.99 (1H, m), 3.03-3.08 (1H, m), 3.20-3.23 (1H, m), 3.95-4.03 (1H, m), 6.39 (1H, d, J=15.3 Hz), 7.36-7.40 (1H, m), 7.56 (1H, d, J=15.3 Hz), 7.58 (2H, d, J=8.6 Hz), 7.63-7.68 (2H, m), 7.94-7.99 (3H, m), 8.33 (1H, d, J=6.7 Hz), 16.75 (1H, brs).

HR-FAB$^+$ (m/z): 482.1344 (+3.9 mmu).

Elemental analysis calcd (%) for C$_{25}$H$_{24}$ClN$_3$O$_3$S.3/5H$_2$O: C, 60.93; H, 5.15; N, 8.53; found: C, 60.64; H, 4.85; N, 8.38.

<Compound of Example 147>

Colorless Powder $^1$H NMR (400 MHz, DMSO-d$_6$) δ 1.31-1.40 (1H, m), 1.52-1.62 (1H, m), 1.74-1.81 (2H, m), 2.35 (3H, s), 2.42 (2H, t, J=7.3 Hz), 2.52-2.57 (1H, m), 2.74-2.80 (1H, m), 3.03 (2H, t, J=7.3 Hz), 3.47-3.52 (1H, m), 3.58 (1H, dd, J=11.6, 2.4 Hz), 3.73-3.82 (1H, m), 7.12 (1H, d, J=7.9 Hz), 7.28 (1H, t, J=7.9 Hz), 7.33 (1H, d, J=7.3 Hz), 7.44 (1H, brs), 7.49 (2H, d, J=8.6 Hz), 7.83 (2H, d, J=8.6 Hz), 7.95 (1H, d, J=7.3 Hz), 12.89 (1H, brs).

HR-FAB$^+$ (m/z): 484.1488 (+2.6 mmu).

Elemental analysis calcd (%) for C$_{25}$H$_{26}$ClN$_3$O$_3$S.1/4H$_2$O: C, 61.47; H, 5.47; N, 8.60; found: C, 61.33; H, 5.29; N, 8.41.

<Compound of Example 148>

Colorless Powder $^1$H NMR (400 MHz, DMSO-d$_6$) δ 1.41-1.48 (1H, m), 1.61-1.68 (1H, m), 1.81-1.93 (2H, m), 2.31 (3H, s), 2.41 (2H, t, J=7.3 Hz), 2.74-2.79 (1H, m), 2.87-2.92 (1H, m), 2.97-3.01 (3H, m), 3.05-3.08 (1H, m), 3.85 (1H, m), 7.36 (1H, t, J=7.3 Hz), 7.48 (2H, d, J=8.6 Hz), 7.54-7.61 (2H, m), 7.77 (2H, d, J=8.6 Hz), 7.95 (1H, d, J=7.3 Hz), 8.03 (1H, d, J=6.1 Hz), 16.83 (1H, brs).

HR-FAB$^+$ (m/z): 484.1485 (+2.3 mmu).

Elemental analysis calcd (%) for C$_{25}$H$_{26}$ClN$_3$O$_3$S.3/10H$_2$O: C, 61.35; H, 5.48; N, 8.59; found: C, 61.28; H, 5.34; N, 8.42.

<Compound of Example 149>

Colorless Powder $^1$H NMR (400 MHz, DMSO-d$_6$) δ 1.32-1.42 (1H, m), 1.51-1.61 (1H, m), 1.74-1.79 (1H, m), 1.82-1.87 (1H, m), 2.43 (3H, s), 2.58-2.63 (1H, m), 2.69-2.75 (1H, m), 3.49-3.56 (2H, m), 3.64-3.67 (1H, m), 5.21 (1H, d, J=13.4 Hz), 5.26 (1H, d, J=13.4 Hz), 7.16 (1H, d, J=7.9 Hz), 7.28-7.34 (2H, m), 7.44 (1H, brs), 7.46 (1H, d, J=7.3 Hz), 7.54 (2H, d, J=8.6 Hz), 7.91 (2H, d, J=8.6 Hz), 12.80 (1H, brs).

HR-FAB$^+$ (m/z): 486.1230 (−2.5 mmu).

<Compound of Example 150>

Colorless Amorphous $^1$H NMR (400 MHz, DMSO-d$_6$) δ 1.42-1.52 (1H, m), 1.60-1.70 (1H, m), 1.85-1.95 (2H, m), 2.42 (3H, s), 2.78-2.83 (1H, m), 2.86-2.91 (1H, m), 2.99-3.02 (1H, m), 3.13 (1H, dd, J=11.0, 3.1 Hz), 3.58-3.67 (1H, m), 5.21 (2H, s), 7.36 (1H, t, J=7.3 Hz), 7.54 (2H, d, J=8.6 Hz), 7.57-7.65 (3H, m), 7.89 (2H, d, J=8.6 Hz), 7.97 (1H, dd, J=7.9, 1.2 Hz), 16.65 (1H, brs).

HR-FAB$^+$ (m/z): 486.1281 (+2.7 mmu).

<Compound of Example 151>

Colorless Powder $^1$H NMR (400 MHz, DMSO-d$_6$) δ 1.52-1.58 (1H, m), 1.62-1.70 (1H, m), 1.75-1.84 (2H, m), 2.30 (3H, s), 3.00 (1H, dd, J=11.6, 7.3 Hz), 3.11-3.16 (1H, m), 3.20-3.26 (1H, m), 3.44 (1H, dd, J=11.6, 2.4 Hz), 3.79-3.87 (1H, m), 6.77 (1H, d, J=7.9 Hz), 7.22 (1H, td, J=7.9, 1.8 Hz), 7.32-7.38 (2H, m), 7.46-7.50 (3H, m), 7.81 (2H, d, J=8.6 Hz), 9.09 (1H, s), 12.80 (1H, brs).

HR-FAB+ (m/z): 471.1260 (+0.2 mmu).
<Compound of Example 152>
Colorless Powder
$^1$H NMR (400 MHz, DMSO-d$_6$) δ 1.49-1.58 (1H, m), 1.68-1.79 (1H, m), 1.89-1.98 (2H, m), 2.32 (3H, s), 2.92 (1H, dd, J=11.0, 8.6 Hz), 2.98-3.06 (2H, m), 3.22 (1H, dd, J=11.0, 3.1 Hz), 3.80-3.88 (1H, m), 6.82 (1H, d, J=6.1 Hz), 7.35 (1H, t, J=7.3 Hz), 7.47 (2H, d, J=8.6 Hz), 7.57-7.65 (2H, m), 7.79 (2H, d, J=8.6 Hz), 7.94 (1H, d, J=7.9 Hz), 9.18 (1H, s), 16.72 (1H, brs).
HR-FAB+ (m/z): 471.1273 (+1.5 mmu).
<Compound of Example 153>
Pale Yellow Powder
$^1$H NMR (400 MHz, DMSO-d$_6$) δ 1.20-1.30 (1H, m), 1.54-1.64 (1H, m), 1.70-1.75 (1H, m), 1.79-1.86 (1H, m), 2.19-2.27 (1H, m), 2.58-2.67 (1H, m), 2.73 (3H, s), 2.79 (1H, td, J=12.2, 3.1 Hz), 2.89 (1H, dd, J=17.1, 6.1 Hz), 3.02 (1H, dd, J=17.1, 6.7 Hz), 3.61 (1H, td, J=12.2, 3.7 Hz), 3.68 (1H, dd, J=12.2, 1.8 Hz), 7.17-7.21 (1H, m), 7.31-7.32 (2H, m), 7.45 (1H, m), 7.60 (2H, d, J=8.6 Hz), 8.02 (2H, d, J=8.6 Hz), 12.77 (1H, brs).
HR-FAB+ (m/z): 455.1192 (−0.4 mmu).
Elemental analysis calcd (%) for C$_{24}$H$_{23}$ClN$_2$O$_3$S.1/4H$_2$O: C, 62.74; H, 5.16; N, 6.10; found: C, 62.71; H, 4.96; N, 5.87.
<Compound of Example 154>
Colorless Powder
$^1$H NMR (400 MHz, DMSO-d$_6$) δ 1.36-1.46 (1H, m), 1.57-1.68 (1H, m), 1.76-1.81 (1H, m), 1.89-1.93 (1H, m), 2.42 (3H, s), 2.46-2.55 (1H, m), 2.69 (1H, dd, J=12.2, 10.4 Hz), 2.76 (1H, td, J=12.2, 2.4 Hz), 3.65 (1H, td, J=12.2, 4.3 Hz), 3.73 (1H, dd, J=11.6, 3.1 Hz), 6.03 (1H, dd, J=15.9, 7.3 Hz), 6.75 (1H, dd, J=15.9, 1.2 Hz), 7.23 (1H, td, J=7.3, 2.4 Hz), 7.30-7.35 (2H, m), 7.48 (1H, m), 7.55 (2H, d, J=8.6 Hz), 7.89 (2H, d, J=8.6 Hz), 12.80 (1H, brs).
HR-FAB+ (m/z): 439.1255 (+0.8 mmu).
Elemental analysis calcd (%) for C$_{24}$H$_{23}$ClN$_2$O$_2$S: C, 65.67; H, 5.28; N, 6.38; found: C, 65.62; H, 5.32; N, 6.15.
<Compound of Example 155>
Colorless Powder
$^1$H NMR (400 MHz, DMSO-d$_6$) δ 1.26-1.36 (1H, m), 1.50-1.61 (1H, m), 1.73-1.80 (1H, m), 1.91-1.98 (1H, m), 1.99-2.10 (1H, m), 2.68 (1H, dd, J=12.2, 10.4 Hz), 2.78 (1H, td, J=11.6, 2.4 Hz), 3.27-3.40 (2H, m), 3.59 (1H, td, J=12.8, 4.3 Hz), 3.76-3.80 (1H, m), 7.17 (1H, ddd, J=7.9, 2.4, 1.2 Hz), 7.28 (1H, t, J=7.3 Hz), 7.31-7.36 (2H, m), 7.42-7.44 (2H, m), 7.46-7.47 (1H, m), 7.92-7.94 (2H, m), 8.03 (1H, s), 12.82 (1H, brs).
HR-FAB+ (m/z): 411.1177 (−2.4 mmu).
Elemental analysis calcd (%) for C$_{22}$H$_{22}$N$_2$O$_2$S: C, 64.36; H, 5.40; N, 6.82; found: C, 64.46; H, 5.35; N, 6.58.
<Compound of Example 156>
Colorless Powder
$^1$H NMR (400 MHz, DMSO-d$_6$) δ 2.49-2.55 (1H, m), 2.63 (3H, s), 2.75 (1H, td, J=11.6, 3.1 Hz), 3.39-3.50 (2H, m), 3.55 (1H, d, J=12.2 Hz), 3.64-3.69 (2H, m), 3.72-3.78 (1H, m), 4.00 (1H, d, J=11.6 Hz), 7.22-7.24 (1H, m), 7.34-7.41 (2H, m), 7.49 (1H, m), 7.59 (2H, d, J=8.6 Hz), 7.97 (2H, d, J=8.6 Hz), 8.47 (1H, t, J=5.5 Hz), 12.88 (1H, brs).
HR-FAB+ (m/z): 472.1117 (+1.9 mmu).
Elemental analysis calcd (%) for C$_{23}$H$_{22}$ClN$_3$O$_4$S.1/5H$_2$O: C, 58.09; H, 4.75; N, 8.84; found: C, 57.95; H, 4.66; N, 8.72.
<Compound of Example 157>
Colorless Powder
$^1$H NMR (400 MHz, DMSO-d$_6$) δ 2.41 (3H, s), 2.73 (1H, dd, J=12.2, 9.8 Hz), 2.83 (1H, td, J=12.2, 3.1 Hz), 3.52 (1H, d, J=11.6 Hz), 3.72-3.78 (2H, m), 4.04 (1H, dt, J=11.0, 2.4 Hz), 4.16 (1H, dd, J=9.8, 3.1 Hz), 4.45 (2H, d, J=6.1 Hz), 7.22-7.25 (1H, m), 7.36 (1H, t, J=7.3 Hz), 7.41-7.42 (1H, d, J=7.3 Hz), 7.47 (1H, m), 7.52 (2H, d, J=8.6 Hz), 7.87 (2H, d, J=8.6 Hz), 8.70 (1H, t, J=5.5 Hz), 12.90 (1H, brs).
HR-FAB+ (m/z): 472.1118 (+2.1 mmu).
Elemental analysis calcd (%) for C$_{23}$H$_{22}$ClN$_3$O$_4$S.2/5H$_2$O: C, 57.65; H, 4.80; N, 8.77; found: C, 57.73; H, 4.69; N, 8.48.
<Compound of Example 158>
Colorless Powder
$^1$H NMR (400 MHz, DMSO-d$_6$) δ 2.40 (3H, s), 2.91 (1H, dd, J=11.6, 10.4 Hz), 2.99-3.08 (2H, m), 3.27-3.43 (1H, m), 3.74-3.80 (1H, m), 4.07 (1H, dt, J=11.6, 2.4 Hz), 4.19 (1H, dd, J=10.4, 2.4 Hz), 4.38-4.48 (2H, m), 7.29 (1H, t, J=7.9 Hz), 7.49-7.54 (3H, m), 7.58 (1H, dd, J=7.3, 1.8 Hz), 7.86-7.89 (3H, m), 8.70 (1H, t, J=6.1 Hz), 14.91 (1H, brs).
HR-FAB+ (m/z): 472.1118 (+2.1 mmu).
Elemental analysis calcd (%) for C$_{23}$H$_{22}$ClN$_3$O$_4$S.1/4H$_2$O: C, 57.98; H, 4.76, N, 8.82; found: C, 57.97; H, 4.61; N, 8.53.
<Compound of Example 159>
Colorless Powder
$^1$H NMR (400 MHz, DMSO-d$_6$) δ 2.40 (3H, s), 2.49-2.55 (1H, m), 2.71 (1H, td, J=11.6, 3.1 Hz), 3.54 (1H, d, J=12.2 Hz), 3.59-3.68 (4H, m), 3.74-3.79 (1H, m), 3.97 (1H, dd, J=11.6, 1.8 Hz), 4.74 (2H, s), 7.20 (1H, dd, J=7.9, 1.2 Hz), 7.34 (1H, t, J=7.9 Hz), 7.39 (1H, d, J=7.9 Hz), 7.46-7.48 (1H, m), 7.54 (2H, d, J=8.6 Hz), 7.91 (2H, d, J=8.6 Hz), 12.87 (1H, brs).
HR-FAB+ (m/z): 459.1186 (+4.1 mmu).
Elemental analysis calcd (%) for C$_{23}$H$_{23}$ClN$_2$O$_4$S.2/5H$_2$O: C, 59.26; H, 5.15; N, 6.01; found: C, 59.29; H, 4.99; N, 5.86.
<Compound of Example 160>
Colorless Powder
$^1$H NMR (400 MHz, DMSO-d$_6$) δ 2.38 (3H, s), 2.86-2.91 (1H, m), 3.00-3.10 (3H, m), 3.52-3.61 (2H, m), 3.70 (1H, td, J=11.0, 3.1 Hz), 3.80-3.85 (1H, m), 4.00-4.03 (1H, m), 4.72 (2H, s), 7.35 (1H, td, J=7.9, 1.2 Hz), 7.54 (2H, d, J=8.6 Hz), 7.57-7.65 (2H, m), 7.90 (2H, d, J=8.6 Hz), 7.95 (1H, dd, J=7.9, 1.2 Hz), 15.97 (1H, brs).
HR-FAB+ (m/z): 459.1193 (+4.8 mmu).
<Compound of Example 161>
Yellow Powder
$^1$H NMR (400 MHz, DMSO-d$_6$) δ 1.50-1.62 (1H, m), 1.66-1.75 (1H, m), 1.78-1.88 (1H, m), 1.92-2.01 (1H, m), 2.58 (3H, s), 3.11-3.21 (2H, m), 3.84-3.95 (2H, m), 4.01 (1H, dd, J=12.8, 2.4 Hz), 7.01 (1H, d, J=2.4 Hz), 7.06 (1H, dd, J=9.2, 2.4 Hz), 7.58 (2H, d, J=8.6 Hz), 7.92-8.01 (3H, m), 8.32 (1H, d, J=7.3 Hz), 13.44 (1H, brs).
HR-FAB+ (m/z): 501.1036 (+3.7 mmu).
<Compound of Example 162>
Colorless Powder
$^1$H NMR (400 MHz, DMSO-d$_6$) δ 1.41-1.54 (1H, m), 1.59-1.73 (1H, m), 1.77-1.85 (1H, m), 1.86-1.94 (1H, m), 2.53-2.64 (5H, m), 3.22-3.37 (2H, m), 3.94-4.07 (1H, m), 6.71 (1H, d, J=9.2 Hz), 7.09 (1H, d, J=7.3 Hz), 7.27 (1H, brs), 7.58 (2H, d, J=8.6 Hz), 7.96 (2H, d, J=8.6 Hz), 8.14-8.59 (3H, m).
HR-FAB+ (m/z): 471.1272 (+1.4 mmu).
<Compound of Example 163>
Pale Yellow Powder
$^1$H NMR (400 MHz, DMSO-d$_6$) δ 1.41-1.60 (2H, m), 1.77-1.84 (1H, m), 1.97-2.04 (1H, m), 2.38 (3H, s), 2.83-2.92 (2H, m), 3.43 (1H, td, J=12.2, 3.7 Hz), 3.58-3.64 (1H, m), 3.70 (1H, dd, J=12.2, 3.7 Hz), 4.79 (2H, s), 7.21 (1H, td, J=7.3, 1.8 Hz), 7.28-7.34 (2H, m), 7.46 (1H, m), 7.54 (2H, d, J=8.6 Hz), 7.90 (2H, d, J=8.6 Hz), 12.82 (1H, brs).

HR-FAB⁺ (m/z): 443.1204 (+0.8 mmu).

Elemental analysis calcd (%) for $C_{23}H_{23}ClN_2O_3S$: C, 62.36; H, 5.23; N, 6.32; found: C, 62.06; H, 5.31; N, 6.06.

$[\alpha]^{28.8°}_D$ −14.1° (C=1.0, DMF)

HPLC (CHIRALCEL OJ (Daicel Chemical Industries, Co., Ltd.) φ 0.46×25 cm, mobile phase: hexane/ethanol=85/15 (0.1% TFA), flowrate: 1 mL/min, Temp.: 40° C.): Rt 27.5 min (>99% ee)

<Compound of Example 164>

Colorless Crystals

¹H NMR (400 MHz, DMSO-d₆) δ 1.46-1.67 (2H, m), 1.75-1.93 (2H, m), 2.58 (3H, s), 2.67-2.78 (2H, m), 3.47 (1H, d, J=12.2 Hz), 3.60 (1H, d, J=12.2 Hz), 3.88-4.02 (1H, m), 7.13 (1H, d, J=9.1 Hz), 7.17-7.24 (1H, m), 7.28-7.33 (1H, m), 7.56 (2H, d, J=8.6 Hz), 7.93 (2H, d, J=8.6 Hz), 8.24 (1H, d, J=7.9 Hz), 13.14 (1H, brs).

HR-FAB⁺ (m/z): 474.1072 (+1.8 mmu).

Elemental analysis calcd (%) for $C_{23}H_{21}ClFN_3O_3S \cdot H_2O$: C, 56.15; H, 4.71; N, 8.54; found: C, 56.05; H, 4.45; N, 8.28.

<Compound of Example 165>

Colorless Crystals

¹H NMR (400 MHz, DMSO-d₆) δ 1.52-1.62 (2H, m), 1.74-1.83 (1H, m), 1.86-1.93 (1H, m), 2.57 (3H, s), 2.66-2.79 (2H, m), 3.58 (1H, d, J=12.2 Hz), 3.70 (1H, d, J=12.2 Hz), 3.86-3.97 (1H, m), 5.10 (2H, s), 6.78-6.83 (1H, m), 6.93 (1H, s), 7.09 (1H, s), 7.23-7.32 (1H, m), 7.36 (2H, t, J=7.3 Hz), 7.43 (2H, d, J=7.3 Hz), 7.56 (2H, d, J=8.6 Hz), 7.93 (2H, d, J=8.6 Hz), 8.23 (1H, d, J=7.3 Hz), 12.85 (1H, brs).

HR-FAB⁺ (m/z): 562.1542 (−2.5 mmu).

Elemental analysis calcd (%) for $C_{30}H_{28}ClN_3O_4S \cdot 3/10H_2O$: C, 63.50; H, 5.08; N, 7.40; found: C, 63.35; H, 5.05; N, 7.40.

Example 166

2-[2-[[2-(4-Chlorophenyl)-4-methylthiazole-5-carbonyl]aminomethyl]morpholin-4-yl]benzoic acid

[Chemical formula 225]

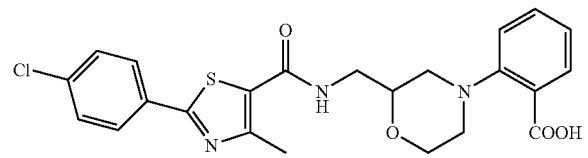

Trifluoroacetic acid (1 mL) was added to tert-butyl 2-[2-[[2-(4-chlorophenyl)-4-methylthiazole-5-carbonyl]aminomethyl]morpholin-4-yl]benzoate (113 mg, 0.214 mmol) in dichloromethane (1 mL). The mixture was stirred at room temperature for 2 hours. Subsequently, the solvent was removed and a 1 mol/L aqueous potassium hydroxide solution was added to the residue to make it basic. The mixture was then made acidic by the addition of 2 mol/L hydrochloric acid. The crystallized powdery product was collected by filtration and washed with water to give 78.2 mg (78%) of the desired compound as a colorless powder.

¹H NMR (400 MHz, DMSO-d₆) δ 2.61 (3H, s), 2.86 (1H, t, J=11.6 Hz), 3.01-3.16 (3H, m), 3.39-3.46 (2H, m), 3.70 (1H, td, J=11.6, 1.8 Hz), 3.79-3.84 (1H, m), 4.05 (1H, d, J=11.6 Hz), 7.36 (1H, t, J=7.3 Hz), 7.57-7.67 (4H, m), 7.94-7.96 (3H, m), 8.40 (1H, t, J=5.5 Hz), 15.96 (1H, brs).

HR-FAB⁺ (m/z): 472.1143 (+4.5 mmu).

Elemental analysis calcd (%) for $C_{23}H_{22}ClN_3O_4S \cdot 3/10H_2O$: C, 57.87; H, 4.77; N, 8.80; found: C, 57.71; H, 4.60; N, 8.50.

Example 167

2-[3-[(Benzothiazol-2-yl)oxymethyl]piperidin-1-yl] benzoic acid

Step 167a) 2-[3-[(Benzothiazol-2-yl)oxymethyl] piperidin-1-yl]benzaldehyde

[Chemical formula 226]

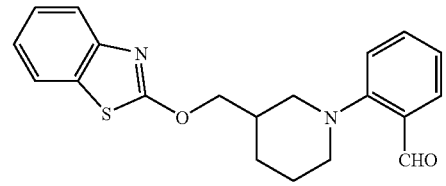

Using 3-[(benzothiazol-2-yl)oxymethyl]piperidine (58.0 mg, 0.234 mmol) and 2-fluorobenzaldehyde (0.0381 mL, 0.351 mmol), the same procedure was followed as in Step 1c of Example 1 to give 10.1 mg (12%) of the desired compound as a colorless oil.

¹H NMR (400 MHz, CDCl₃) δ 1.58-1.62 (1H, m), 1.71-1.82 (1H, m), 1.86-1.93 (1H, m), 2.00-2.06 (1H, m), 2.28-2.38 (1H, m), 3.22 (1H, dd, J=12.8, 10.4 Hz), 3.26-3.33 (1H, m), 4.02-4.09 (3H, m), 4.22-4.26 (1H, m), 6.97 (1H, d, J=8.6 Hz), 7.04-7.09 (2H, m), 7.29 (1H, td, J=7.3, 1.2 Hz), 7.52-7.57 (2H, m), 7.60 (1H, dd, J=7.9, 1.2 Hz), 7.86 (1H, dd, J=7.9, 1.2 Hz), 10.59 (1H, s).

FAB⁺ (m/z): 353 (M+H).

Step 167b) 2-[3-[(Benzothiazol-2-yl)oxymethyl] piperidin-1-yl]benzoic acid

[Chemical formula 227]

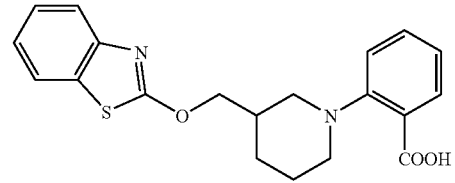

An aqueous solution (1 mL) of sodium chlorite (7.46 mg, 0.0660 mmol) and sodium dihydrogen phosphate (6.89 mg, 0.0574 mmol) was added to a solution of 2-[3-[(benzothiazol-2-yl)oxymethyl]piperidin-1-yl]benzaldehyde (10.1 mg, 0.0287 mmol) and 2-methyl-2-butene (0.00912 mL, 0.0861 mmol) in tert-butanol (3 mL). The mixture was stirred at room temperature for 5 hours. Subsequently, 2 mol/L hydrochloric acid was added to make the mixture acidic. The mixture was then extracted with ethyl acetate and washed with brine. The washed product was dried over magnesium sulfate and the solvent was evaporated. The resulting residue was air-dried to give 7.50 mg (71%) of the desired compound as a colorless powder.

¹H NMR (400 MHz, DMSO-d₆) δ 1.38-1.48 (1H, m), 1.51-1.62 (1H, m), 1.74-1.81 (1H, m), 1.85-1.92 (1H, m), 2.05-2.13 (1H, m), 3.10-3.16 (2H, m), 3.91 (1H, dd, J=9.8, 7.3 Hz), 3.99-4.05 (2H, m), 4.10 (1H, dd, J=12.8, 3.6 Hz), 6.97 (1H, t, J=7.3 Hz), 7.02 (1H, td, J=7.9, 1.2 Hz), 7.10 (1H, d, J=8.6 Hz), 7.23 (1H, td, J=7.9, 1.2 Hz), 7.40 (1H, d, J=7.3 Hz), 7.46 (1H, td, J=7.3, 1.8 Hz), 7.63 (1H, dd, J=7.3, 1.8 Hz), 7.68 (1H, dd, J=7.9, 1.2 Hz).

HR-FAB⁺ (m/z): 369.1250 (−2.3 mmu).

Example 168

2-[3-[(4'-Chlorobiphenyl-4-yl)methoxy]piperidin-1-yl]benzoic acid

Step 168a) 3-[3-[(4'-Chlorobiphenyl-4-yl)methoxy]piperidin-1-yl]benzaldehyde

[Chemical formula 228]

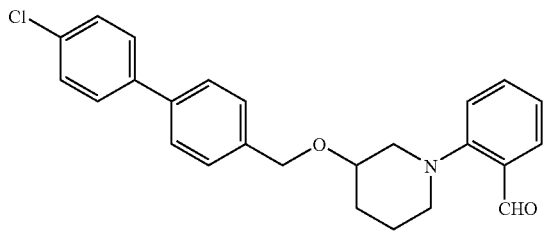

Tetrabutylammonium iodide (26.9 mg, 0.0729 mmol) and potassium carbonate (206 mg, 1.46 mmol) were added to a solution of 3-[(4'-chlorobiphenyl-4-yl)methoxy]piperidine (220 mg, 0.729 mmol) and 2-fluorobenzaldehyde (0.159 mL, 1.46 mmol) in N,N-dimethylformamide (5 mL). The mixture was stirred at 100° C. for 8 hours. Subsequently, water was added and the mixture was extracted with ethyl acetate and washed with brine. The washed product was dried over magnesium sulfate and the solvent was evaporated. Purification of the resulting residue by silica gel column chromatography (hexane:ethyl acetate=40:1->10:1) gave 156 mg (53%) of the desired compound as a pale yellow powder.

¹H NMR (400 MHz, CDCl₃) δ 1.48-1.57 (1H, m), 1.71-1.82 (1H, m), 1.89-1.96 (1H, m), 2.12-2.19 (1H, m), 2.85-2.92 (2H, m), 3.17 (1H, td, J=7.3, 3.6 Hz), 3.46-3.50 (1H, m), 3.70-3.77 (1H, m), 4.62 (1H, d, J=12.2 Hz), 4.65 (1H, d, J=12.2 Hz), 7.09-7.12 (2H, m), 7.39-7.43 (4H, m), 7.49-7.55 (5H, m), 7.80 (1H, dd, J=7.9, 1.2 Hz), 10.31 (1H, s).

FAB⁺ (m/z): 406 (M+H).

Step 168b) 2-[3-[(4'-Chlorobiphenyl-4-yl)methoxy]piperidin-1-yl]benzoic acid

[Chemical formula 229]

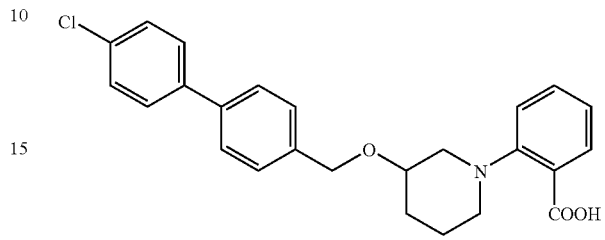

Using 3-[3-[(4'-chlorobiphenyl-4-yl)methoxy]piperidin-1-yl]benzaldehyde (156 mg, 0.384 mmol), the same procedure was followed as in Step 167b of Example 167 to give 95.7 mg (59%) of the desired compound as a colorless powder.

¹H NMR (400 MHz, DMSO-d₆) δ 1.61-1.69 (1H, m), 1.76-1.88 (2H, m), 1.94-2.03 (1H, m), 2.93-3.06 (2H, m), 3.11 (1H, dd, J=11.6, 5.5 Hz), 3.30-3.37 (1H, m), 3.76-3.81 (1H, m), 4.56 (1H, d, J=12.2 Hz), 4.64 (1H, d, J=12.2 Hz), 7.43 (1H, td, J=7.3, 1.2 Hz), 7.47 (2H, d, J=8.6 Hz), 7.51 (2H, d, J=8.6 Hz), 7.65 (2H, d, J=8.6 Hz), 7.68-7.75 (4H, m), 8.04 (1H, dd, J=7.9, 1.2 Hz), 17.39 (1H, brs).

HR-FAB⁺ (m/z): 422.1562 (+3.9 mmu).

Elemental analysis calcd (%) for C₂₅H₂₄ClNO₃.1/10H₂O: C, 70.86; H, 5.76; N, 3.28; found: C, 70.57; H, 5.77; N, 3.19.

Examples 169 Through 179

The procedures were performed in the same manner as in Example 168 to make compounds given in Table 10 below.

TABLE 10

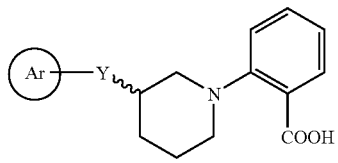

| | Absolute configuration | Ar | Y |
|---|---|---|---|
| Example 169 | Racemic mixture | 4'-methyl-4-chlorobiphenyl | OCH$_2$ |
| Example 170 | Racemic mixture | 4'-methyl-4-chlorobiphenyl | CH$_2$OCH$_2$ |
| Example 171 | Racemic mixture | 4-fluoro-4'-methyldiphenyl ether | CH$_2$O |
| Example 172 | Racemic mixture | 4-fluoro-4'-methyldiphenyl ether | CH$_2$OCH$_2$ |
| Example 173 | Racemic mixture | 2-(4-chlorophenyl)-4,5-dimethylthiazole | COCH$_2$ |
| Example 174 | Racemic mixture | 2-(4-chlorophenyl)-4,5-dimethylthiazole | CH=CHCH$_2$ |
| Example 175 | Racemic mixture | 4-phenyl-2-methylthiazole | SCH$_2$ |
| Example 176 | R | 2-(4-chlorophenyl)-4,5-dimethylthiazole | CONHCH$_2$ |
| Example 177 | S | 2-(4-chlorophenyl)-4,5-dimethylthiazole | CONHCH$_2$ |
| Example 178 | S | 2-(4-chlorophenyl)-4,5-dimethylthiazole | CH$_2$OCH$_2$ |
| Example 179 | R | 2-(4-chlorophenyl)-4,5-dimethylthiazole | CH$_2$OCH$_2$ |

<Compound of Example 169>
Colorless Powder $^1$H NMR (400 MHz, DMSO-d$_6$) δ 1.37-1.45 (1H, m), 1.68-1.77 (1H, m), 1.91-1.98 (2H, m), 2.20-2.30 (1H, m), 2.95-3.11 (3H, m), 3.25 (1H, dd, J=11.6, 3.7 Hz), 3.94 (1H, dd, J=9.8, 7.3 Hz), 4.04 (1H, dd, J=9.8, 5.5 Hz), 7.04 (2H, d, J=8.6 Hz), 7.42-7.48 (3H, m), 7.59 (2H, d, J=8.6 Hz), 7.64 (2H, d, J=8.6 Hz), 7.68 (1H, td, J=7.3, 1.8 Hz), 7.72 (1H, dd, J=8.6, 1.2 Hz), 8.04 (1H, dd, J=7.3, 1.2 Hz), 17.76 (1H, brs).

HR-FAB$^+$ (m/z): 422.1510 (−1.3 mmu).

Elemental analysis calcd (%) for $C_{25}H_{24}ClNO_3 \cdot 1/10H_2O$: C, 70.86; H, 5.76, N, 3.28; found: C, 70.58; H, 5.67; N, 3.21.

<Compound of Example 170>

Colorless Amorphous $^1$H NMR (400 MHz, DMSO-$d_6$) δ 1.22-1.32 (1H, m), 1.60-1.71 (1H, m), 1.79-1.89 (2H, m), 2.00-2.10 (1H, m), 2.82-2.88 (1H, m), 2.94-3.04 (2H, m), 3.10 (1H, dd, J=11.6, 3.7 Hz), 3.35 (1H, dd, J=9.8, 7.3 Hz), 3.42 (1H, dd, J=9.8, 5.5 Hz), 4.47 (2H, s), 7.36 (2H, d, J=8.6 Hz), 7.40 (1H, td, J=7.3, 1.2 Hz), 7.48 (2H, d, J=8.6 Hz), 7.60 (2H, d, J=8.6 Hz), 7.63-7.70 (4H, m), 8.01 (1H, dd, J=7.9, 1.8 Hz), 17.89 (1H, brs).

HR-FAB$^+$ (m/z): 436.1694 (+1.5 mmu).

<Compound of Example 171>

Colorless Oil $^1$H NMR (400 MHz, DMSO-$d_6$) δ 1.59-1.67 (1H, m), 1.71-1.79 (1H, m), 1.80-1.88 (1H, m), 1.91-2.01 (1H, m), 2.92-2.97 (1H, m), 2.99-3.02 (1H, m), 3.04-3.10 (1H, m), 3.28-3.31 (1H, m), 3.73-3.77 (1H, m), 4.48 (1H, d, J=11.6 Hz), 4.56 (1H, d, J=11.6 Hz), 6.96 (2H, d, J=8.6 Hz), 7.05 (2H, dd, J=9.2, 4.9 Hz), 7.22 (2H, t, J=8.6 Hz), 7.38 (2H, d, J=8.6 Hz), 7.43 (1H, td, J=7.3, 1.2 Hz), 7.66-7.74 (2H, m), 8.04 (1H, dd, J=7.9, 1.8 Hz), 17.40 (1H, brs). HR-FAB$^+$ (m/z): 422.1786 (+1.9 mmu).

<Compound of Example 172>

Colorless Oil $^1$H NMR (400 MHz, DMSO-$d_6$) δ 1.23-1.33 (1H, m), 1.61-1.72 (1H, m), 1.79-1.85 (1H, m), 1.86-1.91 (1H, m), 2.01-2.09 (1H, m), 2.83-2.88 (1H, m), 2.96-3.06 (2H, m), 3.10-3.13 (1H, m), 3.29-3.37 (1H, m), 3.42 (1H, dd, J=9.8, 5.5 Hz), 4.42 (2H, s), 6.94 (2H, d, J=8.6 Hz), 7.05 (2H, dd, J=9.2, 4.9 Hz), 7.22 (2H, t, J=8.6 Hz), 7.30 (2H, d, J=8.6 Hz), 7.43 (1H, td, J=7.3, 1.2 Hz), 7.66 (1H, td, J=7.9, 1.8 Hz), 7.71 (1H, dd, J=7.9, 1.2 Hz), 8.03 (1H, dd, J=7.9, 1.8 Hz), 17.76 (1H, brs).

HR-FAB$^+$ (m/z): 436.1937 (+1.3 mmu).

<Compound of Example 173>

Colorless Amorphous $^1$H NMR (400 MHz, DMSO-$d_6$) δ 1.28-1.36 (1H, m), 1.65-1.75 (1H, m), 1.86-1.93 (2H, m), 2.32-2.41 (1H, m), 2.71 (3H, s), 2.88 (1H, t, J=9.4 Hz), 2.98-3.08 (4H, m), 3.13 (1H, dd, J=11.0, 3.7 Hz), 7.40-7.44 (1H, m), 7.60 (2H, d, J=8.6 Hz), 7.64-7.69 (2H, m), 8.01-8.04 (3H, m), 17.78 (1H, brs).

HR-FAB$^+$ (m/z): 455.1192 (−0.4 mmu).

<Compound of Example 174>

Colorless Amorphous $^1$H NMR (400 MHz, DMSO-$d_6$) δ 1.44-1.55 (1H, m), 1.67-1.79 (1H, m), 1.91-2.01 (2H, m), 2.41 (3H, s), 2.63-2.72 (1H, m), 2.97-3.09 (3H, m), 3.19 (1H, dd, J=11.6, 4.3 Hz), 5.97 (1H, dd, J=15.9, 6.7 Hz), 6.77 (1H, dd, J=15.9, 1.2 Hz), 7.43 (1H, td, J=7.9, 1.2 Hz), 7.55 (2H, d, J=8.6 Hz), 7.66-7.74 (2H, m), 7.89 (2H, d, J=8.6 Hz), 8.04 (1H, dd, J=7.9, 1.2 Hz), 17.64 (1H, brs).

HR-FAB$^+$ (m/z): 439.1272 (+2.5 mmu).

<Compound of Example 175>

Colorless Powder $^1$H NMR (400 MHz, DMSO-$d_6$) δ 1.33-1.43 (1H, m), 1.61-1.72 (1H, m), 1.90-1.95 (1H, m), 2.00-2.04 (1H, m), 2.16-2.27 (1H, m), 2.91-2.97 (1H, m), 2.98-3.08 (2H, m), 3.24 (1H, dd, J=11.6, 3.1 Hz), 3.28-3.35 (2H, m), 7.35 (1H, td, J=7.3, 1.8 Hz), 7.40-7.46 (3H, m), 7.64-7.70 (2H, m), 7.90-7.93 (2H, m), 8.02-8.04 (1H, m), 17.47 (1H, brs).

HR-FAB$^+$ (m/z): 411.1174 (−2.7 mmu).

<Compound of Example 176>

Colorless Amorphous $^1$H NMR (400 MHz, DMSO-$d_6$) δ 1.26 (1H, qd, J=11.6, 3.1 Hz), 1.60-1.73 (1H, m), 1.83-1.97 (2H, m), 1.98-2.08 (1H, m), 2.58 (3H, s), 2.85 (1H, t, J=11.0 Hz), 2.99-3.06 (2H, m), 3.10 (1H, dd, J=11.6, 3.7 Hz), 3.16-3.22 (1H, m), 3.25-3.30 (1H, m), 7.44 (1H, td, J=8.6, 1.2 Hz), 7.57 (2H, d, J=8.6 Hz), 7.68 (1H, td, J=7.9, 1.8 Hz), 7.73 (1H, dd, J=7.9, 1.2 Hz), 7.94 (2H, d, J=8.6 Hz), 8.03 (1H, dd, J=7.9 Hz, J=1.2 Hz), 8.37 (1H, t, J=5.5 Hz), 17.90 (1H, brs).

HR-FAB$^+$ (m/z): 470.1336 (+3.1 mmu).

$[\alpha]^{28.6°}_D$−44.3° (C=1.1, DMF)

HPLC (CHIRALCEL OJ (Daicel Chemical Industries, Co., Ltd.) φ 0.46×25 cm, mobile phase: hexane/ethanol=60/40 (0.1% TFA), flow rate: 1 mL/min, Temp.: 40° C.): Rt 12.8 min (>99% ee)

<Compound of Example 177>

Colorless Amorphous $^1$H NMR (400 MHz, DMSO-$d_6$) δ 1.26 (1H, qd, J=11.6, 3.1 Hz), 1.60-1.72 (1H, m), 1.83-1.97 (2H, m), 1.98-2.09 (1H, m), 2.59 (3H, s), 2.85 (1H, t, J=11.0 Hz), 2.99-3.07 (2H, m), 3.10 (1H, dd, J=11.6, 3.7 Hz), 3.16-3.23 (1H, m), 3.25-3.28 (1H, m), 7.44 (1H, td, J=8.6, 1.2 Hz), 7.57 (2H, d, J=8.6 Hz), 7.68 (1H, td, J=7.9, 1.8 Hz), 7.73 (1H, dd, J=7.9, 1.2 Hz), 7.94 (2H, d, J=8.6 Hz), 8.03 (1H, dd, J=7.9 Hz, J=1.2 Hz), 8.37 (1H, t, J=5.5 Hz), 17.89 (1H, brs).

HR-FAB$^+$ (m/z): 470.1313 (+0.7 mmu).

$[\alpha]^{28.8°}_D$+41.4° (C=1.1, DMF)

HPLC (CHIRALCEL OJ (Daicel Chemical Industries, Co., Ltd.) φ 0.46×25 cm, mobile phase: hexane/ethanol=60/40 (0.1% TFA), flow rate: 1 mL/min, Temp.: 40° C.): Rt 7.4 min (93% ee)

<Compound of Example 178>

Colorless Powder $^1$H NMR (400 MHz, DMSO-$d_6$) δ 1.27 (1H, qd, J=11.6, 3.1 Hz), 1.61-1.72 (1H, m), 1.77-1.93 (2H, m), 1.99-2.10 (1H, m), 2.36 (3H, s), 2.85 (1H, t, J=11.0 Hz), 2.96-3.06 (2H, m), 3.09 (1H, dd, J=11.6, 3.1 Hz), 3.39 (1H, dd, J=9.2, 7.3 Hz), 3.47 (1H, dd, J=9.2, 5.5 Hz), 4.66 (2H, s), 7.41-7.45 (1H, m), 7.53 (2H, d, J=8.6 Hz), 7.66 (1H, td, J=7.9, 1.2 Hz), 7.70 (1H, dd, J=7.9, 1.2 Hz), 7.89 (2H, d, J=8.6 Hz), 8.03 (1H, dd, J=7.9, 1.8 Hz), 17.83 (1H, s).

HR-FAB$^+$ (m/z): 457.1327 (−2.6 mmu).

Elemental analysis calcd (%) for $C_{24}H_{25}ClN_2O_3S \cdot 1/10H_2O$: C, 62.83; H, 5.54; N, 6.11; found: C, 62.66; H, 5.47; N, 5.95.

$[\alpha]^{28.6°}_D$+17.2° (C=1.1, CHCl$_3$)

HPLC (CHIRALCEL OJ (Daicel Chemical Industries, Co., Ltd.) φ 0.46×25 cm, mobile phase: hexane/ethanol=90/10 (0.1% TFA), flow rate: 1 mL/min, Temp.: 40° C.): Rt 65.3 min (>99% ee)

<Compound of Example 179>

Colorless Powder $^1$H NMR (400 MHz, DMSO-$d_6$) δ 1.33 (1H, qd, J=11.6, 3.1 Hz), 1.67-1.78 (1H, m), 1.83-1.98 (2H, m), 2.04-2.16 (1H, m), 2.42 (3H, s), 2.90 (1H, t, J=11.0 Hz), 3.01-3.12 (2H, m), 3.15 (1H, dd, J=11.6, 3.1 Hz), 3.45 (1H, dd, J=9.2, 7.3 Hz), 3.52 (1H, dd, J=9.2, 5.5 Hz), 4.72 (2H, s), 7.46-7.50 (1H, m), 7.59 (2H, d, J=8.6 Hz), 7.71 (1H, dt, J=7.9, 1.2 Hz), 7.76 (1H, dd, J=7.9, 1.2 Hz), 7.94 (2H, d, J=8.6 Hz), 8.09 (1H, dd, J=7.9, 1.8 Hz), 17.90 (1H, s).

HR-FAB$^+$ (m/z): 457.1340 (−1.3 mmu).

Elemental analysis calcd (%) for $C_{24}H_{25}ClN_2O_3S \cdot 3/10H_2O$: C, 62.34; H, 5.58; N, 6.06; found: C, 62.33; H, 5.50; N, 5.87.

$[\alpha]^{28.7°}_D$−16.0°(C=0.9, CHCl$_3$)

HPLC (CHIRALCEL OJ (Daicel Chemical Industries, Co., Ltd.) φ 0.46×25 cm, mobile phase: hexane/ethanol=90/10 (0.1% TFA), flow rate: 1 mL/min, Temp.: 40° C.): Rt 57.7 min (>99% ee)

Example 180

3-[3-[2-[2-(4-Chlorophenyl)-4-methylthiazol-5-yl]ethyl]piperidin-1-yl]benzoic acid

[Chemical formula 230]

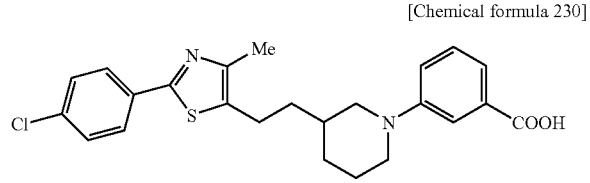

10% Palladium on activated carbon (5 mg) was added to 3-[3-[2-[2-(4-chlorophenyl)-4-methylthiazol-5-yl]ethenyl]piperidin-1-yl]benzoic acid (35.0 mg, 0.0797 mmol) in tetrahydrofuran (5 mL). The reaction mixture was stirred at room temperature for hours in a hydrogen atmosphere. Subsequently, the mixture was filtered through Celite and the solvent was evaporated to give 35.1 mg (quant.) of the desired compound as a colorless powder.

$^1$H NMR (400 MHz, DMSO-$d_6$) δ 1.08-1.18 (1H, m), 1.49-1.58 (2H, m), 1.59-1.67 (2H, m), 1.71-1.76 (1H, m), 1.85-1.89 (1H, m), 2.35 (3H, s), 2.46-2.53 (1H, m), 2.71 (1H, dd, J=11.6, 2.4 Hz), 2.88 (2H, t, J=7.3 Hz), 3.60-3.63 (1H, m), 3.67-3.70 (1H, m), 7.19 (1H, td, J=7.3, 1.8 Hz), 7.27-7.33 (2H, m), 7.45-7.47 (1H, m), 7.52 (2H, d, J=8.6 Hz), 7.86 (2H, d, J=8.6 Hz), 12.78 (1H, brs).

HR-FAB$^+$ (m/z): 441.1441 (+3.7 mmu).

Example 181

2-[3-[2-[2-(4-Chlorophenyl)-4-methylthiazol-5-yl]ethyl]piperidin-1-yl]benzoic acid

[Chemical formula 231]

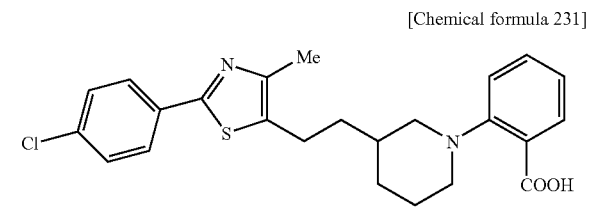

Using 2-[3-[2-[2-(4-chlorophenyl)-4-methylthiazol-5-yl]ethenyl]piperidin-1-yl]benzoic acid (10.0 mg, 0.0228 mmol), the same procedure was followed as in Example 180 to give 8.00 mg (79%) of the desired compound as a colorless oil.

$^1$H NMR (400 MHz, DMSO-$d_6$) δ 1.21-1.30 (1H, m), 1.54-1.71 (3H, m), 1.74-1.83 (1H, m), 1.86-1.95 (2H, m), 2.32 (3H, s), 2.79-2.86 (3H, m), 2.98-3.08 (2H, m), 3.16 (1H, dd, J=11.0, 3.1 Hz), 7.44 (1H, td, J=7.3, 1.2 Hz), 7.52 (2H, d, J=8.6 Hz), 7.67 (1H, td, J=7.9, 1.8 Hz), 7.73 (1H, d, J=7.3 Hz), 7.86 (2H, d, J=8.6 Hz), 8.04 (1H, dd, J=7.9, 1.2 Hz), 18.07 (1H, brs).

HR-FAB$^+$ (m/z): 441.1374 (−3.0 mmu).

Example 181

Methyl (S)-3-[3-[[2-(4-chlorophenyl)-4-methylthiazole-5-carbonyl]methylamino]piperidin-1-yl]benzoate

[Chemical formula 232]

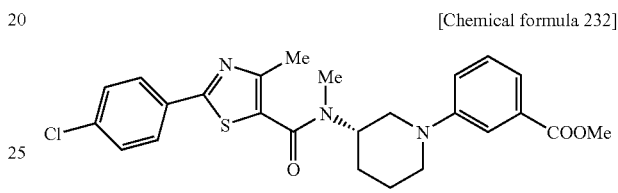

Methyl iodide (0.0530 mL, 0.852 mmol) and silver oxide (197 mg, 0.852 mmol) were added to methyl(S)-3-[3-[[2-(4-chlorophenyl)-4-methylthiazole-5-carbonyl]amino]piperidin-1-yl]benzoate (100 mg, 0.213 mmol) in N,N-dimethylformamide (2 mL). The reaction mixture was stirred at 80° C. for 3 hours. Subsequently, the mixture was filtered through Celite and ethyl acetate was added to the filtrate. The mixture was then washed sequentially with water and brine, followed by drying over magnesium sulfate and evaporation of the solvent. Purification of the resulting residue by silica gel column chromatography (hexane:ethyl acetate=10:1->2:1) gave 59.4 mg (58%) of the desired compound as a colorless oil.

$^1$H NMR (400 MHz, CDCl$_3$) δ 1.52-1.60 (1H, m), 1.74-1.84 (2H, m), 1.88-1.99 (2H, m), 2.51 (3H, s), 2.65-2.71 (1H, m), 2.92 (1H, t, J=11.0 Hz), 3.06 (3H, s), 3.64-3.76 (2H, m), 3.91 (3H, s), 7.12 (1H, m), 7.30 (1H, t, J=7.9 Hz), 7.41 (2H, d, J=8.6 Hz), 7.51 (1H, d, J=7.3 Hz), 7.59 (1H, brs), 7.85 (2H, d, J=8.6 Hz).

Example 182

(S)-3-[3-[[2-(4-Chlorophenyl)-4-methylthiazole-5-carbonyl]methylamino]piperidin-1-yl]benzoic acid

[Chemical formula 233]

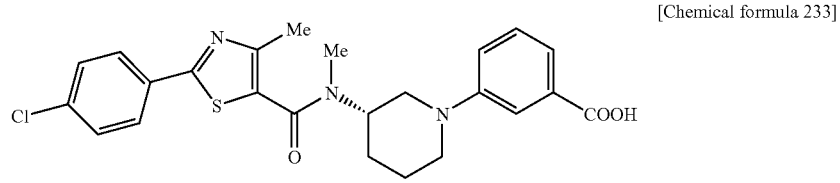

A 1 mol/L aqueous potassium hydroxide solution (1 mL) was added to methyl(S)-3-[3-[[2-(4-chlorophenyl)-4-methylthiazole-5-carbonyl]methylamino]piperidin-1-yl]benzoate (59.4 mg, 0.123 mmol) in methanol (5 mL). The mixture was stirred for 1 hour while being refluxed. The solvent was then evaporated and the residue was dissolved in water. The mixture was made acidic by the addition of 2 mol/L hydrochloric acid. The crystallized powdery product was collected by filtration. Washing this product with water gave 56.4 mg (98%) of the desired product as a colorless amorphous product.

$^1$H NMR (400 MHz, DMSO-$d_6$) δ 1.53-1.69 (1H, m), 1.76-1.90 (3H, m), 2.40 (3H, s), 2.70 (1H, t, J=12.2 Hz), 2.94-3.03 (4H, m), 3.26-3.42 (1H, m), 3.64-3.76 (2H, m), 7.14-7.23 (1H, m), 7.25-7.35 (2H, m), 7.46 (1H, brs), 7.57 (2H, d, J=8.6 Hz), 7.93 (2H, d, J=8.6 Hz), 12.83 (1H, brs).

HR-FAB$^+$ (m/z) 470.1286 (−1.9 mmu).

$[\alpha]^{28.8°}_D$ −58.0° (C=1.0, DMF)

Test Example 1

Activation of Transcription of Human Peroxisome Proliferator-Activated Receptor (PPAR) α

CHO-K1 cells cultured in Ham's F12 medium supplemented with 10% fetal calf serum were cotransfected with the following plasmids: A receptor plasmid encoding a fusion protein consisting of the DNA-binding domain of yeast transcription factor Gal4 fused to the ligand-binding domain of human PPARα (Biochemistry, 1993, 32, 5598), a reporter plasmid (STRATAGENE, firefly luciferase reporter plasmid), and a renilla luciferase plasmid for internal standard (Promega). The cotransfection was performed over a 2-hour period by using Lipofectamine (INVITROGEN) in the absence of serum. Subsequently, a test compound was added in Ham's F12 medium supplemented with 10% defatted bovine serum. The cells were then incubated at 37° C. for 20 hours. The activity of each luciferase was then determined and corrected for internal standard. The results are shown in Table 11 below.

TABLE 11

| Ex. No. | EC$_{50}$ (μmol/L) |
|---------|---------------------|
| 18 | 0.065 |
| 19 | 0.97 |
| 20 | 1.36 |
| 22 | 0.16 |
| 24 | 1.54 |
| 25 | 0.56 |
| 32 | 0.02 |

These results indicate that the cyclic amino benzoic acid derivatives of the present invention are a group of novel compounds that can effectively activate transcription of human PPARα.

INDUSTRIAL APPLICABILITY

The cyclic amino benzoic acid derivatives of the present invention are a group of novel compounds that can effectively activate transcription of human PPARα.

Agonists of the human PPARα, the compounds of the present invention can serve not only as hypolipidemic drugs that are particularly effective in liver, but also as potent suppressants of arteriosclerosis. The compounds of the present invention therefore are of significant pharmaceutical importance.

The invention claimed is:
1. A cyclic amino benzoic acid derivative represented by general formula (1)

[Chemical formula 1]

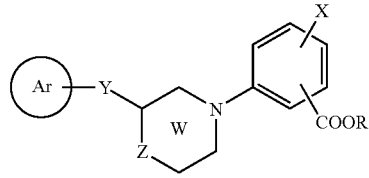

(1)

(wherein
Y represents a C$_1$-C$_4$ alkylene, C$_2$-C$_4$ alkenylene or general formula (2)

[Chemical formula 2]

-T-A-U- (2)

(wherein T represents a single bond, C$_1$-C$_4$ alkylene or C$_2$-C$_4$ alkenylene,
U represents a single bond or C$_1$-C$_4$ alkylene,
A represents a carbonyl group, oxygen atom, —NR$^1$— (R$^1$ represents a hydrogen atom or lower alkyl group), general formula (3)

[Chemical formula 3]

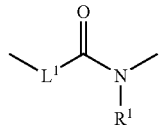

(3)

(wherein L$^1$ represents a single bond or —NR$^1$—, and R$^1$ is as defined above) or general formula (4)

[Chemical formula 4]

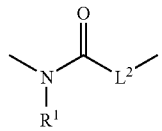

(4)

(wherein L$^2$ represents a single bond, and R$^1$ is as defined above),
Z represents methylene,
X represents a hydrogen atom, halogen atom, lower alkoxy group, nitro group, amino group or benzyloxy group,
R represents a hydrogen atom or lower alkyl group,
—COOR is substituted at ortho position or metha position of binding position of ring W, and
ring Ar represents general formula (5)

[Chemical formula 5]

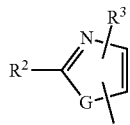

(5)

(wherein $R^2$ represents a phenyl group which may have one or more substituent, where said substituent is the same as or different from each other and represents a halogen atom, lower alkoxy group or trifluoromethyl group, $R^3$ represents a hydrogen atom or lower alkyl group, and G represents a sulfur atom)), or a pharmaceutically acceptable salt thereof.

2. A cyclic amino benzoic acid derivative according to claim 1, wherein in the general formula (1), Y represents a $C_1$-$C_4$ alkylene, $C_2$-$C_4$ alkenylene, C(O)NH, NHC(O)NH, C(O)NH—$C_1$-$C_4$ alkylene, C(O)—$C_1$-$C_4$ alkylene, $C_1$-$C_4$ alkylene-NHC(O), $C_1$-$C_4$ alkylene-C(O)NH, $C_2$-$C_4$ alkenylene-C(O)NH, $C_1$-$C_4$ alkylene-O, $C_1$-$C_4$ alkylene-O—$C_1$-$C_4$ alkylene or $C_1$-$C_4$ alkylene-NH, or a pharmaceutically acceptable salt thereof.

3. A cyclic amino benzoic acid derivative according to claim 1, wherein the compound represented by the general formula (1) is 2-[3-[[2-(4-chlorophenyl)-4-methylthiazol-5-yl]methoxymethyl]piperidin-1-yl] benzoic acid,
3-[3-[[2-(4-chlorophenyl)-4-methylthiazol-5-yl]methoxymethyl]piperidin-1-yl] benzoic acid,
3-[3-[[2-(4-chlorophenyl)-4-methylthiazol-5-yl]methoxy]piperidin-1-yl] benzoic acid,
2-[3-[[2-(4-chlorophenyl)-4-methylthiazol-5-yl]carbonylaminomethyl]piperidin-1-yl] benzoic acid,
3-[3-[[2-(4-chlorophenyl)-4-methylthiazol-5-yl]carbonylaminomethyl]piperidin-1-yl] benzoic acid,
3-[3-[[2-(4-chlorophenyl)-4-methylthiazol-5-yl]carbonylamino]piperidin-1-yl] benzoic acid,
2-[3-[N-[[2-(4-chlorophenyl)-4-methylthiazol-5-yl]methyl] carbamoyl]piperidin-1-yl] benzoic acid,
(S)-2-[3-[[2-(4-chlorophenyl)-4-methylthiazol-5-yl]methoxymethyl]piperidin-1-yl] benzoic acid,
(R)-2-[3-[[2-(4-chlorophenyl)-4-methylthiazol-5-yl]methoxymethyl]piperidin-1-yl] benzoic acid,
(R)-3-[3-[[2-(4-chlorophenyl)-4-methylthiazol-5-yl]methoxy]piperidin-1-yl] benzoic acid,
(S)-2-[3-[[2-(4-chlorophenyl)-4-methylthiazol-5-yl]carbonylaminomethyl]piperidin-1-yl] benzoic acid,
(R)-2-[3-[[2-(4-chlorophenyl)-4-methylthiazol-5-yl]carbonylaminomethyl]piperidin-1-yl] benzoic acid,
(S)-3-[3-[[2-(4-chlorophenyl)-4-methylthiazol-5-yl]carbonylamino]piperidin-1-yl] benzoic acid, or
(R)-3-[3-[[2-(4-chlorophenyl)-4-methylthiazol-5-yl]carbonylamino]piperidin-1-yl] benzoic acid, or a pharmaceutically acceptable salt thereof.

4. A pharmaceutical composition comprising at least one cyclic amino benzoic acid derivative or a pharmaceutically acceptable salt thereof according to claim 1 as an active ingredient.

5. A cyclic amino benzoic acid derivative according to claim 1, wherein the general formula (1) represents general formula (1a)

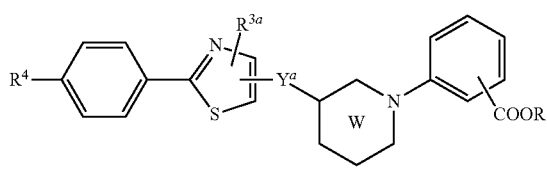

(1a)

(wherein $Y^a$ represents general formula (2d)

$T^a$-$A^a$-U— (2d)

(wherein $T^a$ represents a single bond or $C_1$-$C_4$ alkylene, U represents a single bond or $C_1$-$C_4$ alkylene, $A^a$ represents an oxygen atom, general formula (3b)

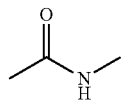

(3b)

or general formula (4b)

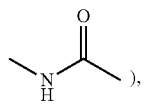

(4b)

R represents a hydrogen atom or lower alkyl group,
COOR is substituted at ortho position or metha position of binding position of the ring W,
$R^{3a}$ represents a lower alkyl group, and
$R^4$ represents a halogen atom), or a pharmaceutically acceptable salt thereof.

6. A cyclic amino benzoic acid derivative according to claim 5, wherein in the general formula (1a), $Y^a$ represents a C(O)NH, C(O)NH—$C_1$-$C_4$ alkylene, $C_1$-$C_4$ alkylene-NHC(O), $C_1$-$C_4$ alkylene-C(O)NH, $C_1$-$C_4$ alkylene-O or $C_1$-$C_4$ alkylene-O—$C_1$-$C_4$ alkylene, or a pharmaceutically acceptable salt thereof.

7. A cyclic amino benzoic acid derivative according to claim 1, wherein the compound represented by the general formula (1) is 2-[3-[[2-(4-chlorophenyl)-4-methylthiazol-5-yl]methoxymethyl]piperidin-1-yl] benzoic acid,
3-[3-[[2-(4-chlorophenyl)-4-methylthiazol-5-yl]methoxymethyl]piperidin-1-yl] benzoic acid,
3-[3-[[2-(4-chlorophenyl)-4-methylthiazol-5-yl]methoxy]piperidin-1-yl] benzoic acid,
2-[3-[[2-(4-chlorophenyl)-4-methylthiazol-5-yl]carbonylaminomethyl]piperidin-1-yl] benzoic acid,
3-[3-[[2-(4-chlorophenyl)-4-methylthiazol-5-yl]carbonylaminomethyl]piperidin-1-yl] benzoic acid,
3-[3-[[2-(4-chlorophenyl)-4-methylthiazol-5-yl]carbonylamino]piperidin-1-yl] benzoic acid,
2-[3-[N-[[2-(4-chlorophenyl)-4-methylthiazol-5-yl]methyl]carbamoyl]piperidin-1-yl] benzoic acid,
(S)-3-[3-[[2-(4-chlorophenyl)-4-methylthiazol-5-yl]carbonylamino]piperidin-1-yl] benzoic acid or
(R)-3-[3-[[2-(4-chlorophenyl)-4-methylthiazol-5-yl]carbonylamino]piperidin-1-yl] benzoic acid, or a pharmaceutically acceptable salt thereof.

8. A pharmaceutical composition comprising at least one cyclic amino benzoic acid derivative or a pharmaceutically acceptable salt thereof according to claim 2 as an active ingredient.

9. A pharmaceutical composition comprising at least one cyclic amino benzoic acid derivative or a pharmaceutically acceptable salt thereof according to claim 3 as an active ingredient.

10. A pharmaceutical composition comprising at least one cyclic amino benzoic acid derivative or a pharmaceutically acceptable salt thereof according to claim 5 as an active ingredient.

11. A pharmaceutical composition comprising at least one cyclic amino benzoic acid derivative or a pharmaceutically acceptable salt thereof according to claim 6 as an active ingredient.

12. A pharmaceutical composition comprising at least one cyclic amino benzoic acid derivative or a pharmaceutically acceptable salt thereof according to claim 7 as an active ingredient.

* * * * *